(12) United States Patent
Cheng et al.

(10) Patent No.: US 7,763,418 B2
(45) Date of Patent: Jul. 27, 2010

(54) DETECTION OF RHO PROTEINS

(75) Inventors: Li Cheng, Denver, CO (US); Ashley Davis, Denver, CO (US); Kim Middleton, Denver, CO (US)

(73) Assignee: Cytoskeleton, Inc., Denver, CO (US)

( * ) Notice: Subject to any disclaimer, the term of this patent is extended or adjusted under 35 U.S.C. 154(b) by 0 days.

(21) Appl. No.: 11/428,415

(22) Filed: Jul. 3, 2006

(65) Prior Publication Data

US 2007/0020687 A1 Jan. 25, 2007

Related U.S. Application Data

(60) Provisional application No. 60/695,844, filed on Jul. 5, 2005.

(51) Int. Cl.
 *C12Q 1/00* (2006.01)
 *G01N 33/53* (2006.01)
 *G01N 33/566* (2006.01)

(52) U.S. Cl. .............. 435/4; 435/7.1; 436/501

(58) Field of Classification Search .............. 435/4, 435/7.1; 436/501
 See application file for complete search history.

(56) References Cited

U.S. PATENT DOCUMENTS

| | | | |
|---|---|---|---|
| 5,912,131 | A | 6/1999 | Eyre |
| 6,300,081 | B1 | 10/2001 | Taylor et al. |
| 6,951,947 | B2 | 10/2005 | Hahn |
| 2004/0029191 | A1* | 2/2004 | Lomas et al. ............ 435/7.9 |
| 2005/0164295 | A1* | 7/2005 | Hoffmann et al. ........ 435/7.1 |

FOREIGN PATENT DOCUMENTS

WO 02/08245 A2 1/2002

OTHER PUBLICATIONS

Kimura et al. J. Biol. Chem. 275(23):17233-17236; 2000.*
Stocklein et al. Sensors & Actuators B 24-25:80-84; 1995.*
Zhang et al. Biol. Pharma Bull. 24(8):970-972; 2001.*
Schreiber et al. Nucl. Acids Res. 17(15):6419; 1989.*
Tu et al. Biochem. Genet. 15(1/2):195-210; 1977.*
Arthur et al., "RhoA inactivation by p190RhoGAP regulates cell spreading and migration by promoting membrane protrusion and polarity," *Mol. Biol. Cell*, (2001) 12(9):2711-2720.
Benard et al., "Characterization of rac and cdc42 activation in chemoattractant-stimulated human neutrophils using a novel assay for active GTPases," *J. Biol. Chem.* (1999) 274(19):13198-13204.
Benard et al., "Assay of Cdc42, Rac, and Rho GTPase activation by affinity methods," *Meth. Enz.*, (2002) 345:349-359.
Bishop et al., "Rho GTPases and their effector proteins," *Biochem J.* (2000) 348 Pt 2:241-255.
Blumenstein, et al. "Models of the cooperative mechanism for Rho effector recognition: implications for RhoA-mediated effector activation." *J. Biol. Chem.* (2004) 279(51):53419-53426.

Chen, et al., "Oncogenic Ras leads to Rho activation by activating the mitogen-activated protein kinase pathway and decreasing Rho-GTPase-activating protein activity." *J. Biol. Chem.* (2003) 278(5):2807-18.
Cheng, et al., "Pleckstrin homology domain-mediated activation of the rho-specific guanine nucleotide exchange factor Dbs by Rac1," *J. Biol. Chem.* (2004) 279(13):12786-93.
Crowther, "Titration of Reagents" *Meth. Mol. Biol.* (2001) 149:83-113.
Edlund et al., "Transforming growth factor-beta-induced mobilization of actin cytoskeleton requires signaling by small GTPases Cdc42 and RhoA," *Mol. Biol. Cell*, (2002) 13(3):902-914.
Fiordalisi et al., "PRL tyrosine phosphatases regulate rho family GTPases to promote invasion and motility," *Canc. Res.* (2006) 66(6):3153-3161.
Fritz et al., "Rho GTPases: promising cellular targets for novel anti-cancer drugs, " *Curr. Cancer Drug Targ.*, (2006) 6(1):1-14.
Fujisawa, "Identification of the Rho-binding domain of p160ROCK, a Rho-associated coiled-coil containing protein kinase," *J. Biol. Chem.* (1996) 271(38):23022-8.
Fujisawa, et al., "Different Regions of Rho Determine Rho-selective Binding of Different Classes of Rho Target Molecules," *J. Biol. Chem.* (1998) 273(30):18943-18949.
Ingham, "Precipitation of proteins with polyethylene glycol," *Meth. Enz.* (1990) 182:301-6.
Itoh et al., "Activation of rac and cdc42 video imaged by fluorescent resonance energy transfer-based single-molecule probes in the membrane of living cells," *Mol. Cell Biol.* (2002) 22(18):6582-6591.
Kimura et al., "Accumulation of GTP-bound RhoA during cytokinesis and a critical role of ECT2 in this accumulation." *J. Biol. Chem.* (2000) 275(23):17233-6.
Klooster et al., "Targeting and activation of Rac1 are mediated by the exchange factor beta-Pix," *J. Cell Biol.*, (2006) 172(5):759-769.
Knaus, et al., "Purification and characterization of Rac 2. A cytosolic GTP-binding protein that regulates human neutrophil NADPH oxidase," *J. Biol. Chem.* (1992) 267(33):23575-82.
Kozer et al., "Effect of crowding on protein-protein association rates: fundamental differences between low and high mass crowding agents," *J. Mol. Biol.*, (2004) 336(3):763-74.
Kranenburg et al., "Activation of RhoA by lysophosphatidic acid and Galpha12/13 subunits in neuronal cells: induction of neurite retraction," *Mol. Biol. Cell* (1999) 10(6):1851-1857.
Takaya et al., "RalA activation at nascent lamellipodia of epidermal growth factor-stimulated Cos7 cells and migrating Madin-Darby canine kidney cells," *Mol. Biol. Cell* (2004) 15(6):2549-57.
Leung et al., "Deleted in liver cancer 2 (DLC2) suppresses cell transformation by means of inhibition of RhoA activity," *Proc. Natl. Acad. Sci. USA* (2005) 102(42):15207-15212.

(Continued)

*Primary Examiner*—Fereydoun G Sajjadi
(74) *Attorney, Agent, or Firm*—Pepper Hamilton LLP

(57) ABSTRACT

The present invention provides methods of detecting activated Rho GTPase proteins by contacting a solid support with a sample comprising an activated Rho GTPase protein. The solid support is linked to an activated Rho GTPase binding peptide. The activated Rho GTPase protein remains associated with the solid support during the detection.

20 Claims, 25 Drawing Sheets

OTHER PUBLICATIONS

Leung, et al., "The nucleotide switch in Cdc42 modulates coupling between the GTPase-binding and allosteric equilibria of Wiskott-Aldrich syndrome protein," *Proc. Natl. Acad. Sci. USA* (2005) 102(16):5685-5690.

Ligeti et al., "Phospholipids can switch the GTPase substrate preference of a GTPase-activating protein," *J. Biol. Chem.* (2004) 279(7):5055-8.

Martin et al., "A novel serine kinase activated by rac1/CDC42Hs-dependent autophosphorylation is related to PAK65 and STE20," *EMBO J.* (1995) 14(9):1970-1978.

Moon et al., "Rho GTPase-activating proteins in cell regulation," *Trends Cell Biol.* (2003) 13(1):13-22.

Nalbant et al., "Activation of endogenous Cdc42 visualized in living cells," *Science* (2004) 305(5690):1615-1619.

Neal et al., "Kinetic analysis of the hydrolysis of GTP by p21N-ras. The basal GTPase mechanism," *Journal of Biological Chemistry* (1988) 263(36):19718-19722.

Nobes et al., "Regulation and function of the Rho subfamily of small GTPases." *Curr. Op. Gen. Dev.* (1994) 4(1):77-81.

Pertz et al., "Designing biosensors for Rho family proteins—deciphering the dynamics of Rho family GTPase activation in living cells," *J. Cell Sci* (2004) 117(Pt 8):1313-1318.

Pertz et al., "Spatiotemporal dynamics of RhoA activity in migrating cells," *Nature* (2006) 440(7087):1069-1072.

Quinn et al., "Translocation of Rac correlates with NADPH oxidase activation. Evidence for equimolar translocation of oxidase components,", *J. Biol. Chem.* (1993) 268(28):20983-7.

Ren et al., "Regulation of the small GTP-binding protein Rho by cell adhesion and the cytoskeleton," *EMBO J.* (1999) 18(3):578-585.

Ren et al., "Determination of GTP loading on Rho," *Meth. Enz.* (2000) 325:264-272.

Riento et al., "RhoE binds to ROCK I and inhibits downstream signaling," *Mol. Cell. Biol.* (2003) 23(12):4219-29.

Schoenwaelder, et al., "Evidence for a calpeptin-sensitive protein-tyrosine phosphatase upstream of the small GTPase Rho. A novel role for the calpain inhibitor calpeptin in the inhibition of protein-tyrosine phosphatases," *J. Biol. Chem.* (1999) 274(20):14359-67.

Schoenwaelder, et al., "The protein tyrosine phosphatase Shp-2 regulates RhoA activity," *Current Biol.* (2000) 10(23):1523-26.

Self et al., "Measurement of intrinsic nucleotide exchange and GTP hydrolysis rates," *Meth. Enz.* (1995) 256:67-76.

Subauste et al., "Rho family proteins modulate rapid apoptosis induced by cytotoxic T lymphocytes and Fas," *J. Biol. Chem.* (2000) 275(13):9725-33.

Sun et al. "Rho and ROCK Signaling in VEGF-Induced Microvascular Endothelial Hyperpermeability," *Microcirculation* (2006) 13(3):237-247.

Takai et al., "Small GTP-binding proteins," *Physiol. Rev.* (2001) 81(1):153-208.

Teusch et al., "A high-content screening assay for the Nogo receptor based on cellular Rho activation," *Assay and Drug Devel. Technol.* (2006) 4(2):133-41.

Kraynov et al., "Localized Rac Activation Dynamics Visualized in Living Cells," *Science* (2000) 290:333-337.

Vetter et al., "The guanine nucleotide-binding switch in three dimensions," *Science* (2001) 294(5545):1299-304.

Vouret-Craviari et al., "Distinct signals via Rho GTPases and Src drive shape changes by thrombin and sphingosine-1-phosphate in endothelial cells," *J. Cell Sci.* (2002) 115(Pt 12):2475-84.

Wakino, et al., "Rho/Rho kinase as a potential target for the treatment of renal disease," *Drug News Perspect.* (2005) 18(10):639-43.

Wells et al., "Identification of potential mechanisms for regulation of p115 RhoGEF through analysis of endogenous and mutant forms of the exchange factor," *J. Biol. Chem.* (2001) 276(31):28897-905.

Werner et al., "Integrins engage mitochondrial function for signal transduction by a mechanism dependent on Rho GTPases," *J. Cell Biol.* (2002) 158(2):357-68.

Xu, et al., "Differing structural requirements for GTPase-activating protein responsiveness and NADPH oxidase activation by Rac," *J. Biol. Chem.* (1994) 269(38):23569-74.

Glogauer et al., "Rac1 Deletion in Mouse Neutrophils Has Selective Effects on Neutrophil Functions," *J Immunol* (2003) 170:5652-5657.

Wennerberg et al., "The Ras superfamily at a glance," *J Cell Sci* (2005) 118:843-846.

Ridley et al., "The small GTP-binding protein rho regulates the assembly of focal adhesions and actin stress fibers in response to growth factors," *Cell* (1992) 70:389-399.

Braga et al., "The small GTPases Rho and Rac are required for the establishment of cadherin-dependent cell-cell contacts," *J Cell Biol* (1997) 137(6):1421-1431.

Coso et al., "The small GTP-binding proteins Rac1 and Cdc42 regulate the activity of the JNK/SAPK signaling pathway," *Cell* (1995) 81:1137-1146.

Aspenstrom et al., "Rho GTPases have diverse effects on the organization of the actin filament system," *Biochem J* (2004) 277:327-337.

Zong et al., "The insert region of RhoA is essential for Rho kinase activation and cellular transformation," *Molecular and Cellular Biology* (2001) 21(16):5287-5298.

Gregorius., K., et al., Hydrocoating: a new method for coupling biomolecules to solid phases, Journal of Immunological Methods, 1995;181:65-73.

Cheng, L., et al., An ELISA based assay to detect activation on Rho family GTPases, Proceedings of the Annual Meeting of the American Association of Cancer Research, Apr. 1, 2006;47:997.

Supplemental European Search Report dated Feb. 1, 2010.

\* cited by examiner

Figure 1A: Coomassie Stained Gel of Recombinant Effector-GBD Peptides
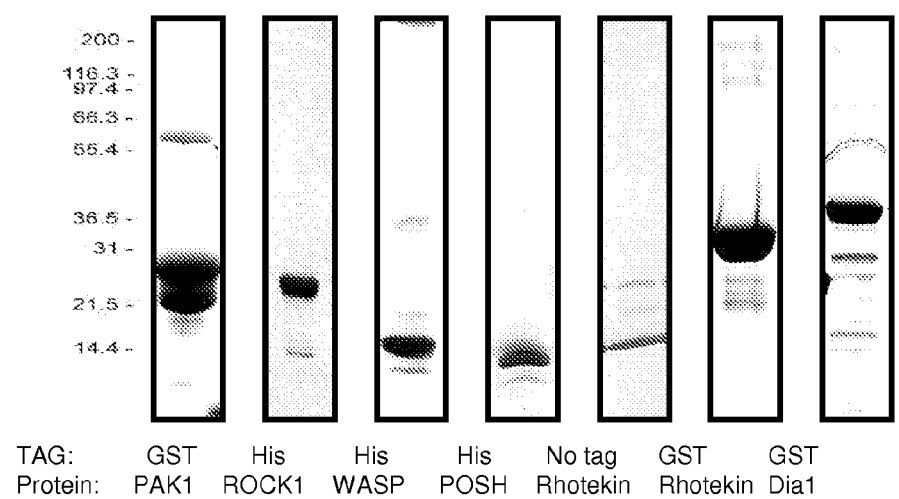

Figure 1B: DNA and Amino Acid Sequence of Modified Rhotekin-GBD

```
Rhotekin wt:    ATCCTGGAGG ACCTCAATAT GCTCTACATC CGGCAGATGG CACTCAGCCT GGAGGACACA GACCTGCAGA
Rhotekin Cys:   ATTCTGGAAG ATCTGAACAT GCTGTACATT CGGCAGATGG CGCTGTCTTT AGAAGATACG GAACTTCAAC
Amino Acid wt:  I  L  E    D  L  N  M    L  Y  I    R  Q  M    A  L  S  L    E  D  T    E  L  Q
Amino Acid Cys: I  L  E    D  L  N  M    L  Y  I    R  Q  M    A  L  S  L    E  D  T    E  L  Q Rhotekin wt:    GGAAACTAGA TCATGAGATC CGGATGAGGG ATGGGGCCTG CAAGCTGCTG GCAGCCTGCT CCCAGCGAGA
Rhotekin Cys:   GTAAATTAGA TCATGAAATC CGCATGCGTG ATGGTGCCGA AAAACTCCTG GCCGCGTTGT CCCAGAGAGA
Amino Acid wt: R  K  L  D    H  E  I    R  M  R    D  G  A  C    K  L  L    A  A  C    S  Q  R  E
Amino Acid Cys:R  K  L  D    H  E  I    R  M  R    D  G  A  E    K  L  L    A  A  L    S  Q  R  E Rhotekin wt:    GCAGGCTCTG GAAGCCACCA AGAGCCTGCT GGTGTGCAAC AGCCGTATTC TCAGCTACAT GGGTGAGCTG
Rhotekin Cys:   ACAGGCACTG GAAGCAACCA AATCATTGCT GGTGTCGAAT AGCCGTATCC TGAGTTATAT GGGCGAACTT
Amino Acid wt:     Q  A  L    E  A  T    K  S  L  L  V    C  N    S  R  I    L  S  Y  M    G  E  L
Amino Acid Cys:    Q  A  L    E  A  T    K  S  L  L  V    S  N    S  R  I    L  S  Y  M    G  E  L Rhotekin wt:    CAGCGGCGAA AGGAGGCCCA GGTGCTGGAG AAGACAGGCA GGCGACCTTC G
Rhotekin Cys:   CAGCGCCGCA AAGAAGCACA AGTTCTCGAA AAAACTGGTG GGGGCTGCTA A
Amino Acid wt:  Q  R  R    K  E  A  Q    V  L  E    K  T  G    R  R  P  S
Amino Acid Cys: Q  R  R    K  E  A  Q    V  L  E    K  T  G    R  R  C  S
```

Figure 1C: Modified Rhotekin-Cys is Able to Selectively Bind to Activated RhoA
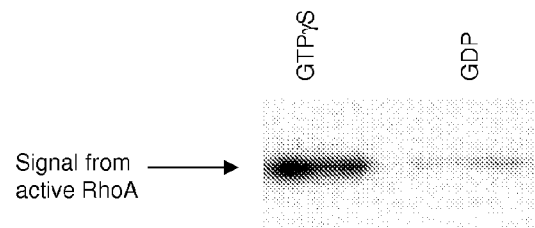

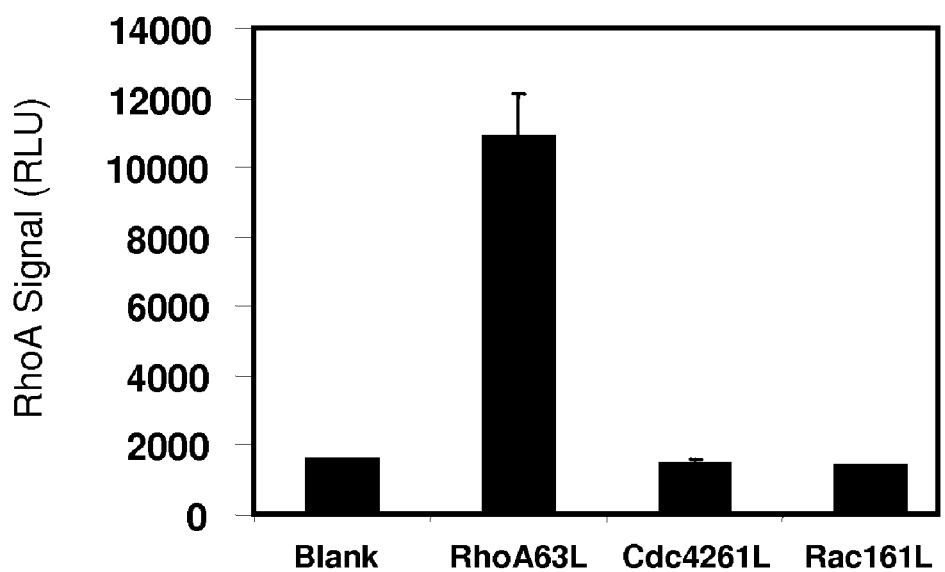
Figure 2A: Utility of ROCK Plates to Detect Active RhoA

Figure 2B: Utility of POSH Plates to Detect Active Rac1
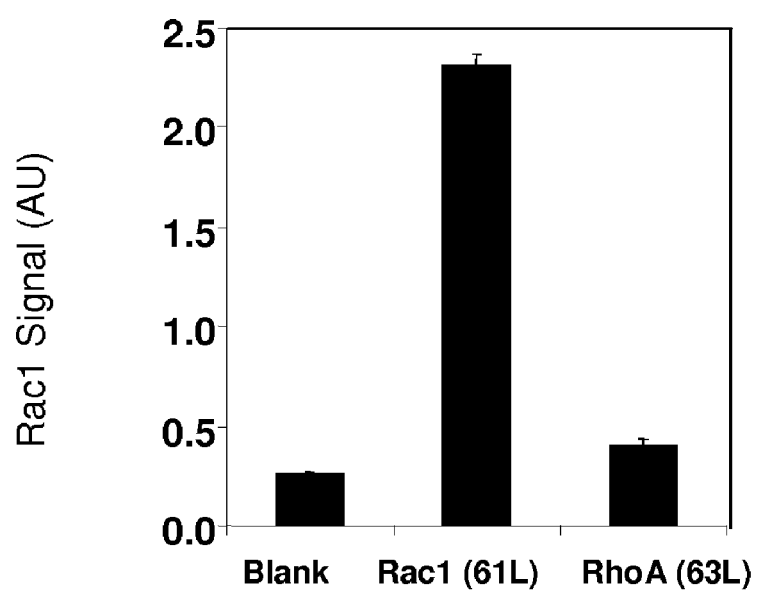

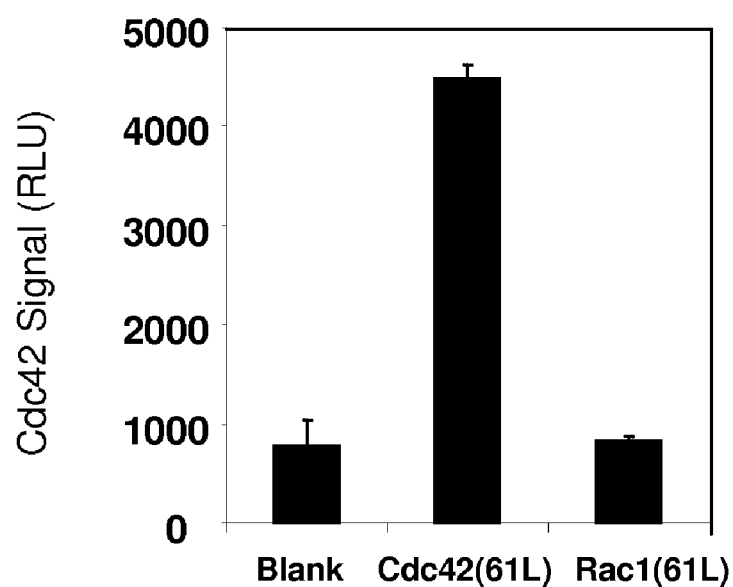
Figure 2C: Utility of WASP Plates to Detect Active Cdc42

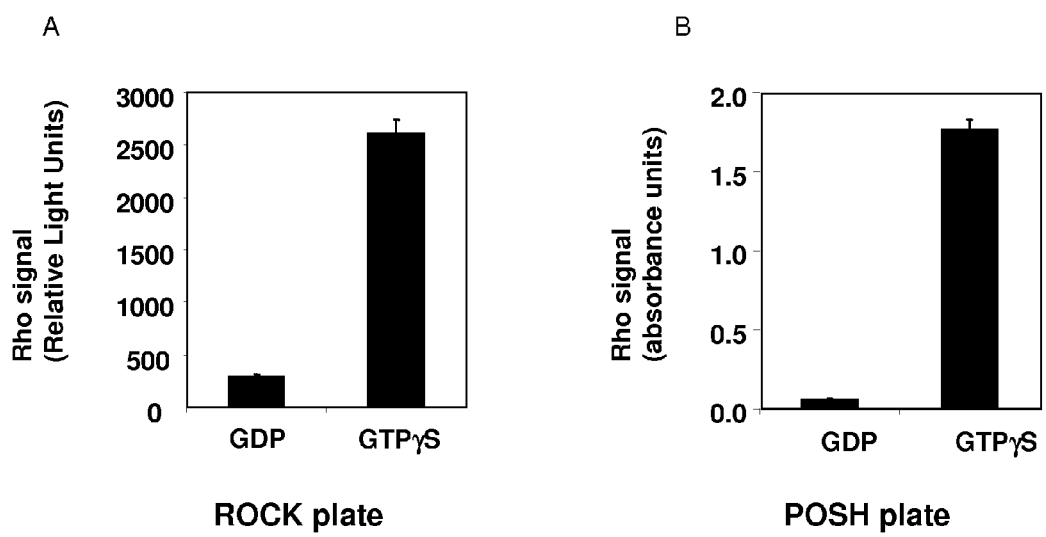
Figure 3: Detection of GTPγS and GDP Loaded Rho GTPases in Platelet Extracts Figure 4: Loss of G-LISA GTPase signal During Antibody Incubations
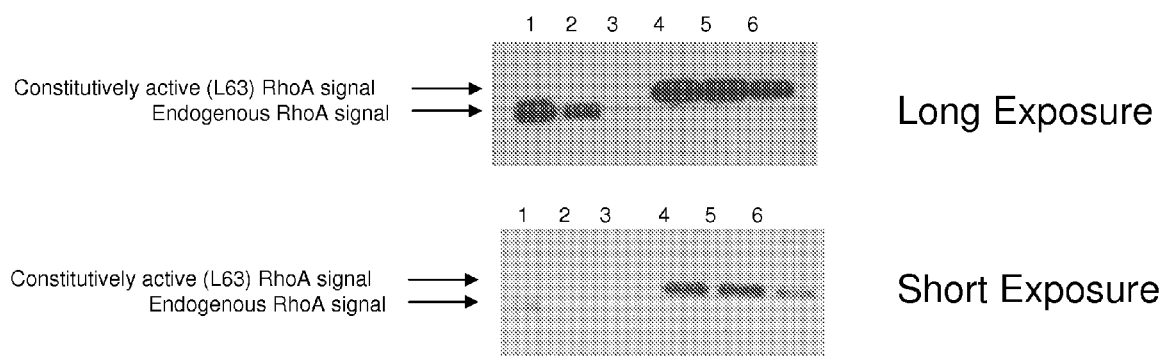

Figure 5A: Development of Antigen Presenting Buffer for RhoA:ROCK G-LISA
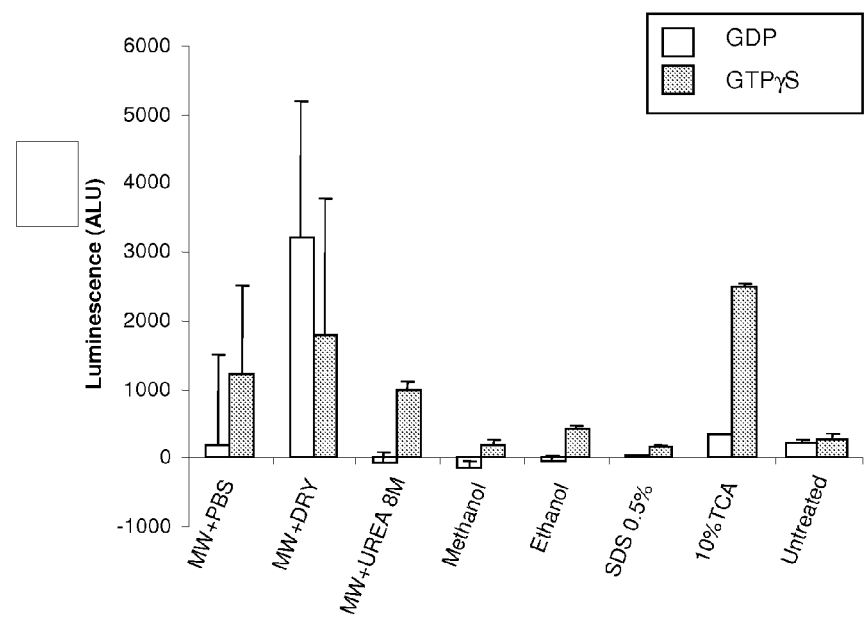

Figure 5B: TCA as Antigen Presenting Buffer in Rac1:POSH G-LISA
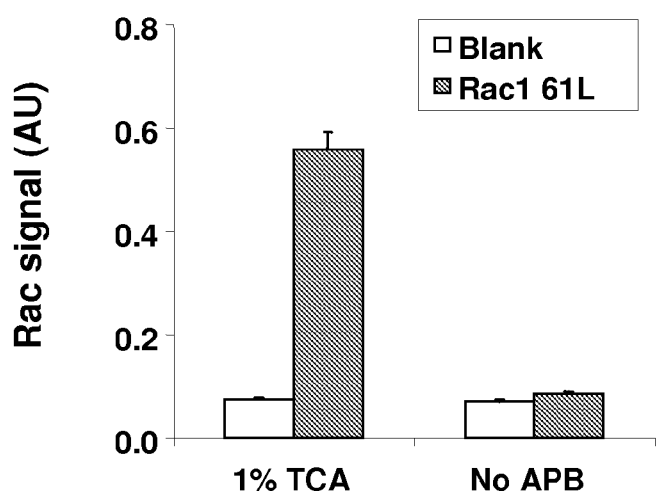

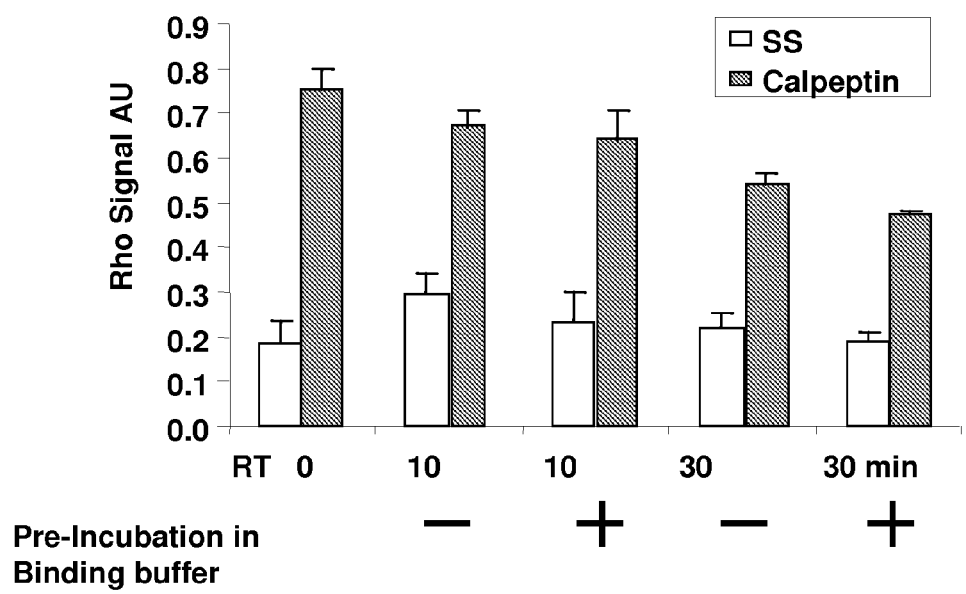
Figure 6A: Stability of Active RhoA in the Presence of Binding Buffer

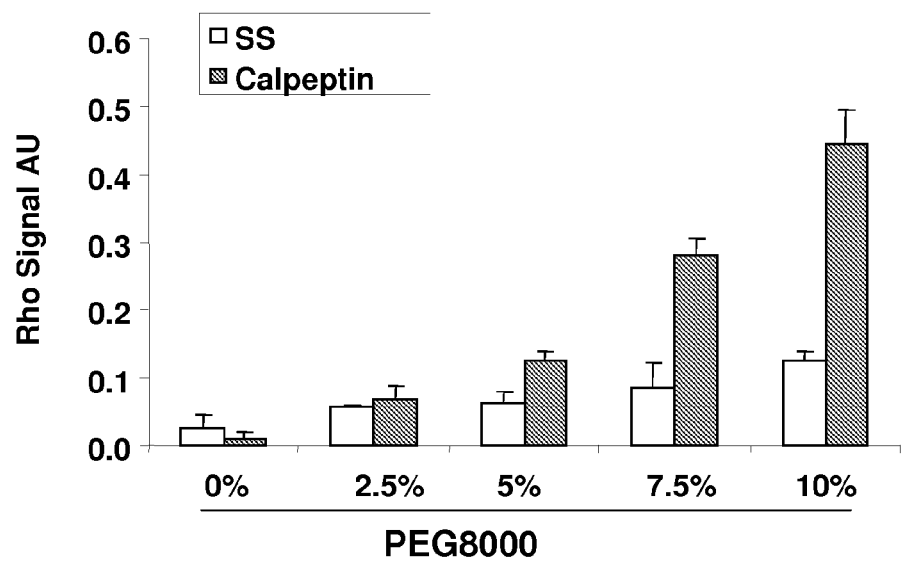
Figure 6B: Enhanced Signal for Active RhoA in the Presence of Binding Buffer

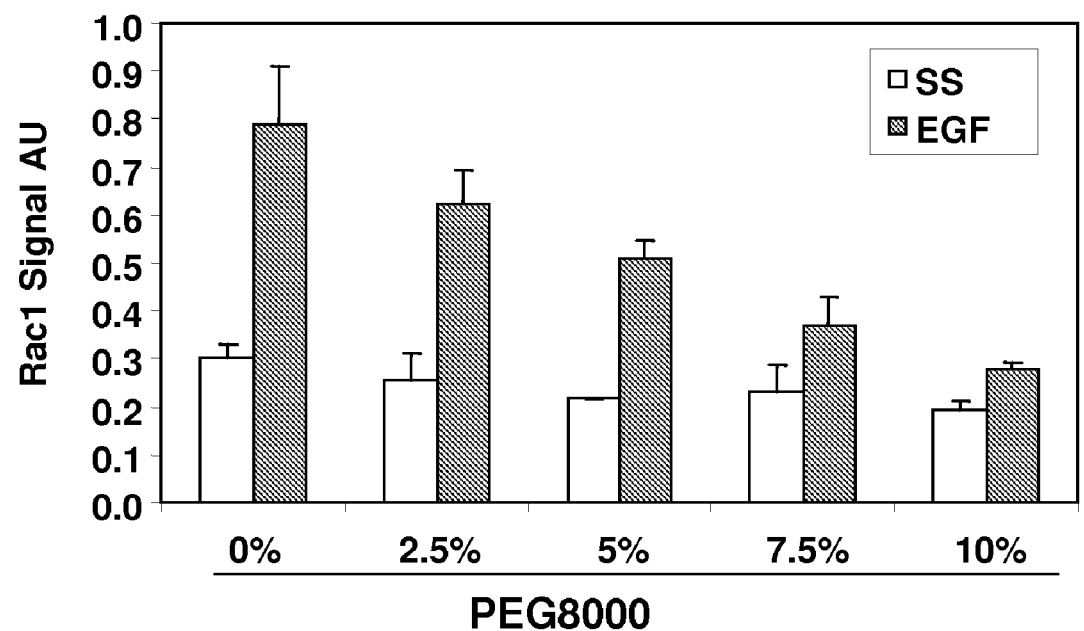
Figure 6C: Effect of Binding Buffer on RAc1 G-LISA Signal

Figure 7A:
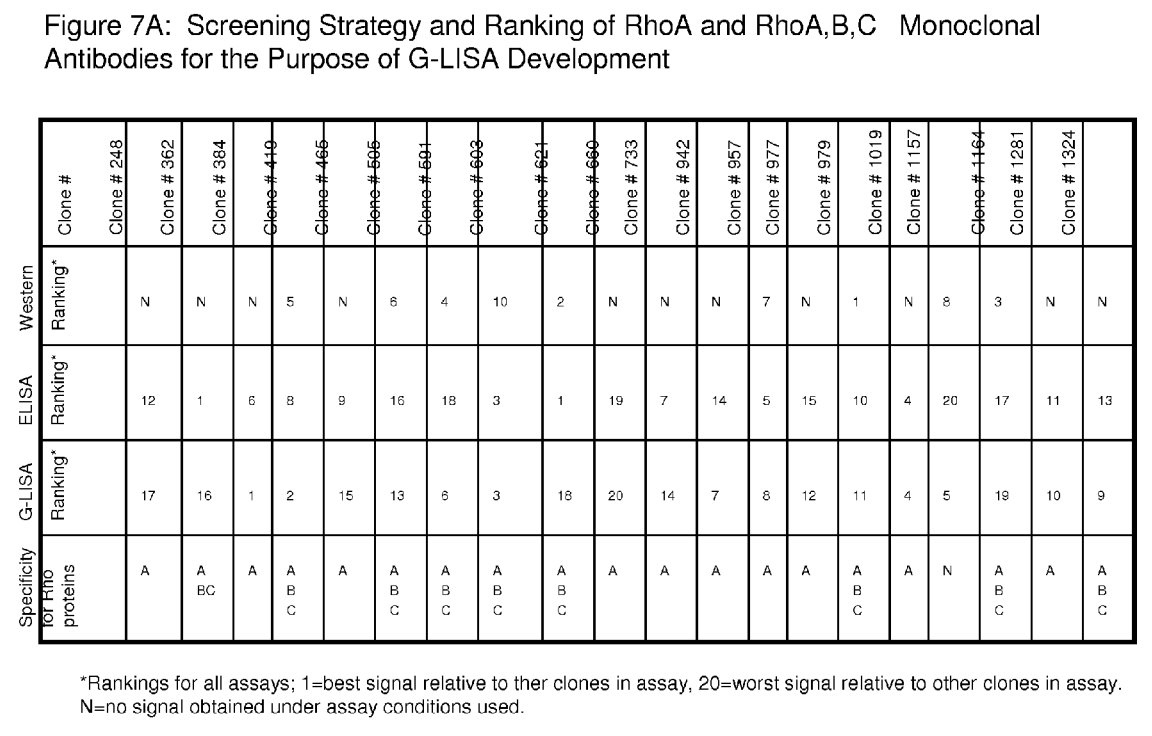

Figure 7A: Screening Strategy and Ranking of RhoA and RhoA,B,C Monoclonal Antibodies for the Purpose of G-LISA Development

| Clone # | Clone # 248 | Clone # 362 | Clone # 384 | Clone # 419 | Clone # 465 | Clone # 505 | Clone # 591 | Clone # 603 | Clone # 621 | Clone # 660 | Clone # 733 | Clone # 942 | Clone # 957 | Clone # 977 | Clone # 979 | Clone # 1019 | Clone # 1157 | Clone # 1164 | Clone # 1281 | Clone # 1324 |
|---|---|---|---|---|---|---|---|---|---|---|---|---|---|---|---|---|---|---|---|---|
| Western Ranking* | N | N | N | 5 | N | 6 | 4 | 10 | 2 | N | N | N | 7 | N | 1 | N | 8 | 3 | N | N |
| ELISA Ranking* | 12 | 1 | 6 | 8 | 9 | 16 | 18 | 3 | 1 | 19 | 7 | 14 | 5 | 15 | 10 | 4 | 20 | 17 | 11 | 13 |
| G-LISA Ranking* | 17 | 16 | 1 | 2 | 15 | 13 | 6 | 3 | 18 | 20 | 14 | 7 | 8 | 12 | 11 | 4 | 5 | 19 | 10 | 9 |
| Specificity for Rho proteins | A | A BC | A | A B C | A | A B C | A B C | A B C | A B C | A | A | A | A | A | A B C | A | N | A B C | A | A B C |

*Rankings for all assays; 1=best signal relative to ther clones in assay, 20=worst signal relative to other clones in assay. N=no signal obtained under assay conditions used.

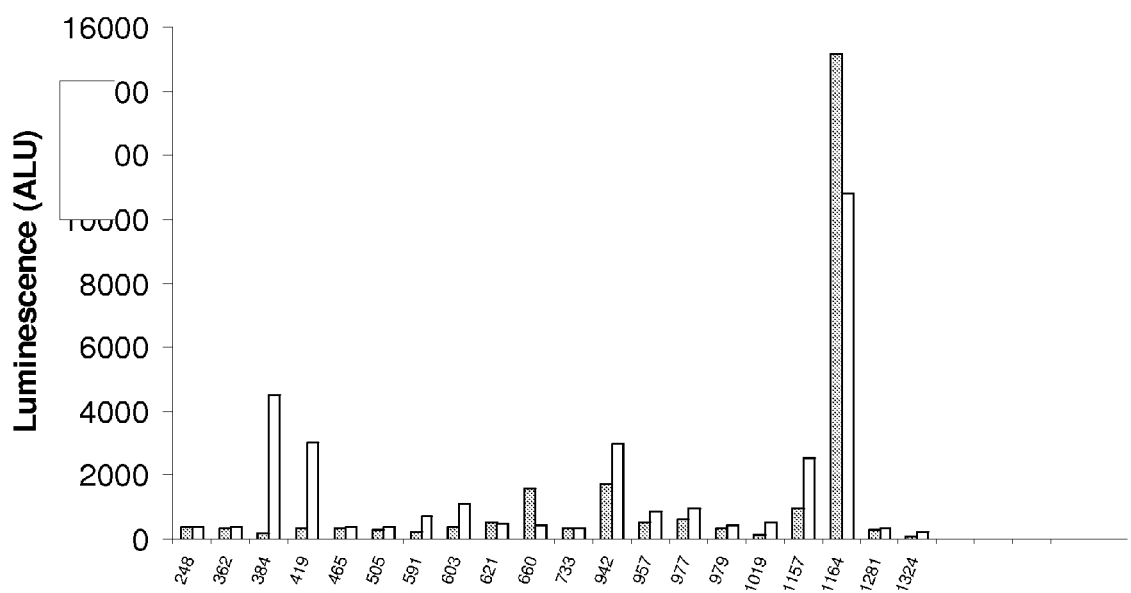
Figure 7B: Raw Data From Monoclonal Antibody G-LISA Screen

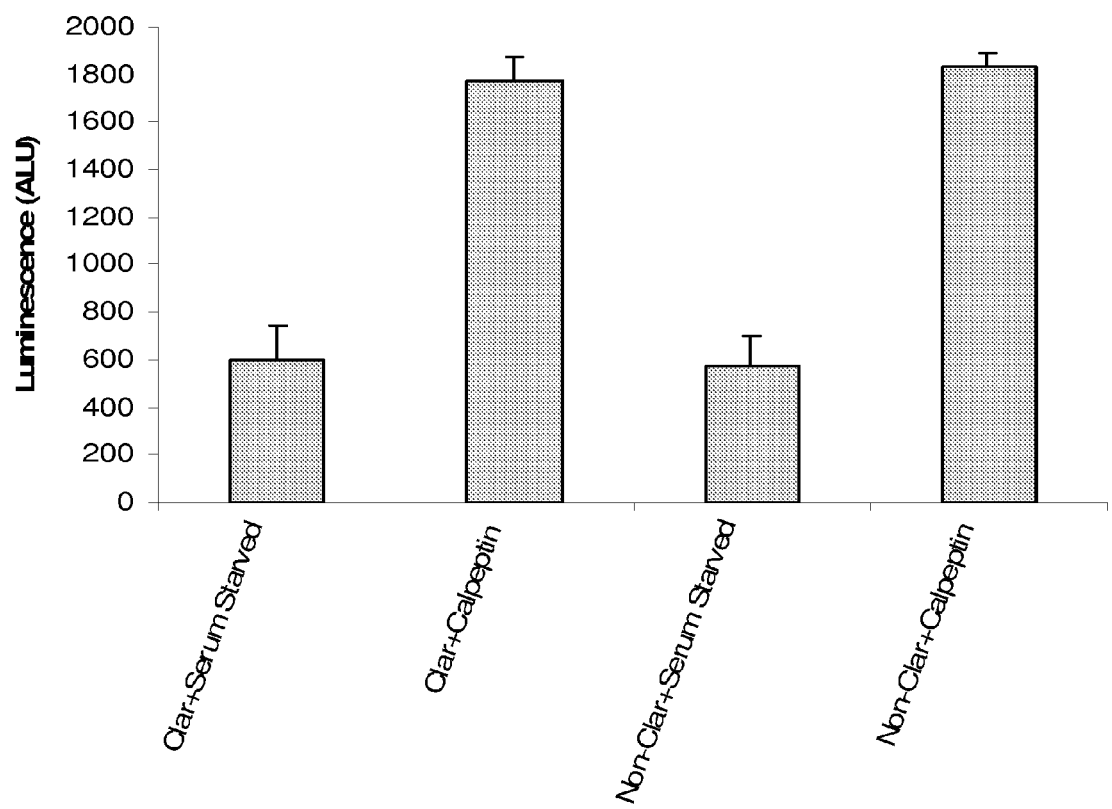
Figure 8: G-LISA Assay Using Non-Clarified Cell Lysates

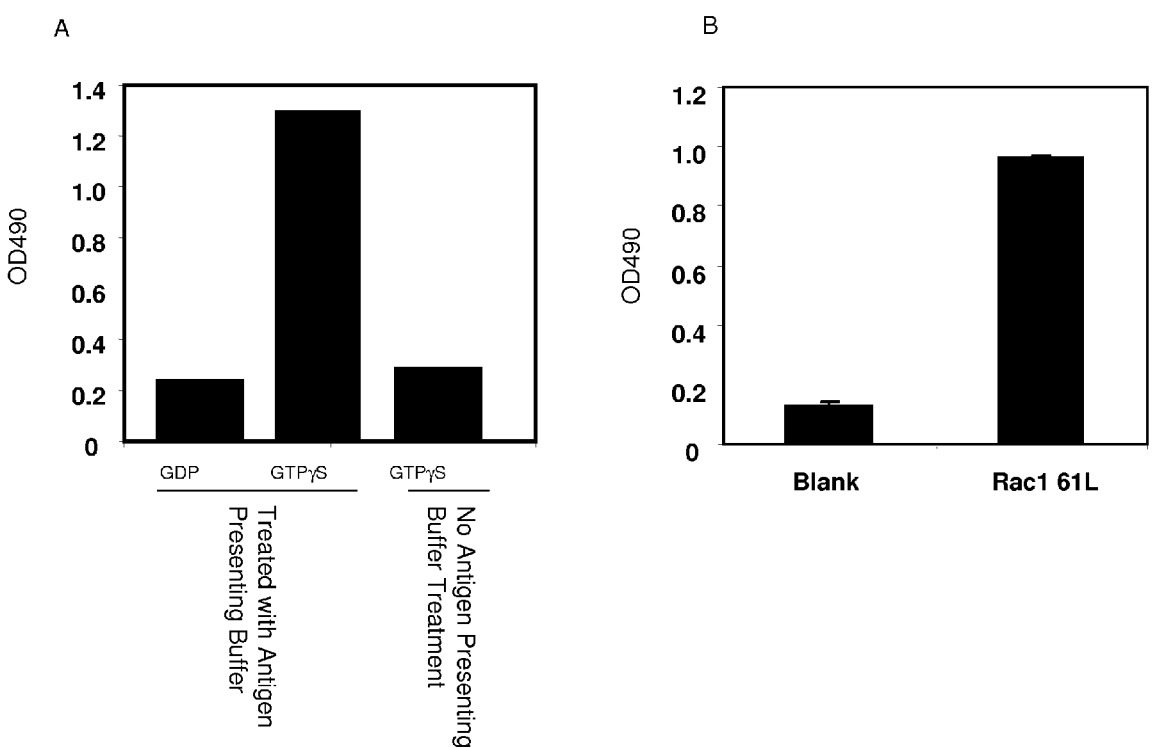
Figure 9: Utility of Non-Covalent PAK Effector-GBD Plates in a G-LISA Assay

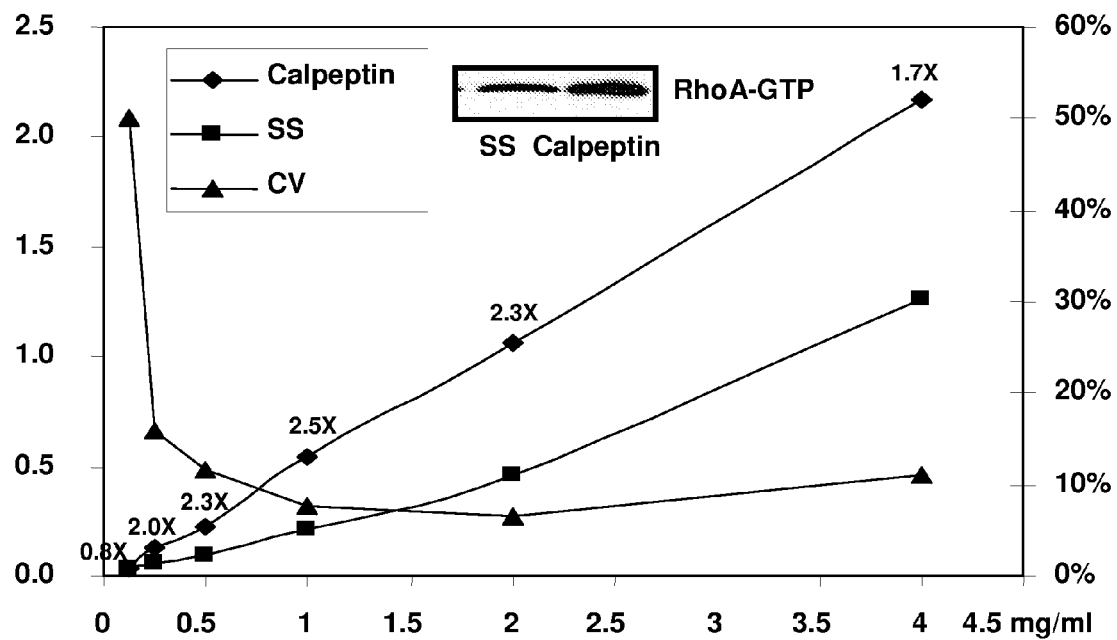
Figure 10: Titration of Cell Lysates in RhoA G-LISA Assay

Figure 11: Titration of Constitutively Active RhoA in G-LISA Assay
A: Full Spectrum Data Points (0 – 2 ng RhoA)
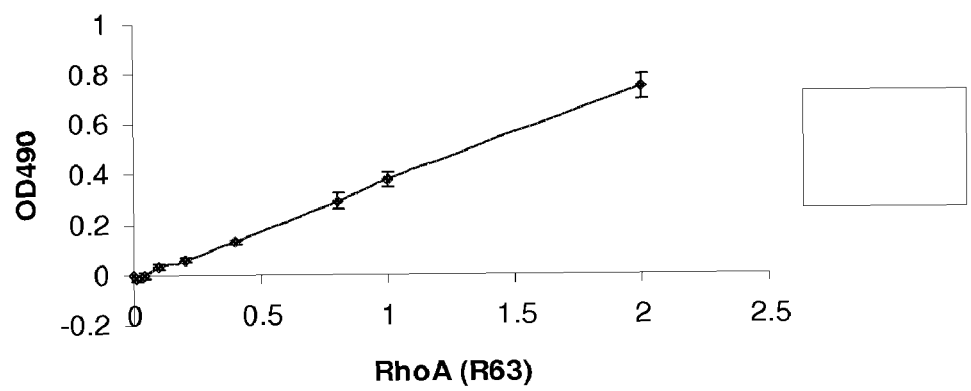
B: Low end Data Points Only (0 – 0.2 ng RhoA)
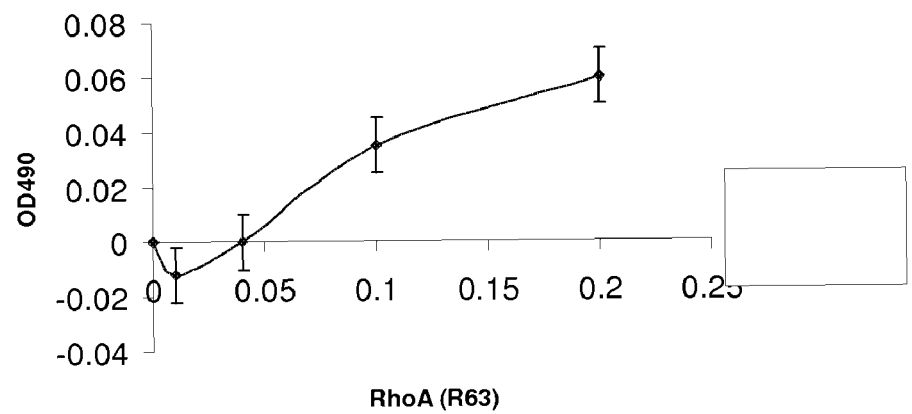

Figure 12: Direct Comparison of Pull-Down Assay and G-LISA Assay for Rac1
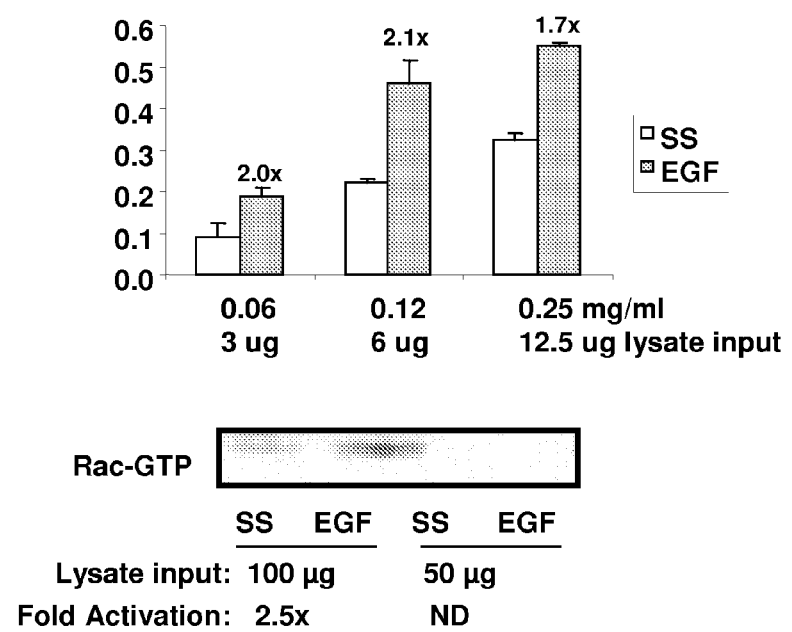

Figure 13A: G-LISA Analysis of In Vivo Activated Rac1 by EGF
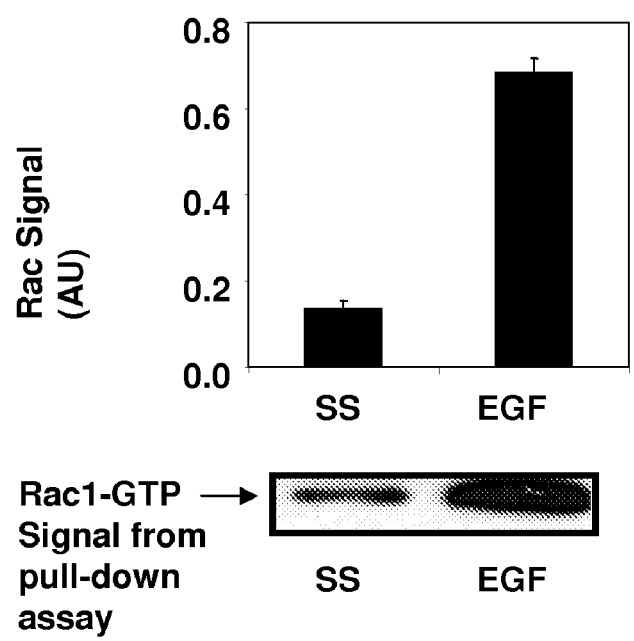

Figure 13B: G-LISA Analysis of In Vivo Activated Cdc42 by EGF
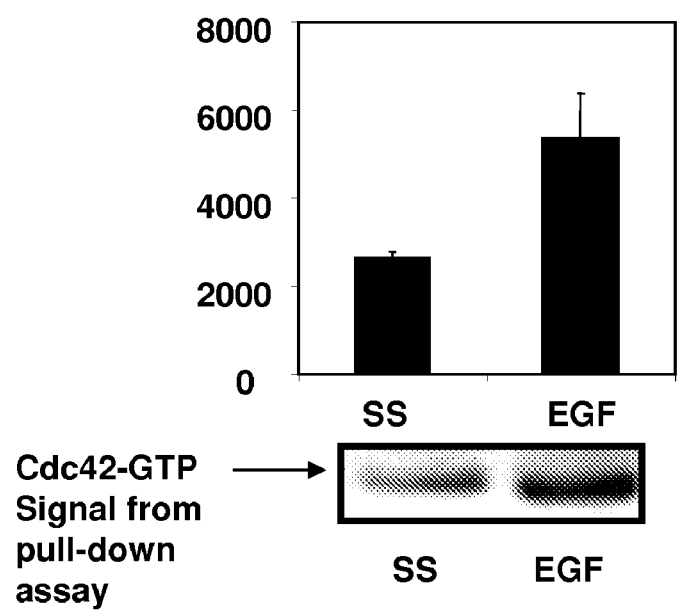

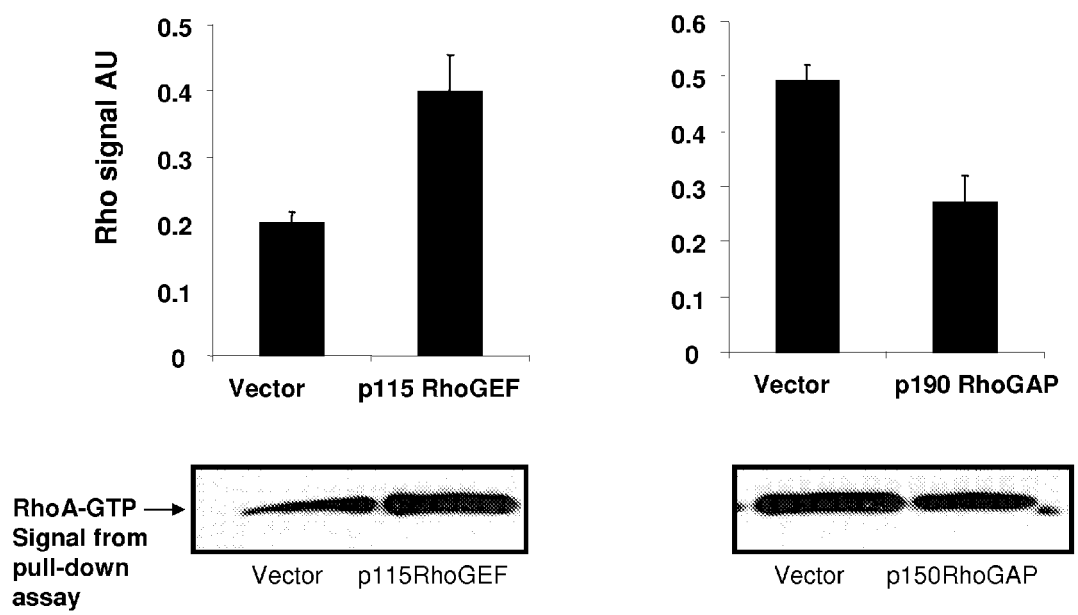
Figure 13C: Analysis of Rho GEF and Rho GAP Transfections with G-LISA Assay

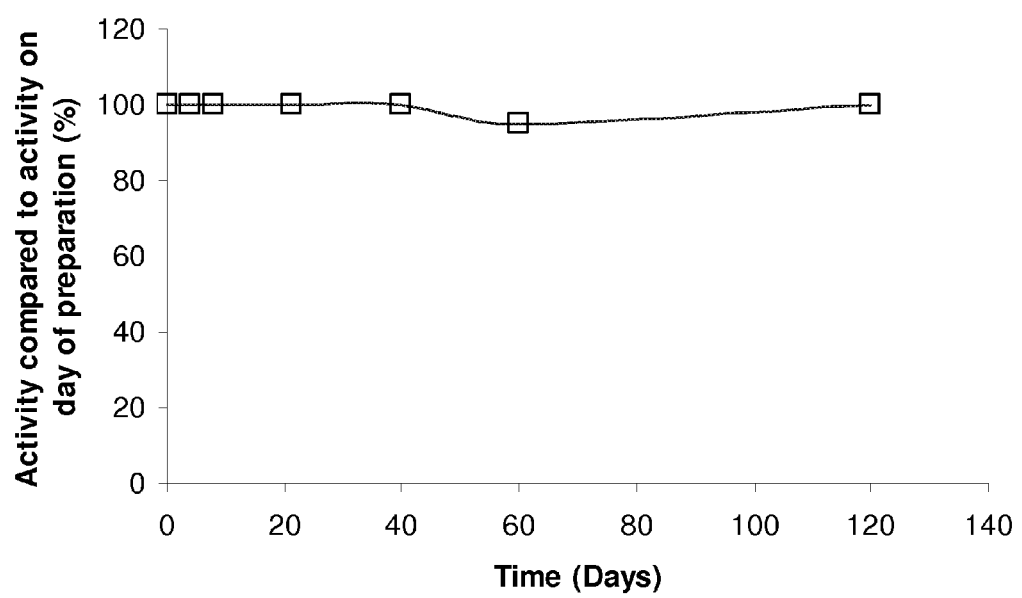
Figure 14: Extended Shelf Life Studies on Lyophilized Effector-GBD Plates Figure 15: Demonstration of POSH-GBD Plate Utilization in Drug Discovery Applications
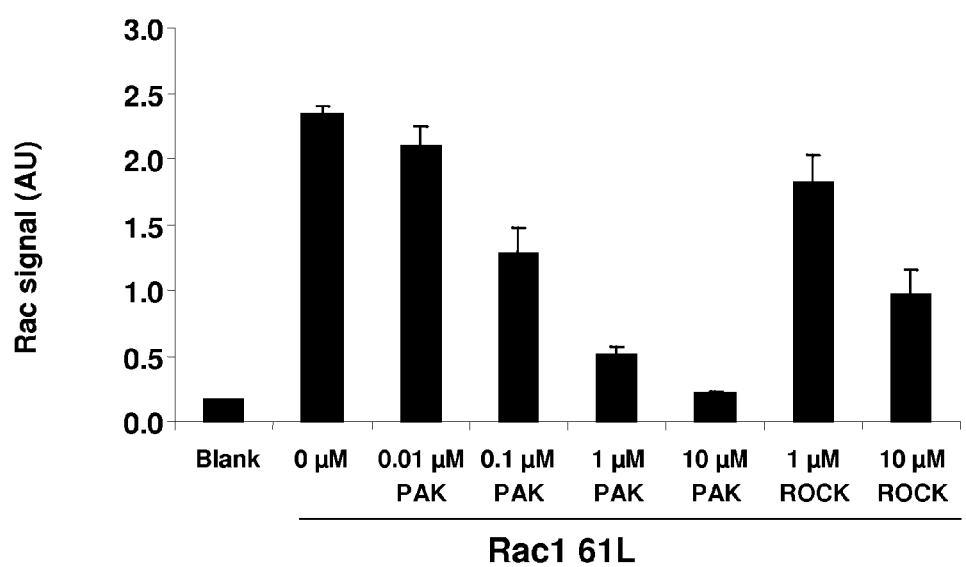

DETECTION OF RHO PROTEINS

CROSS-REFERENCE TO RELATED APPLICATIONS

This application claims priority to U.S. Provisional Application Ser. No. 60/695,844, filed Jul. 5, 2005 which is incorporated herein by reference in its entirety.

FIELD OF THE INVENTION

The present invention is directed, in part, to methods of detecting activated Rho proteins.

BACKGROUND OF THE INVENTION

The Rho GTPases are a structurally and functionally distinct GTPase of the Ras superfamily (Wennerberg et al., 2005, J. Cell Sci., 118:843-846; Takai et al., 2001, Physiol. Rev., 81:153-208). They are involved in a diverse array of cellular functions, including the regulation of actin and tubulin dynamics, cell polarity, membrane transport pathways and transcription factor activities (Ridley et al., 1992, Cell, 70:389-399; Braga et al., 1997, J. Cell Biol., 137:1421-1431; and Coso et al., 1995, Cell, 81:1137-1146). However, some members of the family (e.g., RhoBTB1, RhoBTB2 and RhoH) do not appear to be functionally closely related to the classical members such as RhoA, Rac1 and Cdc42 (Aspenstrom et al., 2004, Biochem J., 377:327-337). It is therefore accepted by those of skill in this area that the Rho GTPase of the Ras superfamily GTPases are most clearly defined by sequence homology.

When all the GTPase domains of the 150+ mammalian Ras superfamily members are aligned and are sorted into a dendrogram based on the alignment, the 20 Rho proteins form one separate branch of the Ras superfamily tree (Wennerberg et al., 2005, J. Cell Sci., 118:843-846). The overall homology within the GTPase domain of the Rho proteins separate them from the other Ras superfamily members. The Rho proteins share between 40-95% homology within the GTPase and they are 30% or less homologous to other Ras superfamily GTPases. In addition, the Rho proteins have one motif that is unique to this GTPase of small GTPases. This motif is called the Rho insert domain and is located between the fifth β strand and the fourth α helix in the small GTPase domain (Zong et al., 2001, Mol. Cell Biol., 21:5287-5298).

Accordingly, a small G-protein is considered a Rho family protein if, when aligned with other Ras superfamily proteins, it falls into the Rho branch (e.g., the protein has at least 40% homology to the other Rho proteins) and contains a Rho insert domain.

The Rho GTPases are known to be involved in the progress of many pathogenic processes such as metastatic invasion, bacterial and viral infections and hypertension (Symons, 1995, Curr. Op. Biotech., 6:668-674; Chen et al., 1996, Science, 274:2115-2118; and Uehata et al., 1997, Nature, 389: 990-994). Because of their multiple roles in both basic cellular functions and in pathogenic processes there is much interest in developing assays that allow researchers to analyse the activity of Rho GTPases in cells. There is furthermore, great interest in developing assays that are compatible with high throughput screening applications for drug discovery targeting Rho GTPases or the Rho GTPase transduction pathways and for assays compatible with diagnostic applications.

The cellular activities mediated by Rho GTPases are dependent upon the activation state of the GTPase. When GTP is bound to Rho GTPases they are in an active state and are able to bind to effectors and propagate the signal cascade leading to a particular cellular response. When GDP is bound to Rho GTPases the Rho protein is inactive (Takai et al., 2001, Physiol. Rev., 81:153-208). Several assays have been developed that monitor the activation state of Rho GTPases.

One assay, the Rho effector pull-down assay, was originally developed for RhoA GTPases by Ren et al. (1999, EMBO J., 18:578-585) and for Rac1/Cdc42 GTPases by Benard et al. (1999, J. Biol. Chem., 274:13198-13204) and is the classical and most widely used assay. The method involves capture of activated Rho GTPase proteins by effectors bound to beads, release of the GTPase protein from the beads, separation of the beads from the released GTPase protein, followed by SDS-PAGE and analysis of the GTPase protein by western blotting. The assay suffers from poor reproducibility due to the multiple manipulations required in the performance of the assay, and low sensitivity. It is also not suitable for high throughput applications (Teusch et al., 2006, Assay and Drug Devel., 4:133).

There are several cell-based assays that use fluorescent bio-probes to detect activated Rho GTPases (Pertz et al., 2004, J. Cell Sci., 117:1313-1318). Several versions of this type of assay rely on a reporter system to monitor in vivo Rho GTPase activation. These cell-based assays, therefore, do not monitor the actual endogenous levels of the GTPase (Itoh et al., 2002, Mol. Cell Biol., 22:6582-6591; Pertz et al., 2006, Nature, 440:1069-1072; and Vadim et al., 2000, Science, 290:333-337). Other versions of cell-based assays use effector domains linked directly to an environmental dye to monitor endogenous in vivo GTPase activation. Because the placing of the environmental dye on any particular probe requires extensive analysis and a particular effector may not be compatible with dye linkage, the usefulness of any particular effector cannot be predicted (Nalbant et al., 2004, Science, 305:1615-1619). Furthermore, because the use of direct effector detection in vivo results in a probe that most often recognizes more than one GTPase, specificity is an issue in these assays. A further issue with this type of assay is that introduction of exogenous effector will actually alter the levels of Rho GTPase activation, which creates a technically challenging assay method (Pertz et al., 2004, J. Cell Sci., 117:1313-1318).

The fluorescent biosensor probes have also been applied to in vitro assays although their sensitivity is fairly low. Furthermore, that the dyes respond to environmental changes poses issues to drug screening applications (Hahn et al., U.S. Pat. No. 6,951,947 B2).

An enzymatic based method to detect Rho activation has been reported (Chen et al., 2003, J. Biol. Chem., 278:2807). The assay utilizes GST-effector-GBD to affinity precipitate active GTP-Rho. GTP is eluted and converted to ATP in a coupled enzymatic assay. ATP is then measured by the firefly luciferase method. This assay is highly dependent on the GST pull-down assay and, thus, has most of the drawbacks associated with this assay. Furthermore, since a Rho-specific antibody is not involved in this method, the specificity of the assay is limited.

An automated cell-based Rho activation assay has also been reported (Teusch et al., 2006, Assay and Drug Devel., 4:133). This assay was developed to replace the GST pull-down assay due to its incompatibility for high throughput screening and poor reproducibility. It is based on the ability of Rho to regulate the actin cytoskeleton. Since actin cytoskeleton is regulated by multiple signal pathways, the specificity for this assay is very limited.

Thus, there is a need for a Rho GTPase activation assay that is simple, specific for a particular GTPase protein, reproducible, sensitive and amenable to high throughput screening applications. The present invention provides for this need as well as others.

SUMMARY OF THE INVENTION

The present invention is directed to methods for detecting an activated Rho GTPase protein by 1) contacting a solid support with a sample comprising an activated Rho GTPase protein, wherein the solid support is linked to an activated Rho GTPase binding peptide, and wherein the activated Rho GTPase in the sample binds the activated Rho GTPase binding peptide; and 2) detecting the activated Rho GTPase protein in the sample, wherein the activated Rho GTPase protein remains associated with the solid support during the detection. In some embodiments, the solid support is a microtiter plate or microarray.

In some embodiments, the sample comprises a cell lysate that comprises endogenous activated Rho GTPase protein. In some embodiments, the sample comprises less than 50 µg of total protein. In some embodiments, the cell lysate is prepared from less than $10^5$ cells. In some embodiments, the cell lysate has not been clarified. In some embodiments, the sample comprises exogenous GTP, GDP or GTPγS.

In some embodiments, prior to detecting the activated Rho GTPase protein in the sample, an Antigen Presenting Buffer is added. The Antigen Presenting Buffer comprises one or more compounds or treatments that can attenuate loss of the activated Rho GTPase protein from the solid support. In some embodiments, the Antigen Presenting Buffer comprises heat denaturation, urea treatment, glutaraldehyde, ethanol, or tricholoracetic acid, or any combination thereof. In some embodiments, the final concentration of trichloroacetic acid is about 0.5% to about 15% v/v.

In some embodiments, prior to detecting the activated Rho GTPase protein in the sample, a Binding Buffer is added. In some embodiments, the Binding Buffer comprises ficoll, dextran, or polyethylene glycol, or any combination thereof. In some embodiments, the polyethylene glycol is PEG 4000 or PEG 8000 at a final concentration of about 2% to about 40% v/v.

In some embodiments, the activated Rho GTPase protein is detected using an antibody specific for one or more activated Rho GTPase proteins.

In some embodiments, the activated Rho GTPase protein is a constitutively active mutant. In some embodiments, the activated Rho GTPase protein is RhoA, RhoB, RhoC, RhoD, Rnd1, Rnd2, Rnd3, Rif, RhoG, Rac1, Rac1b, Rac2, Rac3, Cdc42, TC10, TCL, Wrch-1, Wrch-2, RhoBTB1, or RhoBTB2.

In some embodiments, the activated Rho GTPase binding peptide binds to one or more activated Rho GTPase proteins with an affinity that is at least 2-fold higher for the activated versus inactive form of the Rho GTPase protein. In some embodiments, the activated Rho GTPase binding peptide is a Rhotekin, ROCK1, PAK1, POSH, WASP, or Dia1, or a mutant or multimer of the same. In some embodiments, the activated Rho GTPase binding peptide is linked to the solid support covalently or non-covalently. In some embodiments, the covalent linkage is a disulfide linkage and the non-covalent linkage is a GST linkage. In some embodiments, the activated Rho GTPase binding peptide is lyophilized.

In some embodiments, the methods further comprise quantitating the amount of activated Rho GTPase protein bound to the activated Rho GTPase binding peptide. In some embodiments, the amount of activated Rho GTPase protein is quantitated using an antibody specific for one or more Rho GTPase proteins.

In some embodiments, detection of the activated Rho GTPase protein is carried out by detecting an interaction between the activated Rho GTPase protein and the activated Rho GTPase binding peptide using absorbance, luminescence, or fluorescence.

In some embodiments, the methods further comprise contacting the sample with a test agent and determining whether the test agent modulates an interaction between the activated Rho GTPase protein and the activated Rho GTPase binding peptide.

BRIEF DESCRIPTION OF THE DRAWINGS

FIG. 1A depicts a Coomassie stained SDS gel of recombinant effector-GBD peptides. FIG. 1B depicts DNA and amino acid sequences of wild type (SEQ ID NO:111; SEQ ID NO:112) and modified Rhotekin-Cys-GBD (SEQ ID NO:113; SEQ ID NO:114). FIG. 1C depicts Western Blot analysis of modified Rhotekin-Cys selectively binding to activated RhoA.

FIG. 2A depicts RhoA signal detected by luminometry using ROCK plates to detect active RhoA. FIG. 2B depicts Rac1 signal deteced by absorbance at 490 nm using POSH plates to detect active Rac1. FIG. 2C depicts Cdc42 signal detected by absorbance at 490 nm using WASP plates to detect active Cdc42.

FIG. 3A depicts RhoA signal detected by luminometry using ROCK-GBD maleimide plates. FIG. 3B depicts Rac1 signal detected by absorbance at 490 nm using POSH-GBD maleimide plates.

FIG. 4 depicts Western blot with anti-RhoA antibody showing loss of G-LISA GTPase signal during antibody incubations.

FIG. 5A depicts luminescence detection showing development of Antigen Presenting Buffer for RhoA G-LISA (white bars show GDP signal, grey bars show GTPγS signal). FIG. 5B depicts Rac1 signal detected by absorbance at 490 nm showing TCA as Antigen Presenting Buffer in a Rac1:POSH G-LISA.

FIG. 6A depicts RhoA signal detected by absorbance at 490 nm showing stability of active RhoA in the presence of Binding Buffer (SS is serum starved samples—white bars; RhoA induced samples labeled Calpeptin—grey bars). FIG. 6B depicts active RhoA signal detected by absorbance at 490 nm showing enhanced signal for RhoA in the presence of Binding Buffer (SS is serum starved samples—white bars; RhoA induced samples labeled Calpeptin—grey bars). FIG. 6C depicts Rac1 signal detected by absorbance at 490 nm showing effect of Binding Buffer on Rac1 signal (SS is serum starved samples—white bars; Rac1 induced samples labeled EGF—grey bars).

FIG. 7A depicts a screening strategy and Western ranking of RhoA and RhoA,B,C monoclonal antibodies for the purpose of G-LISA development. FIG. 7B depicts raw data for monoclonal antibody G-LISA screen shown in FIG. 7A.

FIG. 8 depicts luminescence of RhoA G-LISA assay on ROCK maleimide plates using non-clarified cell lysates.

FIG. 9 depcits Rac1 signal detected by absorbance at 490 nm using non-covalent effector-GBD plates in a G-LISA assay.

FIG. 10 depicts titration of cell lysates in RhoA G-LISA as well as Western blot results of a GST-Rhotekin-RBD pull-down assay.

FIG. 11 depicts absorbance detection results of a titration of constitutively activated RhoA in G-LISA.

FIG. 12 depicts direct comparison of pull-down assay and G-LISA assay for Rac1.

FIG. 13A depicts G-LISA analysis of in vivo activated Rac1 by epidermal growth factor (EGF). FIG. 13B depicts G-LISA analysis of in vivo activated Cdc42 by EGF. FIG. 13C depcicts analysis of transfections with G-LISA assay.

FIG. 14 depicts extended shelf life studies on lyophilized effector-GBD plates.

FIG. 15 depicts POSH-GBD plate utilization in drug discovery applications.

DESCRIPTION OF EMBODIMENTS

The present invention provides a Rho GTPase activation assay that is simple, specific for a particular GTPase protein, reproducible, sensitive and amenable to high throughput screening applications that have numerous advantages over traditional pull-down assasys.

As used herein, the term "about" refers to a range of ±5% of the value that is being modified. For example, the phrase "about 10" means a range from 9.5 to 10.5.

As used herein, the term "fragment", when used in reference to a protein, refers to a peptide or polypeptide that is less than the whole. In some embodiments, the fragment comprises at least 5, at least 10, at least 20, at least 30, at least 40, at least 50, at least 60, at least 70, at least 80, at least 90, at least 100, about 5 to about 100, about 5 to about 50, about 5 to about 25, about 100 to about 200, 5 to 100, 5 to 50, 5 to 25, 100 to 200, no more than 200, no more than 100, no more than 75, no more than 50, or no more than 25 amino acid residues. A "fragment" is also referred to as a "portion" of a protein.

As used herein, the term "sample" refers to a composition comprising a Rho GTPase protein (activated and/or inactivated) and/or a Rho GTPase binding peptide. Examples of samples include, but are not limited to, blood, cells, cell lysate, and the like. In some embodiments, the cell lysate is clarified or non-clarified. In some embodiments, the sample comprises exogenous GTP, GDP, or GTPγS.

As used herein, the term "clarified" refers to a sample being cleared, reduced, or filtered to remove non-soluble material that is produced upon lysing a cell. Any method can be used to clarify a cell lysate including, but not limited to, centrifugation, filtration, and the like.

As used herein, the phrase "Rho GTPase protein" (also referred to as "Rho sub-family protein") includes both active and inactive proteins. When GTP is bound to Rho GTPase proteins, they are in an active state and are able to bind to effectors and propagate the signal cascade leading to a particular cellular response. When GDP is bound to Rho GTPases the Rho protein is inactive. The methods of the present invention can be used to detect activated GTPase proteins. Rho GTPase proteins include, but are not limited to, RhoA (SEQ ID NO:1), RhoB (SEQ ID NO:2), RhoC (SEQ ID NO:3), RhoD (SEQ ID NO:4), Rnd3 (SEQ ID NO:5), Rnd1 (SEQ ID NO:6), Rnd2 (SEQ ID NO:7), Rif (SEQ ID NO:8), RhoG (SEQ ID NO:9), RhoH (SEQ ID NO:10), Rac1 (SEQ ID NO:11), Rac1b (SEQ ID NO:84), Rac2 (SEQ ID NO:12), Rac3 (SEQ ID NO:13), Cdc42 (SEQ ID NO:14), TC10 (SEQ ID NO:15), TCL (SEQ ID NO:16), Wrch-1 (SEQ ID NO:17), Wrch-2 (SEQ ID NO:18), RhoBTB1 (SEQ ID NO:19), and RhoBTB2 (SEQ ID NO:20), or any sub-group thereof.

A "Rho GTPase binding peptide" or an "activated Rho GTPase binding peptide" (also referred to as "Rho sub-family binding peptide") is a protein, or a fragment thereof, that is able to bind to an activated Rho GTPase protein. "Rho GTPase binding peptide" does not refer to GTP or an analog thereof. A "Rho GTPase binding peptide" is also referred to herein as an "effector." One of skill in the art can identify a fragment of a Rho GTPase binding peptide that retains its ability to bind to an active Rho GTPase protein by routine experimentation. In some embodiments, the Rho GTPase binding peptide used in the methods provided herein binds to the Rho GTPase protein with at least 2-fold higher affinity for the GTP-bound state than the GDP-bound state of the Rho GTPase protein.

In some embodiments, the Rho GTPase binding peptide can comprise the entire sequence or a portion or fragment of the amino acid sequence of a small G-protein effector such as, for example, ROCK 1, ROCK 2, Citron, DGKθ, Kinectin, Dia1, Dia2, Dia3, PLC-ε, Protein kinase N, Rhophillin, Rhotekin, FHOD, p67Phox, PLC-β, POR-1, POSH, Sra-1, Synaptojanin-2, Ack1, Ack2, CEP1, CEP2, CEP3, CEP4, CEP5, CIP4, Coatamer α, Coatamer γ, MRCKα, MRCKβ, Pak4, Spec1, Spec2, WASP, N-WASP, IRSp53, IQGAP-1, IQGAP-2, MEKK1, MEKK4, MLK2, MLK3, p70 S6 Kinase, Pak1, Pak2, Pak3, Pak4, Pak5, Pak6, PI3K (p85 subunit), PIP5K, PLD-1, or any sub-group or combination thereof. In some embodiments, the Rho GTPase binding peptide is multimerized such that there is more than one unit of the ligand. For example, the Rho GTPase binding peptide can be dimerized or trimerized (3 copies). The Rho GTPase binding peptide can also have 4, 5, 6, 7, 8, 9, or 10 copies of the sequence of the protein that binds to the Rho GTPase protein.

A protein is considered a "Rho GTPase protein" if, when aligned with other Ras superfamily proteins, it falls into the Rho branch (e.g., the protein has at least 40% homology to the other Rho proteins) and contains a Rho insert domain. In some embodiments, a small G-protein is considered to be a Rho family protein if it has at least 40, 50, 60, 70, 80, 90, 95, 96, 97, 98, 99, 40-99, 50-99, 60-99, 70-99, 80-99, 85-99, 90-99, or 95-99% homology to other Rho proteins, such as, but not limited to RhoA, RhoB, RhoC, RhoD, Rnd1, Rnd2, Rnd3, Rif, RhoG, Rac1, Rac1b, Rac2, Rac3, Cdc42, TC10, TCL, Wrch-1, Wrch-2, RhoBTB1, and/or RhoBTB2. Additionally, a protein is considered to have a Rho insert protein when using a method such as a conserved domain finder indicates that the protein comprises a Rho insert protein. A protein that is identified as having a Rho insert domain is considered to be a Rho GTPase protein. Any method or software can be used to determine if a protein comprises a Rho insert protein. As a non-limiting example, one can compare a protein to the conserved domain database using for example, "rpsblast" with the default settings, which can be found on the website of the National Center for Biotechnology Information, for example, at the world wide web address of ncbi"dot""nlm"dot"nih"dot"gov/Structure/cdd/wrpsb"dot"cgi. As used herein, for the purposes of an internet address the term "'dot'" means ".". Examples of Rho GTPase proteins are provided herein and include but are not limited to, RhoA, RhoB, RhoC, RhoD, Rnd1, Rnd2, Rnd3, Rif, RhoG, Rac1, Rac1b, Rac2, Rac3, Cdc42, TC10, TCL, Wrch-1, Wrch-2, RhoBTB1, RhoBTB2, and the like.

Other methods and examples of identifying family members or homologs of proteins include, but are not limited to the following. A number of protein family databases are available for analysis or identification of homologous proteins, domains and motifs. Examples of databases include, but are not limited to, the Simple Modular Architecture Resource Tool (SMART), Protein families database of alignments and HMMs (Pfam), Human Protein Reference Database (HPRD), Online Mendelian Inheritance in Man (OMIM), Cancer Genome Anatomy Project (CGAP), and the Entrez Protein search databases. The SMART database is available at smart"dot"embl-heidelberg"dot"de/. The Pfam database can be accessed through the world wide web of the internet at, for example, sanger"dot"ac"dot"uk/Software/Pfam/search.shtml. OMIM, which is a database of human genetic mutations associated with disease, was developed, in part, for the National Center for Biotechnology Information (NCBI). OMIM can be accessed through the world wide web of the internet at, for example, ncbi"dot"nlm"dot"nih"dot"gov/Omim/. CGAP, which is an interdisciplinary program to establish the information and technological tools required to decipher the molecular anatomy of a cancer cell. CGAP can be accessed through the world wide web of the internet at, for example, ncbi"dot"nlm"dot"nih"dot"gov/ncicgap/. The Entrez Protein search database is available through the world wide web of the internet at ncbi"dot"nlm.nih "dot"gov/entrez/query"dot"fcgi?db=Protein. Some of these databases may contain complete or partial nucleotide or amino acid sequences. In recent years, hidden Markov models (HMMs) have become one of the key technologies used for detection of members of these families. The Pfam, TIGRFAMs and SMART databases use the profile-HMMs provided by the HMMER package. TIGRFAMs is a collection of manually curated protein families consisting of HMMs, multiple sequence alignments, commentary, Gene Ontology (GO) assignments, literature references and pointers to related TIGRFAMs, Pfam and InterPro models. TIGRFAMs contains models of full-length proteins and shorter regions at the levels of superfamilies, subfamilies and equivalogs. TIGRFAMs is available for searching or downloading through the world wide web of the internet at "tigr"dot"org/TIGRFAMs.

The portion of the amino acid sequence of a small G-protein effector can be a domain such as, for example, a Cdc42/Rac Interactive Binding (CRIB) domain, a Rho-binding domain (RhoBD), a Rho-interacting domain (RID), a Rho effector or protein kinase C-related kinase homology region 1 (HR-1), a tetratricopeptide repeat (TPR), or a Pleckstrin homology (PH) domain.

In some embodiments, the Rho GTPase binding peptide used in the methods of the present invention can comprise an effector, or domain thereof, for the RhoA GTPase protein. Examples include, but are not limited to, a RhoBD, an RID and an HR-1 domain. A consensus amino acid sequence of a RhoBD able to bind an activated RhoA GTPase protein is SEQ ID NO:21. A consensus amino acid sequence of an HR-1 domain able to bind an activated Rho GTPase protein is SEQ ID NO:22. A consensus amino acid sequence of an RID domain able to bind an activated Rho GTPase protein is SEQ ID NO:23. Examples of peptides containing a RhoBD that are effectors for the RhoA GTPase protein include, but are not limited to, Citron (SEQ ID NO:24), ROCK 1 (SEQ ID NO:25), and ROCK 2 (SEQ ID NO:26). Examples of peptides containing HR-1 domains that are effectors for the RhoA/B/C GTPase proteins include, but are not limited to, Protein kinase N 1 (SEQ ID NO:27), Protein kinase N 2 (SEQ ID NO:28), ROCK 1 (SEQ ID NO:25), ROCK 2 (SEQ ID NO:26), Rhophilin (SEQ ID NO:29), Rhotekin (SEQ ID NO:30), and Rhotekin 2 (SEQ ID NO:83). Examples of peptides containing RID domains that are effectors for the RhoA GTPase protein include, but are not limited to, ROCK 1 (SEQ ID NO:25) and ROCK 2 (SEQ ID NO:26). Examples of other peptides that are effectors for the RhoA GTPase protein include, but are not limited to, DGKθ (SEQ ID NO:31), kinectin (SEQ ID NO:32), Dia1 (SEQ ID NO:33), Dia2 (SEQ ID NO:34), MBS (SEQ ID NO:82), and PLC-ε (SEQ ID NO:35).

Examples of peptides that are effectors for the RhoB GTPase protein include, but are not limited to, Db1 (SEQ ID NO:93) and p76RBE (SEQ ID NO:94).

In some embodiments, the Rho GTPase binding peptide used in the method of the present invention can comprise an effector for the Rac small G protein. Examples of domains that act as effectors for the Rac small G protein include, but are not limited to, a TPR domain and a PH domain. A consensus amino acid sequence of a TPR domain able to bind an activated Rac small G protein is SEQ ID NO:36. A consensus amino acid sequence of a PH domain able to bind an activated Rac small G protein is SEQ ID NO:37. An example of a peptide containing a TPR domain that is an effector for the Rac small G protein includes, but is not limited to, p67Phox (SEQ ID NO:38). An example of a peptide containing a PH domain that is an effector for the Rac small G protein includes, but is not limited to, PLC-β(SEQ ID NO:39). Examples of other peptides that are Rac small G protein effectors include, but are not limited to, FHOD (SEQ ID NO:40), POR-1 (SEQ ID NO:41), POSH (SEQ ID NO:42), Sra-1 (SEQ ID NO:43), PP5 phosphatase (SEQ ID NO:85), Cinnamolyl-CoA reductase (SEQ ID NO:86), UNC-115 (SEQ ID NO:87), Wave (SEQ ID NO:88), Plexin B1 (SEQ ID NO:89), p35 (SEQ ID NO:90), Tre17 (SEQ ID NO:91), CID (SEQ ID NO:92), and Synaptojanin-2 (SEQ ID NO:44).

In some embodiments, the peptide used in the methods of the present invention can comprise a domain that is an effector for the Cdc42 small G protein. An example of a domain that can act as an effector for the Cdc42 small G protein includes, but is not limited to, a CRIB domain. A consensus amino acid sequence of a CRIB domain able to bind an activated Cdc42 small G protein is SEQ ID NO:45. Examples of peptides containing CRIB domains that are effectors for the Cdc42 small G protein include, but are not limited to, Ack1 (SEQ ID NO:46), Ack2 (SEQ ID NO:47), Pak4 (SEQ ID NO:48), WASP (SEQ ID NO:49), and N-WASP (SEQ ID NO:50). Examples of other peptides that are effectors for the Cdc42 small G protein include, but are not limited to, CEP1 (SEQ ID NO:51), CEP2 (SEQ ID NO:52), CEP3 (SEQ ID NO:53), CEP4 (SEQ ID NO:54), CEP5 (SEQ ID NO:55), CIP4 (SEQ ID NO:56), Coatamer α protein (SEQ ID NO:57), Coatamer γ protein (SEQ ID NO:58), Dia3 (SEQ ID NO:59), MRCKα (SEQ ID NO:60), MRCKβ (SEQ ID NO:61), Spec1 (SEQ ID NO:62), and Spec2 (SEQ ID NO:63).

In some embodiments, the GTPase binding peptide used in the methods of the present invention can comprise a domain that is an effector for both the Rac small G protein and the Cdc42 small G protein. An example of a domain that can act as a Rac small G protein and Cdc42 small G protein effector includes, but is not limited to, a CRIB domain. A consensus amino acid sequence of an CRIB domain able to bind an activated Rac small G protein or an activated Cdc42 small G protein is SEQ ID NO:45. Examples of peptides containing CRIB domains that are effectors for the Rac small G protein and the Cdc42 small G protein include, but are not limited to, MLK2 (SEQ ID NO:64), MLK3 (SEQ ID NO:65), Pak1 (SEQ ID NO:66), Pak2 (SEQ ID NO:67), Pak3 (SEQ ID NO:68), Pak5 (SEQ ID NO:69), Pak6 (SEQ ID NO:70), Tre17 (SEQ ID NO:91), and Par6 (SEQ ID NO:71). Examples of other peptides that are effectors for the Rac small G protein and the Cdc42 small G protein include, but are not limited to, IRSp53 (SEQ ID NO:72), IQGAP-1 (SEQ ID NO:73), IQGAP-2 (SEQ ID NO:74), MEKK1 (SEQ ID NO:75), MEKK4 (SEQ ID NO:76), p70 S6 kinase (SEQ ID NO:77), and PI3k, p85 subunit (SEQ ID NO:78).

In some embodiments, the GTPase binding peptide used in the methods of the present invention can comprise a domain that is an effector for both the Rac small G protein and the RhoA small G protein. An example of a peptide that is an effector for the Rac small G protein and the RhoA small G protein includes, but is not limited to, PIP5K (SEQ ID NO:79).

In some embodiments, the GTPase binding peptide used in the methods of the present invention can comprise a domain that that is a binding protein for the active form of the Rac small G protein, the RhoA small G protein, and the Cdc42 small G protein. An example of this class of peptide includes, but is not limited to, PLD-1 (SEQ ID NO:80), Vav PH, DH, CRD domain (SEQ ID NO 81).

In some embodiments, the GTPase binding peptide used in the methods of the present invention can comprise a domain that that is a binding protein for the active form of the Rnd2 small G protein or TC10 small G protein. An example of this class of peptide includes, but is not limited to, PIST for TC10 (SEQ ID NO:95), Rapostlin for Rnd2 (SEQ ID NO:96) and Pragmin, for Rnd2 (SEQ ID NO:97).

In some embodiments, the Rho GTPase binding peptide or effector is modified such that all or a portion of the internal cysteine residues are mutated to non-cysteine residues. In some embodiments, the Rho GTPase binding peptide or effector is modified such that it comprises a C-terminal cysteine residue. In some embodiments, the Rho GTPase binding peptide comprises a combination of different effectors or fragments of proteins that can bind to a Rho GTPase protein.

It is understood in the art that the amino acid sequence of a peptide or protein need not be 100% identical to another peptide or protein in order for both proteins to be considered to have a common or conserved peptide domain or to be members of a conserved protein family. For example, for a short peptide domain (i.e., less than 50 amino acids), several proteins have been found to have a peptide domain known as the Cdc42/Rac Interactive Binding (CRIB) domain. The CRIB domain is a 14- to 16-amino acid sequence with eight conserved residues that was previously shown to be involved in the binding of signaling molecules to activated GTP-bound forms of Rac and Cdc42. The consensus CRIB domain is I-S-X-P-X(4)-F-X-H-X(2)-H-V-G, where the number in brackets represents the total number of variable (X) amino acid residues.

For larger peptide domains, such as peptides with 50 or more amino acids, when two or more proteins, peptides or domains are homologous, highly conserved, or closely related, the amino acid sequence of a given protein, peptide or domain can be at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of another peptide, protein, or a domain within a given protein.

In general, among sequences and subsequences of greater than 50 residues in length that are less than 50-60% different, the major features of the alignment are reproduced by a wide variety of algorithms. Thus, closely related sequences greater than 50 amino acids in length and protein homologs will share at least 40% amino acid identity, and in some embodiments will share at least between 40% and 50% amino acid identity, and in some embodiments will share at least between 50% and 60% amino acid identity, and in some embodiments will share at least between 60% and 70% amino acid identity, and in some embodiments will share at least between 70% and 80% amino acid identity, and in some embodiments will share at least between 80% and 90% amino acid identity, and in still other embodiments will share at least between 90% and 100% amino acid identity. The homology can be calculated using various publicly available software tools, such as those developed by NCBI (Bethesda, Md.) obtainable through the internet (ftp"dot"ncbi"dot"nlm"dot"nih "dot"gov/pub/). Exemplary tools include, but are not limited to, the BLAST system available through the world wide web of the internet at ncbi-"dot"nlm"dot"nih"dot"gov, and the EMBOSS Pairwise Alignment Algorithms (BLOSUM62 matrix setting) and ClustalW alignments available through the world wide web of the internet at "dot"ebi"dot"ac"dot"uk/emboss/align/ and ebi"dot"ac"dot"uk/clustalw/, respectively.

In some embodiments, the present invention provides methods for detecting an activated Rho GTPase protein comprising contacting a solid support with a sample comprising an activated Rho GTPase protein. The solid support is linked to an activated Rho GTPase binding peptide. The activated Rho GTPase in the sample binds the activated Rho GTPase binding peptide. The activated Rho GTPase protein in the sample is detected. The activated Rho GTPase protein remains associated within the solid support during the detection. As a non-limiting example, the solid support is the well of a microtiter plate to which a Rho GTPase binding peptide is linked and a sample comprising an activated Rho GTPase protein is contacted with the microtiter plate. In this example, the Rho GTPase binding peptide and the activated Rho GTPase protein interact with one another either directly or indirectly through a complex and the remaining proteins or other components of the sample are washed away or removed leaving the activated Rho GTPase protein with the solid support for the detection step. Therefore, in this example, the Rho GTPase protein is considered to remain associated with the solid support. In contrast, in a standard pull-down assay using a bead, wherein a Rho GTPase binding peptide is linked to the bead and contacted with a sample comprising an activated Rho GTPase protein, the activated protein is eluted from the beads and separated from the beads before loading onto a gel or other type of separation medium (e.g., a column) or is separated from the solid support prior to detection. The Rho GTPase protein is then detected but it has been separated away from the solid support (e.g., a bead) and, therefore, in the standard pull-down assay the activated Rho GTPase protein does not remain associated with the solid support during the detecting step.

As used herein, when two proteins or components are referred to as being "bound to one another" this can mean that they are directly in contact with one another or are in a complex with one another but not in direct contact.

The solid support can be any surface to which a Rho GTPase binding peptide can bind. Examples include, but are not limited to, a microtiter plate, beads, discs, microarrays, slides, and the like. In some embodiments, the solid support includes a microtiter plate or microarray bu does not include a bead or a disc. In some embodiments, the solid support is activated or coated with an agent that will covalently attach a protein to the solid support, by for example, forming a disulfide bond. An example of such an agent is, but not limited to, malemide. The solid support can also be coated or modified in such a way that allows a protein to bind or bond with the solid support through a non-covalent interaction. For example, the solid support can comprise glutathione, which will bind to a protein comprising a GST moiety or the solid support can comprise a cations that allow a protein comprising a Histidine tag to bind to it. Other modifications can also be used including, but not limited to, avidin-biotin, HA-hemagluttin, and the like.

In some embodiments, the Rho GTPase binding peptide(s) used in the methods of the present invention are covalently attached to a maleimide activated plate. Maleimide activated plates are available commercially and are designed to immobilize biomolecules through available -SH moieties, usually from a cysteine residue. Examples of maleimide activated microplates include, but are not limited to, polystyrene microplates such as Costar's Sulfhydryl Binding Plates and Strips (Corning, Inc. Corning, N.Y.), Reacti-Bind™ Maleimide Activated Plates (Pierce Biotechnology, Inc. Rockford, Ill.) and maleimide activated microwell plates-sulfhydryl-TRAP™ (NoAb Biodiscoveries, Inc. Mississauga, Ontario, Canada).

In some embodiments, the effector peptide(s) used in the methods of the present invention can be attached to a solid support (e.g. microtiter plate or microarray) with a preactivated covalent surface molecule. Available commercially, the surfaces of these plates are highly specific for their coupling partners thus are used to immobilize biomolecules in a site-directed manner. Examples of these plates are, but not limited to, N-oxysuccinimide (DNA-BIND™) activated plate, Hydrazide (Carbo-BIND™) activated plate, Univer-BIND™ plate (Corning, Inc. Corning N.Y.), Reacti-Bind NeutrAvidin coated plate, Reacti-Bind Streptavidin coated plate, Reacti-Bind anti-GFP coated plate, Reacti-Bind anti-GST coated plate (Pierce Biotechnology, Rockland, Ill.), Biotin-Trap™, GST-Trap™, Amine-Trap™, Sugar-Trap™, Streptavidin-Trap™ plates (NoAb Biodiscoveries, Inc. Mississauga, Ontario, Canada), and the like.

In some embodiments, the effector peptide(s) used in the method of the present invention can be linked (e.g., attached) to a solid support (e.g. microtiter plate) that contains a medium to high binding surface that passively absorbs biomolecules through hydrophobic or ionic interactions. Examples of these plates include, but are not limited to, a series of EIA/RIA plates made by Corning, Inc, (Corning N.Y.) Pierce biotechnology, Inc (Rockland Ill.), and the like.

In some embodiments, the effector peptide(s) used in the method of the present invention can be linked to a microtiter plate that contains an aminated or carboxylated surface. Through these surfaces, covalent coupling is achieved using bifunctional crosslinkers that couple the amine or carboxyl group on the surface to a functional group, such as an amine, thiol or carboxyl group, on the peptide. These microplates include, but not limited to, the series of polystyrene or polypropylene plates made by Corning, Inc (Corning N.Y.).

In some embodiments, the effector peptide(s) used in the method of the present invention can be a plate that is formatted to hold a given reaction volume. Examples include, but are not limited to, 96-well plates, 384-well plates, 1536-well plates, and the like. In some embodiments, the effector peptide(s) of the present invention can be presented in a microarray format.

In some embodiments, the immobilized effector peptide used in the methods of the present invention were formulated to allow them to be lyophilized in the wells or microarray formats and to furthermore, maintain their ability to bind to activated Rho GTPase proteins upon rehydration.

In some embodiments, the immobilized peptide is a Rho GTPase protein which creates a target for an effector or effector-HRP conjugate. In this case, the format is designed to screen for ligands that inhibit or enhance the interaction between these two proteins. In this format, the assay can be used to discover ligands that are useful in drug discovery.

In some embodiments, the assay (method) comprises immobilizing (linking) an active Rho binding peptide or fragment thereof to wells of a microtiter plate. In some embodiments, the method comprises lyophilizing the bound protein in wells to create a highly stable and robust protein matrix; incubating the immobilized binding protein with activated Rho GTPase proteins from clarified or non-clarified cell lysates or from tissue samples or recombinant sources; and quantitating the amount of effector bound activated Rho GTPase protein using a Rho GTPase specific antibody.

The present method has numerous advantages over previous effector based methods for determining the activation state of Rho GTPase proteins and other small G-proteins. First, the assay can produce a stable lyophilized formulation of active Rho GTPase binding peptides attached to a microtiter well or microarray, thereby allowing the whole activation assay to be carried out in a single well format, eliminating the need for constant sample manipulations and consequently creating a far more robust assay. Second, in some embodiments, the method does not require pre-clarification of cell lysates containing activated Rho GTPase proteins, which allows easier handling of multiple samples and minimizes underestimates of Rho activation due to GAP activity. Third, this assay is more sensitive than current assays allowing the use of smaller amounts of cell lysate or total protein, which can be important in cases where minimal raw materials are available and in cases where high throughput assays are required.

In some embodiments, the invention provides methods for the high throughput screening of samples (e.g. biological (tissue, blood, and the like) or cell culture) for quantitation of their activated G-protein status. The invention also provides methods for the high throughput screening of compounds or biomolecules that inhibit or enhance or facilitate the interaction between a small G-protein and its effector protein. Examples of the methods include, but not limited to, compounds that inhibit or enhance the RhoA-Rho kinase interaction, RhoA-Dia interaction, RhoC-Rho kinase interaction, Rac1-Pak interaction, Cdc42-Pak interaction.

In some embodiments, the present invention relates to a solid support (e.g., a microtiter plate or microarray) ELISA based method for detecting activated Rho GTPase proteins. The method comprises, attaching an active Rho GTPase specific binding peptide to wells of a solid support (e.g., microtiter plate or microarray matrix), incubating the immobilized active Rho GTPase binding peptide with a sample (e.g., cell lysates) containing one or more activated Rho GTPase proteins and quantitation of the activated Rho GTPase protein using an antibody (e.g., non-specific or specific) for a particular Rho GTPase protein.

In some embodiments, the antibody used in the methods of the invention is a monoclonal, recombinant or polyclonal antibody for Rho GTPase proteins. These antibodies can be specific for one family member or for several family members. Examples of these antibodies include, but not limited to, mouse monoclonal anti RhoA antibody (Santa Cruz Biotechnology, Santa Cruz Calif.), mouse monoclonal anti pan-Rho antibody (BD Transduction Laborataries, San Diego Calif.), chicken polyclonal anti RhoA antibody (Genway, Inc. San Diego Calif.), mouse monoclonal anti-Rho A,B,C (Cytoskeleton Inc.), mouse anti-RhoA (Cytoskeleton Inc.), and the like.

In some embodiments, the antibody used in the method of the invention can be a monoclonal, recombinant or polyclonal primary antibody conjugated to an enzyme or detectable biomolecules. These detectable conjugated antibodies avoid the use of secondary antibody thus increasing the specificity of the reaction. Examples of the conjugated antibodies include, but not limited to, HRP-conjugated primary antibody, AP-conjugated primary antibody, biotin-conjugated primary antibody previously mixed with a streptavidin-HRP conjugate.

In some embodiments, the antibody used in the method of the invention can be a monoclonal, recombinant or polyclonal antibody to a specific effector of Rho GTPase proteins.

An "antibody specific for a particular Rho GTPase protein" refers to an antibody that is specific for only one Rho GTPase protein and will not react or detect a different Rho GTPase protein. In some embodiments, an antibody can be bi-specific, such that it can bind or detect two Rho different Rho GTPase proteins. In some embodiments, an antibody recognizes one or more Rho GTPase proteins. In some embodiments, a non-specific antibody is used that can detect and bind to more than two Rho GTPase proteins. The antibody can be specific for a particular Rho GTPase protein, but the antibody can also recognize in some embodiments only an activated form of the Rho GTPase protein, an inactive form of the Rho GTPase protein, or in some embodiments the antibody can recognize both active or inactive forms.

In some embodiments, the present invention provides a solid support (e.g., microtiter plate or microarray) ELISA based methods for detecting activated recombinant Rho GTPase proteins. The method can comprise linking a Rho GTPase specific binding peptide (e.g., an effector peptide) to wells of a microtiter plate or microarray matrix; incubating the immobilized effector peptide with one or more activated recombinant Rho GTPase proteins; and quantitation of the activated Rho GTPase protein using an antibody specific for a particular Rho GTPase protein.

In some embodiments, the Rho GTPase protein is a recombinant mutant form of the Rho GTPase and/or a constitutively active mutant. One of skill in the art can create constitutively active mutants of Rho GTPase proteins. In some embodiment, the effector protein or peptide can be incubated with the immobilized Rho GTPase protein and Rho GTPase effector interactions are quantitated using an effector specific antibody.

In some embodiments, the method comprises quantitating the amount of an active Rho GTPase protein.

As used herein, "an effector specific antibody" is an antibody that binds to only one effector and cannot detect or bind to a different effector.

In some embodiments, the cell lysate or sample is formulated in a solution containing a buffer component between pH 5-10, about pH 7.5, or a pH of about 6 to about 8, about 6 to about 9, about 7 to about 8, or about 7. In some embodiments, the sample comprising the effector peptide or the Rho protein can comprise a detergent component. The detergent component can be, for example, a non-ionic detergent such as, but not limited to, Triton X-100. The final concentration of the detergent can be, for example, about 0.1, about 0.2, about 0.3, about 0.4, about 0.5, about 0.6, about 0.7, about 0.8, about 0.9, about 1.0, about 1.5, about 1 to about 2, about 1 to about 3, about 0.5 to about 1.5, about 0.75 to about 1.25, about 1 to about 5, 0.1, 0.2, 0.3, 0.4, 0.5, 0.6, 0.7, 0.8, 0.9, 1.0, 1.5, 1 to 2, 1 to 3, 0.5 to 1.5, 0.75 to 1.25, or 1 to 5%. In some embodiments, the cell lysate or sample comprises magnesium chloride. In some embodiments, the final concentartion of magnesium chloride can be, for example, from about 5 to about 80, about 10 to about 50, about 15 to about 25, about 20, 5 to 80, 10 to 50, 15 to 25, or 20 mM.

The sample or lysis buffer can also comprise a salt component. Examples of a salt component include, but are not limited to sodium chloride, potassium chloride, and the like. The final concentration of the salt component can be, for example, from about 10 to about 700, about 100 to about 500, 10 to 700, or 100 to 500, 100, 200, 300, 400, 500, about 100, about 200, about 300, about 400, about 500 mM.

In some embodiments, the amount of total protein in the sample or cell lysate is from about 1 to about 300, about 20 to about 50, about 1 to about 200, about 1 to about 100, about 1 to about 75, about 1 to about 50, about 1 to about 25, about 1 to about 10, about 20 about 50, less than 100, less than 75, less than 50, less than 25, less than 10, less than 300, or less than 200 µg.

In some embodiments, the sample comprises about $10^3$ to about $10^6$, $10^3$ to about $10^5$, $10^3$ to about $10^4$, $10^4$ to about $10^5$, less than $10^6$, less than $10^5$, or less than $10^4$ cells or a cell lysate prepared from the same number of cells as indicated herein.

The detection of an interaction (e.g., binding) between a Rho GTPase binding peptide and an Rho GTPase protein (e.g., activated or unactivated) can be carried out with any method or machine that one can use to detect such interactions. For example, the detection can use the detection of a change in absorbance, luminescence, fluorescence, combinations thereof, and the like.

In some embodiments of the invention, prior to detecting the activated Rho GTPase protein in the sample, an Antigen Presenting Buffer (APB) (also referred to as "antigen presenting enhancement") is added. The Antigen Presenting Buffer comprises one or more compounds or treatments that can attenuate loss of the activated Rho GTPase protein from the solid support. In some embodiments, the Antigen Presenting Buffer comprises heat denaturation; dry denaturation; urea treatment; crosslinkers such as SMCC and glutaraldehyde; ethanol or methanol; or tricholoracetic acid; or any combination or subgroup thereof. In some embodiments, loss of the activated Rho GTPase protein from the solid support is attenuated by at least 10%, by at least 20%, by at least 30%, by at least 40%, by at least 50%, by at least 60%, by at least 70%, by at least 80%, or by at least 90%. In some embodiments, the final concentration of trichloroacetic acid is about 0.5% to about 15% v/v. In some embodiments, the final concentration of TCA is about 0.5% to about 10%, about 0.5% to about 7.5%, about 0.5% to about 5%, about 0.5% to about 4%, about 0.5% to about 3%, about 0.5% to about 2%, about 0.5% to about 1%, about 0.5%, or about 1%, less than 10%, less than 5%, less than 4%, less than 3%, or less than 2% v/v.

In some embodiments, prior to detecting the activated Rho GTPase protein in the sample, a Binding Buffer (also referred to as a "protein:protein interaction enhancer") is added. In some embodiments, the Binding Buffer increases the binding affinity of the Rho GTPase binding peptide and the Rho GTPase protein at least 10%, 20%, 30%, 40%, 50%, 60%, 70%, 80%, 90%, 2-fold, 3-fold, or more than 3-fold than in the absence of the Binding Buffer. In some embodiments, the Binding Buffer comprises ficoll, dextran, or polyethylene glycol, or any combination or subgroup thereof. In some embodiments, the polyethylene glycol is PEG 4000 or PEG 8000 at a final concentration of about 2% to about 40% v/v. In some embodiments, the final concentration of the PEG is about 2% to about 40%, about 2% to about 30%, about 2% to about 25%, about 2% to about 20%, about 2% to about 10%, about 2% to about 5%, about 2%, about 10%, about 20%, about 30%, about 40%.

In some embodiments, the method further comprises quantitating the amount of activated Rho GTPase protein in the sample. The manner in which the amount of the protein is quantitated is not specific to the present method and any quantitation method can be used. Suitable methods include, but are not limited to, differences in absorbance, luminescence, or fluorescence.

In some embodiments, the method further comprises contacting the sample with a test agent and determining whether the test agent modulates binding of the activated Rho GTPase protein to the activated Rho GTPase binding peptide. In some embodiments, the test agent will increase the binding and in other embodiments the test agent will decrease the binding. A test agent can be any compound or composition such as a protein, peptide, small organic molecule, carbohydrate, and the like. If the test agent inhibits the binding the test agent is considered to be an inhibitor. The binding of the Rho GTPase protein and the Rho GTPase binding peptide can be compared in the absence and the presence of the test agent to determine if the test agent modulates the binding. The binding can be detected or quantitated by any method including those described herein.

In some embodiments, the present invention provides a method for detecting an activated Rho GTPase protein comprising contacting a solid support with a sample comprising an activated Rho GTPase protein, wherein a modified Rho GTPase binding peptide is linked to the solid support, and wherein the modified Rho GTPase binding peptide has a lower $K_d$ (i.e., binds with a greater affinity) with the activated Rho GTPase protein than the unmodified Rho GTPase binding peptide has with the Rho GTPase protein; and detecting the activated Rho GTPase protein in the sample. In some embodiments, the modified Rho GTPase binding peptide is an oligomerized Rho GTPase binding peptide or a mutated Rho GTPase binding peptide. The modified peptide can be any peptide as described herein and known to one of skill in the art including, but not limited to, a modified Rhotekin, modified ROCK1, modified PAK1, modified POSH, or modified WASP.

In some embodiments, the present invention provides methods of detecting an activated Rho GTPase protein comprising contacting a microtiter plate or microarray with a sample comprising an activated Rho GTPase protein, wherein an activated Rho GTPase specific antibody is linked to the microtiter plate or microarray; and detecting the activated Rho GTPase protein in the sample.

In some embodiments, the present invention provides methods of identifying an activated Rho GTPase binding peptide comprising contacting a test agent with an activated Rho GTPase protein optionally in the presence of an Antigen Presenting Buffer; and detecting the binding of the Rho GTPase protein to the test agent, wherein the detection of binding indicates that the test agent is an activated Rho GTPase binding peptide.

In some embodiments, the present invention provides methods further comprising contacting a solid support with a sample comprising an activated Rho GTPase protein, wherein the solid support is linked to the test agent; and detecting the activated Rho GTPase protein in the sample.

In some embodiments, the present invention provides methods of determining whether an Antigen Presenting Buffer is beneficial to detect the binding of an activated Rho GTPase protein to an activated Rho GTPase binding peptide comprising contacting a solid support with a sample comprising the activated Rho GTPase protein, wherein a Rho GTPase binding peptide is linked to the solid support; and detecting the activated Rho GTPase protein in the sample at different time intervals, wherein a decrease in detection at different time intervals indicates that the Antigen Presenting Buffer is beneficial.

In some embodiments, the present invention provides methods of determining whether a test buffer is an Antigen Presenting Buffer comprising contacting a solid support with a test buffer and an activated Rho GTPase protein, wherein an activated Rho GTPase binding peptide is linked to the solid support; and detecting the binding of the activated Rho GTPase protein to the activated Rho GTPase binding peptide at different time intervals, wherein if no decrease in detection is observed in the presence of the test buffer as compared to the absence of the test buffer, then the test buffer is an Antigen Presenting Buffer that facilitates detection of binding of an activated Rho GTPase binding peptide with an activated Rho GTPase protein. In the absence of the test buffer, there is a decrease in detection whereas the presence of the test buffer prevents the decrease in the detection then the test buffer is an APB.

In some embodiments, the present invention provides compositions comprising a solid support; an Antigen Presenting Buffer; an activated Rho GTPase protein; and an activated Rho GTPase binding peptide or a modified Rho GTPase binding peptide.

In some embodiments, the present invention provides kits comprising a solid support and an activated Rho GTPase binding peptide, wherein the activated Rho GTPase binding peptide is optionally linked to the solid support; and optionally an Antigen Presenting Buffer. In some embodiments, the kit comprises a Rho GTPase binding peptide that is covalently linked to the solid support. In some embodiments, the kit further comprises a positive control, wherein the positive control comprises an activated Rho GTPase protein that can bind to the Rho GTPase binding peptide. In some embodiments, the kit comprises an Antigen Presenting Buffer that comprises trichloric acetic acid (TCA). In some embodiments, the kit comprises a Binding Buffer, such as dextran, ficoll, PEG, or combinations thereof.

In some embodiments, the kit comprises a Rho GTPase binding peptide that is Rhotekin, ROCK1, PAK1, POSH, or WASP. In some embodiments, the kit further comprises instructions for carrying out the detection of an activated Rho GTPase protein.

In some embodiments, the kit comprises an agent for detecting binding between the Rho GTPase binding peptide and an activated Rho GTPase protein, wherein the agent is luminescent, fluorescent, or radioactive. In some embodiments, the kit comprises a solid support that is a microtiter plate, microarray, or slide, wherein the solid support is optionally activated with malemide or otherwise activated or coated as described herein to facilitate the binding of the Rho GTPase binding peptide to the solid support.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Production of Effector-GBD Peptides for the G-LISA Assay

There are some sequence motifs that are shared between subgroups of Rho GTPase effectors, for example, the Cdc42/Rac-interacting binding (CRIB) motif is present in many, though not all Rac and Cdc42 binding proteins (Burbelo et al., 1995, J. Biol. Chem., 270:29071-29074) and has been found to be necessary but not sufficient for effector binding (Rudolph et al., 1998, J. Biol. Chem., 273:18067-18076). A further common Rho effector motif is the Rho effector homology (REM) found in PRK1 and PRK2 and the HR1 repeat motif which is found in effectors such as rhophilin and rhotekin (Flynn et al., 1998, J. Biol. Chem., 273:2698-2705). However, there are a large number of effectors that do not contain any of the currently identified GTPase-binding motif/s. These include the POSH, PI3K and DAG effectors (Bishop et al., 2000, Biochem. J., 348:241-255). This type of protein is classified as a Rho effector purely on its functional ability to differentiate between the GTP (active) and GDP (inactive) bound forms of Rho GTPases (Tapon, 1998, EMBO J., 17:1395-1404; and Kobayashi et al., 1998, J. Biol. Chem., 273:291-295). It is therefore accepted by those skilled in the art that Rho effectors are currently defined by their functional ability to selectively recognize the GTP-bound (active) form of Rho GTPases over the inactive GDP form of the GTPase (Vetter et al., 2001, Science, 294:1299-1304; Blumenstein et al., 2004, J. Biol. Chem., 279:53419-53426; Martin et al., 1995, EMBO J., 14:1970-1978; Leung et al., 2005, Proc. Natl. Acad. Sci., 102:5685-5690; Bishop et al., 2000, Biochem. J., 348:241-255; and Fujisawa et al., 1998, J. Biol. Chem., 273:18943-18949).

The example provided herein has utilized six of the most extensively characterized Rho effectors, or more specifically Rho effector-GTPase Binding Domain (GBD) peptides. Table 1 details the effector and the specificity of the effector for activated Rho family proteins.

TABLE 1

Effector Recognition of Activated Rho Family Proteins

| Effector name | Activated Rho family proteins recognized by effector-GBD | References |
|---|---|---|
| Rhotekin | RhoA, RhoB, RhoC | Reid, 1996, J. Biol. Chem., 271: 13556 |
| ROCK1 | RhoA, RhoB, RhoC, RhoE/Rnd3 | Fujisawa, 1996, J. Biol. Chem., 271: 23022<br>Riento, 2003, Mol. Cell. Biol., 23: 4219 |
| PAK1 | Rac1, Rac1b, Rac2, Rac3, Cdc42, Wrch1 | Bagrodia, 1995, J. Biol. Chem., 270: 22731<br>Saras, 2004, J. Exp. Cell Res., 299: 356 |
| POSH | Rac1 | Tapon, 1998, EMBO, 17: 1395 |
| WASP | Cdc42, TC10, TCL, Wrch2/Chp | Symons, 1996, Cell, 84: 723<br>Abe, 2002, J. Cell. Sci., 116: 155<br>Vignal, 2000, J. Biol. Chem., 275: 36457<br>Aronheim, 1998, Curr. Biol., 8: 1125 |
| Dia1 | RhoA, RhoC | Watanabe, 1997, EMBO J., 16: 30444 |

Materials And Methods

Effector cDNA Cloning

For all of the effector proteins and effector GTPase Binding Domains (GBD) provided herein as examples, the full length mammalian cDNA has been previously described (see Table 2). Effector-GBD peptides have been cloned by PCR using the primers and cDNA sources indicated in Table 2. The nucleotide numbering in Table 2 corresponds to the Genbank submission numbering scheme. GTPase Binding Domains (GBDs) were selected based upon published data identifying active Rho binding domains of effectors (see Table 1).

TABLE 2

Effector Cloning Information

| Effector name | Accession number | Primers for cDNA cloning 5' primer 3' primer | Nucleotides included (amino acid) | cDNA source |
|---|---|---|---|---|
| Rhotekin | NM_009106 | 5' caggatccattctggaagatctgaacatgctg (SEQ ID NO: 98)<br>3' cagaattcgcccccaccagttttttcgag (SEQ ID NO: 99) | 19-267 (7-89) | Mouse |
| ROCK1-1 | NM_005406 | 5' accgaattcgaagctgagcaatatttctcg (SEQ ID NO: 100)<br>3' accgaattctca<u>aca</u>ttgtgtattagctttctttctata (SEQ ID NO: 101) | 2539-3070 (847-1024) | Human |
| Dia1-1 | NM_005219 | 5' caggatcctctgcatcatatggggatgat (SEQ ID NO: 102)<br>3' cagaattctcatagaatacaaagagcagaaag (SEQ ID NO: 103) | 187-780 (63-260) | Human |
| PAK1 | NM_002576 | 5' caggatccaaagagaaagagcggccagagat (SEQ ID NO: 104)<br>3' cagaattctca<u>aca</u>ctcagctgacttatctgtaaagctc (SEQ ID NO: 105) | 202-453 (68-151) | Human |
| POSH | NM_020870 | 5' caggatccaagcaccccgacaccaagaag (SEQ ID NO: 106)<br>3' cagaattcacccagtggtgcttatatggacc (SEQ ID NO: 107) | 871-1089 (291-363) | Human |
| WASP | NM_000377 | 5'caggatccgacatccagaaccctgacatcacg (SEQ ID NO: 108)<br>3'cagaattctca<u>aca</u>tcgagatggcggtgggggcggc (SEQ ID NO: 109) | 601-963 (201-321) | Human |

* Cysteine codons are underlined

The sequences from the GenBank accession numbers from Table 2 and anywhere provided herein, are incorporated herein by reference in their entirety.

Modification of Effector-GBD DNA Sequences to Allow Directional Covalent Binding to Maleimide Activated Plates In instances where effector-GBD peptides were linked covalently to maleimide plates (see later in this example and Table 3), the effector-GBD peptide DNA was modified to contain a single cysteine residue at the carboxy terminal. Cysteine codons were engineered into the primer design for ROCK1, PAK1 and WASP (see Table 2, the cysteine codon in the 3' primers are underlined). In the case of POSH, advantage of the cystein codon (position 351) close to the carboxy terminal was taken.

The effector-GBD of rhotekin contains three internal cysteine residues (Table 2 and FIG. 1). To allow directional binding of rhotekin-GBD to maleimide plates the rhotekin-GBD was chemically synthesized (Entelechon GmbH, St. Veit-Weg 2, 93051 Regensburg, Germany), the three internal cysteins were removed and replaced with glutamic acid (aa#43), leucine (aa#49) and serine (aa#65) respectively. A cysteine codon was placed at the carboxy terminal of the modified rhotekin-GBD, immediately upstream of a stop codon. The design of the synthetic rhotekin-GBD sequence was carried out using Leto 1.0 gene optimization software which is based on a proprietary genetic algorithm (Entelechon GmbH, St. Veit-Weg 2, 93051 Regensburg, Germany). The sequence design allowed optimization of codon usage, homogenous GC content, mRNA secondary structure, codon and motif repeats and restriction sites. The synthetic Rhotekin-GBD DNA was supplied by Entelechon GmbH in a pUC18 cloning vector. The DNA was cleaved with restriction enzymes BamH1 and EcoR1 according to the manufacturers instructions (Promega Corp., Madison, Wis.) and the 273 bp DNA fragment containing modified Rhotekin-GBD was cloned directly into the BamH1 and EcoR1 sites of the expression vector pGEX-4T, creating a Rhotekin-GBD domain fused to a Glutathione S Transferase tag at the amino terminal and containing a unique cysteine residue at the carboxy terminal. All molecular biology manipulations were carried out in accordance with general principles outlined in Molecular Cloning, A Laboratory Manual, 1998, Second edition, Cold Spring Harbor Laboratory Press. Ed. Sambrook et al.

Expression Plasmid Vector Backbones and Purification Tag

The example described herein utilizes the expression vectors pRSET-A (Invitrogen Corp., Grand Island, N.Y.) which contains an N-terminal Histidine tag (His-tag) and pGEX-4T (GE Healthcare (Pharmacia Inc.), Piscataway, N.J.) which contains an N-terminal GST-tag. A thrombin protease site between the GST-tagged constructs and effector-GBD peptide of interest allows removal of the GST tag by thrombin cleavage. Table 3 recites the vector used for cloning of each effector-GBD used in the examples. Table 3 also recites the tag used for effector-GBD peptide purification and the method used for linking peptide to microtiter plates. Details of microtiter plate coating is provided in Example 2.

TABLE 3

Effector Purification Tags and Plate Binding Tags

| Effector-GBD | Plasmid Vector Backbone | Purification tag | Peptide Linker for Plate Binding | Plate Chemistry |
|---|---|---|---|---|
| ROCK1 | pRSET-A | Histidine | Unique cystein engineered into carboxy terminal of effector | Maleimide |
| Rhotekin | pGRX-4T | GST | GST tag at amino terminal | Glutathione |
| Rhotekin-Cys | pGEX-4T | GST | Unique cystein engineered into carboxy terminal of effector | Maleimide |
| PAK1 | pGEX-4T | GST | GST tag at amino terminal | Glutathione |
| POSH | pRSET-A | Histidine | Naturally occuring cystein in POSH protein | Maleimide |
| WASP | pRSET-A | Histidine | Unique cystein engineered into carboxy terminal of effector | Maleimide |
| Dia | pGEX-4T | GST | GST tag at amino terminal | Glutathione |

Effector Protein Expression

Bacterial cultures (for example BL21 (DE3) or BL21) containing an expression construct (for example those plasmids described in Table 2) were grown in media (typically LB media) plus a suitable antibiotic (typically ampicillin at 50 µg/ml). Cultures were grown at 37° C. with shaking at 200 rpm until $OD_{600}$ reached approximately 0.6. To induce protein production, IPTG was added to 0.2 mM and shaking was continued at room temperature (typically for 12 hours). Prior to induction, a small sample of bacteria were collected (typically 1 ml) and stored at −20° C. After induction, a small sample of bacteria (typically 1 ml) were collected and stored at −20° C. The remainder of the culture was harvested by pelleting bacteria at 6,000 g. Bacteria pellets could be stored at −20° C. until processed. The 1 ml bacterial samples mentioned above were used to determine efficiency of recombinant protein induction by comparing recombinant protein levels in induced versus uninduced bacterial pellets. Typically this analysis is done by coomassie staining of proteins in an SDS-PAGE system.

Effector Protein Purification

Bacterial pellets were resuspended in lysis buffer (typically 20 ml per liter of culture). Lysis buffer for His tagged proteins was typically 50 mM Tris pH 7.5, 50 mM NaCl, 0.5 mM $MgCl_2$, and 5 mM imidazole. Lysis buffer for GST tagged proteins was typically 50 mM Tris pH 7.5, 150 mM NaCl, and 2 mM EDTA. Resuspended cells were passed through four layers of cheesecloth to remove debris and cells were lysed by passage through a microfluidizer (Model M-110L, Microfluidics). Lysates were clarified by a centrifugation step at 60,000 g.

Histidine tagged proteins were purified by immobilized metal-affinity chromatography (IMAC) (Bomhorst et al., 2000, Methods in Enzymology, 326:245-254). Briefly, lysates were incubated with metal chelated beads (typically nickel or cobalt beads at 1 ml of beads per liter of bacterial culture). The bead/lysate mixture was incubated for 30-60 minutes at 4° C. Beads were washed with wash buffer (50 mM Tris pH 7.5, 0.5 mM NaCl) containing imidazole concentrations ranging from 10 mM to 30 mM. Recombinant effector protein was eluted in 3-5 bead volumes of elution buffer (500 mM imidazole, 200 mM NaCl, 50 mM Tris pH 7.5, 1 mM $MgCl_2$) and stored at −70° C.

GST tagged proteins were purified by glutathione affinity chromatography (Smith, 2000, Methods in Enzymology, 326:254-270). Briefly, lysates were incubated with glutathione beads (typically 1 ml of beads per liter of bacterial culture) at 4° C. for 1 hour. The beads were then washed 3 times with an equal volume of lysis buffer and recombinant GST tagged effector protein was eluted with 3-5 bead volumes of elution buffer (lysis buffer plus 10 mM reduced glutathione) and stored at −70° C.

Thrombin Cleavage of GST tagged Effector-GBD Peptides

The protocol followed the procedure outlined in Meth. Enz. 1995, 256:178. Briefly, GST-tagged protein bound to glutathione beads were washed 3 times in PBS plus 1% Triton X-100 and 3 times in 50 mM Tris pH 7.5, 150 mM NaCl, and 2.5 mM $CaCl_2$. The beads were finally resuspended in an equal volume of calcium buffer. Bovine alpha thrombin (Sigma) was added to the beads at 30 units per mg of protein. The cleavage was carried out for 2-5 hours at 4° C. with rotation. The beads were removed by centrifugation and the cleaved proteins were retained and stored at −70° C.

Pull-Down Assay

Modified GST rhotekin-GBD peptide was bound to glutathione beads and 20 ug of bead bound effector was added to 500 µl (250 µg) of clarified GTPγS or GDP loaded platelet extract (see Example 2 for lysate preparation). The mixture was incubated at 4° C. with rotation for 1 hour. The beads were then washed twice in wash buffer (50 mM Tris pH 7.5, 100 mM NaCl, and 30 mM $MgCl_2$), resuspended in 1 bead volume of SDS sample buffer (75 mM Tris pH 6.8, 2% SDS, 10% glycerol, 5% β-mercaptoethanol, and 2 mg/ml bromophenol blue) and subjected to SDS-PAGE (4-20% gradient). The proteins were transferred to PVDF membranes (Cat# IPVH304F0, Millipore, Bedford, Mass.) and a western blot was perfomed thereafter with anti-RhoA at 0.25 µg/ml (Cat# ARH01, Cytoskeleton Inc., Denver, Colo.), anti-Rac1 at 0.25 µg/ml (Cat# ARC01, Cytoskeleton Inc., Denver, Colo.), anti-Cdc42 at 1 µg/ml (Cat# ACD01, Cytoskeleton Inc., Denver, Colo.). The activated RhoA protein band was detected using primary antibody specifically recognizing RhoA protein and a goat anti-mouse secondary (Jackson Labs., Catalog #115-035-068). The assay was performed at least eight times.

Results

Effector-GBD Cloning

All effector-GBD cDNA sequences described in Table 2 were confirmed to match the published Genbank sequences. In addition, the presence of an engineered carboxy terminal cysteine codon was confirmed for ROCK1, PAK1 and WASP constructs.

FIG. 1B details the sequence of the synthetic rhotekin-Cys-GBD domain. Comparison of the synthetic and wild type rhotekin-RBD sequence confirmed that all three internal cystein residues were removed from the synthetic construct and replaced with glutamic acid (aa#43), leucine (aa#49) and serine (aa#65). The presence of a carboxy terminal cysteine, that was introduced for the purpose of oriented binding to maleimide plates, was also confirmed by sequence analysis (FIG. 1B). cDNAs were cloned using restriction sites recited in Table 2 primers. DNA and amino acid sequence of wild type and modified Rhotekin-Cys-GBD. Amino acid residue changes between wild type and Cys mutant effector-GBD are shown bold and underlined.

Effector Expression and Purity

Typical effector-GBD peptide purities were in the range of 70-80% as determined by scanning densitometry of coomassie stained peptides separated by molecular weight on SDS-PAGE gels (FIG. 1A). Briefly, purified GBD domains of PAK1-GST (30 µg), ROCK1-His (10 µg), WASP-His (20 µg), POSH-His (20 µg), Rhotekin-Cys-no tag (GST tag cleaved with thrombin) (10 µg), Rhotekin wild type GBD-GST (20 µg) and Dia1-GST (15 µg) were loaded on a SDS-PAGE and the protein gel was stained with coomassie blue.

Confirmation of Effector-GBD Biological Activity

The ability of effector-GBD peptides to selectively bind to activated Rho proteins was determined for all effector-GBD peptides with either a GST pull-down (FIG. 1C for the modified Rhotekin-Cys and data not shown) or a G-LISA assay (data not shown and see Example 2). Briefly, 50 µg of purified Rhotekin-Cys GBD mutant beads were incubated with 500 µg GDP or GTPγS loaded platelet extract and the bead precipitated RhoA-GTP was subject to SDS-PAGE and Western blot analysis with anti-RhoA antibody.

Discussion

There are currently 21 members of the Rho family, as defined in Wennerberg et al, 2005, J. Cell Sci., 118:843-6 and Schnelzer et al., 2000, Oncogene, 19:3013-3020. These are RhoA, RhoB, RhoC, RhoD, Rnd3, Rnd1, Rnd2, Rif, RhoG, RhoH, Rac1, Rac1b, Rac2, Rac3, Cdc42, TC10, TCL, Wrch-1, Wrch-2, RhoBTB1 and RhoBTB2.

The combination of effector-GBD peptides used in this example are able to selectively bind to the active form of 13 out of 21 or 62% of all Rho family members (see Table 1). This includes the best characterized Rho proteins, namely RhoA, Rac1 and Cdc42 as indicated from PubMed citations (PubMed citations from 1996-2006; RhoA (2467), Rac1 (1931), Cdc42 (2455), RhoB (283), RhoC (117), RhoD (187), Rnd3 (23), Rnd1(31), Rnd2 (15), Rif (searched as Rif small G-protein) (5), RhoG (83), RhoH (26), Rac2 (219), Rac3 (85), TC10 (70), TCL (searched as TCL small G-protein)(6), Wrch-1 (6), Wrch-2 (4), RhoBTB1 (4), RhoBTB2 (6), Rac1b (22)). Because any given effector will usually bind to more than one Rho GTPase, assay specificity for detection and quantitation of a particular endogenous Rho GTPase depends upon the combination of effector-GBD and a Rho GTPase specific antibody. Using the combination of effector and antibody to obtain Rho GTPase specificity provides this assay an advantage over other active Rho GTPase detection systems that use effector "specificity" only (Pertz et al., 2004, J. Cell Sci., 117:1313-1318).

The effectors here set forth will be referenced throughout the remaining examples, however, it is understood by those of skill in the area that the methods, assays and the like herein disclosed apply equally well to any Rho effector-GBD. This is particularly true when one considers that the definition of a Rho effector, as defined in Vetter et al., 2001, Science, 294: 1299-1304, "Effectors for GTP-binding proteins are operationally defined as molecules interacting more tightly with the GTP-bound than with the GDP-bound form" is accepted by those of skill in the area as the practical definition of a Rho GTPase effector. It will also be understood that the embodiment of this invention is completely dependent upon the practical operational definition of Rho GTPase effectors.

Example 2

Utility of Covalently Linked Effector-GBD Plates in G-LISA Assays

There are many chemistries described in the art for linking a particular peptide to a microtiter plate or microarray (Dent et al., 1998, Bioconjugation, Macmillan Reference Ltd, Chapter 8:505-556). In the broadest terms, linkages can be classified into covalent and non-covalent formats. Both types of linkage are demonstrated herein (see non-covalent linkage, Example 7). The example described herein details a method of covalent linkage through maleimide activated plates.

Covalent linkage of peptides to microtiter plates through activated surface groups occurs when electrons are shared between atoms to generate chemical bonds. While the reactions forming such bonds are always theoretically reversible, the low probability of the reverse reaction occurring in practice results in products that can be thought of as permanent (Dent et al., Bioconjugation, Macmillan Reference Ltd, 1998, p. 218-342). The essentially irreversible nature of peptide linkage has the potential advantage of forming a very stable effector-GBD matrix that will not suffer from biomolecule loss, displacement or surface migration (Larsson et al., 1987, J. Immunol. Meth, 98:129135; Dent et al., 1998, Bioconjugation: Protein Coupling Techniques for the Biomedical Sciences, Chapter 8, Other Categories of protein Coupling, p. 505-556). For this reason, it was decided to pursue a covalent linkage format (but see also non-covalent linkage in Example 7).

There are many types of covalent linkage plate chemistries available to link peptides to plates including, but not limited to, the N-oxysuccinimide (NOS) sufaces that covalently couple primary amine groups (Pierce Biotechnology Inc., Rockford, Ill.) and the Univer-BIND™ plate that reacts with aliphatic carbon-hydrogen bonds (Corning, Inc., N.Y.). The plate chemistry that is described in this example is the maleimide plate, these are available commercially and are designed to immobilize biomolecules through available -SH moieties, usually from a cysteine residue in the coupling peptide. Examples of maleimide activated microplates include, but are not limited to, polystyrene microplates such as Costar's Sulfhydryl Binding Plates and Strips (Corning, Inc. Corning, N.Y.), Reacti-Bind™ Maleimide Activated Plates (Pierce Biotechnology, Inc. Rockford, Ill.) and maleimide activated microwell plates—sulfhydryl-TRAP™ (NoAb Biodiscoveries, Inc. Mississauga, Ontario, Canada). Linkage through a cysteine residue provided the opportunity to engineer peptides that contained a single cysteine and that could, therefore, be oriented on the plate (see Example 1). Homogenous effector orientation is predicted to yield more reproducible plates with lower overall coefficients of variation (Dent et al., 1998, Bioconjugation: Protein Coupling Techniques for the Biomedical Sciences, Chapter 8, Other Categories of protein Coupling, p. 505-556).

Materials and Methods

Covalent Attachment of Effector-GBD Peptides to Maleimide Plates

Effector-GBD peptide (ROCK1, POSH or WASP, see Table 2) was diluted in coating buffer (PBS pH 7.2, plus 1 mM EDTA) to a final concentration 0.05 mg/ml and 5 µg of peptide was added to the wells of maleimide plates (Corning Inc., Catalog #2510). Plates were incubated at 21° C. for 2 hours, washed twice in PBS pH 7.2. Plates were blocked for 1 hour at room temperature with milk (typically 0.1-5%, depending upon effector-GBD). After two washes with PBS (pH 7.2), Lyophilization Buffer was added to each well (5% sucrose and 1% dextran) and the plates were lyophilized and stored desiccated at 4° C.

Constitutively Active Recombinant Rho Proteins

A glutamine to leucine mutation in amino acid 63 of RhoA or amino acid 61 of Rac1 and Cdc42 results in a peptide that is unable to hydrolyse GTP and is therefore constitutively active (Xu et al., 1994, J. Biol. Chem., 269:23569-23574; and Nobes et al., 1994, Curr. Op. Gen. Dev., 4:77-81). The mutant proteins are commercially available as histidine taged peptides (Cytoskeleton Inc. Catalog # R6301 (constitutively active RhoA), R6101 (constitutively active Rac1) and C6101 (constitutively active Cdc42). Typically, constitutively active protein was diluted to 0.2 ng/µl in Cell Lysis buffer (50 mM Tris pH 7.5, 300 mM NaCl, 2% IGEPAL, 0.01% SDS, and 10 mM $MgCl_2$) and 1-5 ng of protein was used in a G-LISA assay.

Production of In Vitro Nucleotide Loaded Cell Lysates

Cell lysates can be loaded with either GTP, GTPγS or GDP and have been widely used as controls for the standard pull-down assays (Knaus et al., 1992, J. Biol. Chem., 267:23575-23582). Artificially loaded lysates also provided robust substrates for the development of a given G-LISA assay. Human platelet extract at 4 mg/ml in Cell Lysis Buffer (50 mM Tris pH 7.5, 300 mM NaCl, 2% IGEPAL, 0.01% SDS, and 10 mM $MgCl_2$) was clarified by centrifugation at 8,000 g, 4° C. for 3 minutes. EDTA was added to a final concentration of 15 mM. GTPγS, GTP or GDP, at 1 mM final concentration, were added to separate aliquots of clarified lysates. Each lysate was incubated for 15 minutes at room temperature to allow the exchange (loading) of nucleotide to Rho proteins. Loading reactions were stopped by the addition of 60 mM $MgCl_2$. Lysates were diluted to 0.5 mg/ml in Cell Lysis Buffer and used in G-LISA assays. Typically 7-15 µg of loaded platelet cell lysate was used for each G-LISA assay. Platelets loaded with GTP are referred to as labile GTP extracts throughout this example.

G-LISA Assays

Active Rho protein (typically 7-15 µg total cell lysate or 1-5 ng of constitutively active recombinant protein) were either added directly to the effector bound G-LISA plate (Rac1 and Cdc42 G-LISAs) or diluted with an equal volume of Binding Buffer (20% PEG 8000, Sigma, St. Louis, Mo.) prior to adding to effector bound plates (RhoA G-LISA). The reactions were incubated for 30 minutes at 4° C. on a microtiter titer plate shaker after which wells were washed once with 200 µl of PBST (PBS pH 7.2, 0.05% Tween-20) and immediately treated with 200 µl of Antigen Presenting Buffer (1% trichloroacetic acid (TCA)) for 2-5 minutes at room temperature. Wells were then washed three times with 200 µl each of PBST and primary antibody is added typically at 1 µg/ml (RhoA specific), 0.25 µg/ml (Rac1 specific), 1 µg/ml (Cdc42 specific) and incubated at room temperature for 45 minutes (incubation at 4° C. gave similar results). Wells are washed three times with 200 µl each of PBST and incubated with appropriate secondary antibody for 45 minutes at room temperature (incubation at 4° C. gave similar results). For RhoA and Rac1 reactions goat anti-mouse secondary at 2 µg/ml is used, for RhoA,B,C reactions donkey anti-chicken secondary at 0.5 µg/ml is used, for Cdc42 reactions goat anti-sheep secondary antibody is used at 0.5 µg/ml. After three washes each of 200 µl PBST the activated Rho proteins are detected using absorbance or luminescence detection as described below.

Measuring G-LISA Assays with Absorbance or Luminometry

Absorbance is measured at OD490 in a spectrophotometer (SpectraMax 250, Molecular Devices) after addition of 50 µl of OPD substrate (Sigma Catalog # P9187) for 15 minutes at 37° C. followed by addition of 50 µl of stop buffer (1M sulfuric acid). Luminescence was measured in a SpectroFluor Plus (Techan Inc.) after addition of 50 µl of lumigen reagent (Lumigen Inc., Catalog # PSA-100), typical settings were 100-150 gain and 10-100 ms integration.

Antibodies

Primary and secondary antibodies used for G-LISA assays in the example set forth and when stated, in other examples set forth are: anti-RhoA (Clone 384 or Part#GL01 in Cat#BK124, Cytoskeleton Inc., Denver, Colo.), anti-RhoA,B,C (clone 419 or Part#GL04 in Cat#BK120) anti-Rac1 (Part# GL06 in Catalog # BK122h, Cytoskeleton Inc., Denver, Colo.), anti-Cdc42 (Catalog #ACD02, Cytoskeleton Inc., Denver, Colo.), goat anti-mouse and donkey anti-sheep (Catalog #115-035-068 and 313-005-045, Jackson ImmunoResearch labs. Inc., West Grove, Pa.).

Results

Utility of Effector-GBD Maleimide Plates for Detection of Specific Rho GTPases

Published estimates of cellular levels of a given Rho GTPase typically fall into the $1 \times 10^{-4}$ ng per cell range (2003, J. Immunol., 170:5652-5657; and Quinn et al., 1993, J. Biol. Chem., 268:20983-20987). Further, based upon published data, one can assume approximately 2-10% of a particular Rho GTPase is typically activated in response to any particular stimulus (Ren et al., 1999, EMBO J., 18:578-585; Bernard et al., 1999, J. Biol. Chem., 274:13198-13204; and Werner et al., 2002, J. Cell Biol., 158:357-368). Further, based upon published data, a standard pull-down assay typically requires $1 \times 10^{6}$ to $1 \times 10^{7}$ cells or 300-800 µg of total cellular protein (Benard et al., 2002, Meth. Enz., 345:349-359; Ren et al., 2000, Meth. Enz., 325:265-272; and Werner et al., 2002, J. Cell Biol., 158:357-368), this amount of lysate is equivalent to approximately 100-1000 ng of a particular Rho protein (both active and inactive conformation combined). Therefore, assuming 2-10% activation of a particular Rho GTPase in response to a particular stimulus, one is looking at a signal for active Rho GTPase in the range of 2-100 ng for a standard pull-down assay.

Taking the above calculations into consideration, initial tests of the G-LISA using 5 ng of recombinant constitutively active Rho GTPases were performed. This amount of protein was considered to be close to the lower levels of detection for the pull-down assay and, because it was desirable to eventually use considerably less than 300-800 µg of cell lysate, the initial tests should be designed such that a fairly stringent level of detection could be obtained. Using the constitutively active forms of the Rho GTPases was a logical choice for initial tests as they present a clearly defined and easily interpretable system.

Rho effectors typically bind to more than one isotype of activated Rho protein (see Example 1, Table 1). For example, ROCK1 (and ROCK1-GBD) recognize the active form of RhoA, RhoB and RhoC and RhoE/Rnd3 (Fujisawa, 1996, J. Biol. Chem., 271:23022; and Riento et al., 2003, Mol. Cell. Biol., 23:4219). Specificity of a particular G-LISA assay is therefore dependent upon the choice of both effector and antibody. Thus, in the example of a ROCK1-GBD plate (FIG. 2A) RhoA specificity is imparted by the use of the ROCK-GBD plate in combination with a RhoA specific antibody (clone 384).

Referring to FIG. 2A, lysis buffer only (Blank), 5 ng of RhoA (63L), Cdc42 (61L) or Rac1 (61L) were subjected to a RhoA G-LISA assay as detailed in materials and methods, and RhoA signal was detected by luminometry as described in materials and methods. FIG. 2A shows that the ROCK1-GBD maleimide plate (ROCK plate) used in combination with a RhoA specific antibody (clone 384) gave a signal 6-fold above background (buffer only) with 5 ng of constitutively active RhoA. Constitutively active Cdc42 and Rac1 did not give a signal above background for this plate. It can therefore be concluded that the ROCK1-GBD plate is able to bind to active RhoA and that the RhoA antibody can specifically detect this level of protein above background. Antibody 384 is specific for RhoA, as demonstrated in FIG. 7A. The rhotekin-Cys effector-GBD was tested to selectively bind to RhoA. This modified effector-GBD gave a signal for constitutively active RhoA 6-fold above background (data not shown).

Referring to FIG. 2B, lysis buffer only (Blank), 5 ng of Rac1 (61L), or RhoA (63L) were subjected to a Rac1 G-LISA assay as detailed in materials and methods (Example 2), and Rac1 signal was detected by absorbance at 490 nm as described in materials and methods (Example 2). In a similar manner, FIG. 2B shows that a POSH bound maleimide plate (POSH plate) used in combination with a Rac1 specific antibody (GL06, Cat# BK122h) gave a signal 9-fold above background with 5 ng of constitutively active Rac 1. As predicted, constitutively active RhoA gave a signal barely above background.

Referring to FIG. 2C, lysis buffer only (Blank), 5 ng of Cdc42 (61L) or Rac1 (61L) were subjected to a Cdc42 G-LISA assay as detailed in materials and methods (Example 2), and Cdc42 signal was detected by absorbance at 490 nm as described in materials and methods (Example 2). FIG. 2C shows that a WASP bound maleimide plate (WASP plate) used in combination with a Cdc42 specific antibody (Catalog # ACD02, Cytoskeleon Inc., Denver, Colo.) gave a signal 5-fold above background with 5 ng of constitutively active Cdc42. As predicted, constitutively active Rac1 did not give a signal above background.

In conclusion, the data in FIG. 2 establishes that the maleimide linked effector-GBD's retain the ability to recognize their target active Rho GTPase. Further, in combination with the appropriate antibody, low nanogram levels of the specific active Rho GTPase can be detected.

Utility of Effector-GBD Maleimide Plates for Discrimination Between Active and Inactive Rho GTPases The G-LISA assays are not only required to detect signal from a particular activated Rho GTPase, they must also be able to distinguish between the active (GTP bound) and inactive (GDP bound) states of a particular Rho protein. The effector-GBD maleimide plates were tested using artificially loaded platelet extracts (see Materials and Methods for details). The artificially loaded extracts in this example have had their endogenous GTPases loaded in vitro with either GTPγS (a slowly hydrolysable GTP analog) or GDP. As the GTPγS is essentially non-hydrolysable the signal from activated samples is very stable. This is in contrast to a normal cell lysate in which the Rho GTPase would be susceptible to GTPase Activating Protein (GAP) enhanced GTP hydrolysis and consequent inactivation (Moon et al, 2003, Trends Cell Biol., 13:13-22). It is accepted by those of skill in the art that lysates containing endogenous Rho proteins artificially loaded in a fixed active state are useful in experiments where one requires robust activation of Rho (typically>10% activation) with limited involvement of Rho hydrolysis (Liseti et al., 2004, J. Biol. Chem., 279:5055).

Referring to FIG. 3A, lysis buffer only, 25 µl of GDP or GTPγS labeled platelet extracts (0.5 mg/ml) (or 15 µg) were mixed with same volume of Binding Buffer and subjected to a standard RhoA G-LISA assay. RhoA signal was detected by luminometry as described in materials and methods. ROCK-GBD maleimide plates were used. The results show that the binding properties of the ROCK plate allow clear differentiation between active RhoA (GTPγS) and inactive (GDP) RhoA, with active RhoA having a 7-fold higher signal than inactive RhoA in this assay.

Referring to FIG. 3B, 50 µl of lysis buffer only, GDP or GTPγS labeled platelet extracts (0.5 mg/ml) (or 15 µg) were subjected to a Rac1 G-LISA assay as detailed in the materials and methods. Rac1 signal was detected by absorbance at 490 nm as described in the materials and methods. POSH-GBD maleimide plates were used. The results show that the binding properties of the POSH plate allow clear differentiation between active Rac1 (GTPγS) and inactive (GDP) Rac1, with active Rac1 having a 30-fold higher signal than inactive Rac1 in this assay.

In conclusion, the data in FIG. 3 establishes that the maleimide linked effector-GBDs retain the ability to distinguish active from inactive forms of a particular Rho GTPase. Furthermore, the active Rho GTPase signal could be detected using luminometry (FIG. 2A) or absorbance (FIG. 2B) based methods.

Example 3

Development of Antigen Presenting Buffer for the G-LISA

Initial attempts to detect active Rho GTPases in the RhoA:ROCK and Rac1:POSH G-LISA assays were not successful because a signal that was significantly above background in either assays (FIGS. 5A (untreated) and 5B (no APB)) could not be obtained. An initial strategy was to develop an ELISA based assay by following a protocol essentially analogous to the original pull-down assays described by Benard et al. for the Rac1:PAK pull-down assay (1999, J. Biol. Chem., 274:13198-13204) and Ren et al. and Kranenburg at al. for the RhoA:Rhotekin pull-down assay (1999, EMBO J., 18:578; and 1999, Mol. Biol. Cell, 10:1851-1857, respectively). The same procedure has been used for pull-down assays using ROCK, Citron, Dia and WASP (Kimura et al., 2000, J. Biol. Chem., 275:17233-17236, and Edlund et al., 2002, Mol. Biol. Cell, 13:902-914). Briefly, maleimide plates were coated with effector, active Rho GTPases in standard pull-down lysis buffer (50 mM Tris, pH 7.2, 1% Triton X-100, 0.5% sodium deoxycholate, 0.1% SDS, 500 mM NaCl, 10 mM $MgCl_2$ for RhoA assays; 50 mM Tris, pH 7.5, 10 mM $MgCl_2$, 200 mM NaCl, 1% Nonidet P-40, 5% glycerol for Rac1 and Cdc42) was introduced into the wells and incubated for 1 hour at 4° C. with shaking (400 rpm), the wells were then washed with standard pull-down wash buffer (50 mM Tris, pH 7.2, 1% Triton X-100, 150 mM NaCl, 10 mM $MgCl_2$ for RhoA; 25 mM Tris, pH 7.6, 1 mM DTT, 30 mM $MgCl_2$, 40 mM NaCl, 1% Nonidet P-40 for Rac1) and the reactions were developed using Rho GTPase specific primary antibodies (Cat.# ARH01, Cytoskeleton Inc. for RhoA, Cat# ARC01, Cytoskeleton Inc. for Rac1) and anti-mouse or anti-rabbit secondary antibodies respectively (Jackson Labs). After 3 washes in TBST, the reactions were developed using absorbance or luminescence detection. Absorbance was measured at $OD_{490}$ in a spectrophotometer (SpectraMax 250, Molecular Devices) after addition of 50 µl of OPD substrate (Sigma Catalog # P9187) for 15 minutes at 37° C. followed by addition of 50 µl of stop buffer (1M sulfuric acid). Luminescence was measured in a SpectroFluor Plus (Techan Inc.) after addition of 50 µl of lumigen reagent (Lumigen Inc., Catalog # PSA-100), typical settings were 100-150 gain and 10-100 ms integration. It should be noted that a standard checkerboard titration for ELISA based antibody concentration optimizations (Crowther, 2001, Meth. Mol. Biol., 149:83-113) was used. In addition, the antibodies used in these G-LISA assays have been shown to work very well in pull-down assays (they are components in Cytoskeleton Pull-Down Assay Kits, Cat# BK034 (Cdc42), BK035 (Rac1) and BK036 (RhoA)). Extensive tests of various blockers, reaction buffers, temperature of incubations, and antibody dilution buffers were also performed. The failure of the G-LISA to work under the standard conditions that have been applied to all pull-down assays suggested that there are one or more fundamental differences between the two assay formats.

Without being bound to any particular theory, one possible reason for failure of the G-LISA approach under standard pull-down conditions could be the fact that very low concentrations of effector bound to the plate were used—this is discussed in the next Example (Use of Binding Buffer in the G-LISA). It was also possible that antibodies capable of recognizing a signal in the western blot analysis of pull-down assays are not able to recognize the Rho GTPase in the G-LISA format—this possibility is discussed in Example 5 (Development of Optimized Antibodies for the G-LISA Assays). A further possibility, and the subject of the Example disclosed herein, was that the G-LISA effector:GTPase complex is lost during the incubation processes of the G-LISA assay.

The pull-down assay captures active Rho GTPases with effector-bound beads or discs and, after a wash step, the active Rho GTPase must be eluted from beads in order to be analysed by western blot detection (Benard et al., 1999, J. Biol. Chem., 274:13198-13204; Ren et al., 1999, EMBO J., 18:578; Kranenburg at al., 1999, Mol. Biol. Cell, 10:1851-1857; and Sun et al., 2006, Microcirculation, 13:237-247). A major difference between the Rho GTPase pull-down assays and the G-LISA assay, is the fact that the G-LISA assay is dependent upon the Rho GTPase being associated with the solid support matrix to which the effector is bound, such as, but not limited to a microtiter plate, throughout the assay. One aim of the experiments in the Example disclosed herein was to a) determine if there was any dissociation of GTPase from the solid matrix throughout the G-LISA, and b) determine ways to prevent loss of the Rho GTPase, if necessary, and, thus, obtain quantitative results for Rho GTPase activation.

Materials and Methods

Western Analysis of G-LISA Rho GTPase Effector Binding

Constitutively active RhoA GTPase protein (R63) and GTP loaded platelet extract capable of GTP hydrolysis was used to examine dissociation of effector:GTPase over time. The G-LISA assay was perfomed as follows: R63 protein (10 ng per assay) or GTP loaded platele extract (25 µg) were incubated with ROCK-GBD effector bound to maleimide plates, incubations were at 4° C. for 30 minutes with shaking at 400 rpm. The reaction was washed twice with 200 µl TBST to remove unbound Rho GTPase. At this point, samples from several wells were eluted with SDS buffer (5% SDS, 63 mM Tris pH 6.8, 5% mercaptoethanol, 10% glycerol) and pooled for later western analysis. The remaining reactions were incubated for 45 minutes in primary anti-RhoA antibody (clone 384) at room temperature with shaking 400 rpm. After 3 washes in TBST, samples from several wells were eluted as above in SDS buffer and saved for later analysis. The remaining reactions were incubated for 45 minutes in secondary anti-chicken antibody at room temperature with shaking 400 rpm. After 3 washes in TBST, samples from several wells were eluted as above in SDS buffer and saved for later analysis. Western analysis was performed using the anti-RhoA mouse monoclonal antibody.

RhoA Antigen Presenting Buffer Tests

Platelet cell lysates loaded with GTPγS or GDP nucleotides (10 μg total cell lysate per assay) were diluted with an equal volume of Binding Buffer (20% PEG 8000, Sigma, St. Louis, Mo.) prior to adding to ROCK effector bound plates. The reactions were incubated for 30 minutes at 4° C. on a microtiter titer plate shaker after which wells were washed once with 200 μl of PBST (PBS pH 7.2, 0.05% Tween-20) and immediately treated with one of the following chemical/physical treatments: microwaving for 3 minutes in the presence of 200 μl PBS; microwaving for 3 minutes dry; microwaving for 3 minutes in the presence of 200 μl of 8M urea; 200 μl methanol for 2 minutes; 200 μl ethanol for 2 minutes; 200 μl of 0.5% SDS for 2 minutes, 200 μl of 10% trichloroacetic acid (TCA) for 2 minutes at room temperature. Wells were then washed three times with 200 μl each of PBST and RhoA primary antibody (B384) was added at 1 μg/ml and incubated at room temperature for 45 minutes. Wells were washed three times with 200 μl each of PBST and incubated with anti-mouse secondary antibody (Jackson Labs) for 45 minutes at room temperature. After three washes each of 200 μl PBST, the activated Rho proteins were detected using luminescence detection. Luminescence was measured in a SpectroFluor Plus (Techan Inc.) after addition of 50 μl of lumigen reagent (Lumigen Inc., Catalog # PSA-100).

Test of TCA Benefit in Rac1 G-LISA

Constitutively active recombinant Rac1 (5 ng) in cell lysis buffer, or cell lysis buffer alone, were added directly to a POSH effector-bound G-LISA plate. The reactions were incubated for 30 minutes at 4° C. on a microtiter titer plate shaker after which wells were washed once with 200 μl of PBST (PBS pH 7.2, 0.05% Tween-20) and immediately treated with 200 μl of Antigen Presenting Buffer (1% trichloroacetic acid (TCA)) for 2-5 minutes at room temperature. Wells were then washed three times with 200 μl each of PBST and primary Rac1 antibody was added at 1 μg/ml and incubated at room temperature for 45 minutes. Wells were washed three times with 200 μl each of PBST and incubated with anti-mouse secondary antibody for 45 minutes at room temperature. After three washes each of 200 μl PBST, the activated Rho proteins were detected using absorbance detection. Absorbance was measured at $OD_{490}$ in a spectrophotometer (SpectraMax 250, Molecular Devices) after addition of 50 μl of OPD substrate (Sigma Catalog # P9187) for 15 minutes at 37° C. followed by addition of 50 μl of stop buffer (1M sulfuric acid).

Results

In order to examine dissociation of GTPase from effector in a system permitting GTP hydrolysis 25 μl of GTP labeled platelet extract (2 mg/ml) was subjected to a standard RhoA G-LISA in a ROCK coated maleimide plate. The bound activated RhoA was eluted with SDS buffer at different stages of G-LISA assay. The bound RhoA was eluted with SDS buffer at different stages of G-LISA assay (after a 30 minute incubation in a ROCK plate (Lane 1), after a 45 minute primary antibody incubation (Lane 2), after a 90 minute secondary antibody incubation (Lane 3)). The eluted Rho was then subjected to SDS-PAGE and Western blot with anti-RhoA antibody. To examine dissociation of GTPase from effector in a system that did not permit GTP hydrolysis 10 ng of RhoA (63L) was subjected to a standard RhoA G-LISA. The bound RhoA (63L) was eluted with SDS buffer at different stages of G-LISA assay (after a 30 minute incubation in a ROCK plate (Lane 4), after a 45 minute primary antibody incubation (Lane 5), after a 90 minute secondary antibody incubation (Lane 6)). The eluted Rho was then subjected to SDS-PAGE and Western blot with anti-RhoA antibody. The top and bottom figures are identical except for the length of exposure of the developing film. The shorter exposure allows a more quantitative look at the 63L signal while the longer exposure is better for viewing the loss of sugnal in the endogenous RhoA samples. The 63L recombinant constitutively active RhoA protein runs higher than endogenous RhoA due to the presence of a His tag on 63L.

The results in FIG. 4 show the active RhoA signal from a hydrolysis deficient mutant RhoA protein (L63) is reduced by 10% after the primary antibody incubation (FIG. 4, compare Lanes 4 and 5) and by 40% at the end of the secondary antibody incubation (FIG. 4, compare Lanes 4 and 6). The reduction in signal in the GTP loaded RhoA samples is 60% after the primary antibody incubation (FIG. 4, compare Lanes 1 and 2) and >90% after the secondary antibody incubation (FIG. 4, compare Lanes 1 and 3). The enhanced loss of signal in the GTP samples is likely due to hydrolysis of the GTPase during the course of the assay (Benard et al., 2002, Meth. Enz., 345:349-359). In this regard, the signal loss over time is also significantly higher in platelet extracts loaded with GTP than in platelets loaded with non-hydrolysable GTPgS samples (data not shown). Taken together the data strongly supports that RhoA signal loss in this assay is due to both simple dissociation and dissociation due to deactivation of the RhoA by GTP hydrolysis. In this regard, an attempt to slow down dissociation by carrying out the antibody incubations at 4° C. and keeping all buffers at 4° C. did not improve the signal to noise of the assays (data not shown).

It was concluded that it was necessary to develop assay conditions that prevented, or minimized, loss of GTPase from the reaction.

Several physical (heat denaturation) and/or chemical treatments for antigen complex stability were evaluated. Crosslinkers such as gluteraldehyde, protein precipitation reagents such as methanol and ethanol and trichloroacetic acid (TCA), chaotrophs such as urea, and denaturants such as sodium dodecyl sulfate (SDS) were chosed for the initial studies.

Referring to FIG. 5A, lysis buffer only (untreated), 15 μg of GDP- or GTPγS-labeled platelet extracts were subjected to a RhoA G-LISA assay. After extract incubation, the plate was treated with MW+PBS, MW/Dry, MW/8 M urea, methanol, ethanol, 0.5% SDS, 10% TCA or no treatment followed by antibody incubation and luminescence detection. MW=5 minute microwave treatment. White bars show GDP signal, grey bars show GTPγS signal. Referring to FIG. 5B, lysis buffer only (Blank) or 5 ng of Rac1 (61L) were subjected to Rac1 G-LISA assay as described in the materials and methods except that the assays were performed either with or without Antigen Presenting Buffer treatment (1% TCA or No APB respectively) Rac1 signal was detected by absorbance at 490 nm as described in the materials and methods.

It was discovered that several chemical and/or physical treatments such as the combination of microwaving (heat denaturation) in the presence of 8M urea dramatically improved the detection of active RhoA proteins in G-LISA assays (MW+UREA 8M, FIG. 5A). Microwaving in PBS gave a greatly increased signal for GTPγS binding. The high cv values, however, were a problem with this method (MW+ PBS, FIG. 5A). Microwaving in the absence of buffer gave poor differentiation between GTPγS and GDP samples (MW+DRY, FIG. 5A). Of the other treatments tested, glutaraldehyde (data not shown) and ethanol gave a consistently positive signal for active RhoA above background (FIG. 5A). Treatment with methanol or 0.5% SDS did not give any significant signal for active RhoA above background. The treatment of the plate with 200 μl of 10% TCA for 2 minutes at room temperature yielded signal for GTPγS RhoA that was approximately 8-fold higher than the GDP RhoA signal (10% TCA, FIG. 5A).

Upon further studies, it was found that out of several acid conditions tested, including acetic acid (data not shown), treatment of the effector:GTPase complex (after washing) with 1% TCA for 2 minutes at room temperature was a suitable choice of Antigen Presenting Buffer treatment for RhoA:ROCK and Rac1:POSH G-LISA assays. The benefit of the Antigen Presenting Buffer in the Rac1:POSH G-LISA is demonstrated in FIG. 5B. A 2 minute incubation in Antigen Presenting Buffer results in a signal from constitutively active Rac1 (5 ng) that is 7-fold above background. Omitting the Antigen Presenting Buffer results in an assay that cannot detect active Rac1 above background (Cell Lysis Buffer alone).

Discussion

Loss of signal during antibody incubations was found to occur in all G-LISA formats tested, however the degree of loss varied according to effector:GTPase pair analysed. For example, RhoA:ROCK, Rac1:POSH, Rac1:PAK1 (FIG. 9), lost>80% of signal in the absence of TCA while Rho-Dia1 only lost approximately 50% and Cdc42:WASP lost only 20% signal (data not shown). Rho effector-GBD peptides can significantly slow down the intrinsic rate of GTP hydrolysis for Rho proteins but do not prevent this process (Leonard et al., 1997, Biochem., 36:1173-1180; and Bernard et al., 1999, J. Biol. Chem., 274:13198-13204). Hence, the degree to which GTPase dissociation occurs will depend upon, amongst other things, the affinity of a particular effector for its active GTPase target and the ability of the effector to prevent GTP hydrolysis of its GTPase target.

A further factor predicted to enhance loss of Rho GTPase signal is a high intrinsic rate of hydrolysis of the GTPase. In this regard, Ras GTPases have a much slower intrinsic rate of GTP hydrolysis than Rho GTPases (Neal et al., 1989, J. Biol. Chem., 261:10963; and Self et al., 1995, Meth. Enz., 256:67-76). Hence, loss of signal due to hydrolysis is unlikely to be as much of an issue with a Ras based G-LISA assay. For example, published affinities for Rac1:PAK and Ras:Raf1 are both approximately 20 nM. Therefore, it would be predicted, despite the similar effector affinities, that the Ras assay will be far less dependent upon Antigen Presenting Buffer than the Rac1:PAK assay that clearly benefit from this step (FIG. 9).

Several chemical and physical treatments were tested for their ability to attenuate loss of Rho GTPase. While many of the treatments, for example 8M urea combined with heat treatment gave enhanced signal, it was discovered that 1% (60 mM) TCA treatment of the complex for 2 minutes at room temperature appeared to be a suitable method of complex stabilization.

TCA treatment was tested with a wide range of effector: GTPase combinations including, RhoA:rhotekin, RhoA: Dia1, RhoA:ROCK, Rac1:PAK and Rac1:POSH. The TCA treatment enhanced signals in all cases tested. Some G-LISAs such as RhoA:ROCK and Rac1:POSH (FIGS. 5A and 5B) showed a great benefit for TCA Antigen Presenting Buffer while others, such as RhoA:Dia1, gave enhanced RhoA signal with TCA treatment (data not shown). The benefit of Antigen Presenting Buffer was also found to apply to G-LISA assays employing the PAK-GST and rhotekin-GST non-covalent plates (see FIG. 9 and data not shown). This suggests that Rho GTPase loss is not likely to be influenced by a particular plate chemistry and, thus, appears to be a general feature of the G-LISA assay format.

The discoveries herein predict that attenuation of Rho GTPase loss from the G-LISA solid support by treatment with Antigen Presenting Buffer or the like is an important parameter in the development of any particular Rho G-LISA assay. In this regard, that dissociation is time dependent can also be utilized in the general developmental scheme of any effector: Rho G-LISA assay. For example, that dissociation was markedly greater after 90 minutes incubation (40% for constitutively active RhoA and 90% for wild type RhoA) than after 45 minutes (10% and 60% respectively) might suggest a scheme where one uses an HRP conjugated primary antibody or the like to minimize assay time. This scheme could possibly aleviate or make redundant the presence of Antigen Presenting Buffer. Thus, one skilled in the art could effectively utilize the information herein disclosed towards the design of any Rho G-LISA assay.

Example 4

Use of Binding Buffer in the G-LISA

As mentioned in the previous Example, the G-LISA assay did not work when simply adapting the pull-down assay to an ELISA type system. The low levels of both effector (<1 μg) and protein lysates (6-15 μg total lysates) were reasoned herein to possibly be below the critical concentration required for effector:GTPase binding. Accordingly, inclusion of a compound or reagent capable of enhancing protein:protein interactions may push the binding equilibrium in favor of effector:GTPase complex formation. Therefore, the effect of protein:protein interaction enhancers, such as polyethyethylene glycol and the like, were examined in the G-LISA reaction (Kozer et al., 2004, J. Mol. Biol., 336:763-740; and Ingham, 1990, Meth. Enz., 182:301-306).

Materials and Methods

Preparation of Activated Cell Lysates

Swiss 3T3 cells were grown in DMEM media supplemented with 10% fetal calf serum until 50% confluent. They were then serum starved for 24 hours prior to treatment with 100 μg/ml calpeptin for 30 minutes to activate RhoA, as described in detail in Example 8. HeLa cells were treated with EGF for 2 minutes to activate Rac 1, as described in detail in Example 8.

Results

In the example set forth, the effect of adding increasing amounts of PEG8000 to RhoA and Rac1 G-LISAs was assessed. In the case of RhoA, increasing amounts of PEG (from zero to 10% final concentration) was found to enhance the active RhoA signal obtained from calpeptin treated Swiss 3T3 cells by over an order of magnitude (FIG. 6B, 0% PEG compared to 10% PEG).

Referring to FIG. 6A, 25 μl of serum starved or Calpeptin treated (RhoA activated) Swiss 3T3 cell lysates (0.5 mg/ml)

were incubated in a room temperature water bath for 0, 10 or 30 min either in the presence (+) or absence (−) of Binding Buffer (10% PEG 8000, final concentration). Samples were then subject to a standard RhoA G-LISA assay in ROCK maleimide plates, quantitated by reading absorbance at 490 nm. SS is serum starved samples (white bars), RhoA induced samples labeled Calpeptin (grey bars). Referring to FIG. 6B, 25 µl of serum starved or Calpeptin treated (RhoA activated) Swiss 3T3 cell lysates (0.5 mg/ml) were diluted with an equal volume of 0%, 5%, 10%, 15% or 20% PEG 8000 and immediately subjected to a standard RhoA G-LISA assay in ROCK maleimide plates, samples were quantitated by reading absorbance at 490 nm. SS is serum starved samples (white bars), RhoA induced samples labeled Calpeptin (grey bars). Referring to FIG. 6C, 25 µl of serum starved or EGF treated (Rac1 activated) Hela cell lysates (1 mg/ml) were diluted with an equal volume of 0%, 5%, 10%, 15% or 20% PEG 8000 and immediately subjected to a standard Rac1 G-LISA assay in POSH maleimide plates. Samples were quantitated by reading absorbance at 490 nm. SS is serum starved samples (white bars), Rac1 induced samples labeled EGF (grey bars). In all cases, AU=Absorbance Units and all readings had buffer only background subtracted.

Rho proteins are very unstable in lysates due to the presence of a large number of GTPase Activating Proteins (GAPs) that act to rapidly hydrolyse Rho proteins (Moon et al., 2003, Trends Cell Biol., 13:13-22). It might therefore be considered likely by one skilled in the art that addition of a protein: protein interaction enhancer to a lysate containing active Rho proteins would be more likely to enhance rapid GTP hydrolysis, by enhancing Rho:GAP interactions, than to enhance Rho:effector interactions (Ren et al., 1999, EMBO J., 18:578). Surprisingly, it was found herein that addition of PEG and the like had an insignificant effect upon RhoA signal after 10 minutes at room temperature (FIG. 6A, +/−10 minutes) and resulted in only a minor loss of RhoA signal after 30 minutes at room temperature (FIG. 6A, +/−30 minutes). The gradual reduction in active RhoA signal over time in FIG. 6A is the result of RhoA inactivation due to GTP hydrolysis (Benard et al., 1999, J. Biol. Chem., 274:13198-13204). Thus, in the RhoA G-LISA, the inclusion of a PEG "Binding Buffer" step was beneficial in producing a highly robust signal from activated RhoA. The benefit of the RhoA G-LISA assay (using a His-ROCK1 plate) for PEG Binding Buffer has been confirmed in several different cell lines, for example 3T3 cells, HeLa cells, Jurkat cells and MDCK cells (data not shown).

In the case of Rac1 increasing amounts of PEG in the G-LISA assay (from zero to 10% final concentration) was found to correlate with a decrease in active Rac1 signal (FIG. 6C). Thus, in this case, PEG appears to be having a negative effect upon the G-LISA signal. It is hypothesised that this is due to enhanced hydrolysis of GTP on active Rac1 due to increased concentrations of Rac GAP proteins. In this regard, it has been reported that Rac1 has a higher intrinsic rate of GTP hydrolysis and a higher affinity towards GAPs than RhoA (Liget et al., 2004, J. Biol. Chem., 279:5055).

Discussion

The degree to which the inclusion of PEG Binding Buffer or the like will improve or inhibit any given G-LISA assay is likely to depend upon a complex mixture of parameters. These include, the effect of Binding Buffer on GAP activated GTP hydrolysis of a particular Rho protein, the binding constant of a particular effector-GBD for a particular active Rho protein and the amount of effector bound per well.

Example 5

Development of Optimized Antibodies for the G-LISA Assays

As mentioned in the previous example, initial attempts to achieve a differential signal between activated and non-activated Rho GTPase proteins in a G-LISA assay did not yield positive results. It was previously determined by western blot analysis of proteins eluted from pooled wells of a G-LISA plate, that the effector-GBD plates could capture constitutively active Rho GTPases (see FIG. 4). This promted the development of a screening strategy for the production of G-LISA optimized monoclonal antibodies. The example below describes the development of a RhoA specific antibody (clone 384) and a Rho A,B,C specific antibody (clone 419).

Materials and Methods

RhoA and RhoA,B,C specific antibodies were developed as follows: a Rho peptide (CDEHTRRELAKMKQEPVKPEEGRD; SEQ ID NO:110) was synthesized (Bachem Inc., King of Prussia, Pa.) and congugated to KLH using an Imject Kit (Pierce, Rockford, Ill. 61105; Catalog #0077610) according to the manufacturer's instructions. Efficiency of KLH-peptide conjugation was determined using Ellman's reagent to measure free cysteins (Sigma, St. Louis, Mo., Catalog # D8130) according to the manufacturer's instructions. Six week old mice (BALB/c) were immunized with 50 µg of KHL-conjugated peptide. Subsequent injections were performed approximately 10-15 days apart. After testing bleeds with a standard ELISA assay and western blot assay against recombinant RhoA (Catalog # RH01, Cytoskeleton Inc., Denver, Colo.), a candidate mouse was selected and given a final boost intravenously in saline solution. The mouse was sacrificed 3 days later. Spleen cells were fused to myeloma cells and hybridomas were selected by ELISA assays against RhoA and RhoC peptides, western blots against RhoA, RhoB, RhoC peptides and platelet extracts and in G-LISA assays. Platelet lysates loaded with GDP or GTPγS were used in the G-LISA screen (method descibed in Example 2). An increase in GTPγS loaded Rho signal over GDP loaded Rho indicated that the antibody may be useful in a G-LISA assay. Clones and purified antibodies were produced by standard procedures outlined in Harlow and Lane, 1988, Antibodies: A Laboratory Manual, Cold Spring Harbor Laboratory, New York.

Secondary antibody, goat anti-mouse was obtained from Jackson Immunoresearch Labs., West Grove, Pa. (Catalog #115-035-068).

Results

Hybridomas were screened in three separate assays, a standard ELISA assay, a standard western blot assay and a Rho G-LISA assay. Results are outlined below and in FIGS. 7A and 7B. Referring to FIG. 7A, standardized dilutions (1:500) of each antibody (clones 248, 362, 384, 419, 465, 505, 591, 603, 621, 660, 733, 942, 957, 977, 979, 1019, 1157, 1164, 1281, and 1324) were analysed by western blotting. Samples of recombinant Rho A, B and C (50 ng each) and 20 µg of platelet extracts were used as samples for analysis of antibody specificity and relative sensitivity (Western Ranking). Goat anti-mouse secondary antibody was used at 1:10,000 dilution. Blots were developed using chemilluminescence detection (Pierce west Dura). The strongest signals from platelet extracts was ranked #1, the lowest was ranked $10^{th}$, N=no signal under conditions used. Standard absorbance ELISA plates were coated with recombinant RhoA or RhoC and the antibodies above were tested in a standard absorbanced based assay against both antigens as described in Antibodies: A Laboratory Manual, Ed. Harlow and Lane, Cold Spring Harbor Press, 1988, Chapter 6:174-194. Antibodies with the strongest ELISA signal for RhoA were ranked highest. For G-LISA assays the antibodies were used in a standard RhoA G-LISA assay to detect signals from 12.5 µg of GDP- or GTPγS-loaded platelet extracts on ROCK maleimide plates. All antibodies were tested at the 1:500 dilution only, anti-mouse secondary antibody was used at 1 µg/ml final concentration. Those antibodies giving the highest ratio of GTPγS to GDP were ranked highest. Referring to FIG. 7B, the raw data generated as described in FIG. 7A is shown.

Clones 362 and 621 gave the strongest ELISA signal and clone 1157 gave the weakest. Antibody specificity could also be determined from this screen, for example clones 362 and 621 reacted strongly in both RhoA and RhoC ELISAs while clones 384 and 465 where RhoA specific.

The western blot screen used RhoA, RhoB and RhoC recombinant proteins and a platelet extract as potential targets for the antibody panel. Clones in FIG. 7A were ranked based upon the RhoA or RhoA,B,C signal generated from platelet extract. For example, clone 979 gave the strongest signal (densitometry) while clones 248, 362, 384, 465, 660, 733, 942, 977, 1019, 1281 and 1324 did not give a detectable signal in platelet extract. All clones (except clone 1157) gave signal with one or more recombinant Rho protein in the western blot analysis and this data was used to determine Rho specificity (FIG. 7A).

The G-LISA assay compared Rho signal from GDP-loaded (inactive Rho) and GTPγS-loaded (active Rho) samples. Clones were ranked according to the ratio of GTPγS to GDP signal where high ratios were considered to be more promising antibodies and so received a correspondingly high ranking. Thus, as detailed in FIG. 7A, clone 384 ranked first in the G-LISA assay with a GTPγS to GDP ratio of 50 while clone 1164 ranked twentieth with a ratio of 0.7.

Discussion

During the course of this development it was discovered that strong reactivity in either western blots or ELISA assays were not predictive of an antibody that would work well in a G-LISA assay (FIGS. 7A and 7B). For example, the two top performing antibodies in a G-LISA screen of 20 hybridomas (clones 384 and 419 respectively), ranked only 6$^{th}$ and 8$^{th}$ out of 20 in the ELISA assay. It is particularly noteworthy that antibodies predicted to work well for pull-down assays, i.e. those ranking highly in the western screen, did not generally work well in G-LISA assays. Indeed the top performing antibody from the G-LISA screen (clone 384) gave no detectable signal in the western blot screen using platelet extracts (FIG. 7A). Similarly, the antibody ranking highest in the ELISA assay (clones 362 and 621) performed very poorly in the G-LISA assay, ranking 16$^{th}$ and 18$^{th}$ out of 20 (FIG. 7A).

Example 6

Use of Non-Clarified Lysates in the G-LISA Assay

In order for the G-LISA assays to be user-friendly in high throughput applications, one would like to eliminate the requirement for a clarification step as this is highly cumbersome and not compatible with HTS formats. In the case of the pull-down assay, a clarification step is necessary because cellular debris cannot be eliminated in the wash steps (beads and debris will pellet together). Also in the pull-down assay, addition of SDS gel loading buffer for SDS-PAGE results in a highly viscous sample (due to DNA release) causing poor sample handling and poor western quantitation. A microtiter plate-based assay such as the G-LISA should not suffer from these drawbacks and one should be able to remove cellular debris with a simple wash step.

Referring to FIG. 8, 25 µl of serum starved or Calpeptin treated (RhoA activated) cell lysates (0.5 mg/ml) were either used directly (Non-Clar samples) or clarified for 5 minutes at 8,000 rpm, 4° C. (Clar. Samples). Lysates were immediately subjected to a standard RhoA G-LISA assay on ROCK maleimide plates. Samples were quantitated by reading luminescence as described in the materials and methods. ALU=Arbitrary Light Units. All readings had buffer only background subtracted.

Results

Calpeptin treated and serum starved cell lysates from Swiss 3T3 cells were prepared as outlined in the materials and methods (Example 8). Half of each lysate was clarified while the other half remained unclarified. All four samples were analysed simultaneously in a RhoA G-LISA assay (as outlined in Example 2). The results in FIG. 8 clearly demonstrate that non-clarified lysates generate activation signals comparable to clarfied lysates.

Discussion

The requirement for a clarification step is an integral component of the pull-down assay protocol (Ren. et al., 1999, EMBO J., 18:578-585; Benard. et al., 1999, J. Biol. Chem., 274:13198-13204; Leung et al., 2005, Proc. Natl. Acad. Sci. USA, 102:15207-15212; Kimura et al., 2000, J. Biol. Chem., 275:17233-17236; Kranenburg et al., 1999, Mol. Biol. Cell, 6:1851-1857; Vouret-Craviari et al., 2002, J. Cell Sci., 115: 2475-2484; and Subauste et al., 2000, J. Biol. Chem., 275: 9725-9733). Attempting to perform the pull-down assay without clarification results in the accumulation of non-specific cellular debris such as cell nuclei and associated proteins. As cellular debris and/or associated proteins cannot be separated from the effector:GTPase complex in this assay, there is a likelihood that samples will be contaminated with inactive GTPase. Further, attempting to omit the clarification step in a pull-down assay will result in the production of a highly viscous material upon addition of SDS sample loading buffer prior to SDS-PAGE and western analysis. The high viscocity is due to lysis of cell nuclei and release of nucleic acids. This results in uneven loading of the SDS-PAGE and consequently highly variable western quantitations. One could reduce viscocity by, for example, DNAse treatment or shear force, however increased manipulatons would further complicate the assay and increase the likelihood of variablity between samples. Yet further, the necessary inclusion of a clarification step in the pull-down assay results in an extra processing step at a point where the GTPase is highly sensitive to GTP hydrolysis (i.e. prior to effector addition). Rho GTPases such as Rac and Cdc42 GTPases that have a high intrinsic rate of hydrolysis are particularly susceptible to this potential problem (Ligeti et al., 2004, J. Biol. Chem., 279: 5055).

The ability to eliminate the clarification step in the G-LISA assay is therefore a non-trivial and important improvement over the pull-down assay. It reduces the sample processing time at a point where the GTPase is most sensitive to deactivation by GTP hydrolysis thereby increasing the assay reproducibility. In this regard, the pull-down assays are known by those in the art to have high cv values (40-60% in our hands, data not shown). Elimination of clarification also allows simple sample processing, compatible with high throughput assays such as would be used for diagnostic or drug discovery applications. The pull-down assay is not suited to these applications.

Example 7

Non-Covalent Attachment of Effector-GBDs to Glutathione Plates

As disclosed throughout these examples, one method of linking effector-GBD peptides to plates was through covalent attachment. Use of non-covalent attachment was also investigated. The example herein describes the use of glutathione S transferase tagged effector-GBD peptides linked to glutathione plates.

Materials and Methods

Non-Covalent Attachment of Effector-GBD to Glutathione Plates

PAK-GBD-GST peptide was diluted in coating buffer (PBS; 140 mM sodium chloride, 2.7 mM potassium chloride, 10 mM sodium phosphate (dibasic), 1.76 mM potassium phosphate (monobasic) pH 7.2) to a final concentration 0.02 mg/ml and 50 µl (1.0 µg) of protein was added per well to GST-Trap Glutathione coated plates (NoAb Biodiscoveries, Ontario, Canada). Plates were incubated at room temperature for 1 hour. Plates were washed twice in PBS and blocked by addition of 0.1% BSA in PBS pH 7.2 for 1 hour at room temperature.

Referring to FIG. 9, PAK-GBD-GST peptide was coated to glutathione plates (NoAb Biodiscoveries) as outlined above. GDP, GTPγS and constitutively active Rac1L61 were assayed using the standard Rac1 G-LISA assay described above (Example 2). Rac1 signal was detected by absorbance at 490 nm as described in materials and methods (Example 2). All readings had buffer only background subtracted Results Constitutively active Rac1, GTPγS- or GDP-loaded platelets were assayed in a G-LISA format (as detailed in Example 2) using PAK-GBD-GST linked plates. The results in FIG. 11 show that the non-covalent G-LISA format is able to identify constitutively active Rac1 above background (buffer only). The constitutively active Rac1 signal is 8-fold above background which is comparable to the signal generated from POSH effector bound covalently to maleimide plates (FIG. 2B, Example 2). The non-covalent PAK-GST assay can differentiate between active and inactive Rac1 protein (FIG. 9, GTPγS (active) and GDP inactive) loaded platelet extract). Although quite sensitive (8-fold activation) the assay is not as robust as the POSH linked maleimide plate G-LISA (30-fold, FIG. 3B, Example 2). The non-covalent PAK-GST assay did not give a signal above background in the absence of Antigen Presenting Buffer (FIG. 9, GTPγS with no Antigen Presenting Buffer).

Discussion

This example demonstrates the utility of a non-covalent plate format for development of G-LISA assays. It can be seen that by following the G-LISA development protocol, one obtains a good signal with the PAK-GST effector linked to glutathione plates (FIG. 9). Interestingly, for this assay, use of Antigen Presenting Buffer (APB) was beneficial for obtaining active Rac1 signal (FIG. 9, GTPγS plus ABP compared to minus APB).

The example describes the use of GST:glutathione linkage, the GTPγS signal generated from the PAK-GST glutathione plate was less than the GTPγS signal generated from a POSH maleimide plate (FIG. 3B) and a PAK maleimide plate (data not shown). For this reason, and the fact that covalent plates generally bind proteins more stably, the covalent maleimide plate format was pursued. However, it has been shown herein that GST:glutathione plates can work well in G-LISAs and it is anticipated that other non-covalent linkages such as polyhistidine:nickel, polyhistidine:cobalt, biotin:streptavidin, biotin:avidin and the like could also be used. Optimization of each plate format could follow the methodologies outlined throughout these examples.

Example 8

Detection Limits and Validation of the G-LISA Assays

All published estimates of the activation (or deactivation) levels of Rho GTPases in cells or tissue samples currently use data generated from standard Rho GTPase pull-down assays (Benard et al., 2002, Meth. Enz., 345:349-359; and Ren et al., 2000, Meth. Enz., 325:265-272). As this assay is clearly established and accepted as the gold standard of quantitation in the field, it was desired to validate the G-LISA by demonstrating that the G-LISA produced activation estimates comparable to those in the pull-down. Thus, it was desired to establish that, while the advantages of the G-LISA assays over the Rho GTPase pull-down assay include greatly enhance the speed, better reproducibility, increased sample throughput, simpler sample handling and smaller sample size, the actual quantitation of active Rho GTPases are comparable in both assays.

Materials and Methods

Production of Activated RhoA Cell Lysates by Induction with Calpeptin

HeLa cells were seeded in DMEM (Gibco. Cat. #10313-021) with 10% FBS. Cells were grown to 50-70% confluency and subsequently serum starved for 24 hours. The cells were then treated with calpeptin (100 ng/µl) for 30 minutes. The cells were harvested in lysis buffer and the lysate protein concentrations were equalized to 4 mg/ml with lysis buffer. The lysates were then diluted accordingly and subjected to a RhoA GLISA assay.

Production of Activated Rac1 and Cdc42 Cell Lysates by Induction with EGF

Hela cells were seeded in DMEM (Gibco. Cat. #10313-021) with 10% FBS. Cells were grown to 50-70% confluency and subsequently serum starved for 24 hours. The cells were then treated with 10 ng/ml epidermal growth factor (EGF) (Sigma. Cat. # E9644) for 2 minutes and harvested in lysis buffer. The lysate concentrations from both serum starved and EGF treated plates were equalized to 1 mg/ml with lysis buffer. The lysates were then subjected to RAC1 or Cdc42 G-LISA assays.

Pull-Down Assays

Assays were performed according to Ren et al. Modified GST rhotekin-GBD peptide was bound to glutathione beads and 20 µg of bead bound effector was added to 500 µl (250 µg) of clarified GTPγS- or GDP-loaded platelet extract (see Example 2 for lysate preparation). The mixture was incubated at 4° C. with rotation for 1 hour. The beads were then washed twice in wash buffer (50 mM Tris pH 7.5, 100 mM NaCl, 30 mM $MgCl_2$) and subjected to SDS-PAGE (4-20% gradient) and western blot procedures. The activated RhoA protein band was detected using primary antibody specifically recognizing RhoA protein and a goat anti-mouse secondary (Jackson Labs., Catalog #115-035-068). The assay was performed at least four times.

Referring to FIG. 10, 25 μl of serum starved or Calpeptin treated (RhoA activated) Hela cell lysate at concentration of 4, 2, 1, 0.5, 0.25, 0.12, 0.06 mg/ml were mixed with same volume of Binding Buffer and subjected to RhoA G-LISA assay followed by absorbance detection. 500 μg of the same lysates were also subjected to GST-Rhotekin-RBD pull-down assay and followed by western blot with anti-RhoA antibody. All readings had buffer only background subtracted.

Referring to FIG. 11, 25 μl of lysis buffer only (0), 0.01, 0.04, 0.1, 0.2, 0.4, 0.8, 1, 2 ng of RhoA (63L) were mixed with same volume of Binding Buffer and subjected to RhoA G-LISA assay and followed by absorbance detection. All readings had buffer only background subtracted.

Referring to FIG. 12, PAK coated GST plates were prepared as outlined in the materials and methods (Example 7). PAK coated glutathione beads were from Cytoskeleton Inc. (Cat. # PAK02). Various amounts of total cell lysates (actual amounts indicated below bar chart and western blot) from serum starved 3T3 cells (SS) or EGF treated 3T3 cells (to activate Rac1) were assayed by either a standard Rac1 G-LISA assay, as described in Example 2, or by a standard PAK-GST bead pull-down assay as described by Benard et al. (J. Biol. Chem., 1999, 274:13198-13204). G-LISA assays were quantitated by absorbance readings at 490 nm as previously described. Rac1 pull-downs were quantitated by densitometry of western blot chemilluminescent signals. Chemilluminescent detection reagent was Supersignal West Dura Extended Duration Substarte (Pierce). The anti-Rac1 antibody used for the pull-down is sold by Cytoskeleton Inc. in their commercial kit for Rac1 pull-down assays (BK035). The figure shows that the detection limit of the Rac1:PAK G-LISA is about 18- to 30-fold lower than that of the Rac1: PAK pull-down assay.

Referring to FIG. 13A, 50 μl of lysis buffer only, serum starved or EGF treated Hela cell lysate (0.5 mg/ml) were subjected to Rac1 G-LISA assay and followed by absorbance detection. Referring to FIG. 13B, 50 μl of serum starved or EGF treated Hela cell lysate (0.5 mg/ml) were subjected to Cdc42 G-LISA assay as described previously and quantitated by luminometry as previously described. A Cdc42 pull-down assay was carried out in parallel using 500 μg of the same lysates. The antibody used in this assay was identical to the one used in the G-LISA (Cat# ACD01, Cytoskeleton Inc.). Fold activation was quantitated by densiometry of film developed by chemilluminescence. Referring to FIG. 13C, Hela cells were transfected with either 5 μg of vector, p115RhoGEF or p190RhoGAP with lipofectamine. 16 hours after transfection, cells were lysed in cell lysis buffer. 25 μl of lysis buffer only, vector, p115RhoGEF, vector, p190RhoGAP transfected cells (1 mg/ml) were then subjected to RhoA G-LISA assay and quantitated by absorbance detection. A Rho pull-down assay was carried out in parallel using 500 μg of the same lysates, fold activation (for p115RhoGEF) or fold inhibition (for p190 GAP) were quantitated by densiometry of film developed by chemilluminescence.

Results

Limits of Detection of RhoA G-LISA

In this example, the limits of G-LISA detection of active RhoA by absorbance based measurements have been determined in two ways. First, the limit of detection of endogenous active (calpeptin induced) RhoA in cell lysates was determined. Second, the limit of detection of pure recombinant constitutively active RhoA was determined.

RhoA activation was induced in serum starved HeLa cells by treatment with calpeptin for 30 minutes (Schoenwaelder et al., 1999, J. Biol. Chem., 274:14359-14367). A standard pull-down assay using 500 μg of each lysate (1 mg/ml lysate concentration) was performed (inset in FIG. 10). Densitometric quantitation of the western blot results showed that RhoA (Calpeptin lane in FIG. 4 inset) had been activated by approximately 2-fold above the serum starved lysate (SS lane in FIG. 10 inset). As expected, this result is in good agreement with published data (Schoenwaelder et al., 2000, Current Biol., 10:1523-1526).

In a parallel G-LISA assay, the serum starved and calpeptin lysates were serially diluted to give protein concentrations of 4, 2, 1, 0.5, 0.25 and 0.125 mg/ml respectively and 25 μl of lysates were tested in a RhoA G-LISA. Lysate concentrations ranging from 0.25 mg/ml to 2 mg/ml (6.25 μg and 50 μg of total cell lysate respectively) gave approximately 2-fold activation of the calpeptin treated samples when compared to serum starved samples (FIG. 10, fold activation is given above calpeptin titration curve). Thus, for protein concentrations as low as 0.25 mg/ml or a total of 6.25 μg of cell lysate, the RhoA G-LISA results agreed very well with published data and with those of the pull-down assay shown in this example.

At protein concentrations between 0.5-2 mg/ml (typically the concentration of cell lysates) the cv ranged from 11-8%. Even at protein amounts as low as 6.25 μg total cell lysates, the cv value of 16% is acceptable. At lower protein concentrations (0.125 mg/ml or 3.1 μg total cell lysate) the cv values became too high to give meaningful results (>50%) in the RhoA assay, while at the highest protein concentration of 4 mg/ml (100 μg lysates) the cv values were 11%, however, the activation level was slightly below 2-fold (1.7-fold). The reduced fold activation at 4 mg/ml is most likely due to the fact that the active RhoA reading is approaching the saturation point of the absorbance assay (2.5 absorbance units). Interestingly, FIG. 12 shows that the Rac1:POSH assay can detect activated Rac1 from as little as 3 μg of total cell lysates with a cv value of 12%.

To determine the limit of G-LISA absorbance detection for recombinant constitutively active RhoA, protein amounts of 0.01, 0.04, 0.1, 0.2, 0.4, 0.8, 1.0, 2.0 and 4.0 ng were added to eight wells each of a ROCK-GBD maleimide plate. The samples were taken through a RhoA G-LISA assay and $OD_{490}$ readings were plotted against protein concentration. The results in FIG. 11 show that the linear range for the absorbance G-LISA is 0.1 ng (cv=6%) to 2 ng (cv=6%). The signal for recombinant constitutively active RhoA appears to begin to be saturated at protein amounts above 4 ng.

To further compare the G-LISA assay with the pull-down assay, the two assays in parallel using the same cell lysates were carried out. HeLa cells were stimulated with epidermal growth factor (EGF) as described in the materials and methods section. It is well documented that EGF transiently activates Rac1, with activation in the range of 2- to 5-fold above unstimulated cells (Kurokawa et al., 2004, Mol. Biol. Cell, 15:100). PAK-GST effector was used in both types of assay and both assays were carried out according to standard methods described in Examples 2 and 3 respectively. It can be seen from FIG. 12 that approximately 2-fold activation from the G-LISA using total lysates protein of 3 μg-12.5 μg was detected while the pull-down assay could detect signal (about 2.5-fold activation) in a 100 μg sample but not in 50 μg of total cell lysates. Thus, the limit of detection in the pull-down assay appears to be about 18-30 times higher than that obtainable with the G-LISA. It is also worth noting that the inventors in this application are highly skilled in the art of pull-down assays and have been responsible for developing a commercial product using this technology. Thus, the head to head comparison of the pull-down and the G-LISA show that both assays give comparable quantitations of Rho activation (about 2-fold), the results clearly establish the G-LISA as the superior assay. The advantages of the G-LISA are not restricted to superior sensitivity, although this is a major advancement, the G-LISA is also faster (<3 h compared to >10 h), requires much smaller sample size and is amenable to HTS applications.

Rac1 and Cdc42 G-LISA Assay Quantitations Compared to Pull-Down Quantitations of Active Rho GTPases To further examine the utility of the G-LISA for in vivo activation of Rho GTPases we compared pull-down data with the G-LISA assay in well-documented examples of Rac1 and Cdc42 activation.

EGF has been shown to activate Rac1 2- to 5-fold above serum starved levels in several cell lines (Kurokawa et al., 2004, Mol. Biol. Cell, 15:100). FIG. 13A shows the results of a comparison between a pull-down assay, using 500 μg of cell lysate and a Rac1 G-LISA using 25 μg of cell lysate. Densitometric quantitation of the pull-down assay western blot indicated a 4-fold activation of Rac 1. The Rac1 G-LISA performed in parallel agreed with this fold activation, giving a result of 4-fold above serum starved cell lysate (FIG. 13A).

It is well documented in the literature that EGF can activate Cdc42 by 2- to 3-fold above serum starved Cdc42 levels (Kurokawa et al., 2004, Mol. Biol. Cell, 15:100). FIG. 13B shows the results of a comparison between a pull-down assay, using 500 μg of cell lysate and a Cdc42 G-LISA using 25 μg of cell lysate. Densitometric quantitation of the pull-down assay western blot indicated a 2-fold activation of Cdc42. The Cdc42 G-LISA performed in parallel agreed with this fold activation, giving a result of 2.2-fold above serum starved cell lysate (FIG. 13B).

Transfection of foreign DNA into cell cultures and subsequent observation of the effects of protein expression on Rho GTPase activation is a common tool in cell and molecular biology (Klooster et al., 2006, J. Cell Biol., 1172:759-769; and Cheng et al., 2004, J. Biol. Chem., 279:12786-12793). The ability of the G-LISA to detect endogenous Rho GTPase activation upon transfection of HeLa cells with a Rho GTP Exchange Factor p115RhoGEF or Rho deactivation upon transfection of HeLa cells with a GTPase Activating Protein p150 RhoGAP (Wells et al., 2001, J. Biol. Chem., 276:28897-28905; and Arthur et al., 2001, Mol. Biol. Cell, 12:2711-2720) was therefore assessed.

The results in FIG. 13C demonstrate that the G-LISA can faithfully detect both an increase (p115RhoGEF) or a decrease (p150RhoGAP) in Rho GTPase activation in the transfection experiments. Furthermore the quantitation of active Rho GTPAse relative to vector only samples is consistent between the pull-down and the G-LISA assay.

Discussion

The results disclosed in Example 3 demonstrate that activation levels obtained from a given Rho GTPase are highly comparable between the pull-down assay and the G-LISA assay. Both assays were compared for quantitation of calpeptin activation of RhoA (FIG. 10), EGF activation of Rac1 (FIG. 13A) and EGF activation of Cdc42 (FIG. 13B) in serum starved HeLa cells. In all cases, the activation of Rho GTPases was similar between the two assays (typically 2- to 4-fold activation) and agreed with published data (Kazuo et al., 2004, Mol. Biol. Cell, 15:1003-1010). Rho activation and deactivation in cell lines transfected with p115RhoGEF (activator) or p190RhoGAP (deactivator) (FIG. 13C) was also compared. Results again showed pull-down and G-LISA assays to be comparable as far as fold activation measurements. Several different cell lines (e.g. Swiss 3T3, Jurkats, MDCK cells) have been analysed in these assays and in all cases the G-LISA quantitations agreed with published pull-down assay estimates (data not shown).

The results shown in FIGS. 10-13 clearly demonstrate that the utility of the G-LISA assays lies in quantitating RhoA activation from small amounts of sample. Thus, the linear range of this assay is approximately 6.25-50 μg of cell lysate (FIG. 10). This corresponds to an estimated 0.04-1.7 ng active RhoA (see example 2, Results section for rationale). The linear range of the pure recombinant constitutively active RhoA was found to be 0.1-2 ng (FIG. 11) which supports the estimates from the cell lysate samples. It should also be noted that the assays described in this example are for absorbance based G-LISAs. In this regard, luminometry based G-LISA assays are more sensitive than absorbance based versions which increase the sensitivity of the assay to below 0.04 ng (data not shown).

In contrast to the G-LISA, it is generally accepted that the quantitation of endogenous activated Rho GTPase's in a standard pull-down assay typically requires $1 \times 10^6$ to $1 \times 10^7$ cells or 300-800 μg of total cellular protein (Benard et al., 2002, Meth. Enz., 345:349-359; and Ren et al., 2000, Meth. Enz., 325:265-272). It is further recognized in the literature that this amount of lysate can be prohibitive for experiments where sample is limiting (Gottig et al., 2006, Eur. J. Immunol., 36:180-189). In this regard, a PAK-GST pull-down assay was directly compared with a PAK-GST G-LISA assay (FIG. 12). The results show that the G-LISA is about 18- to 30-fold more sensitive than the pull-down assay.

Instances requiring the use of small amounts of lysate include analysis of primary cell lines. A further instance would include the processing of high throughput samples cultured in small growth chambers, for example 12 well plates (typically $4 \times 10^5$ cells), 24 well plates (typically $2 \times 10^5$ cells) or 96 well plates (typically $3 \times 10^4$ cells). The G-LISA can detect active RhoA signal from as little as 6 μg of total cell lysate equivalent to $2 \times 10^4$ cells, thus making this assay amenable to the study of Rho GTPase activation even in instances where limiting amounts of sample are available such as in primary cell lines, clinical samples and high throughput applications.

Example 9

Stabilization of Effector-GBD Plates by Lyophilization

Stabilization of effector-GBD peptides confers an advantage to this assay format by creating plates that can be stored desiccated at 4° C. for extended periods of time. Referring to FIG. 14, lyophilzed ROCK-RBD coated microtiter plate were kept at 4° C. and >10% humidity for indicated time points. The activity of the plate was tested by a standard RhoA G-LISA with serum starved or Calpeptin treated cell lysates. In particular, plates were coated with effector-GBD as described in Example 2. After the block and wash step, 50 μl of lyophilization buffer (5% sucrose, 1% dextran in PBS pH 7.2) was added to each well. Plates were frozen to −70° C. and lyophilized using the following procedure:

Stabilize lyophilizer shelf temperature to −40° C. for 5 minutes;

Initiate vacuum to achieve <100 mtorr;

Vacuate for 4 hours at −26° C.;

Vacate for 4 hours at −10° C.;

Vacuate for 4 hours at 0° C.; and
Vacuate for 4 hours at 30° C.

Plates were then removed from the lyophilizer and packaged in containers containing a desiccant bag. Plates were stored at 4° C. and less than 10% humidity. Plates were analysed in a standard Rho:ROCK G-LISA using L63 constitutively active RhoA (5 ng per well) at the time intervals shown in FIG. 14. The % activity of each plate was plotted with reference to the plate assayed at time zero (100% activity). It was found that the plates remained very stable over at least 120 days under these conditions. Plates that were allowed to get damp lost activity after 1-2 hours (data not shown).

Discussion

Formulating a stable G-LISA plate has many advantages, including ease of storage and handling in HTS formats. As this assay is also presented in a kit format, the lyophilization of the plate contents allows shipping in the absence of dry ice and the like.

Example 10

Application of G-LISA Assay to Drug Discovery

It is well documented in the literature that Rho family proteins and their effector proteins are involved in a variety of human disease including cancer and renal disease (Fiordalisi et al., 2006, Canc. Res., 66:3153-3161; Fritz et al., 2006, Curr. Cancer Drug Targ., 1: 1-14; and Wakino et al., 2005, Drug Newa Perspect., 18:639-643). It would therefore be valuable to create a screen capable of identifying direct Rho GTPase modulators and compounds directly modulating the interaction of Rho GTPases with effectors. The application of the G-LISA technology has therefore been extended herein to include such screens.

Referring to FIG. 15, lysis buffer only (Blank) or 5 ng of Rac1 (61L) was subjected to a standard Rac1:POSH G-LISA. PAK-GST was included in the reaction at the lysates incubation stage of the assay. The PAK peptide should be a competitive inhibitor for POSH binding to Rac1 GTPase and thereby lower the G-LISA signal. ROCK-GST was included in some reactions a negative control "inhibitor". The molar values of the PAK- and ROCK-GST peptides are given in µM. As predicted the PAK peptide was a more efficient competitor of Rac1:POSH reactions ($IC_{50}$ of 0.1 µM compared to 8 µM).

Results

The example shown in FIG. 15 depicts G-LISA data from 5 ng of constitutively active Rac1 (61L) bound to a POSH-GBD maleimide plate. The G-LISA was performed as described previously except that the reaction was carried out in the presence or absence of PAK-GBD-GST which should act as a competitive inhibitor of Rac1:POSH binding. PAK-GBD-GST was added to the reaction at 0 µM to 10 µM. FIG. 15 shows that the $IC_{50}$ for PAK is approximately 0.1 µM. The RhoA effector ROCK-GBD was also tested in the assay. The $IC_{50}$ for this peptide was approximately 80 times higher than for PAK (8 µM). This example serves to demonstrate the utility of the G-LISA assays in drug discovery.

Discussion

This example describes the application of the G-LISA to drug discovery. The assay format uses purified constitutively active Rho GTPases and purified effector-GBD peptides, it is therefore a well defined system that will generate results of immediate mechanistic relevance. It should be noted that the G-LISA assays are also amenable to the identification of compounds that modulate the activity of endogenous Rho GTPases. This assay (or kit) format would be carried out as follows: cells would be grown in a suitable HTS compatible vessel such as a 96 well plate, cells would be treated with a library of compounds (serum starving of cells prior to treatment is optional), cells would be lysed in 25 µl of lysis buffer (protein quantitation at this point is optional) and transferred to a G-LISA plate either in the presence or absence of 20% PEG 8000. Plates are incubated at 4° C. for 30 minutes then washed at room temperature and treated with Antigen Presenting Buffer for 2-5 minutes. Plates are washed and Rho GTPase in the wells is quantitated. Quantitation can be with a Rho-specific antibody or by some other means. HTS methodology can also employ robotics systems commonly used with microtiter plates or microarrays.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method for detecting an activated Rho GTPase protein comprising:
    contacting a solid support with a sample comprising an activated Rho GTPase protein, wherein the solid support is linked to an activated Rho GTPase binding peptide, and wherein the activated Rho GTPase in the sample binds the activated Rho GTPase binding peptide;
    attenuating Rho GTPase protein loss from the solid support by adding an Antigen Presenting Buffer, wherein the Antigen Presenting Buffer comprises tricholoracetic acid;
    detecting the activated Rho GTPase protein in the sample, wherein the activated Rho GTPase protein remains associated with the solid support during the detection; and
    wherein prior to detecting the activated Rho GTPase protein in the sample, a Binding Buffer is added when the Rho GTPase binding peptide is ROCK1 or ROCK2.

2. The method of claim 1 wherein the sample comprises a cell lysate comprising endogenous activated Rho GTPase protein.

3. The method of claim 2 wherein the sample comprises less than 50 µg of total protein.

4. The method of claim 2 wherein the cell lysate is prepared from less than $10^5$ cells.

5. The method of claim 2 wherein the cell lysate has not been clarified.

6. The method of claim 1 wherein the final concentration of trichloroacetic acid is about 0.5% to about 15% v/v.

7. The method of claim 1 wherein the activated Rho GTPase protein is detected using an antibody specific for one or more activated Rho GTPase proteins.

8. The method of claim 1 wherein the activated Rho GTPase protein is a constitutively active mutant.

9. The method of claim 1 wherein the sample comprises exogenous GTP, GDP or GTPγS.

10. The method of claim 1 wherein the activated Rho GTPase protein is RhoA, RhoB, RhoC, RhoD, Rnd1, Rnd2, Rnd3, Rif, RhoG, Rac1, Rac1b, Rac2, Rac3, Cdc42, TC10, TCL, Wrch-1, Wrch-2, RhoBTB1, or RhoBTB2.

11. The method of claim 1 wherein the activated Rho GTPase binding peptide is a Rhotekin, ROCK1, ROCK2, PAK1, POSH, WASP, or Dia1, or a mutant or multimer of the same.

12. The method of claim 1 wherein the activated Rho GTPase binding peptide is linked to the solid support by a disulfide linkage or a GST linkage.

13. The method of claim 1 wherein the activated Rho GTPase binding peptide is lyophilized.

14. The method of claim 1 wherein the solid support is a microtiter plate or microarray.

15. The method of claim 1 further comprising quantitating the amount of activated Rho GTPase protein bound to the activated Rho GTPase binding peptide.

16. The method of claim 1 wherein detection of the activated Rho GTPase protein is carried out by detecting an interaction between the activated Rho GTPase protein and the activated Rho GTPase binding peptide using absorbance, luminescence, or fluorescence.

17. The method of claim 1 further comprising contacting the sample with a test agent and determining whether the test agent modulates an interaction between the activated Rho GTPase protein and the activated Rho GTPase binding peptide.

18. The method of claim 1 wherein the activated Rho GTPase binding peptide is a Rhotekin, ROCK1, ROCK2, PAK1, POSH, WASP, or Dia1, or a mutant or multimer of the same.

19. The method of claim 1 wherein the Binding Buffer comprises ficoll, dextran, or polyethylene glycol, or any combination thereof.

20. The method of claim 19 wherein the polyethylene glycol is PEG 4000 or PEG 8000 at a final concentration of about 2% to about 40% v/v.

* * * * *

SEQUENCE LISTING

```
<160> NUMBER OF SEQ ID NOS: 114

<210> SEQ ID NO 1
<211> LENGTH: 193
<212> TYPE: PRT
<213> ORGANISM: Homo sapiens

<400> SEQUENCE: 1

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
```

```
            50                  55                  60
Asp Tyr Asp Arg Leu Arg Pro Leu Ser Tyr Pro Asp Thr Asp Val Ile
 65                  70                  75                  80

Leu Met Cys Phe Ser Ile Asp Ser Pro Asp Ser Leu Glu Asn Ile Pro
                 85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
            115                 120                 125

Arg Glu Leu Ala Lys Met Lys Gln Glu Pro Val Lys Pro Glu Glu Gly
130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Ser Gly Cys Leu Val
                180                 185                 190

Leu

<210> SEQ ID NO 2
<211> LENGTH: 196
<212> TYPE: PRT
<213> ORGANISM: Homo sapiens

<400> SEQUENCE: 2

Met Ala Ala Ile Arg Lys Lys Leu Val Val Gly Asp Gly Ala Cys
 1               5                  10                  15

Gly Lys Thr Cys Leu Leu Ile Val Phe Ser Lys Asp Glu Phe Pro Glu
            20                  25                  30

Val Tyr Val Pro Thr Val Phe Glu Asn Tyr Val Ala Asp Ile Glu Val
                35                  40                  45

Asp Gly Lys Gln Val Glu Leu Ala Leu Trp Asp Thr Ala Gly Gln Glu
 50                  55                  60

Asp Tyr Asp Arg Leu Arg Pro Leu Ser Tyr Pro Asp Thr Asp Val Ile
 65                  70                  75                  80

Leu Met Cys Phe Ser Val Asp Ser Pro Asp Ser Leu Glu Asn Ile Pro
                 85                  90                  95

Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
            115                 120                 125

Thr Glu Leu Ala Arg Met Lys Gln Glu Pro Val Arg Thr Asp Asp Gly
            130                 135                 140

Arg Ala Met Ala Val Arg Ile Gln Ala Tyr Asp Tyr Leu Glu Cys Ser
145                 150                 155                 160

Ala Lys Thr Lys Glu Gly Val Arg Glu Val Phe Glu Thr Ala Thr Arg
                165                 170                 175

Ala Ala Leu Gln Lys Arg Tyr Gly Ser Gln Asn Gly Cys Ile Asn Cys
                180                 185                 190

Cys Lys Val Leu
        195

<210> SEQ ID NO 3
<211> LENGTH: 193
<212> TYPE: PRT
```

<213> ORGANISM: Homo sapiens

<400> SEQUENCE: 3

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Ile Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Gln Asp Glu His Thr Arg
        115                 120                 125

Arg Glu Leu Ala Lys Met Lys Gln Glu Pro Val Arg Ser Glu Glu Gly
    130                 135                 140

Arg Asp Met Ala Asn Arg Ile Ser Ala Phe Gly Tyr Leu Glu Cys Ser
145                 150                 155                 160

Ala Lys Thr Lys Glu Gly Val Arg Glu Val Phe Glu Met Ala Thr Arg
                165                 170                 175

Ala Gly Leu Gln Val Arg Lys Asn Lys Arg Arg Arg Gly Cys Pro Ile
            180                 185                 190

Leu

<210> SEQ ID NO 4
<211> LENGTH: 210
<212> TYPE: PRT
<213> ORGANISM: Homo sapiens

<400> SEQUENCE: 4

Met Thr Ala Ala Gln Ala Ala Gly Glu Glu Ala Pro Pro Gly Val Arg
1               5                   10                  15

Ser Val Lys Val Val Leu Val Gly Asp Gly Gly Cys Gly Lys Thr Ser
            20                  25                  30

Leu Leu Met Val Phe Ala Asp Gly Ala Phe Pro Glu Ser Tyr Thr Pro
        35                  40                  45

Thr Val Phe Glu Arg Tyr Met Val Asn Leu Gln Val Lys Gly Lys Pro
    50                  55                  60

Val His Leu His Ile Trp Asp Thr Ala Gly Gln Asp Asp Tyr Asp Arg
65                  70                  75                  80

Leu Arg Pro Leu Phe Tyr Pro Asp Ala Ser Val Leu Leu Leu Cys Phe
                85                  90                  95

Asp Val Thr Ser Pro Asn Ser Phe Asp Asn Ile Phe Asn Arg Trp Tyr
            100                 105                 110

Pro Glu Val Asn His Phe Cys Lys Lys Val Pro Ile Ile Val Val Gly
        115                 120                 125

Cys Lys Thr Asp Leu Arg Lys Asp Lys Ser Leu Val Asn Lys Leu Arg
    130                 135                 140

Arg Asn Gly Leu Glu Pro Val Thr Tyr His Arg Gly Gln Glu Met Ala
145                 150                 155                 160

```
Arg Ser Val Gly Ala Val Ala Tyr Leu Glu Cys Ser Ala Arg Leu His
            165                 170                 175

Asp Asn Val His Ala Val Phe Gln Glu Ala Ala Glu Val Ala Leu Ser
            180                 185                 190

Ser Arg Gly Arg Asn Phe Trp Arg Ile Thr Gln Gly Phe Cys Val
        195                 200                 205

Val Thr
    210

<210> SEQ ID NO 5
<211> LENGTH: 244
<212> TYPE: PRT
<213> ORGANISM: Homo sapiens

<400> SEQUENCE: 5

Met Lys Glu Arg Arg Ala Ser Gln Lys Leu Ser Ser Lys Ser Ile Met
1               5                   10                  15

Asp Pro Asn Gln Asn Val Lys Cys Lys Ile Val Val Gly Asp Ser
            20                  25                  30

Gln Cys Gly Lys Thr Ala Leu Leu His Val Phe Ala Lys Asp Cys Phe
        35                  40                  45

Pro Glu Asn Tyr Val Pro Thr Val Phe Glu Asn Tyr Thr Ala Ser Phe
    50                  55                  60

Glu Ile Asp Thr Gln Arg Ile Glu Leu Ser Leu Trp Asp Thr Ser Gly
65                  70                  75                  80

Ser Pro Tyr Tyr Asp Asn Val Arg Pro Leu Ser Tyr Pro Asp Ser Asp
                85                  90                  95

Ala Val Leu Ile Cys Phe Asp Ile Ser Arg Pro Glu Thr Leu Asp Ser
            100                 105                 110

Val Leu Lys Lys Trp Lys Gly Glu Ile Gln Glu Phe Cys Pro Asn Thr
        115                 120                 125

Lys Met Leu Leu Val Gly Cys Lys Ser Asp Leu Arg Thr Asp Val Ser
130                 135                 140

Thr Leu Val Glu Leu Ser Asn His Arg Gln Thr Pro Val Ser Tyr Asp
145                 150                 155                 160

Gln Gly Ala Asn Met Ala Lys Gln Ile Gly Ala Ala Thr Tyr Ile Glu
                165                 170                 175

Cys Ser Ala Leu Gln Ser Glu Asn Ser Val Arg Asp Ile Phe His Val
            180                 185                 190

Ala Thr Leu Ala Cys Val Asn Lys Thr Asn Lys Asn Val Lys Arg Asn
        195                 200                 205

Lys Ser Gln Arg Ala Thr Lys Arg Ile Ser His Met Pro Ser Arg Pro
    210                 215                 220

Glu Leu Ser Ala Val Ala Thr Asp Leu Arg Lys Asp Lys Ala Lys Ser
225                 230                 235                 240

Cys Thr Val Met

<210> SEQ ID NO 6
<211> LENGTH: 232
<212> TYPE: PRT
<213> ORGANISM: Homo sapiens

<400> SEQUENCE: 6

Met Lys Glu Arg Arg Ala Pro Gln Pro Val Val Ala Arg Cys Lys Leu
1               5                   10                  15
```

-continued

Val Leu Val Gly Asp Val Gln Cys Gly Lys Thr Ala Met Leu Gln Val
            20                  25                  30

Leu Ala Lys Asp Cys Tyr Pro Glu Thr Tyr Val Pro Thr Val Phe Glu
        35                  40                  45

Asn Tyr Thr Ala Cys Leu Glu Thr Glu Gln Arg Val Glu Leu Ser
 50                  55                  60

Leu Trp Asp Thr Ser Gly Ser Pro Tyr Tyr Asp Asn Val Arg Pro Leu
 65                  70                  75                  80

Cys Tyr Ser Asp Ser Asp Ala Val Leu Leu Cys Phe Asp Ile Ser Arg
                85                  90                  95

Pro Glu Thr Val Asp Ser Ala Leu Lys Lys Trp Arg Thr Glu Ile Leu
            100                 105                 110

Asp Tyr Cys Pro Ser Thr Arg Val Leu Leu Ile Gly Cys Lys Thr Asp
        115                 120                 125

Leu Arg Thr Asp Leu Ser Thr Leu Met Glu Leu Ser His Gln Lys Gln
130                 135                 140

Ala Pro Ile Ser Tyr Glu Gln Gly Cys Ala Ile Ala Lys Gln Leu Gly
145                 150                 155                 160

Ala Glu Ile Tyr Leu Glu Gly Ser Ala Phe Thr Ser Glu Lys Ser Ile
                165                 170                 175

His Ser Ile Phe Arg Thr Ala Ser Met Leu Cys Leu Asn Lys Pro Ser
            180                 185                 190

Pro Leu Pro Gln Lys Ser Pro Val Arg Ser Leu Ser Lys Arg Leu Leu
        195                 200                 205

His Leu Pro Ser Arg Ser Glu Leu Ile Ser Ser Thr Phe Lys Lys Glu
210                 215                 220

Lys Ala Lys Ser Cys Ser Ile Met
225                 230

<210> SEQ ID NO 7
<211> LENGTH: 227
<212> TYPE: PRT
<213> ORGANISM: Homo sapiens

<400> SEQUENCE: 7

Met Glu Gly Gln Ser Gly Arg Cys Lys Ile Val Val Val Gly Asp Ala
1               5                   10                  15

Glu Cys Gly Lys Thr Ala Leu Leu Gln Val Phe Ala Lys Asp Ala Tyr
            20                  25                  30

Pro Gly Ser Tyr Val Pro Thr Val Phe Glu Asn Tyr Thr Ala Ser Phe
        35                  40                  45

Glu Ile Asp Lys Arg Arg Ile Glu Leu Asn Met Trp Asp Thr Ser Gly
    50                  55                  60

Ser Ser Tyr Tyr Asp Asn Val Arg Pro Leu Ala Tyr Pro Asp Ser Asp
65                  70                  75                  80

Ala Val Leu Ile Cys Phe Asp Ile Ser Arg Pro Glu Thr Leu Asp Ser
                85                  90                  95

Val Leu Lys Lys Trp Gln Gly Glu Thr Gln Glu Phe Cys Pro Asn Ala
            100                 105                 110

Lys Val Val Leu Val Gly Cys Lys Leu Asp Met Arg Thr Asp Leu Ala
        115                 120                 125

Thr Leu Arg Glu Leu Ser Lys Gln Arg Leu Ile Pro Val Thr His Glu
130                 135                 140

Gln Gly Thr Val Leu Ala Lys Gln Val Gly Ala Val Ser Tyr Val Glu
145                 150                 155                 160

```
Cys Ser Ser Arg Ser Ser Glu Arg Ser Val Arg Asp Val Phe His Val
                165                 170                 175

Ala Thr Val Ala Ser Leu Gly Arg Gly His Arg Gln Leu Arg Arg Thr
            180                 185                 190

Asp Ser Arg Arg Gly Met Gln Arg Ser Ala Gln Leu Ser Gly Arg Pro
        195                 200                 205

Asp Arg Gly Asn Glu Gly Glu Ile His Lys Asp Arg Ala Lys Ser Cys
    210                 215                 220

Asn Leu Met
225

<210> SEQ ID NO 8
<211> LENGTH: 211
<212> TYPE: PRT
<213> ORGANISM: Homo sapiens

<400> SEQUENCE: 8

Met Asp Ala Pro Gly Ala Leu Ala Gln Thr Ala Ala Pro Gly Pro Gly
1               5                   10                  15

Arg Lys Glu Leu Lys Ile Val Ile Val Gly Asp Gly Gly Cys Gly Lys
            20                  25                  30

Thr Ser Leu Leu Met Val Tyr Ser Gln Gly Ser Phe Pro Glu His Tyr
        35                  40                  45

Ala Pro Ser Val Phe Glu Lys Tyr Thr Ala Ser Val Thr Val Gly Ser
    50                  55                  60

Lys Glu Val Thr Leu Asn Leu Tyr Asp Thr Ala Gly Gln Glu Asp Tyr
65                  70                  75                  80

Asp Arg Leu Arg Pro Leu Ser Tyr Gln Asn Thr His Leu Val Leu Ile
                85                  90                  95

Cys Tyr Asp Val Met Asn Pro Thr Ser Tyr Asp Asn Val Leu Ile Lys
            100                 105                 110

Trp Phe Pro Glu Val Thr His Phe Cys Arg Gly Ile Pro Met Val Leu
        115                 120                 125

Ile Gly Cys Lys Thr Asp Leu Arg Lys Asp Lys Glu Gln Leu Arg Lys
    130                 135                 140

Leu Arg Ala Ala Gln Leu Glu Pro Ile Thr Tyr Met Gln Gly Leu Ser
145                 150                 155                 160

Ala Cys Glu Gln Ile Arg Ala Ala Leu Tyr Leu Glu Cys Ser Ala Lys
                165                 170                 175

Phe Arg Glu Asn Val Glu Asp Val Phe Arg Glu Ala Ala Lys Val Ala
            180                 185                 190

Leu Ser Ala Leu Lys Lys Ala Gln Arg Gln Lys Lys Arg Arg Leu Cys
        195                 200                 205

Leu Leu Leu
    210

<210> SEQ ID NO 9
<211> LENGTH: 191
<212> TYPE: PRT
<213> ORGANISM: Homo sapiens

<400> SEQUENCE: 9

Met Gln Ser Ile Lys Cys Val Val Val Gly Asp Gly Ala Val Gly Lys
1               5                   10                  15

Thr Cys Leu Leu Ile Cys Tyr Thr Thr Asn Ala Phe Pro Lys Glu Tyr
            20                  25                  30
```

```
Ile Pro Thr Val Phe Asp Asn Tyr Ser Ala Gln Ser Ala Val Asp Gly
        35                  40                  45

Arg Thr Val Asn Leu Asn Leu Trp Asp Thr Ala Gly Gln Glu Glu Tyr
 50                  55                  60

Asp Arg Leu Arg Thr Leu Ser Tyr Pro Gln Thr Asn Val Phe Val Ile
 65                  70                  75                  80

Cys Phe Ser Ile Ala Ser Pro Pro Ser Tyr Glu Asn Val Arg His Lys
                 85                  90                  95

Trp His Pro Glu Val Cys His His Cys Pro Asp Val Pro Ile Leu Leu
                100                 105                 110

Val Gly Thr Lys Lys Asp Leu Arg Ala Gln Pro Asp Thr Leu Arg Arg
            115                 120                 125

Leu Lys Glu Gln Gly Gln Ala Pro Ile Thr Pro Gln Gln Gly Gln Ala
130                 135                 140

Leu Ala Lys Gln Ile His Ala Val Arg Tyr Leu Glu Cys Ser Ala Leu
145                 150                 155                 160

Gln Gln Asp Gly Val Lys Glu Val Phe Ala Glu Ala Val Arg Ala Val
                165                 170                 175

Leu Asn Pro Thr Pro Ile Lys Arg Gly Arg Ser Cys Ile Leu Leu
                180                 185                 190

<210> SEQ ID NO 10
<211> LENGTH: 191
<212> TYPE: PRT
<213> ORGANISM: Homo sapiens

<400> SEQUENCE: 10

Met Leu Ser Ser Ile Lys Cys Val Leu Val Gly Asp Ser Ala Val Gly
 1               5                  10                  15

Lys Thr Ser Leu Leu Val Arg Phe Thr Ser Glu Thr Phe Pro Glu Ala
                20                  25                  30

Tyr Lys Pro Thr Val Tyr Glu Asn Thr Gly Val Asp Val Phe Met Asp
            35                  40                  45

Gly Ile Gln Ile Ser Leu Gly Leu Trp Asp Thr Ala Gly Asn Asp Ala
        50                  55                  60

Phe Arg Ser Ile Arg Pro Leu Ser Tyr Gln Gln Ala Asp Val Val Leu
 65                  70                  75                  80

Met Cys Tyr Ser Val Ala Asn His Asn Ser Phe Leu Asn Leu Lys Asn
                 85                  90                  95

Lys Trp Ile Gly Glu Ile Arg Ser Asn Leu Pro Cys Thr Pro Val Leu
                100                 105                 110

Val Val Ala Thr Gln Thr Asp Gln Arg Glu Met Gly Pro His Arg Ala
            115                 120                 125

Ser Cys Val Asn Ala Met Glu Gly Lys Lys Leu Ala Gln Asp Val Arg
130                 135                 140

Ala Lys Gly Tyr Leu Glu Cys Ser Ala Leu Ser Asn Arg Gly Val Gln
145                 150                 155                 160

Gln Val Phe Glu Cys Ala Val Arg Thr Ala Val Asn Gln Ala Arg Arg
                165                 170                 175

Arg Asn Arg Arg Arg Leu Phe Ser Ile Asn Glu Cys Lys Ile Phe
                180                 185                 190

<210> SEQ ID NO 11
<211> LENGTH: 192
<212> TYPE: PRT
```

<213> ORGANISM: Homo sapiens

<400> SEQUENCE: 11

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
                35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
                115                 120                 125

Leu Lys Glu Lys Lys Leu Thr Pro Ile Thr Tyr Pro Gln Gly Leu Ala
        130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
                180                 185                 190

<210> SEQ ID NO 12
<211> LENGTH: 192
<212> TYPE: PRT
<213> ORGANISM: Homo sapiens

<400> SEQUENCE: 12

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Ser
                35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
                100                 105                 110

Val Gly Thr Lys Leu Asp Leu Arg Asp Asp Lys Asp Thr Ile Glu Lys
                115                 120                 125

Leu Lys Glu Lys Lys Leu Ala Pro Ile Thr Tyr Pro Gln Gly Leu Ala
        130                 135                 140

Leu Ala Lys Glu Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val

```
                                165                  170                 175
Leu Cys Pro Gln Pro Thr Arg Gln Lys Arg Ala Cys Ser Leu Leu
            180                 185                 190

<210> SEQ ID NO 13
<211> LENGTH: 192
<212> TYPE: PRT
<213> ORGANISM: Homo sapiens

<400> SEQUENCE: 13

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro His Thr Pro Ile Leu Leu
            100                 105                 110

Val Gly Thr Lys Leu Asp Leu Arg Asp Asp Lys Asp Thr Ile Glu Arg
        115                 120                 125

Leu Arg Asp Lys Lys Leu Ala Pro Ile Thr Tyr Pro Gln Gly Leu Ala
    130                 135                 140

Met Ala Arg Glu Ile Gly Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Pro Gly Lys Lys Cys Thr Val Phe
            180                 185                 190

<210> SEQ ID NO 14
<211> LENGTH: 191
<212> TYPE: PRT
<213> ORGANISM: Homo sapiens

<400> SEQUENCE: 14

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
```

```
                115                 120                 125
Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 15
<211> LENGTH: 205
<212> TYPE: PRT
<213> ORGANISM: Homo sapiens

<400> SEQUENCE: 15

Met Ala His Gly Pro Gly Ala Leu Met Leu Lys Cys Val Val Val Gly
1               5                   10                  15

Asp Gly Ala Val Gly Lys Thr Cys Leu Leu Met Ser Tyr Ala Asn Asp
            20                  25                  30

Ala Phe Pro Glu Glu Tyr Val Pro Thr Val Phe Asp His Tyr Ala Val
        35                  40                  45

Ser Val Thr Val Gly Gly Lys Gln Tyr Leu Leu Gly Leu Tyr Asp Thr
    50                  55                  60

Ala Gly Gln Glu Asp Tyr Asp Arg Leu Arg Pro Leu Ser Tyr Pro Met
65                  70                  75                  80

Thr Asp Val Phe Leu Ile Cys Phe Ser Val Val Asn Pro Ala Ser Phe
                85                  90                  95

Gln Asn Val Lys Glu Glu Trp Val Pro Glu Leu Lys Glu Tyr Ala Pro
            100                 105                 110

Asn Val Pro Phe Leu Leu Ile Gly Thr Gln Ile Asp Leu Arg Asp Asp
        115                 120                 125

Pro Lys Thr Leu Ala Arg Leu Asn Asp Met Lys Glu Lys Pro Ile Cys
    130                 135                 140

Val Glu Gln Gly Gln Lys Leu Ala Lys Glu Ile Gly Ala Cys Cys Tyr
145                 150                 155                 160

Val Glu Cys Ser Ala Leu Thr Gln Lys Gly Leu Lys Thr Val Phe Asp
                165                 170                 175

Glu Ala Ile Ile Ala Ile Leu Thr Pro Lys Lys His Thr Val Lys Lys
            180                 185                 190

Arg Ile Gly Ser Arg Cys Ile Asn Cys Cys Leu Ile Thr
        195                 200                 205

<210> SEQ ID NO 16
<211> LENGTH: 214
<212> TYPE: PRT
<213> ORGANISM: Homo sapiens

<400> SEQUENCE: 16

Met Asn Cys Lys Glu Gly Thr Asp Ser Ser Cys Gly Cys Arg Gly Asn
1               5                   10                  15

Asp Glu Lys Lys Met Leu Lys Cys Val Val Val Gly Asp Gly Ala Val
            20                  25                  30

Gly Lys Thr Cys Leu Leu Met Ser Tyr Ala Asn Asp Ala Phe Pro Glu
        35                  40                  45

Glu Tyr Val Pro Thr Val Phe Asp His Tyr Ala Val Thr Val Thr Val
```

```
              50                  55                  60
Gly Gly Lys Gln His Leu Leu Gly Leu Tyr Asp Thr Ala Gly Gln Glu
 65                  70                  75                  80

Asp Tyr Asn Gln Leu Arg Pro Leu Ser Tyr Pro Asn Thr Asp Val Phe
                 85                  90                  95

Leu Ile Cys Phe Ser Val Val Asn Pro Ala Ser Tyr His Asn Val Gln
                100                 105                 110

Glu Glu Trp Val Pro Glu Leu Lys Asp Cys Met Pro His Val Pro Tyr
            115                 120                 125

Val Leu Ile Gly Thr Gln Ile Asp Leu Arg Asp Asp Pro Lys Thr Leu
130                 135                 140

Ala Arg Leu Leu Tyr Met Lys Glu Lys Pro Leu Thr Tyr Glu His Gly
145                 150                 155                 160

Val Lys Leu Ala Lys Ala Ile Gly Ala Gln Cys Tyr Leu Glu Cys Ser
                165                 170                 175

Ala Leu Thr Gln Lys Gly Leu Lys Ala Val Phe Asp Glu Ala Ile Leu
            180                 185                 190

Thr Ile Phe His Pro Lys Lys Lys Lys Arg Cys Ser Glu Gly His
        195                 200                 205

Ser Cys Cys Ser Ile Ile
        210

<210> SEQ ID NO 17
<211> LENGTH: 258
<212> TYPE: PRT
<213> ORGANISM: Homo sapiens

<400> SEQUENCE: 17

Met Pro Pro Gln Gln Gly Asp Pro Ala Phe Pro Asp Arg Cys Glu Ala
 1               5                  10                  15

Pro Pro Val Pro Pro Arg Arg Glu Arg Gly Gly Arg Gly Gly Arg Gly
                20                  25                  30

Pro Gly Glu Pro Gly Gly Arg Gly Arg Ala Gly Gly Ala Glu Gly Arg
            35                  40                  45

Gly Val Lys Cys Val Leu Val Gly Asp Gly Ala Val Gly Lys Thr Ser
 50                  55                  60

Leu Val Val Ser Tyr Thr Thr Asn Gly Tyr Pro Thr Glu Tyr Ile Pro
 65                  70                  75                  80

Thr Ala Phe Asp Asn Phe Ser Ala Val Val Ser Val Asp Gly Arg Pro
                 85                  90                  95

Val Arg Leu Gln Leu Cys Asp Thr Ala Gly Gln Asp Glu Phe Asp Lys
                100                 105                 110

Leu Arg Pro Leu Cys Tyr Thr Asn Thr Asp Ile Phe Leu Leu Cys Phe
            115                 120                 125

Ser Val Val Ser Pro Ser Ser Phe Gln Asn Val Ser Glu Lys Trp Val
130                 135                 140

Pro Glu Ile Arg Cys His Cys Pro Lys Ala Pro Ile Ile Leu Val Gly
145                 150                 155                 160

Thr Gln Ser Asp Leu Arg Glu Asp Val Lys Val Leu Ile Glu Leu Asp
                165                 170                 175

Lys Cys Lys Glu Lys Pro Val Pro Glu Glu Ala Ala Lys Leu Cys Ala
            180                 185                 190

Glu Glu Ile Lys Ala Ala Ser Tyr Ile Glu Cys Ser Ala Leu Thr Gln
        195                 200                 205
```

```
Lys Asn Leu Lys Glu Val Phe Asp Ala Ala Ile Val Ala Gly Ile Gln
        210                 215                 220

Tyr Ser Asp Thr Gln Gln Pro Lys Lys Ser Lys Ser Arg Thr Pro
225                 230                 235                 240

Asp Lys Met Lys Asn Leu Ser Lys Ser Trp Trp Lys Lys Tyr Cys Cys
                245                 250                 255

Phe Val

<210> SEQ ID NO 18
<211> LENGTH: 236
<212> TYPE: PRT
<213> ORGANISM: Homo sapiens

<400> SEQUENCE: 18

Met Pro Pro Arg Glu Leu Ser Glu Ala Glu Pro Pro Leu Arg Ala
1               5                   10                  15

Pro Thr Pro Pro Arg Arg Arg Ser Ala Pro Pro Glu Leu Gly Ile
                20                  25                  30

Lys Cys Val Leu Val Gly Asp Gly Ala Val Gly Lys Ser Ser Leu Ile
            35                  40                  45

Val Ser Tyr Thr Cys Asn Gly Tyr Pro Ala Arg Tyr Arg Pro Thr Ala
50                  55                  60

Leu Asp Thr Phe Ser Val Gln Val Leu Val Asp Gly Ala Pro Val Arg
65                  70                  75                  80

Ile Glu Leu Trp Asp Thr Ala Gly Gln Glu Asp Phe Asp Arg Leu Arg
                85                  90                  95

Ser Leu Cys Tyr Pro Asp Thr Asp Val Phe Leu Ala Cys Phe Ser Val
            100                 105                 110

Val Gln Pro Ser Ser Phe Gln Asn Ile Thr Glu Lys Trp Leu Pro Glu
        115                 120                 125

Ile Arg Thr His Asn Pro Gln Ala Pro Val Leu Leu Val Gly Thr Gln
    130                 135                 140

Ala Asp Leu Arg Asp Asp Val Asn Val Leu Ile Gln Leu Asp Gln Gly
145                 150                 155                 160

Gly Arg Glu Gly Pro Val Pro Gln Pro Gln Ala Gln Gly Leu Ala Glu
                165                 170                 175

Arg Ile Arg Ala Cys Cys Tyr Leu Glu Cys Ser Ala Leu Thr Gln Lys
            180                 185                 190

Asn Leu Lys Glu Val Phe Asp Ser Ala Ile Leu Ser Ala Ile Glu His
        195                 200                 205

Lys Ala Arg Leu Glu Lys Lys Leu Asn Ala Lys Gly Val Arg Thr Leu
    210                 215                 220

Ser Arg Cys Arg Trp Lys Lys Phe Phe Cys Phe Val
225                 230                 235

<210> SEQ ID NO 19
<211> LENGTH: 696
<212> TYPE: PRT
<213> ORGANISM: Homo sapiens

<400> SEQUENCE: 19

Met Asp Ala Asp Met Asp Tyr Glu Arg Pro Asn Val Glu Thr Ile Lys
1               5                   10                  15

Cys Val Val Val Gly Asp Asn Ala Val Gly Lys Thr Arg Leu Ile Cys
            20                  25                  30

Ala Arg Ala Cys Asn Thr Thr Leu Thr Gln Tyr Gln Leu Leu Ala Thr
```

-continued

```
                35                  40                  45
His Val Pro Thr Val Trp Ala Ile Asp Gln Tyr Arg Val Cys Gln Glu
 50                  55                  60
Val Leu Glu Arg Ser Arg Asp Val Val Asp Glu Val Ser Val Ser Leu
 65                  70                  75                  80
Arg Leu Trp Asp Thr Phe Gly Asp His His Lys Asp Arg Arg Phe Ala
                 85                  90                  95
Tyr Gly Arg Ser Asp Val Val Leu Cys Phe Ser Ile Ala Asn Pro
                100                 105                 110
Asn Ser Leu Asn His Val Lys Ser Met Trp Tyr Pro Glu Ile Lys His
                115                 120                 125
Phe Cys Pro Arg Thr Pro Val Ile Leu Val Gly Cys Gln Leu Asp Leu
130                 135                 140
Arg Tyr Ala Asp Leu Glu Ala Val Asn Arg Ala Arg Arg Pro Leu Ala
145                 150                 155                 160
Arg Pro Ile Lys Arg Gly Asp Ile Leu Pro Pro Glu Lys Gly Arg Glu
                165                 170                 175
Val Ala Lys Glu Leu Gly Leu Pro Tyr Tyr Glu Thr Ser Val Phe Asp
                180                 185                 190
Gln Phe Gly Ile Lys Asp Val Phe Asp Asn Ala Ile Arg Ala Ala Leu
                195                 200                 205
Ile Ser Arg Arg His Leu Gln Phe Trp Lys Ser His Leu Lys Lys Val
                210                 215                 220
Gln Lys Pro Leu Leu Gln Ala Pro Phe Leu Pro Pro Lys Ala Pro Pro
225                 230                 235                 240
Pro Val Ile Lys Ile Pro Glu Cys Pro Ser Met Gly Thr Asn Glu Ala
                245                 250                 255
Ala Cys Leu Leu Asp Asn Pro Leu Cys Ala Asp Val Leu Phe Ile Leu
                260                 265                 270
Gln Asp Gln Glu His Ile Phe Ala His Arg Ile Tyr Leu Ala Thr Ser
                275                 280                 285
Ser Ser Lys Phe Tyr Asp Leu Phe Leu Met Glu Cys Glu Glu Ser Pro
                290                 295                 300
Asn Gly Ser Glu Gly Ala Cys Glu Lys Glu Lys Gln Ser Arg Asp Phe
305                 310                 315                 320
Gln Gly Arg Ile Leu Ser Val Asp Pro Glu Glu Arg Glu Glu Gly
                325                 330                 335
Pro Pro Arg Ile Pro Gln Ala Asp Gln Trp Lys Ser Ser Asn Lys Ser
                340                 345                 350
Leu Val Glu Ala Leu Gly Leu Glu Ala Glu Gly Ala Val Pro Glu Thr
                355                 360                 365
Gln Thr Leu Thr Gly Trp Ser Lys Gly Phe Ile Gly Met His Arg Glu
                370                 375                 380
Met Gln Val Asn Pro Ile Ser Lys Arg Met Gly Pro Met Thr Val Val
385                 390                 395                 400
Arg Met Asp Ala Ser Val Gln Pro Gly Pro Phe Arg Thr Leu Leu Gln
                405                 410                 415
Phe Leu Tyr Thr Gly Gln Leu Asp Glu Lys Glu Lys Asp Leu Val Gly
                420                 425                 430
Leu Ala Gln Ile Ala Glu Val Leu Glu Met Phe Asp Leu Arg Met Met
                435                 440                 445
Val Glu Asn Ile Met Asn Lys Glu Ala Phe Met Asn Gln Glu Ile Thr
                450                 455                 460
```

```
Lys Ala Phe His Val Arg Lys Ala Asn Arg Ile Lys Glu Cys Leu Ser
465                 470                 475                 480

Lys Gly Thr Phe Ser Asp Val Thr Phe Lys Leu Asp Asp Gly Ala Ile
                485                 490                 495

Ser Ala His Lys Pro Leu Leu Ile Cys Ser Cys Glu Trp Met Ala Ala
            500                 505                 510

Met Phe Gly Gly Ser Phe Val Glu Ser Ala Asn Ser Glu Val Tyr Leu
        515                 520                 525

Pro Asn Ile Asn Lys Ile Ser Met Gln Ala Val Leu Asp Tyr Leu Tyr
    530                 535                 540

Thr Lys Gln Leu Ser Pro Asn Leu Asp Leu Asp Pro Leu Glu Leu Ile
545                 550                 555                 560

Ala Leu Ala Asn Arg Phe Cys Leu Pro His Leu Val Ala Leu Ala Glu
                565                 570                 575

Gln His Ala Val Gln Glu Leu Thr Lys Ala Ala Thr Ser Gly Val Gly
            580                 585                 590

Ile Asp Gly Glu Val Leu Ser Tyr Leu Glu Leu Ala Gln Phe His Asn
        595                 600                 605

Ala His Gln Leu Ala Ala Trp Cys Leu His His Ile Cys Thr Asn Tyr
    610                 615                 620

Asn Ser Val Cys Ser Lys Phe Arg Lys Glu Ile Lys Ser Lys Ser Ala
625                 630                 635                 640

Asp Asn Gln Glu Tyr Phe Glu Arg His Arg Trp Pro Pro Val Trp Tyr
                645                 650                 655

Leu Lys Glu Glu Asp His Tyr Gln Arg Val Lys Arg Glu Arg Glu Lys
            660                 665                 670

Glu Asp Ile Ala Leu Asn Lys His Arg Ser Arg Arg Lys Trp Cys Phe
        675                 680                 685

Trp Asn Ser Ser Pro Ala Val Ala
    690                 695

<210> SEQ ID NO 20
<211> LENGTH: 727
<212> TYPE: PRT
<213> ORGANISM: Homo sapiens

<400> SEQUENCE: 20

Met Asp Ser Asp Met Asp Tyr Glu Arg Pro Asn Val Glu Thr Ile Lys
1               5                   10                  15

Cys Val Val Val Gly Asp Asn Ala Val Gly Lys Thr Arg Leu Ile Cys
                20                  25                  30

Ala Arg Ala Cys Asn Ala Thr Leu Thr Gln Tyr Gln Leu Leu Ala Thr
            35                  40                  45

His Val Pro Thr Val Trp Ala Ile Asp Gln Tyr Arg Val Cys Gln Glu
        50                  55                  60

Val Leu Glu Arg Ser Arg Asp Val Val Asp Val Ser Val Ser Leu
65                  70                  75                  80

Arg Leu Trp Asp Thr Phe Gly Asp His His Lys Asp Arg Arg Phe Ala
                85                  90                  95

Tyr Gly Arg Ser Asp Val Val Leu Cys Phe Ser Ile Ala Asn Pro
            100                 105                 110

Asn Ser Leu His His Val Lys Thr Met Trp Tyr Pro Glu Ile Lys His
        115                 120                 125

Phe Cys Pro Arg Ala Pro Val Ile Leu Val Gly Cys Gln Leu Asp Leu
```

```
            130                 135                 140
Arg Tyr Ala Asp Leu Glu Ala Val Asn Arg Ala Arg Arg Pro Leu Ala
145                 150                 155                 160

Arg Pro Ile Lys Pro Asn Glu Ile Leu Pro Pro Glu Lys Gly Arg Glu
                165                 170                 175

Val Ala Lys Glu Leu Gly Ile Pro Tyr Tyr Glu Thr Ser Val Val Ala
                180                 185                 190

Gln Phe Gly Ile Lys Asp Val Phe Asp Asn Ala Ile Arg Ala Ala Leu
                195                 200                 205

Ile Ser Arg Arg His Leu Gln Phe Trp Lys Ser His Leu Arg Asn Val
210                 215                 220

Gln Arg Pro Leu Leu Gln Ala Pro Phe Leu Pro Pro Lys Pro Pro Pro
225                 230                 235                 240

Pro Ile Ile Val Val Pro Asp Pro Pro Ser Ser Ser Glu Glu Gly Pro
                245                 250                 255

Ala His Leu Leu Glu Asp Pro Leu Cys Ala Asp Val Ile Leu Val Leu
                260                 265                 270

Gln Glu Arg Val Arg Ile Phe Ala His Lys Ile Tyr Leu Ser Thr Ser
        275                 280                 285

Ser Ser Lys Phe Tyr Asp Leu Phe Leu Met Asp Leu Ser Glu Gly Glu
        290                 295                 300

Leu Gly Gly Pro Ser Glu Pro Gly Gly Thr His Pro Glu Asp His Gln
305                 310                 315                 320

Gly His Ser Asp Gln His His His His His His His His Gly Arg
                325                 330                 335

Asp Phe Leu Leu Arg Ala Ala Ser Phe Asp Val Cys Glu Ser Val Asp
                340                 345                 350

Glu Ala Gly Gly Ser Gly Pro Ala Gly Leu Arg Ala Ser Thr Ser Asp
                355                 360                 365

Gly Ile Leu Arg Gly Asn Gly Thr Gly Tyr Leu Pro Gly Arg Gly Arg
                370                 375                 380

Val Leu Ser Ser Trp Ser Arg Ala Phe Val Ser Ile Gln Glu Glu Met
385                 390                 395                 400

Ala Glu Asp Pro Leu Thr Tyr Lys Ser Arg Leu Met Val Val Lys
                405                 410                 415

Met Asp Ser Ser Ile Gln Pro Gly Pro Phe Arg Ala Val Leu Lys Tyr
                420                 425                 430

Leu Tyr Thr Gly Glu Leu Asp Glu Asn Glu Arg Asp Leu Met His Ile
                435                 440                 445

Ala His Ile Ala Glu Leu Leu Glu Val Phe Asp Leu Arg Met Met Val
450                 455                 460

Ala Asn Ile Leu Asn Asn Glu Ala Phe Met Asn Gln Glu Ile Thr Lys
465                 470                 475                 480

Ala Phe His Val Arg Arg Thr Asn Arg Val Lys Glu Cys Leu Ala Lys
                485                 490                 495

Gly Thr Phe Ser Asp Val Thr Phe Ile Leu Asp Gly Thr Ile Ser
                500                 505                 510

Ala His Lys Pro Leu Leu Ile Ser Ser Cys Asp Trp Met Ala Ala Met
                515                 520                 525

Phe Gly Gly Pro Phe Val Glu Ser Ser Arg Glu Val Val Phe Pro
        530                 535                 540

Tyr Thr Ser Lys Ser Cys Met Arg Ala Val Leu Glu Tyr Leu Tyr Thr
545                 550                 555                 560
```

-continued

```
Gly Met Phe Thr Ser Ser Pro Asp Leu Asp Asp Met Lys Leu Ile Ile
            565                 570                 575

Leu Ala Asn Arg Leu Cys Leu Pro His Leu Val Ala Leu Thr Glu Gln
            580                 585                 590

Tyr Thr Val Thr Gly Leu Met Glu Ala Thr Gln Met Met Val Asp Ile
        595                 600                 605

Asp Gly Asp Val Leu Val Phe Leu Glu Leu Ala Gln Phe His Cys Ala
    610                 615                 620

Tyr Gln Leu Ala Asp Trp Cys Leu His His Ile Cys Thr Asn Tyr Asn
625                 630                 635                 640

Asn Val Cys Arg Lys Phe Pro Arg Asp Met Lys Ala Met Ser Pro Glu
                645                 650                 655

Asn Gln Glu Tyr Phe Glu Lys His Arg Trp Pro Pro Val Trp Tyr Leu
            660                 665                 670

Lys Glu Glu Asp His Tyr Gln Arg Ala Arg Lys Glu Arg Glu Lys Glu
        675                 680                 685

Asp Tyr Leu His Leu Lys Arg Gln Pro Lys Arg Arg Trp Leu Phe Trp
    690                 695                 700

Asn Ser Pro Ser Ser Pro Ser Ser Ala Ala Ser Ser Ser Ser Pro
705                 710                 715                 720

Ser Ser Ser Ser Ala Val Val
                725

<210> SEQ ID NO 21
<211> LENGTH: 17
<212> TYPE: PRT
<213> ORGANISM: Homo sapiens
<220> FEATURE:
<221> NAME/KEY: misc_feature
<222> LOCATION: (4), (10)..(13), (15)
<223> OTHER INFORMATION: Xaa is any amino acid residue

<400> SEQUENCE: 21

Thr Glu Arg Xaa Leu Lys Thr Gln Ala Xaa Xaa Xaa Xaa Ala Xaa Ile
1               5                   10                  15

Leu

<210> SEQ ID NO 22
<211> LENGTH: 64
<212> TYPE: PRT
<213> ORGANISM: Homo sapiens
<220> FEATURE:
<221> NAME/KEY: misc_feature
<222> LOCATION: (2)..(4), (7), (9)..(11), (13), (19), (21), (22),
      (25)..(32), (34), (37), (38), (40), (42), (45), (48),
      (50), (51), (53), (54), (57), (61)
<223> OTHER INFORMATION: Xaa is any amino acid

<400> SEQUENCE: 22

Leu Xaa Xaa Xaa Leu Asp Xaa Glu Xaa Xaa Xaa Phe Xaa Gly Ala Glu
1               5                   10                  15

Leu Leu Xaa Leu Xaa Xaa Glu Lys Xaa Xaa Xaa Xaa Xaa Xaa Xaa Xaa
            20                  25                  30

Glu Xaa Gln Arg Xaa Xaa Asp Xaa Glu Xaa Leu Lys Xaa Arg Asn Xaa
        35                  40                  45

Glu Xaa Xaa Val Xaa Xaa Leu Lys Xaa Gln Leu Glu Xaa Leu Lys Lys
    50                  55                  60

<210> SEQ ID NO 23
```

```
<211> LENGTH: 63
<212> TYPE: PRT
<213> ORGANISM: Homo sapiens
<220> FEATURE:
<221> NAME/KEY: misc_feature
<222> LOCATION: (2)..(4), (7)..(13), (15)..(19), (21), (24)..28),
      (30)..(35), (37)..(44), (46)..(53), (55)..(62)
<223> OTHER INFORMATION: Xaa is any amino acid

<400> SEQUENCE: 23
```

Leu Xaa Xaa Xaa Leu Glu Xaa Xaa Xaa Xaa Xaa Xaa Thr Xaa Xaa
1               5                   10                  15

Xaa Xaa Xaa Val Xaa Glu Leu Xaa Xaa Xaa Xaa Glu Xaa Xaa Xaa
                20                  25                  30

Xaa Xaa Xaa Glu Xaa Xaa Xaa Xaa Xaa Xaa Xaa Gln Xaa Xaa Xaa
            35                  40                  45

Xaa Xaa Xaa Xaa Xaa Leu Xaa Xaa Xaa Xaa Xaa Xaa Xaa Thr
        50                  55                  60

```
<210> SEQ ID NO 24
<211> LENGTH: 2027
<212> TYPE: PRT
<213> ORGANISM: Homo sapiens

<400> SEQUENCE: 24
```

Met Leu Lys Phe Lys Tyr Gly Ala Arg Asn Pro Leu Asp Ala Gly Ala
1               5                   10                  15

Ala Glu Pro Ile Ala Ser Arg Ala Ser Arg Leu Asn Leu Phe Phe Gln
                20                  25                  30

Gly Lys Pro Pro Phe Met Thr Gln Gln Gln Met Ser Pro Leu Ser Arg
            35                  40                  45

Glu Gly Ile Leu Asp Ala Leu Phe Val Leu Phe Glu Glu Cys Ser Gln
    50                  55                  60

Pro Ala Leu Met Lys Ile Lys His Val Ser Asn Phe Val Arg Lys Tyr
65                  70                  75                  80

Ser Asp Thr Ile Ala Glu Leu Gln Glu Leu Gln Pro Ser Ala Lys Asp
                85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
        115                 120                 125

Lys Lys Lys Ala Leu Leu Ala Gln Glu Gln Val Ser Phe Phe Glu Glu
130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr
                165                 170                 175

Gln Pro Gly Gly Asp Leu Leu Ser Leu Leu Asn Arg Tyr Glu Asp Gln
            180                 185                 190

Leu Asp Glu Asn Leu Ile Gln Phe Tyr Leu Ala Glu Leu Ile Leu Ala
        195                 200                 205

Val His Ser Val His Leu Met Gly Tyr Val His Arg Asp Ile Lys Pro
210                 215                 220

Glu Asn Ile Leu Val Asp Arg Thr Gly His Ile Lys Leu Val Asp Phe
225                 230                 235                 240

Gly Ser Ala Ala Lys Met Asn Ser Asn Lys Met Val Asn Ala Lys Leu
                245                 250                 255

-continued

```
Pro Ile Gly Thr Pro Asp Tyr Met Ala Pro Glu Val Leu Thr Val Met
            260                 265                 270
Asn Gly Asp Gly Lys Gly Thr Tyr Gly Leu Asp Cys Asp Trp Trp Ser
        275                 280                 285
Val Gly Val Ile Ala Tyr Glu Met Ile Tyr Gly Arg Ser Pro Phe Ala
    290                 295                 300
Glu Gly Thr Ser Ala Arg Thr Phe Asn Asn Ile Met Asn Phe Gln Arg
305                 310                 315                 320
Phe Leu Lys Phe Pro Asp Asp Pro Lys Val Ser Ser Asp Phe Leu Asp
                325                 330                 335
Leu Ile Gln Ser Leu Leu Cys Gly Gln Lys Glu Arg Leu Lys Phe Glu
            340                 345                 350
Gly Leu Cys Cys His Pro Phe Phe Ser Lys Ile Asp Trp Asn Asn Ile
        355                 360                 365
Arg Asn Ser Pro Pro Pro Phe Val Pro Thr Leu Lys Ser Asp Asp Asp
    370                 375                 380
Thr Ser Asn Phe Asp Glu Pro Glu Lys Asn Ser Trp Val Ser Ser Ser
385                 390                 395                 400
Pro Cys Gln Leu Ser Pro Ser Gly Phe Ser Gly Glu Glu Leu Pro Phe
                405                 410                 415
Val Gly Phe Ser Tyr Ser Lys Ala Leu Gly Ile Leu Gly Arg Ser Glu
            420                 425                 430
Ser Val Val Ser Gly Leu Asp Ser Pro Ala Lys Thr Ser Ser Met Glu
        435                 440                 445
Lys Lys Leu Leu Ile Lys Ser Lys Glu Leu Gln Asp Ser Gln Asp Lys
    450                 455                 460
Cys His Lys Met Glu Gln Glu Met Thr Arg Leu His Arg Arg Val Ser
465                 470                 475                 480
Glu Val Glu Ala Val Leu Ser Gln Lys Glu Val Glu Leu Lys Ala Ser
                485                 490                 495
Glu Thr Gln Arg Ser Leu Leu Glu Gln Asp Leu Ala Thr Tyr Ile Thr
            500                 505                 510
Glu Cys Ser Ser Leu Lys Arg Ser Leu Glu Gln Ala Arg Met Glu Val
        515                 520                 525
Ser Gln Glu Asp Asp Lys Ala Leu Gln Leu Leu His Asp Ile Arg Glu
    530                 535                 540
Gln Ser Arg Lys Leu Gln Glu Ile Lys Glu Gln Glu Tyr Gln Ala Gln
545                 550                 555                 560
Val Glu Glu Met Arg Leu Met Met Asn Gln Leu Glu Glu Asp Leu Val
                565                 570                 575
Ser Ala Arg Arg Arg Ser Asp Leu Tyr Glu Ser Glu Leu Arg Glu Ser
            580                 585                 590
Arg Leu Ala Ala Glu Glu Phe Lys Arg Lys Ala Thr Glu Cys Gln His
        595                 600                 605
Lys Leu Leu Lys Ala Lys Asp Gln Gly Lys Pro Glu Val Gly Glu Tyr
    610                 615                 620
Ala Lys Leu Glu Lys Ile Asn Ala Glu Gln Leu Lys Ile Gln Glu
625                 630                 635                 640
Leu Gln Glu Lys Leu Glu Lys Ala Val Lys Ala Ser Thr Glu Ala Thr
                645                 650                 655
Glu Leu Leu Gln Asn Ile Arg Gln Ala Lys Glu Arg Ala Glu Arg Glu
            660                 665                 670
Leu Glu Lys Leu Gln Asn Arg Glu Asp Ser Ser Glu Gly Ile Arg Lys
```

-continued

```
                675                 680                 685
Lys Leu Val Glu Ala Glu Glu Leu Glu Lys His Arg Glu Ala Gln
        690                 695                 700
Val Ser Ala Gln His Leu Glu Val His Leu Lys Gln Lys Glu Gln His
705                 710                 715                 720
Tyr Glu Glu Lys Ile Lys Val Leu Asp Asn Gln Ile Lys Lys Asp Leu
                725                 730                 735
Ala Asp Lys Glu Thr Leu Glu Asn Met Met Gln Arg His Glu Glu Glu
            740                 745                 750
Ala His Glu Lys Gly Lys Ile Leu Ser Glu Gln Lys Ala Met Ile Asn
                755                 760                 765
Ala Met Asp Ser Lys Ile Arg Ser Leu Glu Gln Arg Ile Val Glu Leu
        770                 775                 780
Ser Glu Ala Asn Lys Leu Ala Ala Asn Ser Ser Leu Phe Thr Gln Arg
785                 790                 795                 800
Asn Met Lys Ala Gln Glu Glu Met Ile Ser Glu Leu Arg Gln Gln Lys
                805                 810                 815
Phe Tyr Leu Glu Thr Gln Ala Gly Lys Leu Glu Ala Gln Asn Arg Lys
            820                 825                 830
Leu Glu Glu Gln Leu Glu Lys Ile Ser His Gln Asp His Ser Asp Lys
                835                 840                 845
Asn Arg Leu Leu Glu Leu Glu Thr Arg Leu Arg Glu Val Ser Leu Glu
        850                 855                 860
His Glu Glu Gln Lys Leu Glu Leu Lys Arg Gln Leu Thr Glu Leu Gln
865                 870                 875                 880
Leu Ser Leu Gln Glu Arg Glu Ser Gln Leu Thr Ala Leu Gln Ala Ala
                885                 890                 895
Arg Ala Ala Leu Glu Ser Gln Leu Arg Gln Ala Lys Thr Glu Leu Glu
            900                 905                 910
Glu Thr Thr Ala Glu Ala Glu Glu Ile Gln Ala Leu Thr Ala His
                915                 920                 925
Arg Asp Glu Ile Gln Arg Lys Phe Asp Ala Leu Arg Asn Ser Cys Thr
        930                 935                 940
Val Ile Thr Asp Leu Glu Glu Gln Leu Asn Gln Leu Thr Glu Asp Asn
945                 950                 955                 960
Ala Glu Leu Asn Asn Gln Asn Phe Tyr Leu Ser Lys Gln Leu Asp Glu
                965                 970                 975
Ala Ser Gly Ala Asn Asp Glu Ile Val Gln Leu Arg Ser Glu Val Asp
            980                 985                 990
His Leu Arg Arg Glu Ile Thr Glu Arg Glu Met Gln Leu Thr Ser Gln
                995                 1000                1005
Lys Gln Thr Met Glu Ala Leu Lys Thr Thr Cys Thr Met Leu Glu Glu
        1010                1015                1020
Gln Val Met Asp Leu Glu Ala Leu Asn Asp Glu Leu Leu Glu Lys Glu
1025                1030                1035                1040
Arg Gln Trp Glu Ala Trp Arg Ser Val Leu Gly Asp Glu Lys Ser Gln
                1045                1050                1055
Phe Glu Cys Arg Val Arg Glu Leu Gln Arg Met Leu Asp Thr Glu Lys
            1060                1065                1070
Gln Ser Arg Ala Arg Ala Asp Gln Arg Ile Thr Glu Ser Arg Gln Val
        1075                1080                1085
Val Glu Leu Ala Val Lys Glu His Lys Ala Glu Ile Leu Ala Leu Gln
        1090                1095                1100
```

```
Gln Ala Leu Lys Glu Gln Lys Leu Lys Ala Glu Ser Leu Ser Asp Lys
1105                1110                1115                1120

Leu Asn Asp Leu Glu Lys Lys His Ala Met Leu Glu Met Asn Ala Arg
            1125                1130                1135

Ser Leu Gln Gln Lys Leu Glu Thr Glu Arg Glu Leu Lys Gln Arg Leu
        1140                1145                1150

Leu Glu Glu Gln Ala Lys Leu Gln Gln Met Asp Leu Gln Lys Asn
    1155                1160                1165

His Ile Phe Arg Leu Thr Gln Gly Leu Gln Glu Ala Leu Asp Arg Ala
    1170                1175                1180

Asp Leu Leu Lys Thr Glu Arg Ser Asp Leu Glu Tyr Gln Leu Glu Asn
1185                1190                1195                1200

Ile Gln Val Leu Tyr Ser His Glu Lys Val Lys Met Glu Gly Thr Ile
                1205                1210                1215

Ser Gln Gln Thr Lys Leu Ile Asp Phe Leu Gln Ala Lys Met Asp Gln
                1220                1225                1230

Pro Ala Lys Lys Lys Lys Gly Leu Phe Ser Arg Arg Lys Glu Asp Pro
                1235                1240                1245

Ala Leu Pro Thr Gln Val Pro Leu Gln Tyr Asn Glu Leu Lys Leu Ala
    1250                1255                1260

Leu Glu Lys Glu Lys Ala Arg Cys Ala Glu Leu Glu Glu Ala Leu Gln
1265                1270                1275                1280

Lys Thr Arg Ile Glu Leu Arg Ser Ala Arg Glu Glu Ala Ala His Arg
                1285                1290                1295

Lys Ala Thr Asp His Pro His Pro Ser Thr Pro Ala Thr Ala Arg Gln
                1300                1305                1310

Gln Ile Ala Met Ser Ala Ile Val Arg Ser Pro Glu His Gln Pro Ser
                1315                1320                1325

Ala Met Ser Leu Leu Ala Pro Pro Ser Ser Arg Arg Lys Glu Ser Ser
                1330                1335                1340

Thr Pro Glu Glu Phe Ser Arg Arg Leu Lys Glu Arg Met His His Asn
1345                1350                1355                1360

Ile Pro His Arg Phe Asn Val Gly Leu Asn Met Arg Ala Thr Lys Cys
                1365                1370                1375

Ala Val Cys Leu Asp Thr Val His Phe Gly Arg Gln Ala Ser Lys Cys
                1380                1385                1390

Leu Glu Cys Gln Val Met Cys His Pro Lys Cys Ser Thr Cys Leu Pro
            1395                1400                1405

Ala Thr Cys Gly Leu Pro Ala Glu Tyr Ala Thr His Phe Thr Glu Ala
    1410                1415                1420

Phe Cys Arg Asp Lys Met Asn Ser Pro Gly Leu Gln Thr Lys Glu Pro
1425                1430                1435                1440

Ser Ser Ser Leu His Leu Glu Gly Trp Met Lys Val Pro Arg Asn Asn
                1445                1450                1455

Lys Arg Gly Gln Gln Gly Trp Asp Arg Lys Tyr Ile Val Leu Glu Gly
                1460                1465                1470

Ser Lys Val Leu Ile Tyr Asp Asn Glu Ala Arg Glu Ala Gly Gln Arg
            1475                1480                1485

Pro Val Glu Glu Phe Glu Leu Cys Leu Pro Asp Gly Asp Val Ser Ile
    1490                1495                1500

His Gly Ala Val Gly Ala Ser Glu Leu Ala Asn Thr Ala Lys Ala Asp
1505                1510                1515                1520
```

-continued

```
Val Pro Tyr Ile Leu Lys Met Glu Ser His Pro His Thr Thr Cys Trp
            1525                1530                1535

Pro Gly Arg Thr Leu Tyr Leu Leu Ala Pro Ser Phe Pro Asp Lys Gln
            1540                1545                1550

Arg Trp Val Thr Ala Leu Glu Ser Val Ala Gly Gly Arg Val Ser
            1555                1560                1565

Arg Glu Lys Ala Glu Ala Asp Ala Lys Leu Leu Gly Asn Ser Leu Leu
            1570                1575                1580

Lys Leu Glu Gly Asp Asp Arg Leu Asp Met Asn Cys Thr Leu Pro Phe
1585                1590                1595                1600

Ser Asp Gln Val Val Leu Val Gly Thr Glu Glu Gly Leu Tyr Ala Leu
            1605                1610                1615

Asn Val Leu Lys Asn Ser Leu Thr His Val Pro Gly Ile Gly Ala Val
            1620                1625                1630

Phe Gln Ile Tyr Ile Ile Lys Asp Leu Glu Lys Leu Met Ile Ala Gly
            1635                1640                1645

Glu Glu Arg Ala Leu Cys Leu Val Asp Val Lys Lys Val Lys Gln Ser
            1650                1655                1660

Leu Ala Gln Ser His Leu Pro Ala Gln Pro Asp Ile Ser Pro Asn Ile
1665                1670                1675                1680

Phe Glu Ala Val Lys Gly Cys His Leu Phe Gly Ala Gly Lys Ile Glu
            1685                1690                1695

Asn Gly Leu Cys Ile Cys Ala Ala Met Pro Ser Lys Val Val Ile Leu
            1700                1705                1710

Arg Tyr Asn Glu Asn Leu Ser Lys Tyr Cys Ile Arg Lys Glu Ile Glu
            1715                1720                1725

Thr Ser Glu Pro Cys Ser Cys Ile His Phe Thr Asn Tyr Ser Ile Leu
            1730                1735                1740

Ile Gly Thr Asn Lys Phe Tyr Glu Ile Asp Met Lys Gln Tyr Thr Leu
1745                1750                1755                1760

Glu Glu Phe Leu Asp Lys Asn Asp His Ser Leu Ala Pro Ala Val Phe
            1765                1770                1775

Ala Ala Ser Ser Asn Ser Phe Pro Val Ser Ile Val Gln Val Asn Ser
            1780                1785                1790

Ala Gly Gln Arg Glu Glu Tyr Leu Leu Cys Phe His Glu Phe Gly Val
            1795                1800                1805

Phe Val Asp Ser Tyr Gly Arg Arg Ser Arg Thr Asp Asp Leu Lys Trp
            1810                1815                1820

Ser Arg Leu Pro Leu Ala Phe Ala Tyr Arg Glu Pro Tyr Leu Phe Val
1825                1830                1835                1840

Thr His Phe Asn Ser Leu Glu Val Ile Glu Ile Gln Ala Arg Ser Ser
            1845                1850                1855

Ala Gly Thr Pro Ala Arg Ala Tyr Leu Asp Ile Pro Asn Pro Arg Tyr
            1860                1865                1870

Leu Gly Pro Ala Ile Ser Ser Gly Ala Ile Tyr Leu Ala Ser Ser Tyr
            1875                1880                1885

Gln Asp Lys Leu Arg Val Ile Cys Cys Lys Gly Asn Leu Val Lys Glu
            1890                1895                1900

Ser Gly Thr Glu His His Arg Gly Pro Ser Thr Ser Arg Lys Ser Ser
1905                1910                1915                1920

Pro Asn Lys Arg Gly Pro Pro Thr Tyr Asn Glu His Ile Thr Lys Arg
            1925                1930                1935

Val Ala Ser Ser Pro Ala Pro Pro Glu Gly Pro Ser His Pro Arg Glu
```

```
                   1940              1945              1950
Pro Ser Thr Pro His Arg Tyr Arg Glu Gly Arg Thr Glu Leu Arg Arg
        1955              1960              1965

Asp Lys Ser Pro Gly Arg Pro Leu Glu Arg Glu Lys Ser Pro Gly Arg
        1970              1975              1980

Met Leu Ser Thr Arg Arg Glu Arg Ser Pro Gly Arg Leu Phe Glu Asp
1985              1990              1995              2000

Ser Ser Arg Gly Arg Leu Pro Ala Gly Ala Val Arg Thr Pro Leu Ser
                2005              2010              2015

Gln Val Asn Lys Val Trp Asp Gln Ser Ser Val
                2020              2025

<210> SEQ ID NO 25
<211> LENGTH: 1354
<212> TYPE: PRT
<213> ORGANISM: Homo sapiens

<400> SEQUENCE: 25

Met Ser Thr Gly Asp Ser Phe Glu Thr Arg Phe Glu Lys Met Asp Asn
1               5                   10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
                85                  90                  95

Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
        115                 120                 125

Ala Phe Ala Asn Ser Pro Trp Val Val Gln Leu Phe Tyr Ala Phe Gln
    130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                165                 170                 175

Phe Tyr Thr Ala Glu Val Val Leu Ala Leu Asp Ala Ile His Ser Met
            180                 185                 190

Gly Phe Ile His Arg Asp Val Lys Pro Asp Asn Met Leu Leu Asp Lys
        195                 200                 205

Ser Gly His Leu Lys Leu Ala Asp Phe Gly Thr Cys Met Lys Met Asn
    210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                245                 250                 255

Arg Glu Cys Asp Trp Trp Ser Val Gly Val Phe Leu Tyr Glu Met Leu
            260                 265                 270

Val Gly Asp Thr Pro Phe Tyr Ala Asp Ser Leu Val Gly Thr Tyr Ser
        275                 280                 285
```

```
Lys Ile Met Asn His Lys Asn Ser Leu Thr Phe Pro Asp Asn Asp
290                 295                 300
Ile Ser Lys Glu Ala Lys Asn Leu Ile Cys Ala Phe Leu Thr Asp Arg
305                 310                 315                 320
Glu Val Arg Leu Gly Arg Asn Gly Val Glu Glu Ile Lys Arg His Leu
                325                 330                 335
Phe Phe Lys Asn Asp Gln Trp Ala Trp Glu Thr Leu Arg Asp Thr Val
                340                 345                 350
Ala Pro Val Val Pro Asp Leu Ser Ser Asp Ile Asp Thr Ser Asn Phe
                355                 360                 365
Asp Asp Leu Glu Glu Asp Lys Gly Glu Glu Thr Phe Pro Ile Pro
370                 375                 380
Lys Ala Phe Val Gly Asn Gln Leu Pro Phe Val Gly Phe Thr Tyr Tyr
385                 390                 395                 400
Ser Asn Arg Arg Tyr Leu Ser Ser Ala Asn Pro Asn Asp Asn Arg Thr
                405                 410                 415
Ser Ser Asn Ala Asp Lys Ser Leu Gln Glu Ser Leu Gln Lys Thr Ile
                420                 425                 430
Tyr Lys Leu Glu Glu Gln Leu His Asn Glu Met Gln Leu Lys Asp Glu
                435                 440                 445
Met Glu Gln Lys Cys Arg Thr Ser Asn Ile Lys Leu Asp Lys Ile Met
450                 455                 460
Lys Glu Leu Asp Glu Glu Gly Asn Gln Arg Arg Asn Leu Glu Ser Thr
465                 470                 475                 480
Val Ser Gln Ile Glu Lys Glu Lys Met Leu Leu Gln His Arg Ile Asn
                485                 490                 495
Glu Tyr Gln Arg Lys Ala Glu Gln Glu Asn Glu Lys Arg Arg Asn Val
                500                 505                 510
Glu Asn Glu Val Ser Thr Leu Lys Asp Gln Leu Glu Asp Leu Lys Lys
                515                 520                 525
Val Ser Gln Asn Ser Gln Leu Ala Asn Glu Lys Leu Ser Gln Leu Gln
530                 535                 540
Lys Gln Leu Glu Glu Ala Asn Asp Leu Leu Arg Thr Glu Ser Asp Thr
545                 550                 555                 560
Ala Val Arg Leu Arg Lys Ser His Thr Glu Met Ser Lys Ser Ile Ser
                565                 570                 575
Gln Leu Glu Ser Leu Asn Arg Glu Leu Gln Glu Arg Asn Arg Ile Leu
                580                 585                 590
Glu Asn Ser Lys Ser Gln Thr Asp Lys Asp Tyr Tyr Gln Leu Gln Ala
                595                 600                 605
Ile Leu Glu Ala Glu Arg Arg Asp Arg Gly His Asp Ser Glu Met Ile
610                 615                 620
Gly Asp Leu Gln Ala Arg Ile Thr Ser Leu Gln Glu Glu Val Lys His
625                 630                 635                 640
Leu Lys His Asn Leu Glu Lys Val Glu Gly Glu Arg Lys Glu Ala Gln
                645                 650                 655
Asp Met Leu Asn His Ser Glu Lys Lys Asn Asn Leu Glu Ile Asp
                660                 665                 670
Leu Asn Tyr Lys Leu Lys Ser Leu Gln Gln Arg Leu Glu Gln Glu Val
                675                 680                 685
Asn Glu His Lys Val Thr Lys Ala Arg Leu Thr Asp Lys His Gln Ser
                690                 695                 700
Ile Glu Glu Ala Lys Ser Val Ala Met Cys Glu Met Glu Lys Lys Leu
```

```
                      705                 710                 715                 720
Lys Glu Glu Arg Glu Ala Arg Glu Lys Ala Glu Asn Arg Val Val Gln
                725                 730                 735
Ile Glu Lys Gln Cys Ser Met Leu Asp Val Asp Leu Lys Gln Ser Gln
                740                 745                 750
Gln Lys Leu Glu His Leu Thr Gly Asn Lys Glu Arg Met Glu Asp Glu
                755                 760                 765
Val Lys Asn Leu Thr Leu Gln Leu Glu Gln Glu Ser Asn Lys Arg Leu
                770                 775                 780
Leu Leu Gln Asn Glu Leu Lys Thr Gln Ala Phe Glu Ala Asp Asn Leu
785                 790                 795                 800
Lys Gly Leu Glu Lys Gln Met Lys Gln Glu Ile Asn Thr Leu Leu Glu
                805                 810                 815
Ala Lys Arg Leu Leu Glu Phe Glu Leu Ala Gln Leu Thr Lys Gln Tyr
                820                 825                 830
Arg Gly Asn Glu Gly Gln Met Arg Glu Leu Gln Asp Gln Leu Glu Ala
                835                 840                 845
Glu Gln Tyr Phe Ser Thr Leu Tyr Lys Thr Gln Val Lys Glu Leu Lys
                850                 855                 860
Glu Glu Ile Glu Glu Lys Asn Arg Glu Asn Leu Lys Lys Ile Gln Glu
865                 870                 875                 880
Leu Gln Asn Glu Lys Glu Thr Leu Ala Thr Gln Leu Asp Leu Ala Glu
                885                 890                 895
Thr Lys Ala Glu Ser Glu Gln Leu Ala Arg Gly Leu Leu Glu Glu Gln
                900                 905                 910
Tyr Phe Glu Leu Thr Gln Glu Ser Lys Lys Ala Ala Ser Arg Asn Arg
                915                 920                 925
Gln Glu Ile Thr Asp Lys Asp His Thr Val Ser Arg Leu Glu Glu Ala
                930                 935                 940
Asn Ser Met Leu Thr Lys Asp Ile Glu Ile Leu Arg Arg Glu Asn Glu
945                 950                 955                 960
Glu Leu Thr Glu Lys Met Lys Lys Ala Glu Glu Glu Tyr Lys Leu Glu
                965                 970                 975
Lys Glu Glu Glu Ile Ser Asn Leu Lys Ala Ala Phe Glu Lys Asn Ile
                980                 985                 990
Asn Thr Glu Arg Thr Leu Lys Thr Gln Ala Val Asn Lys Leu Ala Glu
                995                 1000                1005
Ile Met Asn Arg Lys Asp Phe Lys Ile Asp Arg Lys Lys Ala Asn Thr
                1010                1015                1020
Gln Asp Leu Arg Lys Lys Glu Lys Glu Asn Arg Lys Leu Gln Leu Glu
1025                1030                1035                1040
Leu Asn Gln Glu Arg Glu Lys Phe Asn Gln Met Val Val Lys His Gln
                1045                1050                1055
Lys Glu Leu Asn Asp Met Gln Ala Gln Leu Val Glu Glu Cys Ala His
                1060                1065                1070
Arg Asn Glu Leu Gln Met Gln Leu Ala Ser Lys Glu Ser Asp Ile Glu
                1075                1080                1085
Gln Leu Arg Ala Lys Leu Leu Asp Leu Ser Asp Ser Thr Ser Val Ala
                1090                1095                1100
Ser Phe Pro Ser Ala Asp Glu Thr Asp Gly Asn Leu Pro Glu Ser Arg
1105                1110                1115                1120
Ile Glu Gly Trp Leu Ser Val Pro Asn Arg Gly Asn Ile Lys Arg Tyr
                1125                1130                1135
```

```
Gly Trp Lys Lys Gln Tyr Val Val Ser Ser Lys Ile Leu Phe
            1140                1145                1150

Tyr Asn Asp Glu Gln Asp Lys Glu Gln Ser Asn Pro Ser Met Val Leu
            1155                1160                1165

Asp Ile Asp Lys Leu Phe His Val Arg Pro Val Thr Gln Gly Asp Val
            1170                1175                1180

Tyr Arg Ala Glu Thr Glu Glu Ile Pro Lys Ile Phe Gln Ile Leu Tyr
1185                1190                1195                1200

Ala Asn Glu Gly Glu Cys Arg Lys Asp Val Glu Met Glu Pro Val Gln
                1205                1210                1215

Gln Ala Glu Lys Thr Asn Phe Gln Asn His Lys Gly His Glu Phe Ile
                1220                1225                1230

Pro Thr Leu Tyr His Phe Pro Ala Asn Cys Asp Ala Cys Ala Lys Pro
            1235                1240                1245

Leu Trp His Val Phe Lys Pro Pro Ala Leu Glu Cys Arg Arg Cys
            1250                1255                1260

His Val Lys Cys His Arg Asp His Leu Asp Lys Lys Glu Asp Leu Ile
1265                1270                1275                1280

Cys Pro Cys Lys Val Ser Tyr Asp Val Thr Ser Ala Arg Asp Met Leu
                1285                1290                1295

Leu Leu Ala Cys Ser Gln Asp Glu Gln Lys Lys Trp Val Thr His Leu
            1300                1305                1310

Val Lys Lys Ile Pro Lys Asn Pro Pro Ser Gly Phe Val Arg Ala Ser
            1315                1320                1325

Pro Arg Thr Leu Ser Thr Arg Ser Thr Ala Asn Gln Ser Phe Arg Lys
            1330                1335                1340

Val Val Lys Asn Thr Ser Gly Lys Thr Ser
1345                1350

<210> SEQ ID NO 26
<211> LENGTH: 1388
<212> TYPE: PRT
<213> ORGANISM: Homo sapiens

<400> SEQUENCE: 26

Met Ser Arg Pro Pro Thr Gly Lys Met Pro Gly Ala Pro Glu Thr
1               5                   10                  15

Ala Pro Gly Asp Gly Ala Gly Ala Ser Arg Gln Arg Lys Leu Glu Ala
                20                  25                  30

Leu Ile Arg Asp Pro Arg Ser Pro Ile Asn Val Glu Ser Leu Leu Asp
            35                  40                  45

Gly Leu Asn Ser Leu Val Leu Asp Leu Asp Phe Pro Ala Leu Arg Lys
        50                  55                  60

Asn Lys Asn Ile Asp Asn Phe Leu Asn Arg Tyr Glu Lys Ile Val Lys
65                  70                  75                  80

Lys Ile Arg Gly Leu Gln Met Lys Ala Glu Asp Tyr Asp Val Val Lys
                85                  90                  95

Val Ile Gly Arg Gly Ala Phe Gly Glu Val Gln Leu Val Arg His Lys
            100                 105                 110

Ala Ser Gln Lys Val Tyr Ala Met Lys Leu Leu Ser Lys Phe Glu Met
        115                 120                 125

Ile Lys Arg Ser Asp Ser Ala Phe Phe Trp Glu Glu Arg Asp Ile Met
    130                 135                 140

Ala Phe Ala Asn Ser Pro Trp Val Val Gln Leu Phe Tyr Ala Phe Gln
```

-continued

```
            145                 150                 155                 160
Asp Asp Arg Tyr Leu Tyr Met Val Met Glu Tyr Met Pro Gly Gly Asp
                165                 170                 175
Leu Val Asn Leu Met Ser Asn Tyr Asp Val Pro Glu Lys Trp Ala Lys
            180                 185                 190
Phe Tyr Thr Ala Glu Val Val Leu Ala Leu Asp Ala Ile His Ser Met
            195                 200                 205
Gly Leu Ile His Arg Asp Val Lys Pro Asp Asn Met Leu Leu Asp Lys
        210                 215                 220
His Gly His Leu Lys Leu Ala Asp Phe Gly Thr Cys Met Lys Met Asp
225                 230                 235                 240
Glu Thr Gly Met Val His Cys Asp Thr Ala Val Gly Thr Pro Asp Tyr
                245                 250                 255
Ile Ser Pro Glu Val Leu Lys Ser Gln Gly Gly Asp Gly Phe Tyr Gly
                260                 265                 270
Arg Glu Cys Asp Trp Trp Ser Val Gly Val Phe Leu Tyr Glu Met Leu
            275                 280                 285
Val Gly Asp Thr Pro Phe Tyr Ala Asp Ser Leu Val Gly Thr Tyr Ser
        290                 295                 300
Lys Ile Met Asp His Lys Asn Ser Leu Cys Phe Pro Glu Asp Ala Glu
305                 310                 315                 320
Ile Ser Lys His Ala Lys Asn Leu Ile Cys Ala Phe Leu Thr Asp Arg
                325                 330                 335
Glu Val Arg Leu Gly Arg Asn Gly Val Glu Glu Ile Arg Gln His Pro
            340                 345                 350
Phe Phe Lys Asn Asp Gln Trp His Trp Asp Asn Ile Arg Glu Thr Ala
            355                 360                 365
Ala Pro Val Val Pro Glu Leu Ser Ser Asp Ile Asp Ser Ser Asn Phe
        370                 375                 380
Asp Asp Ile Glu Asp Asp Lys Gly Asp Val Glu Thr Phe Pro Ile Pro
385                 390                 395                 400
Lys Ala Phe Val Gly Asn Gln Leu Pro Phe Ile Gly Phe Thr Tyr Tyr
                405                 410                 415
Arg Glu Asn Leu Leu Leu Ser Asp Ser Pro Ser Cys Arg Glu Thr Asp
            420                 425                 430
Ser Ile Gln Ser Arg Lys Asn Glu Glu Ser Gln Glu Ile Gln Lys Lys
        435                 440                 445
Leu Tyr Thr Leu Glu Glu His Leu Ser Asn Glu Met Gln Ala Lys Glu
        450                 455                 460
Glu Leu Glu Gln Lys Cys Lys Ser Val Asn Thr Arg Leu Glu Lys Thr
465                 470                 475                 480
Ala Lys Glu Leu Glu Glu Glu Ile Thr Leu Arg Lys Ser Val Glu Ser
                485                 490                 495
Ala Leu Arg Gln Leu Glu Arg Glu Lys Ala Leu Leu Gln His Lys Asn
            500                 505                 510
Ala Glu Tyr Gln Arg Lys Ala Asp His Glu Ala Asp Lys Lys Arg Asn
            515                 520                 525
Leu Glu Asn Asp Val Asn Ser Leu Lys Asp Gln Leu Glu Asp Leu Lys
        530                 535                 540
Lys Arg Asn Gln Asn Ser Gln Ile Ser Thr Glu Lys Val Asn Gln Leu
545                 550                 555                 560
Gln Arg Gln Leu Asp Glu Thr Asn Ala Leu Leu Arg Thr Glu Ser Asp
                565                 570                 575
```

```
Thr Ala Ala Arg Leu Arg Lys Thr Gln Ala Glu Ser Ser Lys Gln Ile
            580                 585                 590

Gln Gln Leu Glu Ser Asn Asn Arg Asp Leu Gln Asp Lys Asn Cys Leu
        595                 600                 605

Leu Glu Thr Ala Lys Leu Lys Leu Glu Lys Glu Phe Ile Asn Leu Gln
        610                 615                 620

Ser Ala Leu Glu Ser Glu Arg Arg Asp Arg Thr His Gly Ser Glu Ile
625                 630                 635                 640

Ile Asn Asp Leu Gln Gly Arg Ile Cys Gly Leu Glu Glu Asp Leu Lys
                645                 650                 655

Asn Gly Lys Ile Leu Leu Ala Lys Val Glu Leu Glu Lys Arg Gln Leu
            660                 665                 670

Gln Glu Arg Phe Thr Asp Leu Glu Lys Glu Lys Ser Asn Met Glu Ile
        675                 680                 685

Asp Met Thr Tyr Gln Leu Lys Val Ile Gln Gln Ser Leu Glu Gln Glu
        690                 695                 700

Glu Ala Glu His Lys Ala Thr Lys Ala Arg Leu Ala Asp Lys Asn Lys
705                 710                 715                 720

Ile Tyr Glu Ser Ile Glu Glu Ala Lys Ser Glu Ala Met Lys Glu Met
                725                 730                 735

Glu Lys Lys Leu Leu Glu Glu Arg Thr Leu Lys Gln Lys Val Glu Asn
            740                 745                 750

Leu Leu Leu Glu Ala Glu Lys Arg Cys Ser Leu Leu Asp Cys Asp Leu
        755                 760                 765

Lys Gln Ser Gln Gln Lys Ile Asn Glu Leu Leu Lys Gln Lys Asp Val
        770                 775                 780

Leu Asn Glu Asp Val Arg Asn Leu Thr Leu Lys Ile Glu Gln Glu Thr
785                 790                 795                 800

Gln Lys Arg Cys Leu Thr Gln Asn Asp Leu Lys Met Gln Thr Gln Gln
                805                 810                 815

Val Asn Thr Leu Lys Met Ser Glu Lys Gln Leu Lys Gln Glu Asn Asn
            820                 825                 830

His Leu Met Glu Met Lys Met Asn Leu Glu Lys Gln Asn Ala Glu Leu
        835                 840                 845

Arg Lys Glu Arg Gln Asp Ala Asp Gly Gln Met Lys Glu Leu Gln Asp
        850                 855                 860

Gln Leu Glu Ala Glu Gln Tyr Phe Ser Thr Leu Tyr Lys Thr Gln Val
865                 870                 875                 880

Arg Glu Leu Lys Glu Glu Cys Glu Glu Lys Thr Lys Leu Gly Lys Glu
                885                 890                 895

Leu Gln Gln Lys Lys Gln Glu Leu Gln Asp Glu Arg Asp Ser Leu Ala
            900                 905                 910

Ala Gln Leu Glu Ile Thr Leu Thr Lys Ala Asp Ser Glu Gln Leu Ala
        915                 920                 925

Arg Ser Ile Ala Glu Glu Gln Tyr Ser Asp Leu Glu Lys Glu Lys Ile
        930                 935                 940

Met Lys Glu Leu Glu Ile Lys Glu Met Met Ala Arg His Lys Gln Glu
945                 950                 955                 960

Leu Thr Glu Lys Asp Ala Thr Ile Ala Ser Leu Glu Glu Thr Asn Arg
                965                 970                 975

Thr Leu Thr Ser Asp Val Ala Asn Leu Ala Asn Glu Lys Glu Glu Leu
            980                 985                 990
```

```
Asn Asn Lys Leu Lys Asp Val Gln Glu Gln Leu Ser Arg Leu Lys Asp
            995                 1000                1005

Glu Glu Ile Ser Ala Ala Ala Ile Lys Ala Gln Phe Glu Lys Gln Leu
        1010                1015                1020

Leu Thr Glu Arg Thr Leu Lys Thr Gln Ala Val Asn Lys Leu Ala Glu
1025                1030                1035                1040

Ile Met Asn Arg Lys Glu Pro Val Lys Arg Gly Asn Asp Thr Asp Val
            1045                1050                1055

Arg Arg Lys Glu Lys Glu Asn Arg Lys Leu His Met Glu Leu Lys Ser
            1060                1065                1070

Glu Arg Glu Lys Leu Thr Gln Gln Met Ile Lys Tyr Gln Lys Glu Leu
            1075                1080                1085

Asn Glu Met Gln Ala Gln Ile Ala Glu Glu Ser Gln Ile Arg Ile Glu
            1090                1095                1100

Leu Gln Met Thr Leu Asp Ser Lys Asp Ser Asp Ile Glu Gln Leu Arg
1105                1110                1115                1120

Ser Gln Leu Gln Ala Leu His Ile Gly Leu Asp Ser Ser Ser Ile Gly
            1125                1130                1135

Ser Gly Pro Gly Asp Ala Glu Ala Asp Asp Gly Phe Pro Glu Ser Arg
            1140                1145                1150

Leu Glu Gly Trp Leu Ser Leu Pro Val Arg Asn Asn Thr Lys Lys Phe
            1155                1160                1165

Gly Trp Val Lys Lys Tyr Val Ile Val Ser Ser Lys Lys Ile Leu Phe
            1170                1175                1180

Tyr Asp Ser Glu Gln Asp Lys Glu Gln Ser Asn Pro Tyr Met Val Leu
1185                1190                1195                1200

Asp Ile Asp Lys Leu Phe His Val Arg Pro Val Thr Gln Thr Asp Val
            1205                1210                1215

Tyr Arg Ala Asp Ala Lys Glu Ile Pro Arg Ile Phe Gln Ile Leu Tyr
            1220                1225                1230

Ala Asn Glu Gly Glu Ser Lys Lys Glu Gln Glu Phe Pro Val Glu Pro
            1235                1240                1245

Val Gly Glu Lys Ser Asn Tyr Ile Cys His Lys Gly His Glu Phe Ile
            1250                1255                1260

Pro Thr Leu Tyr His Phe Pro Thr Asn Cys Glu Ala Cys Met Lys Pro
1265                1270                1275                1280

Leu Trp His Met Phe Lys Pro Pro Ala Leu Glu Cys Arg Arg Cys
            1285                1290                1295

His Ile Lys Cys His Lys Asp His Met Asp Lys Lys Glu Glu Ile Ile
            1300                1305                1310

Ala Pro Cys Lys Val Tyr Tyr Asp Ile Ser Thr Ala Lys Asn Leu Leu
            1315                1320                1325

Leu Leu Ala Asn Ser Thr Glu Glu Gln Gln Lys Trp Val Ser Arg Leu
            1330                1335                1340

Val Lys Lys Ile Pro Lys Lys Pro Pro Ala Pro Asp Pro Phe Ala Arg
1345                1350                1355                1360

Ser Ser Pro Arg Thr Ser Met Lys Ile Gln Gln Asn Gln Ser Ile Arg
            1365                1370                1375

Arg Pro Ser Arg Gln Leu Ala Pro Asn Lys Pro Ser
            1380                1385

<210> SEQ ID NO 27
<211> LENGTH: 948
<212> TYPE: PRT
```

<213> ORGANISM: Homo sapiens

<400> SEQUENCE: 27

```
Met Ala Glu Ala Asn Asn Pro Ser Glu Gln Glu Leu Glu Ser Glu Pro
1               5                   10                  15

Arg Ser Trp Ser Leu Leu Glu Gln Leu Gly Leu Ala Gly Ala Asp Leu
            20                  25                  30

Ala Ala Pro Gly Val Gln Gln Leu Glu Leu Glu Arg Glu Arg Leu
        35                  40                  45

Arg Arg Glu Ile Arg Lys Glu Leu Lys Leu Lys Glu Gly Ala Glu Asn
    50                  55                  60

Leu Arg Arg Ala Thr Thr Asp Leu Gly Arg Ser Leu Gly Pro Val Glu
65                  70                  75                  80

Leu Leu Leu Arg Gly Ser Ser Arg Arg Leu Asp Leu Leu His Gln Gln
                85                  90                  95

Leu Gln Glu Leu His Ala His Val Val Leu Pro Asp Pro Ala Ala Thr
            100                 105                 110

His Asp Gly Pro Gln Ser Pro Gly Ala Gly Gly Pro Thr Cys Ser Ala
        115                 120                 125

Thr Asn Leu Ser Arg Val Ala Gly Leu Glu Lys Gln Leu Ala Ile Glu
    130                 135                 140

Leu Lys Val Lys Gln Gly Ala Glu Asn Met Ile Gln Thr Tyr Ser Asn
145                 150                 155                 160

Gly Ser Thr Lys Asp Arg Lys Leu Leu Leu Thr Ala Gln Gln Met Leu
                165                 170                 175

Gln Asp Ser Lys Thr Lys Ile Asp Ile Ile Arg Met Gln Leu Arg Arg
            180                 185                 190

Ala Leu Gln Ala Gly Gln Leu Glu Asn Gln Ala Ala Pro Asp Asp Thr
        195                 200                 205

Gln Gly Ser Pro Asp Leu Gly Ala Val Glu Leu Arg Ile Glu Glu Leu
    210                 215                 220

Arg His His Phe Arg Val Glu His Ala Val Ala Glu Gly Ala Lys Asn
225                 230                 235                 240

Val Leu Arg Leu Leu Ser Ala Ala Lys Ala Pro Asp Arg Lys Ala Val
                245                 250                 255

Ser Glu Ala Gln Glu Lys Leu Thr Glu Ser Asn Gln Lys Leu Gly Leu
            260                 265                 270

Leu Arg Glu Ala Leu Glu Arg Arg Leu Gly Glu Leu Pro Ala Asp His
        275                 280                 285

Pro Lys Gly Arg Leu Leu Arg Glu Glu Leu Ala Ala Ala Ser Ser Ala
    290                 295                 300

Ala Phe Ser Thr Arg Leu Ala Gly Pro Phe Pro Ala Thr His Tyr Ser
305                 310                 315                 320

Thr Leu Cys Lys Pro Ala Pro Leu Thr Gly Thr Leu Glu Val Arg Val
                325                 330                 335

Val Gly Cys Arg Asp Leu Pro Glu Thr Ile Pro Trp Asn Pro Thr Pro
            340                 345                 350

Ser Met Gly Gly Pro Gly Thr Pro Asp Ser Arg Pro Pro Phe Leu Ser
        355                 360                 365

Arg Pro Ala Arg Gly Leu Tyr Ser Arg Ser Gly Ser Leu Ser Gly Arg
    370                 375                 380

Ser Ser Leu Lys Ala Glu Ala Glu Asn Thr Ser Glu Val Ser Thr Val
385                 390                 395                 400
```

-continued

```
Leu Lys Leu Asp Asn Thr Val Val Gly Gln Thr Ser Trp Lys Pro Cys
                405                 410                 415
Gly Pro Asn Ala Trp Asp Gln Ser Phe Thr Leu Glu Leu Glu Arg Ala
            420                 425                 430
Arg Glu Leu Glu Leu Ala Val Phe Trp Arg Asp Gln Arg Gly Leu Cys
        435                 440                 445
Ala Leu Lys Phe Leu Lys Leu Glu Asp Phe Leu Asp Asn Glu Arg His
    450                 455                 460
Glu Val Gln Leu Asp Met Glu Pro Gln Gly Cys Leu Val Ala Glu Val
465                 470                 475                 480
Thr Phe Arg Asn Pro Val Ile Glu Arg Ile Pro Arg Leu Arg Arg Gln
                485                 490                 495
Lys Lys Ile Phe Ser Lys Gln Gln Gly Lys Ala Phe Gln Arg Ala Arg
            500                 505                 510
Gln Met Asn Ile Asp Val Ala Thr Trp Val Arg Leu Leu Arg Arg Leu
        515                 520                 525
Ile Pro Asn Ala Thr Gly Thr Gly Thr Phe Ser Pro Gly Ala Ser Pro
    530                 535                 540
Gly Ser Glu Ala Arg Thr Thr Gly Asp Ile Ser Val Glu Lys Leu Asn
545                 550                 555                 560
Leu Gly Thr Asp Ser Asp Ser Ser Pro Gln Lys Ser Ser Arg Asp Pro
                565                 570                 575
Pro Ser Ser Pro Ser Ser Leu Ser Ser Pro Ile Gln Glu Ser Thr Ala
            580                 585                 590
Pro Glu Leu Pro Ser Glu Thr Gln Glu Thr Pro Gly Pro Ala Leu Cys
        595                 600                 605
Ser Pro Leu Arg Lys Ser Pro Leu Thr Leu Glu Asp Phe Lys Phe Leu
    610                 615                 620
Ala Val Leu Gly Arg Gly His Phe Gly Lys Val Leu Leu Ser Glu Phe
625                 630                 635                 640
Arg Pro Ser Gly Glu Leu Phe Ala Ile Lys Ala Leu Lys Lys Gly Asp
                645                 650                 655
Ile Val Ala Arg Asp Glu Val Glu Ser Leu Met Cys Glu Lys Arg Ile
            660                 665                 670
Leu Ala Ala Val Thr Ser Ala Gly His Pro Phe Leu Val Asn Leu Phe
        675                 680                 685
Gly Cys Phe Gln Thr Pro Glu His Val Cys Phe Val Met Glu Tyr Ser
    690                 695                 700
Ala Gly Gly Asp Leu Met Leu His Ile His Ser Asp Val Phe Ser Glu
705                 710                 715                 720
Pro Arg Ala Ile Phe Tyr Ser Ala Cys Val Val Leu Gly Leu Gln Phe
                725                 730                 735
Leu His Glu His Lys Ile Val Tyr Arg Asp Leu Lys Leu Asp Asn Leu
            740                 745                 750
Leu Leu Asp Thr Glu Gly Tyr Val Lys Ile Ala Asp Phe Gly Leu Cys
        755                 760                 765
Lys Glu Gly Met Gly Tyr Gly Asp Arg Thr Ser Thr Phe Cys Gly Thr
    770                 775                 780
Pro Glu Phe Leu Ala Pro Glu Val Leu Thr Asp Thr Ser Tyr Thr Arg
785                 790                 795                 800
Ala Val Asp Trp Trp Gly Leu Gly Val Leu Leu Tyr Glu Met Leu Val
                805                 810                 815
Gly Glu Ser Pro Phe Pro Gly Asp Asp Glu Glu Glu Val Phe Asp Ser
```

```
                      820                 825                 830
Ile Val Asn Asp Glu Val Arg Tyr Pro Arg Phe Leu Ser Ala Glu Ala
            835                 840                 845
Ile Gly Ile Met Arg Arg Leu Leu Arg Arg Asn Pro Glu Arg Arg Leu
        850                 855                 860
Gly Ser Ser Glu Arg Asp Ala Glu Asp Val Lys Lys Gln Pro Phe Phe
865                 870                 875                 880
Arg Thr Leu Gly Trp Glu Ala Leu Leu Ala Arg Arg Leu Pro Pro Pro
                885                 890                 895
Phe Val Pro Thr Leu Ser Gly Arg Thr Asp Val Ser Asn Phe Asp Glu
            900                 905                 910
Glu Phe Thr Gly Glu Ala Pro Thr Leu Ser Pro Pro Arg Asp Ala Arg
        915                 920                 925
Pro Leu Thr Ala Ala Glu Gln Ala Ala Phe Leu Asp Phe Asp Phe Val
930                 935                 940
Ala Gly Gly Cys
945

<210> SEQ ID NO 28
<211> LENGTH: 984
<212> TYPE: PRT
<213> ORGANISM: Homo sapiens

<400> SEQUENCE: 28

Met Ala Ser Asn Pro Glu Arg Gly Glu Ile Leu Leu Thr Glu Leu Gln
1               5                   10                  15
Gly Asp Ser Arg Ser Leu Pro Phe Ser Glu Asn Val Ser Ala Val Gln
            20                  25                  30
Lys Leu Asp Phe Ser Asp Thr Met Val Gln Gln Lys Leu Asp Asp Ile
        35                  40                  45
Lys Asp Arg Ile Lys Arg Glu Ile Arg Lys Glu Leu Lys Ile Lys Glu
    50                  55                  60
Gly Ala Glu Asn Leu Arg Lys Val Thr Thr Asp Lys Lys Ser Leu Ala
65                  70                  75                  80
Tyr Val Asp Asn Ile Leu Lys Lys Ser Asn Lys Lys Leu Glu Glu Leu
                85                  90                  95
His His Lys Leu Gln Glu Leu Asn Ala His Ile Val Val Ser Asp Pro
            100                 105                 110
Glu Asp Ile Thr Asp Cys Pro Arg Thr Pro Asp Thr Pro Asn Asn Asp
        115                 120                 125
Pro Arg Cys Ser Thr Ser Asn Asn Arg Leu Lys Ala Leu Gln Lys Gln
    130                 135                 140
Leu Asp Ile Glu Leu Lys Val Lys Gln Gly Ala Glu Asn Met Ile Gln
145                 150                 155                 160
Met Tyr Ser Asn Gly Ser Ser Lys Asp Arg Lys Leu His Gly Thr Ala
                165                 170                 175
Gln Gln Leu Leu Gln Asp Ser Lys Thr Lys Ile Glu Val Ile Arg Met
            180                 185                 190
Gln Ile Leu Gln Ala Val Gln Thr Asn Glu Leu Ala Phe Asp Asn Ala
        195                 200                 205
Lys Pro Val Ile Ser Pro Leu Glu Leu Arg Met Glu Glu Leu Arg His
    210                 215                 220
His Phe Arg Ile Glu Phe Ala Val Ala Glu Gly Ala Lys Asn Val Met
225                 230                 235                 240
```

```
Lys Leu Leu Gly Ser Gly Lys Val Thr Asp Arg Lys Ala Leu Ser Glu
                245                 250                 255

Ala Gln Ala Arg Phe Asn Glu Ser Ser Gln Lys Leu Asp Leu Leu Lys
            260                 265                 270

Tyr Ser Leu Glu Gln Arg Leu Asn Glu Val Pro Lys Asn His Pro Lys
        275                 280                 285

Ser Arg Ile Ile Ile Glu Glu Leu Ser Leu Val Ala Ala Ser Pro Thr
    290                 295                 300

Leu Ser Pro Arg Gln Ser Met Ile Ser Thr Gln Asn Gln Tyr Ser Thr
305                 310                 315                 320

Leu Ser Lys Pro Ala Ala Leu Thr Gly Thr Leu Glu Val Arg Leu Met
                325                 330                 335

Gly Cys Gln Asp Ile Leu Glu Asn Val Pro Gly Arg Ser Lys Ala Thr
            340                 345                 350

Ser Val Ala Leu Pro Gly Trp Ser Pro Ser Glu Thr Arg Ser Ser Phe
        355                 360                 365

Met Ser Arg Thr Ser Lys Ser Lys Ser Gly Ser Ser Arg Asn Leu Leu
    370                 375                 380

Lys Thr Asp Asp Leu Ser Asn Asp Val Cys Ala Val Leu Lys Leu Asp
385                 390                 395                 400

Asn Thr Val Val Gly Gln Thr Ser Trp Lys Pro Ile Ser Asn Gln Ser
                405                 410                 415

Trp Asp Gln Lys Phe Thr Leu Glu Leu Asp Arg Ser Arg Glu Leu Glu
            420                 425                 430

Ile Ser Val Tyr Trp Arg Asp Trp Arg Ser Leu Cys Ala Val Lys Phe
        435                 440                 445

Leu Arg Leu Glu Asp Phe Leu Asp Asn Gln Arg His Gly Met Cys Leu
    450                 455                 460

Tyr Leu Glu Pro Gln Gly Thr Leu Phe Ala Glu Val Thr Phe Phe Asn
465                 470                 475                 480

Pro Val Ile Glu Arg Arg Pro Lys Leu Gln Arg Gln Lys Lys Ile Phe
                485                 490                 495

Ser Lys Gln Gln Gly Lys Thr Phe Leu Arg Ala Pro Gln Met Asn Ile
            500                 505                 510

Asn Ile Ala Thr Trp Gly Arg Leu Val Arg Arg Ala Ile Pro Thr Val
        515                 520                 525

Asn His Ser Gly Thr Phe Ser Pro Gln Ala Pro Val Pro Thr Thr Val
    530                 535                 540

Pro Val Val Asp Val Arg Ile Pro Gln Leu Ala Pro Pro Ala Ser Asp
545                 550                 555                 560

Ser Thr Val Thr Lys Leu Asp Phe Asp Leu Glu Pro Glu Pro Pro Pro
                565                 570                 575

Ala Pro Pro Arg Ala Ser Ser Leu Gly Glu Ile Asp Glu Ser Ser Glu
            580                 585                 590

Leu Arg Val Leu Asp Ile Pro Gly Gln Asp Ser Glu Thr Val Phe Asp
        595                 600                 605

Ile Gln Asn Asp Arg Asn Ser Ile Leu Pro Lys Ser Gln Ser Glu Tyr
    610                 615                 620

Lys Pro Asp Thr Pro Gln Ser Gly Leu Glu Tyr Ser Gly Ile Gln Glu
625                 630                 635                 640

Leu Glu Asp Arg Arg Ser Gln Gln Arg Phe Gln Phe Asn Leu Gln Asp
                645                 650                 655

Phe Arg Cys Cys Ala Val Leu Gly Arg Gly His Phe Gly Lys Val Leu
```

-continued

```
            660                 665                 670
Leu Ala Glu Tyr Lys Asn Thr Asn Glu Met Phe Ala Ile Lys Ala Leu
        675                 680                 685

Lys Lys Gly Asp Ile Val Ala Arg Asp Glu Val Asp Ser Leu Met Cys
        690                 695                 700

Glu Lys Arg Ile Phe Glu Thr Val Asn Ser Val Arg His Pro Phe Leu
705                 710                 715                 720

Val Asn Leu Phe Ala Cys Phe Gln Thr Lys Glu His Val Cys Phe Val
                725                 730                 735

Met Glu Tyr Ala Ala Gly Gly Asp Leu Met Met His Ile His Thr Asp
            740                 745                 750

Val Phe Ser Glu Pro Arg Ala Val Phe Tyr Ala Ala Cys Val Val Leu
        755                 760                 765

Gly Leu Gln Tyr Leu His Glu His Lys Ile Val Tyr Arg Asp Leu Lys
        770                 775                 780

Leu Asp Asn Leu Leu Leu Asp Thr Glu Gly Phe Val Lys Ile Ala Asp
785                 790                 795                 800

Phe Gly Leu Cys Lys Glu Gly Met Gly Tyr Gly Asp Arg Thr Ser Thr
                805                 810                 815

Phe Cys Gly Thr Pro Glu Phe Leu Ala Pro Glu Val Leu Thr Glu Thr
            820                 825                 830

Ser Tyr Thr Arg Ala Val Asp Trp Trp Gly Leu Gly Val Leu Ile Tyr
        835                 840                 845

Glu Met Leu Val Gly Glu Ser Pro Phe Pro Gly Asp Asp Glu Glu Glu
        850                 855                 860

Val Phe Asp Ser Ile Val Asn Asp Glu Val Arg Tyr Pro Arg Phe Leu
865                 870                 875                 880

Ser Thr Glu Ala Ile Ser Ile Met Arg Arg Leu Leu Arg Arg Asn Pro
                885                 890                 895

Glu Arg Arg Leu Gly Ala Ser Glu Lys Asp Ala Glu Asp Val Lys Lys
            900                 905                 910

His Pro Phe Phe Arg Leu Ile Asp Trp Ser Ala Leu Met Asp Lys Lys
        915                 920                 925

Val Lys Pro Pro Phe Ile Pro Thr Ile Arg Gly Arg Glu Asp Val Ser
        930                 935                 940

Asn Phe Asp Asp Glu Phe Thr Ser Glu Ala Pro Ile Leu Thr Pro Pro
945                 950                 955                 960

Arg Glu Pro Arg Ile Leu Ser Glu Glu Gln Glu Met Phe Arg Asp
                965                 970                 975

Phe Asp Tyr Ile Ala Asp Trp Cys
            980

<210> SEQ ID NO 29
<211> LENGTH: 686
<212> TYPE: PRT
<213> ORGANISM: Homo sapiens

<400> SEQUENCE: 29

Met Thr Asp Ala Leu Leu Pro Ala Ala Pro Gln Pro Leu Glu Lys Lys
1               5                   10                  15

Asn Asp Gly Tyr Phe Arg Lys Gly Cys Asn Pro Leu Ala Gln Thr Gly
            20                  25                  30

Arg Ser Lys Leu Gln Asn Gln Arg Ala Ala Leu Asn Gln Gln Ile Leu
        35                  40                  45
```

```
Lys Ala Val Arg Met Arg Thr Gly Ala Glu Asn Leu Leu Lys Val Ala
 50                  55                  60

Thr Asn Ser Lys Val Arg Glu Gln Val Arg Leu Glu Leu Ser Phe Val
 65                  70                  75                  80

Asn Ser Asp Leu Gln Met Leu Lys Glu Leu Glu Gly Leu Asn Ile
                     85                  90                  95

Ser Val Gly Val Tyr Gln Asn Thr Glu Glu Ala Phe Thr Ile Pro Leu
                100                 105                 110

Ile Pro Leu Gly Leu Lys Glu Thr Lys Asp Val Asp Phe Ala Val Val
                115                 120                 125

Leu Lys Asp Phe Ile Leu Glu His Tyr Ser Glu Asp Gly Tyr Leu Tyr
    130                 135                 140

Glu Asp Glu Ile Ala Asp Leu Met Asp Leu Arg Gln Ala Cys Arg Thr
145                 150                 155                 160

Pro Ser Arg Asp Glu Ala Gly Val Glu Leu Leu Met Thr Tyr Phe Ile
                165                 170                 175

Gln Leu Gly Phe Val Glu Ser Arg Phe Phe Pro Thr Arg Gln Met
                180                 185                 190

Gly Leu Leu Phe Thr Trp Tyr Asp Ser Leu Thr Gly Val Pro Val Ser
                195                 200                 205

Gln Gln Asn Leu Leu Glu Lys Ala Ser Val Leu Phe Asn Thr Gly
    210                 215                 220

Ala Leu Tyr Thr Gln Ile Gly Thr Arg Cys Asp Arg Gln Thr Gln Ala
225                 230                 235                 240

Gly Leu Glu Ser Ala Ile Asp Ala Phe Gln Arg Ala Gly Val Leu
                245                 250                 255

Asn Tyr Leu Lys Asp Thr Phe Thr His Thr Pro Ser Tyr Asp Met Ser
                260                 265                 270

Pro Ala Met Leu Ser Val Leu Val Lys Met Met Leu Ala Gln Ala Gln
                275                 280                 285

Glu Ser Val Phe Glu Lys Ile Ser Leu Pro Gly Ile Arg Asn Glu Phe
                290                 295                 300

Phe Met Leu Val Lys Val Ala Gln Glu Ala Ala Lys Val Gly Glu Val
305                 310                 315                 320

Tyr Gln Gln Leu His Ala Ala Met Ser Gln Ala Pro Val Lys Glu Asn
                325                 330                 335

Ile Pro Tyr Ser Trp Ala Ser Leu Ala Cys Val Lys Ala His His Tyr
                340                 345                 350

Ala Ala Leu Ala His Tyr Phe Thr Ala Ile Leu Leu Ile Asp His Gln
    355                 360                 365

Val Lys Pro Gly Thr Asp Leu Asp His Gln Glu Lys Cys Leu Ser Gln
    370                 375                 380

Leu Tyr Asp His Met Pro Glu Gly Leu Thr Pro Leu Ala Thr Leu Lys
385                 390                 395                 400

Asn Asp Gln Gln Arg Arg Gln Leu Gly Lys Ser His Leu Arg Arg Ala
                405                 410                 415

Met Ala His His Glu Glu Ser Val Arg Glu Ala Ser Leu Cys Lys Lys
                420                 425                 430

Leu Arg Ser Ile Glu Val Leu Gln Lys Val Leu Cys Ala Ala Gln Glu
    435                 440                 445

Arg Ser Arg Leu Thr Tyr Ala Gln His Gln Glu Glu Asp Asp Leu Leu
    450                 455                 460

Asn Leu Ile Asp Ala Pro Ser Val Val Ala Lys Thr Glu Gln Glu Val
```

```
                465                 470                 475                 480
Asp Ile Ile Leu Pro Gln Phe Ser Lys Leu Thr Val Thr Asp Phe Phe
                    485                 490                 495

Gln Lys Leu Gly Pro Leu Ser Val Phe Ser Ala Asn Lys Arg Trp Thr
                500                 505                 510

Pro Pro Arg Ser Ile Arg Phe Thr Ala Glu Glu Gly Asp Leu Gly Phe
                515                 520                 525

Thr Leu Arg Gly Asn Ala Pro Val Gln Val His Phe Leu Asp Pro Tyr
            530                 535                 540

Cys Ser Ala Ser Val Ala Gly Ala Arg Glu Gly Asp Tyr Ile Val Ser
545                 550                 555                 560

Ile Gln Leu Val Asp Cys Lys Trp Leu Thr Leu Ser Glu Val Met Lys
                565                 570                 575

Leu Leu Lys Ser Phe Gly Glu Asp Glu Ile Glu Met Lys Val Val Ser
                580                 585                 590

Leu Leu Asp Ser Thr Ser Ser Met His Asn Lys Ser Ala Thr Tyr Ser
            595                 600                 605

Val Gly Met Gln Lys Thr Tyr Ser Met Ile Cys Leu Ala Ile Asp Asp
        610                 615                 620

Asp Asp Lys Thr Asp Lys Thr Lys Lys Ile Ser Lys Lys Leu Ser Phe
625                 630                 635                 640

Leu Ser Trp Gly Thr Asn Lys Asn Arg Gln Lys Ser Ala Ser Thr Leu
                645                 650                 655

Cys Leu Pro Ser Val Gly Ala Ala Arg Pro Gln Val Lys Lys Lys Leu
            660                 665                 670

Pro Ser Pro Phe Ser Leu Leu Asn Ser Asp Ser Ser Trp Tyr
        675                 680                 685

<210> SEQ ID NO 30
<211> LENGTH: 550
<212> TYPE: PRT
<213> ORGANISM: Homo sapiens

<400> SEQUENCE: 30

Met Gln Asp Arg Leu His Ile Leu Glu Asp Leu Asn Met Leu Tyr Ile
1               5                   10                  15

Arg Gln Met Ala Leu Ser Leu Glu Asp Thr Glu Leu Gln Arg Lys Leu
            20                  25                  30

Asp His Glu Ile Arg Met Arg Glu Gly Ala Cys Lys Leu Leu Ala Ala
        35                  40                  45

Cys Ser Gln Arg Glu Gln Ala Leu Glu Ala Thr Lys Ser Leu Leu Val
    50                  55                  60

Cys Asn Ser Arg Ile Leu Ser Tyr Met Gly Glu Leu Gln Arg Arg Lys
65                  70                  75                  80

Glu Ala Gln Val Leu Gly Lys Thr Ser Arg Arg Pro Ser Asp Ser Gly
                85                  90                  95

Pro Pro Ala Glu Arg Ser Pro Cys Arg Gly Arg Val Cys Ile Ser Asp
            100                 105                 110

Leu Arg Ile Pro Leu Met Trp Lys Asp Thr Glu Tyr Phe Lys Asn Lys
        115                 120                 125

Gly Asp Leu His Arg Trp Ala Val Phe Leu Leu Gln Leu Gly Glu
    130                 135                 140

His Ile Gln Asp Thr Glu Met Ile Leu Val Asp Arg Thr Leu Thr Asp
145                 150                 155                 160
```

```
Ile Ser Phe Gln Ser Asn Val Leu Phe Ala Glu Ala Gly Pro Asp Phe
            165                 170                 175

Glu Leu Arg Leu Glu Leu Tyr Gly Ala Cys Val Glu Glu Glu Gly Ala
        180                 185                 190

Leu Thr Gly Gly Pro Lys Arg Leu Ala Thr Lys Leu Ser Ser Ser Leu
    195                 200                 205

Gly Arg Ser Ser Gly Arg Arg Val Arg Ala Ser Leu Asp Ser Ala Gly
210                 215                 220

Gly Ser Gly Ser Ser Pro Ile Leu Leu Pro Thr Pro Val Val Gly Gly
225                 230                 235                 240

Pro Arg Tyr His Leu Leu Ala His Thr Thr Leu Thr Leu Ala Ala Val
                245                 250                 255

Gln Asp Gly Phe Arg Thr His Asp Leu Thr Leu Ala Ser His Glu Glu
            260                 265                 270

Asn Pro Ala Trp Leu Pro Leu Tyr Gly Ser Val Cys Cys Arg Leu Ala
        275                 280                 285

Ala Gln Pro Leu Cys Met Thr Gln Pro Thr Ala Ser Gly Thr Leu Arg
    290                 295                 300

Val Gln Gln Ala Gly Glu Met Gln Asn Trp Ala Gln Val His Gly Val
305                 310                 315                 320

Leu Lys Gly Thr Asn Leu Phe Cys Tyr Arg Gln Pro Glu Asp Ala Asp
                325                 330                 335

Thr Gly Glu Glu Pro Leu Leu Thr Ile Ala Val Asn Lys Glu Thr Arg
            340                 345                 350

Val Arg Ala Gly Glu Leu Asp Gln Ala Leu Gly Arg Pro Phe Thr Leu
        355                 360                 365

Ser Ile Ser Asn Gln Tyr Gly Asp Asp Glu Val Thr His Thr Leu Gln
    370                 375                 380

Thr Glu Ser Arg Glu Ala Leu Gln Ser Trp Met Glu Ala Leu Trp Gln
385                 390                 395                 400

Leu Phe Phe Asp Met Ser Gln Trp Lys Gln Cys Cys Asp Glu Ile Met
                405                 410                 415

Lys Ile Glu Thr Pro Ala Pro Arg Lys Pro Pro Gln Ala Leu Ala Lys
            420                 425                 430

Gln Gly Ser Leu Tyr His Glu Met Ala Ile Glu Pro Leu Asp Asp Ile
        435                 440                 445

Ala Ala Val Thr Asp Ile Leu Thr Gln Arg Glu Gly Ala Arg Leu Glu
    450                 455                 460

Thr Pro Pro Pro Trp Leu Ala Met Phe Thr Asp Gln Pro Ala Leu Pro
465                 470                 475                 480

Asn Pro Cys Ser Pro Ala Ser Val Ala Pro Ala Pro Asp Trp Thr His
                485                 490                 495

Pro Leu Pro Trp Gly Arg Pro Arg Thr Phe Ser Leu Asp Ala Val Pro
            500                 505                 510

Pro Asp His Ser Pro Arg Ala Arg Ser Val Ala Pro Leu Pro Pro Gln
        515                 520                 525

Arg Ser Pro Arg Thr Arg Gly Leu Cys Ser Lys Gly Gln Pro Arg Thr
    530                 535                 540

Trp Leu Gln Ser Pro Val
545                 550

<210> SEQ ID NO 31
<211> LENGTH: 942
<212> TYPE: PRT
```

<213> ORGANISM: Homo sapiens

<400> SEQUENCE: 31

```
Met Ala Ala Ala Ala Glu Pro Gly Ala Arg Ala Trp Leu Gly Gly Gly
1               5                   10                  15

Ser Pro Arg Pro Gly Ser Pro Ala Cys Ser Pro Val Leu Gly Ser Gly
            20                  25                  30

Gly Arg Ala Arg Pro Gly Pro Gly Pro Gly Pro Glu Arg Ala
        35                  40                  45

Gly Val Arg Ala Pro Gly Pro Ala Ala Pro Gly His Ser Phe Arg
    50                  55                  60

Lys Val Thr Leu Thr Lys Pro Thr Phe Cys His Leu Cys Ser Asp Phe
65                  70                  75                  80

Ile Trp Gly Leu Ala Gly Phe Leu Cys Asp Val Cys Asn Phe Met Ser
                85                  90                  95

His Glu Lys Cys Leu Lys His Val Arg Ile Pro Cys Thr Ser Val Ala
            100                 105                 110

Pro Ser Leu Val Arg Val Pro Val Ala His Cys Phe Gly Pro Arg Gly
        115                 120                 125

Leu His Lys Arg Lys Phe Cys Ala Val Cys Arg Lys Val Leu Glu Ala
    130                 135                 140

Pro Ala Leu His Cys Glu Val Cys Glu Leu His Leu His Pro Asp Cys
145                 150                 155                 160

Val Pro Phe Ala Cys Ser Asp Cys Arg Gln Cys His Gln Asp Gly His
                165                 170                 175

Gln Asp His Asp Thr His His His Trp Arg Glu Gly Asn Leu Pro
            180                 185                 190

Ser Gly Ala Arg Cys Glu Val Cys Arg Lys Thr Cys Gly Ser Ser Asp
        195                 200                 205

Val Leu Ala Gly Val Arg Cys Glu Trp Cys Gly Val Gln Ala His Ser
    210                 215                 220

Leu Cys Ser Ala Ala Leu Ala Pro Glu Cys Gly Phe Gly Arg Leu Arg
225                 230                 235                 240

Ser Leu Val Leu Pro Pro Ala Cys Val Arg Leu Pro Gly Gly Phe
                245                 250                 255

Ser Lys Thr Gln Ser Phe Arg Ile Val Glu Ala Ala Glu Pro Gly Glu
            260                 265                 270

Gly Gly Asp Gly Ala Asp Gly Ser Ala Ala Val Gly Pro Gly Arg Glu
        275                 280                 285

Thr Gln Ala Thr Pro Glu Ser Gly Lys Gln Thr Leu Lys Ile Phe Asp
    290                 295                 300

Gly Asp Asp Ala Val Arg Arg Ser Gln Phe Arg Leu Val Thr Val Ser
305                 310                 315                 320

Arg Leu Ala Gly Ala Glu Glu Val Leu Glu Ala Leu Arg Ala His
                325                 330                 335

His Ile Pro Glu Asp Pro Gly His Leu Glu Leu Cys Arg Leu Pro Pro
            340                 345                 350

Ser Ser Gln Ala Cys Asp Ala Trp Ala Gly Lys Ala Gly Ser Ala
        355                 360                 365

Val Ile Ser Glu Glu Gly Arg Ser Pro Gly Ser Gly Glu Ala Thr Pro
    370                 375                 380

Glu Ala Trp Val Ile Arg Ala Leu Pro Arg Ala Gln Glu Val Leu Lys
385                 390                 395                 400
```

-continued

```
Ile Tyr Pro Gly Trp Leu Lys Val Gly Val Ala Tyr Val Ser Val Arg
            405                 410                 415

Val Thr Pro Lys Ser Thr Ala Arg Ser Val Val Leu Glu Val Leu Pro
            420                 425                 430

Leu Leu Gly Arg Gln Ala Glu Ser Pro Glu Ser Phe Gln Leu Val Glu
            435                 440                 445

Val Ala Met Gly Cys Arg His Val Gln Arg Thr Met Leu Met Asp Glu
            450                 455                 460

Gln Pro Leu Leu Asp Arg Leu Gln Asp Ile Arg Gln Met Ser Val Arg
465                 470                 475                 480

Gln Val Ser Gln Thr Arg Phe Tyr Val Ala Glu Ser Arg Asp Val Ala
                    485                 490                 495

Pro His Val Ser Leu Phe Val Gly Gly Leu Pro Pro Gly Leu Ser Pro
                500                 505                 510

Glu Glu Tyr Ser Ser Leu Leu His Glu Ala Gly Ala Thr Lys Ala Thr
            515                 520                 525

Val Val Ser Val Ser His Ile Tyr Ser Ser Gln Gly Ala Val Val Leu
            530                 535                 540

Asp Val Ala Cys Phe Ala Glu Ala Glu Arg Leu Tyr Met Leu Leu Lys
545                 550                 555                 560

Asp Met Ala Val Arg Gly Arg Leu Leu Thr Ala Leu Val Leu Pro Asp
                    565                 570                 575

Leu Leu His Ala Lys Leu Pro Pro Asp Ser Cys Pro Leu Leu Val Phe
                580                 585                 590

Val Asn Pro Lys Ser Gly Gly Leu Lys Gly Arg Asp Leu Leu Cys Ser
            595                 600                 605

Phe Arg Lys Leu Leu Asn Pro His Gln Val Phe Asp Leu Thr Asn Gly
            610                 615                 620

Gly Pro Leu Pro Gly Leu His Leu Phe Ser Gln Val Pro Cys Phe Arg
625                 630                 635                 640

Val Leu Val Cys Gly Gly Asp Gly Thr Val Gly Trp Val Leu Gly Ala
                    645                 650                 655

Leu Glu Glu Thr Arg Tyr Arg Leu Ala Cys Pro Glu Pro Ser Val Ala
                660                 665                 670

Ile Leu Pro Leu Gly Thr Gly Asn Asp Leu Gly Arg Val Leu Arg Trp
            675                 680                 685

Gly Ala Gly Tyr Ser Gly Glu Asp Pro Phe Ser Val Leu Leu Ser Val
            690                 695                 700

Asp Glu Ala Asp Ala Val Leu Met Asp Arg Trp Thr Ile Leu Leu Asp
705                 710                 715                 720

Ala His Glu Ala Gly Ser Ala Glu Asn Asp Thr Ala Asp Ala Glu Pro
                    725                 730                 735

Pro Lys Ile Val Gln Met Ser Asn Tyr Cys Gly Ile Gly Ile Asp Ala
                740                 745                 750

Glu Leu Ser Leu Asp Phe His Gln Ala Arg Glu Glu Pro Gly Lys
            755                 760                 765

Phe Thr Ser Arg Leu His Asn Lys Gly Val Tyr Val Arg Val Gly Leu
            770                 775                 780

Gln Lys Ile Ser His Ser Arg Ser Leu His Lys Gln Ile Arg Leu Gln
785                 790                 795                 800

Val Glu Arg Gln Glu Val Glu Leu Pro Ser Ile Glu Gly Leu Ile Phe
                    805                 810                 815

Ile Asn Ile Pro Ser Trp Gly Ser Gly Ala Asp Leu Trp Gly Ser Asp
```

```
                            820                 825                 830
Ser Asp Thr Arg Phe Glu Lys Pro Arg Met Asp Asp Gly Leu Leu Glu
            835                 840                 845

Val Val Gly Val Thr Gly Val His Met Gly Gln Val Gln Gly Gly
850                 855                 860

Leu Arg Ser Gly Ile Arg Ile Ala Gln Gly Ser Tyr Phe Arg Val Thr
865                 870                 875                 880

Leu Leu Lys Ala Thr Pro Val Gln Val Asp Gly Glu Pro Trp Val Gln
            885                 890                 895

Ala Pro Gly His Met Ile Ile Ser Ala Ala Gly Pro Lys Val His Met
            900                 905                 910

Leu Arg Lys Ala Lys Gln Lys Pro Arg Arg Ala Gly Thr Thr Arg Asp
            915                 920                 925

Ala Arg Ala Asp Ala Ala Pro Ala Pro Glu Ser Asp Pro Arg
            930                 935                 940

<210> SEQ ID NO 32
<211> LENGTH: 1357
<212> TYPE: PRT
<213> ORGANISM: Homo sapiens

<400> SEQUENCE: 32

Met Glu Phe Tyr Glu Ser Ala Tyr Phe Ile Val Leu Ile Pro Ser Ile
1               5                   10                  15

Val Ile Thr Val Ile Phe Leu Phe Phe Trp Leu Phe Met Lys Glu Thr
                20                  25                  30

Leu Tyr Asp Glu Val Leu Ala Lys Gln Lys Arg Glu Gln Lys Leu Ile
            35                  40                  45

Pro Thr Lys Thr Asp Lys Lys Lys Ala Glu Lys Lys Asn Lys Lys
        50                  55                  60

Lys Glu Ile Gln Asn Gly Asn Leu His Glu Ser Asp Ser Glu Ser Val
65                  70                  75                  80

Pro Arg Asp Phe Lys Leu Ser Asp Ala Leu Ala Val Glu Asp Asp Gln
                85                  90                  95

Val Ala Pro Val Pro Leu Asn Val Val Glu Thr Ser Ser Ser Val Arg
            100                 105                 110

Glu Arg Lys Lys Lys Glu Lys Lys Gln Lys Pro Val Leu Glu Glu Gln
        115                 120                 125

Val Ile Lys Glu Ser Asp Ala Ser Lys Ile Pro Gly Lys Lys Val Glu
    130                 135                 140

Pro Val Pro Val Thr Lys Gln Pro Thr Pro Pro Ser Glu Ala Ala Ala
145                 150                 155                 160

Ser Lys Lys Lys Pro Gly Gln Lys Lys Ser Lys Asn Gly Ser Asp Asp
                165                 170                 175

Gln Asp Lys Lys Val Glu Thr Leu Met Val Pro Ser Lys Arg Gln Glu
            180                 185                 190

Ala Leu Pro Leu His Gln Glu Thr Lys Gln Glu Ser Gly Ser Gly Lys
        195                 200                 205

Lys Lys Ala Ser Ser Lys Lys Gln Lys Thr Glu Asn Val Phe Val Asp
    210                 215                 220

Glu Pro Leu Ile His Ala Thr Thr Tyr Ile Pro Leu Met Asp Asn Ala
225                 230                 235                 240

Asp Ser Ser Pro Val Val Asp Lys Arg Glu Val Ile Asp Leu Leu Lys
                245                 250                 255
```

-continued

```
Pro Asp Gln Val Glu Gly Ile Gln Lys Ser Gly Thr Lys Leu Lys
            260                 265                 270

Thr Glu Thr Asp Lys Glu Asn Ala Glu Val Lys Phe Lys Asp Phe Leu
            275                 280                 285

Leu Ser Leu Lys Thr Met Met Phe Ser Glu Asp Glu Ala Leu Cys Val
            290                 295                 300

Val Asp Leu Leu Lys Glu Lys Ser Gly Val Ile Gln Asp Ala Leu Lys
305                 310                 315                 320

Lys Ser Ser Lys Gly Glu Leu Thr Thr Leu Ile His Gln Leu Gln Glu
                325                 330                 335

Lys Asp Lys Leu Leu Ala Ala Val Lys Glu Asp Ala Ala Thr Lys
                340                 345                 350

Asp Arg Cys Lys Gln Leu Thr Gln Glu Met Met Thr Glu Lys Glu Arg
                355                 360                 365

Ser Asn Val Val Ile Thr Arg Met Lys Asp Arg Ile Gly Thr Leu Glu
            370                 375                 380

Lys Glu His Asn Val Phe Gln Asn Lys Ile His Val Ser Tyr Gln Glu
385                 390                 395                 400

Thr Gln Gln Met Gln Met Lys Phe Gln Gln Val Arg Glu Gln Met Glu
                405                 410                 415

Ala Glu Ile Ala His Leu Lys Gln Glu Asn Gly Ile Leu Arg Asp Ala
                420                 425                 430

Val Ser Asn Thr Thr Asn Gln Leu Glu Ser Lys Gln Ser Ala Glu Leu
            435                 440                 445

Asn Lys Leu Arg Gln Asp Tyr Ala Arg Leu Val Asn Glu Leu Thr Glu
            450                 455                 460

Lys Thr Gly Lys Leu Gln Gln Glu Glu Val Gln Lys Lys Asn Ala Glu
465                 470                 475                 480

Gln Ala Ala Thr Gln Leu Lys Val Gln Leu Gln Glu Ala Glu Arg Arg
                485                 490                 495

Trp Glu Glu Val Gln Ser Tyr Ile Arg Lys Arg Thr Ala Glu His Glu
                500                 505                 510

Ala Ala Gln Gln Asp Leu Gln Ser Lys Phe Val Ala Lys Glu Asn Glu
            515                 520                 525

Val Gln Ser Leu His Ser Lys Leu Thr Asp Thr Leu Val Ser Lys Gln
            530                 535                 540

Gln Leu Glu Gln Arg Leu Met Gln Leu Met Glu Ser Glu Gln Lys Arg
545                 550                 555                 560

Val Asn Lys Glu Glu Ser Leu Gln Met Gln Val Gln Asp Ile Leu Glu
                565                 570                 575

Gln Asn Glu Ala Leu Lys Ala Gln Ile Gln Gln Phe His Ser Gln Ile
            580                 585                 590

Ala Ala Gln Thr Ser Ala Ser Val Leu Ala Glu Glu Leu His Lys Val
            595                 600                 605

Ile Ala Glu Lys Asp Lys Gln Ile Lys Gln Thr Glu Asp Ser Leu Ala
610                 615                 620

Ser Glu Arg Asp Arg Leu Thr Ser Lys Glu Glu Leu Lys Asp Ile
625                 630                 635                 640

Gln Asn Met Asn Phe Leu Leu Lys Ala Glu Val Gln Lys Leu Gln Ala
                645                 650                 655

Leu Ala Asn Glu Gln Ala Ala Ala Ala His Glu Leu Glu Lys Met Gln
            660                 665                 670

Gln Ser Val Tyr Val Lys Asp Asp Lys Ile Arg Leu Leu Glu Glu Gln
```

-continued

```
                675                 680                 685
Leu Gln His Glu Ile Ser Asn Lys Met Glu Glu Phe Lys Ile Leu Asn
    690                 695                 700
Asp Gln Asn Lys Ala Leu Lys Ser Glu Val Gln Lys Leu Gln Thr Leu
705                 710                 715                 720
Val Ser Glu Gln Pro Asn Lys Asp Val Val Glu Gln Met Glu Lys Cys
                725                 730                 735
Ile Gln Glu Lys Asp Glu Lys Leu Lys Thr Val Glu Glu Leu Leu Glu
            740                 745                 750
Thr Gly Leu Ile Gln Val Ala Thr Lys Glu Glu Leu Asn Ala Ile
            755                 760                 765
Arg Thr Glu Asn Ser Ser Leu Thr Lys Glu Val Gln Asp Leu Lys Ala
    770                 775                 780
Lys Gln Asn Asp Gln Val Ser Phe Ala Ser Leu Val Glu Glu Leu Lys
785                 790                 795                 800
Lys Val Ile His Glu Lys Asp Gly Lys Ile Lys Ser Val Glu Glu Leu
                805                 810                 815
Leu Glu Ala Glu Leu Leu Lys Val Ala Asn Lys Glu Lys Thr Val Gln
            820                 825                 830
Asp Leu Lys Gln Glu Ile Lys Ala Leu Lys Glu Glu Ile Gly Asn Val
            835                 840                 845
Gln Leu Glu Lys Ala Gln Gln Leu Ser Ile Thr Ser Lys Val Gln Glu
    850                 855                 860
Leu Gln Asn Leu Leu Lys Gly Lys Glu Glu Gln Met Asn Thr Met Lys
865                 870                 875                 880
Ala Val Leu Glu Glu Lys Glu Lys Asp Leu Ala Asn Thr Gly Lys Trp
                885                 890                 895
Leu Gln Asp Leu Gln Glu Glu Asn Glu Ser Leu Lys Ala His Val Gln
            900                 905                 910
Glu Val Ala Gln His Asn Leu Lys Glu Ala Ser Ser Ala Ser Gln Phe
            915                 920                 925
Glu Glu Leu Glu Ile Val Leu Lys Glu Lys Glu Asn Glu Leu Lys Arg
    930                 935                 940
Leu Glu Ala Met Leu Lys Glu Arg Glu Ser Asp Leu Ser Ser Lys Thr
945                 950                 955                 960
Gln Leu Leu Gln Asp Val Gln Asp Glu Asn Lys Leu Phe Lys Ser Gln
                965                 970                 975
Ile Glu Gln Leu Lys Gln Asn Tyr Gln Ala Ser Ser Phe Pro
            980                 985                 990
Pro His Glu Leu Leu Lys Val Ile Ser Glu Arg Glu Lys Glu Ile
            995                 1000                1005
Ser Gly Leu Trp Asn Glu Leu Asp Ser Leu Lys Asp Ala Val Glu His
    1010                1015                1020
Gln Arg Lys Lys Asn Asn Asp Leu Arg Glu Lys Asn Trp Glu Ala Met
1025                1030                1035                1040
Glu Ala Leu Ala Ser Thr Glu Lys Met Leu Gln Asp Lys Val Asn Lys
                1045                1050                1055
Thr Ser Lys Glu Arg Gln Gln Val Glu Ala Val Glu Leu Glu Ala
            1060                1065                1070
Lys Glu Val Leu Lys Lys Leu Phe Pro Lys Val Ser Val Pro Ser Asn
            1075                1080                1085
Leu Ser Tyr Gly Glu Trp Leu His Gly Phe Glu Lys Lys Ala Lys Glu
    1090                1095                1100
```

Cys Met Ala Gly Thr Ser Gly Ser Glu Glu Val Lys Val Leu Glu His
1105                1110                1115                1120

Lys Leu Lys Glu Ala Asp Glu Met His Thr Leu Leu Gln Leu Glu Cys
            1125                1130                1135

Glu Lys Tyr Lys Ser Val Leu Ala Glu Thr Glu Gly Ile Leu Gln Lys
            1140                1145                1150

Leu Gln Arg Ser Val Gln Glu Glu Asn Lys Trp Lys Val Lys Val
        1155                1160                1165

Asp Glu Ser His Lys Thr Ile Lys Gln Met Gln Ser Ser Phe Thr Ser
        1170                1175                1180

Ser Glu Gln Glu Leu Glu Arg Leu Arg Ser Glu Asn Lys Asp Ile Glu
1185                1190                1195                1200

Asn Leu Arg Arg Glu Arg Glu His Leu Glu Met Glu Leu Glu Lys Ala
            1205                1210                1215

Glu Met Glu Arg Ser Thr Tyr Val Thr Glu Val Arg Glu Leu Lys Asp
            1220                1225                1230

Leu Leu Thr Glu Leu Gln Lys Lys Leu Asp Asp Ser Tyr Ser Glu Ala
            1235                1240                1245

Val Arg Gln Asn Glu Glu Leu Asn Leu Leu Lys Ala Gln Leu Asn Glu
        1250                1255                1260

Thr Leu Thr Lys Leu Arg Thr Glu Gln Asn Glu Arg Gln Lys Val Ala
1265                1270                1275                1280

Gly Asp Leu His Lys Ala Gln Gln Ser Leu Glu Leu Ile Gln Ser Lys
            1285                1290                1295

Ile Val Lys Ala Ala Gly Asp Thr Thr Val Ile Glu Asn Ser Asp Val
            1300                1305                1310

Ser Pro Glu Thr Glu Ser Ser Glu Lys Glu Thr Met Ser Val Ser Leu
            1315                1320                1325

Asn Gln Thr Val Thr Gln Leu Gln Gln Leu Leu Gln Ala Val Asn Gln
            1330                1335                1340

Gln Leu Thr Lys Glu Lys Glu His Tyr Gln Val Leu Glu
1345                1350                1355

<210> SEQ ID NO 33
<211> LENGTH: 1248
<212> TYPE: PRT
<213> ORGANISM: Homo sapiens

<400> SEQUENCE: 33

Met Glu Pro Pro Gly Gly Ser Leu Gly Pro Gly Arg Gly Thr Arg Asp
1               5                   10                  15

Lys Lys Lys Gly Arg Ser Pro Asp Glu Leu Pro Ser Ala Gly Gly Asp
            20                  25                  30

Gly Gly Lys Ser Lys Lys Phe Leu Glu Arg Phe Thr Ser Met Arg Ile
        35                  40                  45

Lys Lys Glu Lys Glu Lys Pro Asn Ser Ala His Arg Asn Ser Ser Ala
    50                  55                  60

Ser Tyr Gly Asp Asp Pro Thr Ala Gln Ser Leu Gln Asp Val Ser Asp
65                  70                  75                  80

Glu Gln Val Leu Val Leu Phe Glu Gln Met Leu Leu Asp Met Asn Leu
                85                  90                  95

Asn Glu Glu Lys Gln Gln Pro Leu Arg Glu Lys Asp Ile Ile Ile Lys
            100                 105                 110

Arg Glu Met Val Ser Gln Tyr Leu Tyr Thr Ser Lys Ala Gly Met Ser

-continued

```
            115                 120                 125
Gln Lys Glu Ser Ser Lys Ser Ala Met Met Tyr Ile Gln Glu Leu Arg
        130                 135                 140

Ser Gly Leu Arg Asp Met Pro Leu Leu Ser Cys Leu Glu Ser Leu Arg
145                 150                 155                 160

Val Ser Leu Asn Asn Asn Pro Val Ser Trp Val Gln Thr Phe Gly Ala
                165                 170                 175

Glu Gly Leu Ala Ser Leu Leu Asp Ile Leu Lys Arg Leu His Asp Glu
            180                 185                 190

Lys Glu Glu Thr Ala Gly Ser Tyr Asp Ser Arg Asn Lys His Glu Ile
        195                 200                 205

Ile Arg Cys Leu Lys Ala Phe Met Asn Asn Lys Phe Gly Ile Lys Thr
    210                 215                 220

Met Leu Glu Thr Glu Glu Gly Ile Leu Leu Leu Val Arg Ala Met Asp
225                 230                 235                 240

Pro Ala Val Pro Asn Met Met Ile Asp Ala Ala Lys Leu Leu Ser Ala
                245                 250                 255

Leu Cys Ile Leu Pro Gln Pro Glu Asp Met Asn Glu Arg Val Leu Glu
            260                 265                 270

Ala Met Thr Glu Arg Ala Glu Met Asp Glu Val Glu Arg Phe Gln Pro
        275                 280                 285

Leu Leu Asp Gly Leu Lys Ser Gly Thr Thr Ile Ala Leu Lys Val Gly
    290                 295                 300

Cys Leu Gln Leu Ile Asn Ala Leu Ile Thr Pro Ala Glu Glu Leu Asp
305                 310                 315                 320

Phe Arg Val His Ile Arg Ser Glu Leu Met Arg Leu Gly Leu His Gln
                325                 330                 335

Val Leu Gln Asp Leu Arg Glu Ile Glu Asn Glu Asp Met Arg Val Gln
            340                 345                 350

Leu Asn Val Phe Asp Glu Gln Gly Glu Glu Asp Ser Tyr Asp Leu Lys
        355                 360                 365

Gly Arg Leu Asp Asp Ile Arg Met Glu Met Asp Asp Phe Asn Glu Val
    370                 375                 380

Phe Gln Ile Leu Leu Asn Thr Val Lys Asp Ser Lys Ala Glu Pro His
385                 390                 395                 400

Phe Leu Ser Ile Leu Gln His Leu Leu Leu Val Arg Asn Asp Tyr Glu
                405                 410                 415

Ala Arg Pro Gln Tyr Tyr Lys Leu Ile Glu Glu Cys Ile Ser Gln Ile
            420                 425                 430

Val Leu His Lys Asn Gly Ala Asp Pro Asp Phe Lys Cys Arg His Leu
        435                 440                 445

Gln Ile Glu Ile Glu Gly Leu Ile Asp Gln Met Ile Asp Lys Thr Lys
    450                 455                 460

Val Glu Lys Ser Glu Ala Lys Ala Ala Glu Leu Glu Lys Lys Leu Asp
465                 470                 475                 480

Ser Glu Leu Thr Ala Arg His Glu Leu Gln Val Glu Met Lys Lys Met
                485                 490                 495

Glu Ser Asp Phe Glu Gln Lys Leu Gln Asp Leu Gln Gly Glu Lys Asp
            500                 505                 510

Ala Leu His Ser Glu Lys Gln Gln Ile Ala Thr Glu Lys Gln Asp Leu
        515                 520                 525

Glu Ala Glu Val Ser Gln Leu Thr Gly Glu Val Ala Lys Leu Thr Lys
    530                 535                 540
```

-continued

```
Glu Leu Glu Asp Ala Lys Lys Glu Met Ala Ser Leu Ser Ala Ala Ala
545                 550                 555                 560
Ile Thr Val Pro Pro Ser Val Pro Ser Arg Ala Pro Val Pro Pro Ala
                565                 570                 575
Pro Pro Leu Pro Gly Asp Ser Gly Thr Ile Ile Pro Pro Pro Pro Ala
            580                 585                 590
Pro Gly Asp Ser Thr Thr Pro Pro Pro Pro Pro Pro Pro Pro Pro Pro
        595                 600                 605
Pro Pro Pro Leu Pro Gly Gly Thr Ala Ile Ser Pro Pro Pro Pro Leu
    610                 615                 620
Ser Gly Asp Ala Thr Ile Pro Pro Pro Pro Leu Pro Glu Gly Val
625                 630                 635                 640
Gly Ile Pro Ser Pro Ser Ser Leu Pro Gly Gly Thr Ala Ile Pro Pro
                645                 650                 655
Pro Pro Pro Leu Pro Gly Ser Ala Arg Ile Pro Pro Pro Pro Pro Pro
            660                 665                 670
Leu Pro Gly Ser Ala Gly Ile Pro Pro Pro Pro Pro Leu Pro Gly
            675                 680                 685
Glu Ala Gly Met Pro Pro Pro Pro Pro Leu Pro Gly Gly Pro Gly
690                 695                 700
Ile Pro Pro Pro Pro Phe Pro Gly Gly Pro Gly Ile Pro Pro Pro
705                 710                 715                 720
Pro Pro Gly Met Gly Met Pro Pro Pro Pro Phe Gly Phe Gly Val
            725                 730                 735
Pro Ala Ala Pro Val Leu Pro Phe Gly Leu Thr Pro Lys Lys Leu Tyr
            740                 745                 750
Lys Pro Glu Val Gln Leu Arg Arg Pro Asn Trp Ser Lys Leu Val Ala
            755                 760                 765
Glu Asp Leu Ser Gln Asp Cys Phe Trp Thr Lys Val Lys Glu Asp Arg
770                 775                 780
Phe Glu Asn Asn Glu Leu Phe Ala Lys Leu Thr Leu Thr Phe Ser Ala
785                 790                 795                 800
Gln Thr Lys Thr Lys Lys Asp Gln Glu Gly Gly Glu Lys Lys Ser
            805                 810                 815
Val Gln Lys Lys Lys Val Lys Glu Leu Lys Val Leu Asp Ser Lys Thr
            820                 825                 830
Ala Gln Asn Leu Ser Ile Phe Leu Gly Ser Phe Arg Met Pro Tyr Gln
            835                 840                 845
Glu Ile Lys Asn Val Ile Leu Glu Val Asn Glu Ala Val Leu Thr Glu
850                 855                 860
Ser Met Ile Gln Asn Leu Ile Lys Gln Met Pro Glu Pro Glu Gln Leu
865                 870                 875                 880
Lys Met Leu Ser Glu Leu Lys Asp Glu Tyr Asp Asp Leu Ala Glu Ser
                885                 890                 895
Glu Gln Phe Gly Val Val Met Gly Thr Val Pro Arg Leu Arg Pro Arg
            900                 905                 910
Leu Asn Ala Ile Leu Phe Lys Leu Gln Phe Ser Glu Gln Val Glu Asn
            915                 920                 925
Ile Lys Pro Glu Ile Val Ser Val Thr Ala Ala Cys Glu Glu Leu Arg
            930                 935                 940
Lys Ser Glu Ser Phe Ser Asn Leu Leu Glu Ile Thr Leu Leu Val Gly
945                 950                 955                 960
```

```
Asn Tyr Met Asn Ala Gly Ser Arg Asn Ala Gly Ala Phe Gly Phe Asn
                965                 970                 975

Ile Ser Phe Leu Cys Lys Leu Arg Asp Thr Lys Ser Thr Asp Gln Lys
            980                 985                 990

Met Thr Leu Leu His Phe Leu Ala Glu Leu Cys Glu Asn Asp Tyr Pro
        995                1000                1005

Asp Val Leu Lys Phe Pro Asp Glu Leu Ala His Val Glu Lys Ala Ser
    1010                1015                1020

Arg Val Ser Ala Glu Asn Leu Gln Lys Asn Leu Asp Gln Met Lys Lys
1025                1030                1035                1040

Gln Ile Ser Asp Val Glu Arg Asp Val Gln Asn Phe Pro Ala Ala Thr
            1045                1050                1055

Asp Glu Lys Asp Lys Phe Val Glu Lys Met Thr Ser Phe Val Lys Asp
            1060                1065                1070

Ala Gln Glu Gln Tyr Asn Lys Leu Arg Met Met His Ser Asn Met Glu
        1075                1080                1085

Thr Leu Tyr Lys Glu Leu Gly Glu Tyr Phe Leu Phe Asp Pro Lys Lys
    1090                1095                1100

Leu Ser Val Glu Glu Phe Phe Met Asp Leu His Asn Phe Arg Asn Met
1105                1110                1115                1120

Phe Leu Gln Ala Val Lys Glu Asn Gln Lys Arg Arg Glu Thr Glu Glu
            1125                1130                1135

Lys Met Arg Arg Ala Lys Leu Ala Lys Glu Lys Ala Glu Lys Glu Arg
            1140                1145                1150

Leu Glu Lys Gln Gln Lys Arg Glu Gln Leu Ile Asp Met Asn Ala Glu
        1155                1160                1165

Gly Asp Glu Thr Gly Val Met Asp Ser Leu Leu Glu Ala Leu Gln Ser
    1170                1175                1180

Gly Ala Ala Phe Arg Arg Lys Arg Gly Pro Arg Gln Ala Asn Arg Lys
1185                1190                1195                1200

Ala Gly Cys Ala Val Thr Ser Leu Leu Ala Ser Glu Leu Thr Lys Asp
            1205                1210                1215

Asp Ala Met Ala Ala Val Pro Ala Lys Val Ser Lys Asn Ser Glu Thr
            1220                1225                1230

Phe Pro Thr Ile Leu Glu Glu Ala Lys Glu Leu Val Gly Arg Ala Ser
            1235                1240                1245

<210> SEQ ID NO 34
<211> LENGTH: 1101
<212> TYPE: PRT
<213> ORGANISM: Homo sapiens

<400> SEQUENCE: 34

Met Glu Gln Pro Gly Ala Ala Ala Ser Gly Ala Gly Gly Gly Ser Glu
1               5                   10                  15

Glu Pro Gly Gly Gly Arg Ser Asn Lys Arg Ser Ala Gly Asn Arg Ala
            20                  25                  30

Ala Asn Glu Glu Glu Thr Lys Asn Lys Pro Lys Leu Asn Ile Gln Ile
        35                  40                  45

Lys Thr Leu Ala Asp Asp Val Arg Asp Arg Ile Thr Ser Phe Arg Lys
    50                  55                  60

Ser Thr Val Lys Lys Glu Lys Pro Leu Ile Gln His Pro Ile Asp Ser
65                  70                  75                  80

Gln Val Ala Met Ser Glu Phe Pro Ala Ala Gln Pro Leu Tyr Asp Glu
            85                  90                  95
```

-continued

```
Arg Ser Leu Asn Leu Ser Glu Lys Glu Val Leu Asp Leu Phe Glu Lys
            100                 105                 110

Met Met Glu Asp Met Asn Leu Asn Glu Glu Lys Lys Ala Pro Leu Arg
            115                 120                 125

Asn Lys Asp Phe Thr Thr Lys Arg Glu Met Val Val Gln Tyr Ile Ser
            130                 135                 140

Ala Thr Ala Lys Ser Gly Gly Leu Lys Asn Ser Lys His Glu Cys Thr
145                 150                 155                 160

Leu Ser Ser Gln Glu Tyr Val His Glu Leu Arg Ser Gly Ile Ser Asp
                    165                 170                 175

Glu Lys Leu Leu Asn Cys Leu Glu Ser Leu Arg Val Ser Leu Thr Ser
            180                 185                 190

Asn Pro Val Ser Trp Val Asn Asn Phe Gly His Glu Gly Leu Gly Leu
            195                 200                 205

Leu Leu Asp Glu Leu Glu Lys Leu Leu Asp Lys Lys Gln Gln Glu Asn
210                 215                 220

Ile Asp Lys Lys Asn Gln Tyr Lys Leu Ile Gln Cys Leu Lys Ala Phe
225                 230                 235                 240

Met Asn Asn Lys Phe Gly Leu Gln Arg Ile Leu Gly Asp Glu Arg Ser
                    245                 250                 255

Leu Leu Leu Leu Ala Arg Ala Ile Asp Pro Lys Gln Pro Asn Met Met
            260                 265                 270

Thr Glu Ile Val Lys Ile Leu Ser Ala Ile Cys Ile Val Gly Glu Glu
            275                 280                 285

Asn Ile Leu Asp Lys Leu Leu Gly Ala Ile Thr Thr Ala Ala Glu Arg
290                 295                 300

Asn Asn Arg Glu Arg Phe Ser Pro Ile Val Glu Gly Leu Glu Asn Gln
305                 310                 315                 320

Glu Ala Leu Gln Leu Gln Val Ala Cys Met Gln Phe Ile Asn Ala Leu
                    325                 330                 335

Val Thr Ser Pro Tyr Glu Leu Asp Phe Arg Ile His Leu Arg Asn Glu
            340                 345                 350

Phe Leu Arg Ser Gly Leu Lys Thr Met Leu Pro Asp Leu Lys Glu Lys
            355                 360                 365

Glu Asn Asp Glu Leu Asp Ile Gln Leu Lys Val Phe Asp Glu Asn Lys
            370                 375                 380

Glu Asp Asp Leu Thr Glu Leu Ser His Arg Leu Asn Asp Ile Arg Ala
385                 390                 395                 400

Glu Met Asp Asp Met Asn Glu Val Tyr His Leu Leu Tyr Asn Met Leu
                    405                 410                 415

Lys Asp Thr Ala Ala Glu Asn Tyr Phe Leu Ser Ile Leu Gln His Phe
            420                 425                 430

Leu Leu Ile Arg Asn Asp Tyr Tyr Ile Arg Pro Gln Tyr Tyr Lys Ile
            435                 440                 445

Ile Glu Glu Cys Val Ser Gln Ile Val Leu His Cys Ser Gly Met Asp
450                 455                 460

Pro Asp Phe Lys Tyr Arg Gln Arg Leu Asp Ile Asp Leu Thr His Leu
465                 470                 475                 480

Ile Asp Ser Cys Val Asn Lys Ala Lys Val Glu Glu Ser Glu Gln Lys
                    485                 490                 495

Ala Ala Glu Phe Ser Lys Lys Phe Asp Glu Glu Phe Thr Ala Arg Gln
            500                 505                 510
```

```
Glu Ala Gln Ala Glu Leu Gln Lys Arg Asp Glu Lys Ile Lys Glu Leu
                515                 520                 525
Glu Ala Glu Ile Gln Gln Leu Arg Thr Gln Ala Gln Val Leu Ser Ser
            530                 535                 540
Ser Ser Gly Ile Pro Gly Pro Pro Ala Pro Pro Leu Pro Gly Val
545                 550                 555                 560
Gly Pro Pro Pro Pro Pro Ala Pro Pro Leu Pro Gly Gly Ala Pro
                565                 570                 575
Leu Pro Pro Pro Pro Pro Leu Pro Gly Met Met Gly Ile Pro Pro
                580                 585                 590
Pro Pro Pro Pro Pro Leu Leu Phe Gly Gly Pro Pro Pro Pro Pro
            595                 600                 605
Leu Gly Gly Val Pro Pro Pro Gly Ile Ser Leu Asn Leu Pro Tyr
    610                 615                 620
Gly Met Lys Gln Lys Lys Met Tyr Lys Pro Glu Val Ser Met Lys Arg
625                 630                 635                 640
Ile Asn Trp Ser Lys Ile Glu Pro Thr Glu Leu Ser Glu Asn Cys Phe
                645                 650                 655
Trp Leu Arg Val Lys Glu Asp Lys Phe Glu Asn Pro Asp Leu Phe Ala
            660                 665                 670
Lys Leu Ala Leu Asn Phe Ala Thr Gln Ile Lys Val Gln Lys Asn Ala
        675                 680                 685
Glu Ala Leu Glu Glu Lys Lys Thr Gly Pro Thr Lys Lys Val Lys
    690                 695                 700
Glu Leu Arg Ile Leu Asp Pro Lys Thr Ala Gln Asn Leu Ser Ile Phe
705                 710                 715                 720
Leu Gly Ser Tyr Arg Met Pro Tyr Glu Asp Ile Arg Asn Val Ile Leu
                725                 730                 735
Glu Val Asn Glu Asp Met Leu Ser Glu Ala Leu Ile Gln Asn Leu Val
            740                 745                 750
Lys His Leu Pro Glu Gln Lys Ile Leu Asn Glu Leu Ala Glu Leu Lys
        755                 760                 765
Asn Glu Tyr Asp Asp Leu Cys Glu Pro Glu Gln Phe Gly Val Val Met
    770                 775                 780
Ser Ser Val Lys Met Leu Gln Pro Arg Leu Ser Ser Ile Leu Phe Lys
785                 790                 795                 800
Leu Thr Phe Glu Glu His Ile Asn Asn Ile Lys Pro Ser Ile Ile Ala
                805                 810                 815
Val Thr Leu Ala Cys Glu Glu Leu Lys Lys Ser Glu Ser Phe Asn Arg
            820                 825                 830
Leu Leu Glu Leu Val Leu Leu Val Gly Asn Tyr Met Asn Ser Gly Ser
        835                 840                 845
Arg Asn Ala Gln Ser Leu Gly Phe Lys Ile Asn Phe Leu Cys Lys Ile
    850                 855                 860
Arg Asp Thr Lys Ser Ala Asp Gln Lys Thr Thr Leu Leu His Phe Ile
865                 870                 875                 880
Ala Asp Ile Cys Glu Glu Lys Tyr Arg Asp Ile Leu Lys Phe Pro Glu
                885                 890                 895
Glu Leu Glu His Val Glu Ser Ala Ser Lys Val Ser Ala Gln Ile Leu
            900                 905                 910
Lys Ser Asn Leu Ala Ser Met Glu Gln Gln Ile Val His Leu Glu Arg
        915                 920                 925
Asp Ile Lys Lys Phe Pro Gln Ala Glu Asn Gln His Asp Lys Phe Val
```

```
                930                 935                 940
Glu Lys Met Thr Ser Phe Thr Lys Thr Ala Arg Glu Gln Tyr Glu Lys
945                 950                 955                 960

Leu Ser Thr Met His Asn Asn Met Met Lys Leu Tyr Glu Asn Leu Gly
                965                 970                 975

Glu Tyr Phe Ile Phe Asp Ser Lys Thr Val Ser Ile Glu Glu Phe Phe
            980                 985                 990

Gly Asp Leu Asn Asn Phe Arg Thr Leu Phe Leu Glu Ala Val Arg Glu
        995                 1000                1005

Asn Asn Lys Arg Arg Glu Met Glu Glu Lys Thr Arg Arg Ala Lys Leu
    1010                1015                1020

Ala Lys Glu Lys Ala Glu Gln Glu Lys Leu Glu Arg Gln Lys Lys Lys
1025                1030                1035                1040

Lys Gln Leu Ile Asp Ile Asn Lys Glu Gly Asp Glu Thr Gly Val Met
            1045                1050                1055

Asp Asn Leu Leu Glu Ala Leu Gln Ser Gly Ala Ala Phe Arg Asp Arg
        1060                1065                1070

Arg Lys Arg Ile Pro Arg Asn Pro Asp Asn Arg Val Pro Leu Glu
    1075                1080                1085

Arg Ser Arg Ser Arg His Asn Gly Ala Ile Ser Ser Lys
    1090                1095                1100

<210> SEQ ID NO 35
<211> LENGTH: 2303
<212> TYPE: PRT
<213> ORGANISM: Homo sapiens

<400> SEQUENCE: 35

Met Thr Ser Glu Glu Met Thr Ala Ser Val Leu Ile Pro Val Thr Gln
1               5                   10                  15

Arg Lys Val Val Ser Ala Gln Ser Ala Ala Asp Glu Ser Ser Glu Lys
            20                  25                  30

Val Ser Asp Ile Asn Ile Ser Lys Ala His Thr Val Arg Arg Ser Gly
        35                  40                  45

Glu Thr Ser His Thr Ile Ser Gln Leu Asn Lys Leu Lys Glu Glu Pro
    50                  55                  60

Ser Gly Ser Asn Leu Pro Lys Ile Leu Ser Ile Ala Arg Glu Lys Ile
65                  70                  75                  80

Val Ser Asp Glu Asn Ser Asn Glu Lys Cys Trp Glu Lys Ile Met Pro
                85                  90                  95

Asp Ser Ala Lys Asn Leu Asn Ile Asn Cys Asn Asn Ile Leu Arg Asn
            100                 105                 110

His Gln His Gly Leu Pro Gln Arg Gln Phe Tyr Glu Met Tyr Asn Ser
        115                 120                 125

Val Ala Glu Glu Asp Leu Cys Leu Glu Thr Gly Ile Pro Ser Pro Leu
    130                 135                 140

Glu Arg Lys Val Phe Pro Gly Ile Gln Leu Glu Leu Asp Arg Pro Ser
145                 150                 155                 160

Met Gly Ile Ser Pro Leu Gly Asn Gln Ser Val Ile Ile Glu Thr Gly
                165                 170                 175

Arg Ala His Pro Asp Ser Arg Arg Ala Val Phe His Phe His Tyr Glu
            180                 185                 190

Val Asp Arg Arg Met Ser Asp Thr Phe Cys Thr Leu Ser Glu Asn Leu
        195                 200                 205
```

```
Ile Leu Asp Asp Cys Gly Asn Cys Val Pro Leu Pro Gly Gly Glu Glu
    210                 215                 220

Lys Gln Lys Lys Asn Tyr Val Ala Tyr Thr Cys Lys Leu Met Glu Leu
225                 230                 235                 240

Ala Lys Asn Cys Asp Asn Lys Asn Glu Gln Leu Gln Cys Asp His Cys
                245                 250                 255

Asp Thr Leu Asn Asp Lys Tyr Phe Cys Phe Glu Gly Ser Cys Glu Lys
            260                 265                 270

Val Asp Met Val Tyr Ser Gly Asp Ser Phe Cys Arg Lys Asp Phe Thr
        275                 280                 285

Asp Ser Gln Ala Ala Lys Thr Phe Leu Ser His Phe Glu Asp Phe Pro
    290                 295                 300

Asp Asn Cys Asp Asp Val Glu Glu Asp Ala Phe Lys Ser Lys Lys Glu
305                 310                 315                 320

Arg Ser Thr Leu Leu Val Arg Arg Phe Cys Lys Asn Asp Arg Glu Val
                325                 330                 335

Lys Lys Ser Val Tyr Thr Gly Thr Arg Ala Ile Val Arg Thr Leu Pro
            340                 345                 350

Ser Gly His Ile Gly Leu Thr Ala Trp Ser Tyr Ile Asp Gln Lys Arg
        355                 360                 365

Asn Gly Pro Leu Leu Pro Cys Gly Arg Val Met Glu Pro Pro Ser Thr
    370                 375                 380

Val Glu Ile Arg Gln Asp Gly Ser Gln Arg Leu Ser Glu Ala Gln Trp
385                 390                 395                 400

Tyr Pro Ile Tyr Asn Ala Val Arg Arg Glu Glu Thr Glu Asn Thr Val
                405                 410                 415

Gly Ser Leu Leu His Phe Leu Thr Lys Leu Pro Ala Ser Glu Thr Ala
            420                 425                 430

His Gly Arg Ile Ser Val Gly Pro Cys Leu Lys Gln Cys Val Arg Asp
        435                 440                 445

Thr Val Cys Glu Tyr Arg Ala Thr Leu Gln Arg Thr Ser Ile Ser Gln
    450                 455                 460

Tyr Ile Thr Gly Ser Leu Leu Glu Ala Thr Thr Ser Leu Gly Ala Arg
465                 470                 475                 480

Ser Gly Leu Leu Ser Thr Phe Gly Gly Ser Thr Gly Arg Met Met Leu
                485                 490                 495

Lys Glu Arg Gln Pro Gly Pro Ser Val Ala Asn Ser Asn Ala Leu Pro
            500                 505                 510

Ser Ser Ser Ala Gly Ile Ser Lys Glu Leu Ile Asp Leu Gln Pro Leu
        515                 520                 525

Ile Gln Phe Pro Glu Glu Val Ala Ser Ile Leu Met Glu Gln Glu Gln
    530                 535                 540

Thr Ile Tyr Arg Arg Val Leu Pro Val Asp Tyr Leu Cys Phe Leu Thr
545                 550                 555                 560

Arg Asp Leu Gly Thr Pro Glu Cys Gln Ser Ser Leu Pro Cys Leu Lys
                565                 570                 575

Ala Ser Ile Ser Ala Ser Ile Leu Thr Thr Gln Asn Gly Glu His Asn
            580                 585                 590

Ala Leu Glu Asp Leu Val Met Arg Phe Asn Glu Val Ser Ser Trp Val
        595                 600                 605

Thr Trp Leu Ile Leu Thr Ala Gly Ser Met Glu Glu Lys Arg Glu Val
    610                 615                 620

Phe Ser Tyr Leu Val His Val Ala Lys Cys Cys Trp Asn Met Gly Asn
```

-continued

```
            625                 630                 635                 640
Tyr Asn Ala Val Met Glu Phe Leu Ala Gly Leu Arg Ser Arg Lys Val
                    645                 650                 655
Leu Lys Met Trp Gln Phe Met Asp Gln Ser Asp Ile Glu Thr Met Arg
                    660                 665                 670
Ser Leu Lys Asp Ala Met Ala Gln His Glu Ser Ser Cys Glu Tyr Arg
                    675                 680                 685
Lys Val Val Thr Arg Ala Leu His Ile Pro Gly Cys Lys Val Val Pro
                    690                 695                 700
Phe Cys Gly Val Phe Leu Lys Glu Leu Cys Glu Val Leu Asp Gly Ala
705                 710                 715                 720
Ser Gly Leu Met Lys Leu Cys Pro Arg Tyr Asn Ser Gln Glu Glu Thr
                    725                 730                 735
Leu Glu Phe Val Ala Asp Tyr Ser Gly Gln Asp Asn Phe Leu Gln Arg
                    740                 745                 750
Val Gly Gln Asn Gly Leu Lys Asn Ser Glu Lys Glu Ser Thr Val Asn
                    755                 760                 765
Ser Ile Phe Gln Val Ile Arg Ser Cys Asn Arg Ser Leu Glu Thr Asp
                    770                 775                 780
Glu Glu Asp Ser Pro Ser Glu Gly Asn Ser Ser Arg Lys Ser Ser Leu
785                 790                 795                 800
Lys Asp Lys Ser Arg Trp Gln Phe Ile Ile Gly Asp Leu Leu Asp Ser
                    805                 810                 815
Asp Asn Asp Ile Phe Glu Gln Ser Lys Glu Tyr Asp Ser His Gly Ser
                    820                 825                 830
Glu Asp Ser Gln Lys Ala Phe Asp His Gly Thr Glu Leu Ile Pro Trp
                    835                 840                 845
Tyr Val Leu Ser Ile Gln Ala Asp Val His Gln Phe Leu Leu Gln Gly
                    850                 855                 860
Ala Thr Val Ile His Tyr Asp Gln Asp Thr His Leu Ser Ala Arg Cys
865                 870                 875                 880
Phe Leu Gln Leu Gln Pro Asp Asn Ser Thr Leu Thr Trp Val Lys Pro
                    885                 890                 895
Thr Thr Ala Ser Pro Ala Ser Ser Lys Ala Lys Leu Gly Val Leu Asn
                    900                 905                 910
Asn Thr Ala Glu Pro Gly Lys Phe Pro Leu Leu Gly Asn Ala Gly Leu
                    915                 920                 925
Ser Ser Leu Thr Glu Gly Val Leu Asp Leu Phe Ala Val Lys Ala Val
                    930                 935                 940
Tyr Met Gly His Pro Gly Ile Asp Ile His Thr Val Cys Val Gln Asn
945                 950                 955                 960
Lys Leu Gly Ser Met Phe Leu Ser Glu Thr Gly Val Thr Leu Leu Tyr
                    965                 970                 975
Gly Leu Gln Thr Thr Asp Asn Arg Leu Leu His Phe Val Ala Pro Lys
                    980                 985                 990
His Thr Ala Lys Met Leu Phe Ser Gly Leu Leu Glu Leu Thr Arg Ala
                    995                 1000                1005
Val Arg Lys Met Arg Lys Phe Pro Asp Gln Arg Gln Trp Leu Arg
                    1010                1015                1020
Lys Gln Tyr Val Ser Leu Tyr Gln Glu Asp Gly Arg Tyr Glu Gly Pro
1025                1030                1035                1040
Thr Leu Ala His Ala Val Glu Leu Phe Gly Gly Arg Arg Trp Ser Ala
                    1045                1050                1055
```

```
Arg Asn Pro Ser Pro Gly Thr Ser Ala Lys Asn Ala Glu Lys Pro Asn
            1060                1065                1070

Met Gln Arg Asn Asn Thr Leu Gly Ile Ser Thr Lys Lys Lys
        1075                1080                1085

Lys Ile Leu Met Arg Gly Glu Ser Gly Glu Val Thr Asp Glu Met
        1090                1095                1100

Ala Thr Arg Lys Ala Lys Met His Lys Glu Cys Arg Ser Arg Ser Gly
1105                1110                1115                1120

Ser Asp Pro Gln Asp Ile Asn Glu Gln Glu Ser Glu Val Asn Ala
            1125                1130                1135

Ile Ala Asn Pro Pro Asn Pro Leu Pro Ser Arg Arg Ala His Ser Leu
            1140                1145                1150

Thr Thr Ala Gly Ser Pro Asn Leu Ala Ala Gly Thr Ser Ser Pro Ile
            1155                1160                1165

Arg Pro Val Ser Ser Pro Val Leu Ser Ser Asn Lys Ser Pro Ser
            1170                1175                1180

Ser Ala Trp Ser Ser Ser Ser Trp His Gly Arg Ile Lys Gly Gly Met
1185                1190                1195                1200

Lys Gly Phe Gln Ser Phe Met Val Ser Asp Ser Asn Met Ser Phe Val
            1205                1210                1215

Glu Phe Val Glu Leu Phe Lys Ser Phe Ser Val Arg Ser Arg Lys Asp
            1220                1225                1230

Leu Lys Asp Leu Phe Asp Val Tyr Ala Val Pro Cys Asn Arg Ser Gly
            1235                1240                1245

Ser Glu Ser Ala Pro Leu Tyr Thr Asn Leu Thr Ile Asp Glu Asn Thr
            1250                1255                1260

Ser Asp Leu Gln Pro Asp Leu Asp Leu Leu Thr Arg Asn Val Ser Asp
1265                1270                1275                1280

Leu Gly Leu Phe Ile Lys Ser Lys Gln Gln Leu Ser Asp Asn Gln Arg
            1285                1290                1295

Gln Ile Ser Asp Ala Ile Ala Ala Ala Ser Ile Val Thr Asn Gly Thr
            1300                1305                1310

Gly Ile Glu Ser Thr Ser Leu Gly Ile Phe Gly Val Gly Ile Leu Gln
            1315                1320                1325

Leu Asn Asp Phe Leu Val Asn Cys Gln Gly Glu His Cys Thr Tyr Asp
            1330                1335                1340

Glu Ile Leu Ser Ile Ile Gln Lys Phe Glu Pro Ser Ile Ser Met Cys
1345                1350                1355                1360

His Gln Gly Leu Met Ser Phe Glu Gly Phe Ala Arg Phe Leu Met Asp
            1365                1370                1375

Lys Glu Asn Phe Ala Ser Lys Asn Asp Glu Ser Gln Glu Asn Ile Lys
            1380                1385                1390

Glu Leu Gln Leu Pro Leu Ser Tyr Tyr Ile Glu Ser Ser His Asn
            1395                1400                1405

Thr Tyr Leu Thr Gly His Gln Leu Lys Gly Glu Ser Ser Val Glu Leu
            1410                1415                1420

Tyr Ser Gln Val Leu Leu Gln Gly Cys Arg Ser Val Glu Leu Asp Cys
1425                1430                1435                1440

Trp Asp Gly Asp Asp Gly Met Pro Ile Ile Tyr His Gly His Thr Pro
                1445                1450                1455

Thr Thr Lys Ile Pro Phe Lys Glu Val Val Glu Ala Ile Asp Arg Ser
                1460                1465                1470
```

-continued

```
Ala Phe Ile Asn Ser Asp Leu Pro Ile Ile Ser Ile Glu Asn His
        1475                1480                1485

Cys Ser Leu Pro Gln Gln Arg Lys Met Ala Glu Ile Phe Lys Thr Val
1490                1495                1500

Phe Gly Glu Lys Leu Val Thr Lys Phe Leu Phe Glu Thr Asp Phe Ser
1505                1510                1515                1520

Asp Asp Pro Met Leu Pro Ser Pro Asp Gln Leu Arg Lys Lys Val Leu
                1525                1530                1535

Leu Lys Asn Lys Lys Leu Lys Ala His Gln Thr Pro Val Asp Ile Leu
            1540                1545                1550

Lys Gln Lys Ala His Gln Leu Ala Ser Met Gln Val Gln Ala Tyr Asn
        1555                1560                1565

Gly Gly Asn Ala Asn Pro Arg Pro Ala Asn Glu Glu Glu Asp
    1570                1575                1580

Glu Glu Asp Glu Tyr Asp Tyr Asp Tyr Glu Ser Leu Ser Asp Asn
1585                1590                1595                1600

Ile Leu Glu Asp Arg Pro Glu Asn Lys Ser Cys Asn Asp Lys Leu Gln
                1605                1610                1615

Phe Glu Tyr Asn Glu Glu Ile Pro Lys Arg Ile Lys Lys Ala Asp Asn
            1620                1625                1630

Ser Ala Cys Asn Lys Gly Lys Val Tyr Asp Met Glu Leu Gly Glu Glu
        1635                1640                1645

Phe Tyr Leu Asp Gln Asn Lys Lys Glu Ser Arg Gln Ile Ala Pro Glu
    1650                1655                1660

Leu Ser Asp Leu Val Ile Tyr Arg Gln Ala Val Lys Phe Pro Gly Leu
1665                1670                1675                1680

Ser Thr Leu Asn Ala Ser Gly Ser Ser Arg Gly Lys Glu Arg Lys Ser
                1685                1690                1695

Arg Lys Ser Ile Phe Gly Asn Asn Pro Gly Arg Met Ser Pro Gly Glu
            1700                1705                1710

Thr Ala Ser Phe Asn Lys Thr Ser Gly Lys Ser Ser Cys Glu Gly Ile
        1715                1720                1725

Arg Gln Thr Trp Glu Glu Ser Ser Pro Leu Asn Pro Thr Thr Ser
    1730                1735                1740

Leu Ser Ala Ile Ile Arg Thr Pro Lys Cys Tyr His Ile Ser Ser Leu
1745                1750                1755                1760

Asn Glu Asn Ala Ala Lys Arg Leu Cys Arg Arg Tyr Ser Gln Lys Leu
                1765                1770                1775

Ile Gln His Thr Ala Cys Gln Leu Leu Arg Thr Tyr Pro Ala Ala Thr
            1780                1785                1790

Arg Ile Asp Ser Ser Asn Pro Asn Pro Leu Met Phe Trp Leu His Gly
        1795                1800                1805

Ile Gln Leu Val Ala Leu Asn Tyr Gln Thr Asp Asp Leu Pro Leu His
    1810                1815                1820

Leu Asn Ala Ala Met Phe Glu Ala Asn Gly Gly Cys Gly Tyr Val Leu
1825                1830                1835                1840

Lys Pro Pro Val Leu Trp Asp Lys Asn Cys Pro Met Tyr Gln Lys Phe
                1845                1850                1855

Ser Pro Leu Glu Arg Asp Leu Asp Ser Met Asp Pro Ala Val Tyr Ser
            1860                1865                1870

Leu Thr Ile Val Ser Gly Gln Asn Val Cys Pro Ser Asn Ser Met Gly
        1875                1880                1885

Ser Pro Cys Ile Glu Val Asp Val Leu Gly Met Pro Leu Asp Ser Cys
```

-continued

```
               1890                1895                1900

His Phe Arg Thr Lys Pro Ile His Arg Asn Thr Leu Asn Pro Met Trp
1905                1910                1915                1920

Asn Glu Gln Phe Leu Phe Arg Val His Phe Glu Asp Leu Val Phe Leu
            1925                1930                1935

Arg Phe Ala Val Val Glu Asn Asn Ser Ser Ala Val Thr Ala Gln Arg
            1940                1945                1950

Ile Ile Pro Leu Lys Ala Leu Lys Arg Gly Tyr Arg His Leu Gln Leu
            1955                1960                1965

Arg Asn Leu His Asn Glu Val Leu Glu Ile Ser Ser Leu Phe Ile Asn
1970                1975                1980

Ser Arg Arg Met Glu Glu Asn Ser Ser Gly Asn Thr Met Ser Ala Ser
1985                1990                1995                2000

Ser Met Phe Asn Thr Glu Glu Arg Lys Cys Leu Gln Thr His Arg Val
            2005                2010                2015

Thr Val His Gly Val Pro Gly Pro Glu Pro Phe Thr Val Phe Thr Ile
            2020                2025                2030

Asn Gly Gly Thr Lys Ala Lys Gln Leu Leu Gln Gln Ile Leu Thr Asn
            2035                2040                2045

Glu Gln Asp Ile Lys Pro Val Thr Thr Asp Tyr Phe Leu Met Glu Glu
            2050                2055                2060

Lys Tyr Phe Ile Ser Lys Glu Lys Asn Glu Cys Arg Lys Gln Pro Phe
2065                2070                2075                2080

Gln Arg Ala Ile Gly Pro Glu Glu Ile Met Gln Ile Leu Ser Ser
            2085                2090                2095

Trp Phe Pro Glu Glu Gly Tyr Met Gly Arg Ile Val Leu Lys Thr Gln
            2100                2105                2110

Gln Glu Asn Leu Glu Glu Lys Asn Ile Val Gln Asp Asp Lys Glu Val
            2115                2120                2125

Ile Leu Ser Ser Glu Glu Glu Ser Phe Phe Val Gln Val His Asp Val
            2130                2135                2140

Ser Pro Glu Gln Pro Arg Thr Val Ile Lys Ala Pro Arg Val Ser Thr
2145                2150                2155                2160

Ala Gln Asp Val Ile Gln Gln Thr Leu Cys Lys Ala Lys Tyr Ser Tyr
            2165                2170                2175

Ser Ile Leu Ser Asn Pro Asn Pro Ser Asp Tyr Val Leu Leu Glu Glu
            2180                2185                2190

Val Val Lys Asp Thr Thr Asn Lys Lys Thr Thr Thr Pro Lys Ser Ser
            2195                2200                2205

Gln Arg Val Leu Leu Asp Gln Glu Cys Val Phe Gln Ala Gln Ser Lys
            2210                2215                2220

Trp Lys Gly Ala Gly Lys Phe Ile Leu Lys Leu Lys Glu Gln Val Gln
2225                2230                2235                2240

Ala Ser Arg Glu Asp Lys Lys Gly Ile Ser Phe Ala Ser Glu Leu
            2245                2250                2255

Lys Lys Leu Thr Lys Ser Thr Lys Gln Pro Arg Gly Leu Thr Ser Pro
            2260                2265                2270

Ser Gln Leu Leu Thr Ser Glu Ser Ile Gln Thr Lys Glu Glu Lys Pro
            2275                2280                2285

Val Gly Gly Leu Ser Pro Val Thr Gln Trp Ile Thr Asp Ser Asp
            2290                2295                2300

<210> SEQ ID NO 36
```

<211> LENGTH: 31
<212> TYPE: PRT
<213> ORGANISM: Homo sapiens
<220> FEATURE:
<221> NAME/KEY: misc_feature
<222> LOCATION: (2), (3), (5), (6), (10), (11), (13)..(17), (19), (20),
      (24), (25), (27), (28)
<223> OTHER INFORMATION: Xaa is any amino acid

<400> SEQUENCE: 36

Ala Xaa Xaa Tyr Xaa Xaa Ile Leu Gly Xaa Xaa Tyr Xaa Xaa Xaa Xaa
1               5                   10                  15

Xaa Tyr Xaa Xaa Ala Ile Leu Xaa Xaa Phe Xaa Xaa Ala Ile Leu
            20                  25                  30

<210> SEQ ID NO 37
<211> LENGTH: 86
<212> TYPE: PRT
<213> ORGANISM: Homo sapiens
<220> FEATURE:
<221> NAME/KEY: misc_feature
<222> LOCATION: (1)..(4), (6), (8)..(15), (17), (18), (20)..(22),
      (24)..(27), (29)..(44), (46)..(62), (64)..(81), (83)..(85)
<223> OTHER INFORMATION: Xaa is any amino acid

<400> SEQUENCE: 37

Xaa Xaa Xaa Xaa Gly Xaa Leu Xaa Xaa Xaa Xaa Xaa Xaa Xaa Trp
1               5                   10                  15

Xaa Xaa Arg Xaa Xaa Xaa Leu Xaa Xaa Xaa Leu Xaa Xaa Xaa Xaa
            20                  25                  30

Xaa Xaa Xaa Xaa Xaa Xaa Xaa Xaa Xaa Xaa Leu Xaa Xaa Xaa
        35                  40                  45

Xaa Xaa Xaa Xaa Xaa Xaa Xaa Xaa Xaa Xaa Xaa Xaa Phe Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Glu Xaa Xaa Xaa Trp
            85

<210> SEQ ID NO 38
<211> LENGTH: 526
<212> TYPE: PRT
<213> ORGANISM: Homo sapiens

<400> SEQUENCE: 38

Met Ser Leu Val Glu Ala Ile Ser Leu Trp Asn Glu Gly Val Leu Ala
1               5                   10                  15

Ala Asp Lys Lys Asp Trp Lys Gly Ala Leu Asp Ala Phe Ser Ala Val
            20                  25                  30

Gln Asp Pro His Ser Arg Ile Cys Phe Asn Ile Gly Cys Met Tyr Thr
        35                  40                  45

Ile Leu Lys Asn Met Thr Glu Ala Glu Lys Ala Phe Thr Arg Ser Ile
    50                  55                  60

Asn Arg Asp Lys His Leu Ala Val Ala Tyr Phe Gln Arg Gly Met Leu
65                  70                  75                  80

Tyr Tyr Gln Thr Glu Lys Tyr Asp Leu Ala Ile Lys Asp Leu Lys Glu
                85                  90                  95

Ala Leu Ile Gln Leu Arg Gly Asn Gln Leu Ile Asp Tyr Lys Ile Leu
            100                 105                 110

Gly Leu Gln Phe Lys Leu Phe Ala Cys Glu Val Leu Tyr Asn Ile Ala
        115                 120                 125

```
Phe Met Tyr Ala Lys Lys Glu Glu Trp Lys Lys Ala Glu Glu Gln Leu
            130                 135                 140

Ala Leu Ala Thr Ser Met Lys Ser Glu Pro Arg His Ser Lys Ile Asp
145                 150                 155                 160

Lys Ala Met Glu Cys Val Trp Lys Gln Lys Leu Tyr Glu Pro Val Val
                165                 170                 175

Ile Pro Val Gly Lys Leu Phe Arg Pro Asn Glu Arg Gln Val Ala Gln
            180                 185                 190

Leu Ala Lys Lys Asp Tyr Leu Gly Lys Ala Thr Val Val Ala Ser Val
        195                 200                 205

Val Asp Gln Asp Ser Phe Ser Gly Phe Ala Pro Leu Gln Pro Gln Ala
210                 215                 220

Ala Glu Pro Pro Arg Pro Lys Thr Pro Glu Ile Phe Arg Ala Leu
225                 230                 235                 240

Glu Gly Glu Ala His Arg Val Leu Phe Gly Phe Val Pro Glu Thr Lys
                245                 250                 255

Glu Glu Leu Gln Val Met Pro Gly Asn Ile Val Phe Val Leu Lys Lys
            260                 265                 270

Gly Asn Asp Asn Trp Ala Thr Val Met Phe Asn Gly Gln Lys Gly Leu
        275                 280                 285

Val Pro Cys Asn Tyr Leu Glu Pro Val Glu Leu Arg Ile His Pro Gln
290                 295                 300

Gln Gln Pro Gln Glu Glu Ser Ser Pro Gln Ser Asp Ile Pro Ala Pro
305                 310                 315                 320

Pro Ser Ser Lys Ala Pro Gly Arg Pro Gln Leu Ser Pro Gly Gln Lys
                325                 330                 335

Gln Lys Glu Glu Pro Lys Glu Val Lys Leu Ser Val Pro Met Pro Tyr
            340                 345                 350

Thr Leu Lys Val His Tyr Lys Tyr Thr Val Val Met Lys Thr Gln Pro
        355                 360                 365

Gly Leu Pro Tyr Ser Gln Val Arg Asp Met Val Ser Lys Lys Leu Glu
370                 375                 380

Leu Arg Leu Glu His Thr Lys Leu Ser Tyr Arg Pro Arg Asp Ser Asn
385                 390                 395                 400

Glu Leu Val Pro Leu Ser Glu Asp Ser Met Lys Asp Ala Trp Gly Gln
                405                 410                 415

Val Lys Asn Tyr Cys Leu Thr Leu Trp Cys Glu Asn Thr Val Gly Asp
            420                 425                 430

Gln Gly Phe Pro Asp Glu Pro Lys Glu Ser Glu Lys Ala Asp Ala Asn
        435                 440                 445

Asn Gln Thr Thr Glu Pro Gln Leu Lys Lys Gly Ser Gln Val Glu Ala
450                 455                 460

Leu Phe Ser Tyr Glu Ala Thr Gln Pro Glu Asp Leu Glu Phe Gln Glu
465                 470                 475                 480

Gly Asp Ile Ile Leu Val Leu Ser Lys Val Asn Glu Glu Trp Leu Glu
                485                 490                 495

Gly Glu Cys Lys Gly Lys Val Gly Ile Phe Pro Lys Val Phe Val Glu
            500                 505                 510

Asp Cys Ala Thr Thr Asp Leu Glu Ser Thr Arg Arg Glu Val
        515                 520                 525

<210> SEQ ID NO 39
<211> LENGTH: 1216
```

<212> TYPE: PRT
<213> ORGANISM: Homo sapiens

<400> SEQUENCE: 39

```
Met Ala Gly Ala Gln Pro Gly Val His Ala Leu Gln Leu Lys Pro Val
1               5                   10                  15

Cys Val Ser Asp Ser Leu Lys Lys Gly Thr Lys Phe Val Lys Trp Asp
                20                  25                  30

Asp Asp Ser Thr Ile Val Thr Pro Ile Ile Leu Arg Thr Asp Pro Gln
            35                  40                  45

Gly Phe Phe Phe Tyr Trp Thr Asp Gln Asn Lys Glu Thr Glu Leu Leu
        50                  55                  60

Asp Leu Ser Leu Val Lys Asp Ala Arg Cys Gly Arg His Ala Lys Ala
65                  70                  75                  80

Pro Lys Asp Pro Lys Leu Arg Glu Leu Leu Asp Val Gly Asn Ile Gly
                85                  90                  95

Arg Leu Glu Gln Arg Met Ile Thr Val Val Tyr Gly Pro Asp Leu Val
            100                 105                 110

Asn Ile Ser His Leu Asn Leu Val Ala Phe Gln Glu Glu Val Ala Lys
        115                 120                 125

Glu Trp Thr Asn Glu Val Phe Ser Leu Ala Thr Asn Leu Leu Ala Gln
130                 135                 140

Asn Met Ser Arg Asp Ala Phe Leu Glu Lys Ala Tyr Thr Lys Leu Lys
145                 150                 155                 160

Leu Gln Val Thr Pro Glu Gly Arg Ile Pro Leu Lys Asn Ile Tyr Arg
                165                 170                 175

Leu Phe Ser Ala Asp Arg Lys Arg Val Glu Thr Ala Leu Glu Ala Cys
            180                 185                 190

Ser Leu Pro Ser Ser Arg Asn Asp Ser Ile Pro Gln Glu Asp Phe Thr
        195                 200                 205

Pro Glu Val Tyr Arg Val Phe Leu Asn Asn Leu Cys Pro Arg Pro Glu
210                 215                 220

Ile Asp Asn Ile Phe Ser Glu Phe Gly Ala Lys Ser Lys Pro Tyr Leu
225                 230                 235                 240

Thr Val Asp Gln Met Met Asp Phe Ile Asn Leu Lys Gln Arg Asp Pro
                245                 250                 255

Arg Leu Asn Glu Ile Leu Tyr Pro Pro Leu Lys Gln Glu Gln Val Gln
            260                 265                 270

Val Leu Ile Glu Lys Tyr Glu Pro Asn Asn Ser Leu Ala Arg Lys Gly
        275                 280                 285

Gln Ile Ser Val Asp Gly Phe Met Arg Tyr Leu Ser Gly Glu Glu Asn
290                 295                 300

Gly Val Val Ser Pro Glu Lys Leu Asp Leu Asn Glu Asp Met Ser Gln
305                 310                 315                 320

Pro Leu Ser His Tyr Phe Ile Asn Ser Ser His Asn Thr Tyr Leu Thr
                325                 330                 335

Ala Gly Gln Leu Ala Gly Asn Ser Ser Val Glu Met Tyr Arg Gln Val
            340                 345                 350

Leu Leu Ser Gly Cys Arg Cys Val Glu Leu Asp Cys Trp Lys Gly Arg
        355                 360                 365

Thr Ala Glu Glu Glu Pro Val Ile Thr His Gly Phe Thr Met Thr Thr
370                 375                 380

Glu Ile Ser Phe Lys Glu Val Ile Glu Ala Ile Ala Glu Cys Ala Phe
385                 390                 395                 400
```

```
Lys Thr Ser Pro Phe Pro Ile Leu Leu Ser Phe Glu Asn His Val Asp
                405                 410                 415
Ser Pro Lys Gln Gln Ala Lys Met Ala Glu Tyr Cys Arg Leu Ile Phe
            420                 425                 430
Gly Asp Ala Leu Leu Met Glu Pro Leu Glu Lys Tyr Pro Leu Glu Ser
            435                 440                 445
Gly Val Pro Leu Pro Ser Pro Met Asp Leu Met Tyr Lys Ile Leu Val
        450                 455                 460
Lys Asn Lys Lys Lys Ser His Lys Ser Ser Glu Gly Ser Gly Lys Lys
465                 470                 475                 480
Lys Leu Ser Glu Gln Ala Ser Asn Thr Tyr Ser Asp Ser Ser Ser Met
                485                 490                 495
Phe Glu Pro Ser Ser Pro Gly Ala Gly Glu Ala Asp Thr Glu Ser Asp
            500                 505                 510
Asp Asp Asp Asp Asp Asp Cys Lys Lys Ser Ser Met Asp Glu Gly Gly
            515                 520                 525
Thr Ala Gly Ser Glu Ala Met Ala Thr Glu Glu Met Ser Asn Leu Val
        530                 535                 540
Asn Tyr Ile Gln Pro Val Lys Phe Glu Ser Phe Glu Ile Ser Lys Lys
545                 550                 555                 560
Arg Asn Lys Ser Phe Glu Met Ser Ser Phe Val Glu Thr Lys Gly Leu
                565                 570                 575
Glu Gln Leu Thr Lys Ser Pro Val Glu Phe Val Glu Tyr Asn Lys Met
            580                 585                 590
Gln Leu Ser Arg Ile Tyr Pro Lys Gly Thr Arg Val Asp Ser Ser Asn
            595                 600                 605
Tyr Met Pro Gln Leu Phe Trp Asn Ala Gly Cys Gln Met Val Ala Leu
        610                 615                 620
Asn Phe Gln Thr Met Asp Leu Ala Met Gln Ile Asn Met Gly Met Tyr
625                 630                 635                 640
Glu Tyr Asn Gly Lys Ser Gly Tyr Arg Leu Lys Pro Glu Phe Met Arg
                645                 650                 655
Arg Pro Asp Lys His Phe Asp Pro Phe Thr Glu Gly Ile Val Asp Gly
            660                 665                 670
Ile Val Ala Asn Thr Leu Ser Val Lys Ile Ile Ser Gly Gln Phe Leu
            675                 680                 685
Ser Asp Lys Lys Val Gly Thr Tyr Val Glu Val Asp Met Phe Gly Leu
        690                 695                 700
Pro Val Asp Thr Arg Arg Lys Ala Phe Lys Thr Lys Thr Ser Gln Gly
705                 710                 715                 720
Asn Ala Val Asn Pro Val Trp Glu Glu Pro Ile Val Phe Lys Lys
                725                 730                 735
Val Val Leu Pro Thr Leu Ala Cys Leu Arg Ile Ala Val Tyr Glu Glu
            740                 745                 750
Gly Gly Lys Phe Ile Gly His Arg Ile Leu Pro Val Gln Ala Ile Arg
            755                 760                 765
Pro Gly Tyr His Tyr Ile Cys Leu Arg Asn Glu Arg Asn Gln Pro Leu
        770                 775                 780
Thr Leu Pro Ala Val Phe Val Tyr Ile Glu Val Lys Asp Tyr Val Pro
785                 790                 795                 800
Asp Thr Tyr Ala Asp Val Ile Glu Ala Leu Ser Asn Pro Ile Arg Tyr
                805                 810                 815
```

-continued

Val Asn Leu Met Glu Gln Arg Ala Lys Gln Leu Ala Ala Leu Thr Leu
                820                 825                 830

Glu Asp Glu Glu Val Lys Lys Glu Ala Asp Pro Gly Glu Thr Pro
    835                 840                 845

Ser Glu Ala Pro Ser Glu Ala Arg Thr Thr Pro Ala Glu Asn Gly Val
    850                 855                 860

Asn His Thr Thr Thr Leu Thr Pro Lys Pro Pro Ser Gln Ala Leu His
865                 870                 875                 880

Ser Gln Pro Ala Pro Gly Ser Val Lys Ala Pro Ala Lys Thr Glu Asp
                885                 890                 895

Leu Ile Gln Ser Val Leu Thr Glu Val Glu Ala Gln Thr Ile Glu Glu
                900                 905                 910

Leu Lys Gln Gln Lys Ser Phe Val Lys Leu Gln Lys Lys His Tyr Lys
                915                 920                 925

Glu Met Lys Asp Leu Val Lys Arg His His Lys Lys Thr Thr Asp Leu
    930                 935                 940

Ile Lys Glu His Thr Thr Lys Tyr Asn Glu Ile Gln Asn Asp Tyr Leu
945                 950                 955                 960

Arg Arg Arg Ala Ala Leu Glu Lys Ser Ala Lys Lys Asp Ser Lys Lys
                965                 970                 975

Lys Ser Glu Pro Ser Ser Pro Asp His Gly Ser Ser Thr Ile Glu Gln
    980                 985                 990

Asp Leu Ala Ala Leu Asp Ala Glu Met Thr Gln Lys Leu Ile Asp Leu
                995                 1000                1005

Lys Asp Lys Gln Gln Gln Gln Leu Leu Asn Leu Arg Gln Glu Gln Tyr
    1010                1015                1020

Tyr Ser Glu Lys Tyr Gln Lys Arg Glu His Ile Lys Leu Leu Ile Gln
1025                1030                1035                1040

Lys Leu Thr Asp Val Ala Glu Glu Cys Gln Asn Asn Gln Leu Lys Lys
                1045                1050                1055

Leu Lys Glu Ile Cys Glu Lys Glu Lys Lys Glu Leu Lys Lys Lys Met
                1060                1065                1070

Asp Lys Lys Arg Gln Glu Lys Ile Thr Glu Ala Lys Ser Lys Asp Lys
    1075                1080                1085

Ser Gln Met Glu Glu Glu Lys Thr Glu Met Ile Arg Ser Tyr Ile Gln
    1090                1095                1100

Glu Val Val Gln Tyr Ile Lys Arg Leu Glu Glu Ala Gln Ser Lys Arg
1105                1110                1115                1120

Gln Glu Lys Leu Val Glu Lys His Lys Glu Ile Arg Gln Ile Leu
                1125                1130                1135

Asp Glu Lys Pro Lys Leu Gln Val Glu Leu Glu Gln Glu Tyr Gln Asp
    1140                1145                1150

Lys Phe Lys Arg Leu Pro Leu Glu Ile Leu Glu Phe Val Gln Glu Ala
    1155                1160                1165

Met Lys Gly Lys Ile Ser Glu Asp Ser Asn His Gly Ser Ala Pro Leu
    1170                1175                1180

Ser Leu Ser Ser Asp Pro Gly Lys Val Asn His Lys Thr Pro Ser Ser
1185                1190                1195                1200

Glu Glu Leu Gly Gly Asp Ile Pro Gly Lys Glu Phe Asp Thr Pro Leu
                1205                1210                1215

<210> SEQ ID NO 40
<211> LENGTH: 1164
<212> TYPE: PRT

<213> ORGANISM: Homo sapiens

<400> SEQUENCE: 40

```
Met Ala Gly Gly Glu Asp Arg Gly Asp Gly Glu Pro Val Ser Val Val
1               5                   10                  15

Thr Val Arg Val Gln Tyr Leu Glu Asp Thr Asp Pro Phe Ala Cys Ala
            20                  25                  30

Asn Phe Pro Glu Pro Arg Arg Ala Pro Thr Cys Ser Leu Asp Gly Ala
        35                  40                  45

Leu Pro Leu Gly Ala Gln Ile Pro Ala Val His Arg Leu Leu Gly Ala
    50                  55                  60

Pro Leu Lys Leu Glu Asp Cys Ala Leu Gln Val Ser Pro Ser Gly Tyr
65                  70                  75                  80

Tyr Leu Asp Thr Glu Leu Ser Leu Glu Glu Gln Arg Glu Met Leu Glu
                85                  90                  95

Gly Phe Tyr Glu Glu Ile Ser Lys Gly Arg Lys Pro Thr Leu Ile Leu
            100                 105                 110

Arg Thr Gln Leu Ser Val Arg Val Asn Ala Ile Leu Glu Lys Leu Tyr
        115                 120                 125

Ser Ser Ser Gly Pro Glu Leu Arg Arg Ser Leu Phe Ser Leu Lys Gln
130                 135                 140

Ile Phe Gln Glu Asp Lys Asp Leu Val Pro Glu Phe Val His Ser Glu
145                 150                 155                 160

Gly Leu Ser Cys Leu Ile Arg Val Gly Ala Ala Asp His Asn Tyr
                165                 170                 175

Gln Ser Tyr Ile Leu Arg Ala Leu Gly Gln Leu Met Leu Phe Val Asp
            180                 185                 190

Gly Met Leu Gly Val Val Ala His Ser Asp Thr Ile Gln Trp Leu Tyr
        195                 200                 205

Thr Leu Cys Ala Ser Leu Ser Arg Leu Val Val Lys Thr Ala Leu Lys
    210                 215                 220

Leu Leu Leu Val Phe Val Glu Tyr Ser Glu Asn Asn Ala Pro Leu Phe
225                 230                 235                 240

Ile Arg Ala Val Asn Ser Val Ala Thr Thr Thr Gly Ala Pro Pro Trp
                245                 250                 255

Ala Asn Leu Val Ser Ile Leu Glu Glu Lys Asn Gly Ala Asp Pro Glu
            260                 265                 270

Leu Leu Val Tyr Thr Val Thr Leu Ile Asn Lys Thr Leu Ala Ala Leu
        275                 280                 285

Pro Asp Gln Asp Ser Phe Tyr Asp Val Thr Asp Ala Leu Glu Gln Gln
    290                 295                 300

Gly Met Asp Thr Leu Val Gln Arg His Leu Gly Thr Ala Gly Thr Asp
305                 310                 315                 320

Val Asp Leu Arg Thr Gln Leu Val Leu Tyr Glu Asn Ala Leu Lys Leu
                325                 330                 335

Glu Asp Gly Asp Ile Glu Glu Ala Pro Gly Ala Gly Arg Arg Glu
            340                 345                 350

Arg Arg Lys Pro Ser Ser Glu Glu Gly Lys Arg Ser Arg Arg Ser Leu
        355                 360                 365

Glu Gly Gly Gly Cys Pro Ala Arg Ala Pro Glu Pro Gly Pro Thr Gly
    370                 375                 380

Pro Ala Ser Pro Val Gly Pro Thr Ser Ser Thr Gly Pro Ala Leu Leu
385                 390                 395                 400
```

```
Thr Gly Pro Ala Ser Ser Pro Val Gly Pro Pro Ser Gly Leu Gln Ala
            405                 410                 415
Ser Val Asn Leu Phe Pro Thr Ile Ser Val Ala Pro Ser Ala Asp Thr
        420                 425                 430
Ser Ser Glu Arg Ser Ile Tyr Lys Ala Arg Phe Leu Glu Asn Val Ala
    435                 440                 445
Ala Ala Glu Thr Glu Lys Gln Val Ala Leu Ala Gln Gly Arg Ala Glu
450                 455                 460
Thr Leu Ala Gly Ala Met Pro Asn Glu Ala Gly Gly His Pro Asp Ala
465                 470                 475                 480
Arg Gln Leu Trp Asp Ser Pro Glu Thr Ala Pro Ala Arg Thr Pro
                485                 490                 495
Gln Ser Pro Ala Pro Cys Val Leu Leu Arg Ala Gln Arg Ser Leu Ala
            500                 505                 510
Pro Glu Pro Lys Glu Pro Leu Ile Pro Ala Ser Pro Lys Ala Glu Pro
        515                 520                 525
Ile Trp Glu Leu Pro Thr Arg Ala Pro Arg Leu Ser Ile Gly Asp Leu
    530                 535                 540
Asp Phe Ser Asp Leu Gly Glu Asp Glu Asp Gln Asp Met Leu Asn Val
545                 550                 555                 560
Glu Ser Val Glu Ala Gly Lys Asp Ile Pro Ala Pro Ser Pro Pro Leu
                565                 570                 575
Pro Leu Leu Ser Gly Val Pro Pro Pro Leu Pro Pro Pro
            580                 585                 590
Pro Ile Lys Gly Pro Phe Pro Pro Pro Leu Pro Leu Ala Ala
        595                 600                 605
Pro Leu Pro His Ser Val Pro Asp Ser Ser Ala Leu Pro Thr Lys Arg
    610                 615                 620
Lys Thr Val Lys Leu Phe Trp Arg Asp Val Lys Leu Ala Gly His
625                 630                 635                 640
Gly Val Ser Ala Ser Arg Phe Gly Pro Cys Ala Thr Leu Trp Ala Ser
                645                 650                 655
Leu Asp Pro Val Ser Val Asp Thr Ala Arg Leu Glu His Leu Phe Glu
            660                 665                 670
Ser Arg Ala Lys Glu Val Leu Pro Ser Lys Ala Gly Glu Gly Arg
        675                 680                 685
Arg Thr Met Thr Thr Val Leu Asp Pro Lys Arg Thr Asn Ala Ile Asn
    690                 695                 700
Ile Gly Leu Thr Thr Leu Pro Pro Val His Val Ile Lys Ala Ala Leu
705                 710                 715                 720
Leu Asn Phe Asp Glu Phe Ala Val Ser Lys Asp Gly Ile Glu Lys Leu
                725                 730                 735
Leu Thr Met Met Pro Thr Glu Glu Arg Gln Lys Ile Glu Gly Ala
            740                 745                 750
Gln Leu Ala Asn Pro Asp Ile Pro Leu Gly Pro Ala Glu Asn Phe Leu
        755                 760                 765
Met Thr Leu Ala Ser Ile Gly Gly Leu Ala Ala Arg Leu Gln Leu Trp
    770                 775                 780
Ala Phe Lys Leu Asp Tyr Asp Ser Met Glu Arg Glu Ile Ala Glu Pro
785                 790                 795                 800
Leu Phe Asp Leu Lys Val Gly Met Glu Gln Leu Val Gln Asn Ala Thr
                805                 810                 815
Phe Arg Cys Ile Leu Ala Thr Leu Leu Ala Val Gly Asn Phe Leu Asn
```

-continued

```
                820                 825                 830
Gly Ser Gln Ser Ser Gly Phe Glu Leu Ser Tyr Leu Glu Lys Val Ser
            835                 840                 845
Asp Val Lys Asp Thr Val Arg Arg Gln Ser Leu Leu His His Leu Cys
        850                 855                 860
Ser Leu Val Leu Gln Thr Arg Pro Glu Ser Ser Asp Leu Tyr Ser Glu
865                 870                 875                 880
Ile Pro Ala Leu Thr Arg Cys Ala Lys Val Asp Phe Glu Gln Leu Thr
                885                 890                 895
Glu Asn Leu Gly Gln Leu Glu Arg Arg Ser Arg Ala Ala Glu Glu Ser
            900                 905                 910
Leu Arg Ser Leu Ala Lys His Glu Leu Ala Pro Ala Leu Arg Ala Arg
        915                 920                 925
Leu Thr His Phe Leu Asp Gln Cys Ala Arg Arg Val Ala Met Leu Arg
    930                 935                 940
Ile Val His Arg Arg Val Cys Asn Arg Phe His Ala Phe Leu Leu Tyr
945                 950                 955                 960
Leu Gly Tyr Thr Pro Gln Ala Ala Arg Glu Val Arg Ile Met Gln Phe
                965                 970                 975
Cys His Thr Leu Arg Glu Phe Ala Leu Glu Tyr Arg Thr Cys Arg Glu
            980                 985                 990
Arg Val Leu Gln Gln Gln Gln Lys Gln Ala Thr Tyr Arg Glu Arg Asn
        995                1000                1005
Lys Thr Arg Gly Arg Met Ile Thr Glu Thr Lys Phe Ser Gly Val
    1010                1015                1020
Ala Gly Glu Ala Pro Ser Asn Pro Ser Val Pro Val Ala Val Ser Ser
1025                1030                1035                1040
Gly Pro Gly Arg Gly Asp Ala Asp Ser His Ala Ser Met Lys Ser Leu
                1045                1050                1055
Leu Thr Ser Arg Leu Glu Asp Thr Thr His Asn Arg Arg Ser Arg Gly
            1060                1065                1070
Met Val Gln Ser Ser Ser Pro Ile Met Pro Thr Val Gly Pro Ser Thr
        1075                1080                1085
Ala Ser Pro Glu Glu Pro Pro Gly Ser Ser Leu Pro Ser Asp Thr Ser
    1090                1095                1100
Asp Glu Ile Met Asp Leu Leu Val Gln Ser Val Thr Lys Ser Ser Pro
1105                1110                1115                1120
Arg Ala Leu Ala Ala Arg Glu Arg Lys Arg Ser Arg Gly Asn Arg Lys
                1125                1130                1135
Ser Leu Arg Arg Thr Leu Lys Ser Gly Leu Gly Asp Asp Leu Val Gln
            1140                1145                1150
Ala Leu Gly Leu Ser Lys Gly Pro Gly Leu Glu Val
        1155                1160

<210> SEQ ID NO 41
<211> LENGTH: 341
<212> TYPE: PRT
<213> ORGANISM: Homo sapiens

<400> SEQUENCE: 41

Met Thr Asp Gly Ile Leu Gly Lys Ala Ala Thr Met Glu Ile Pro Ile
1               5                   10                  15
His Gly Asn Gly Glu Ala Arg Gln Leu Pro Glu Asp Asp Gly Leu Glu
            20                  25                  30
```

-continued

```
Gln Asp Leu Gln Gln Val Met Val Ser Gly Pro Asn Leu Asn Glu Thr
         35                  40                  45
Ser Ile Val Ser Gly Gly Tyr Gly Ser Gly Asp Gly Leu Ile Pro
 50                  55                  60
Thr Gly Ser Gly Arg His Pro Ser His Ser Thr Pro Ser Gly Pro
 65                  70                  75                  80
Gly Asp Glu Val Ala Arg Gly Ile Ala Gly Glu Lys Phe Asp Ile Val
                 85                  90                  95
Lys Lys Trp Gly Ile Asn Thr Tyr Lys Cys Thr Lys Gln Leu Leu Ser
                100                 105                 110
Glu Arg Phe Gly Arg Gly Ser Arg Thr Val Asp Leu Glu Leu Glu Leu
                115                 120                 125
Gln Ile Glu Leu Leu Arg Glu Thr Lys Arg Lys Tyr Glu Ser Val Leu
    130                 135                 140
Gln Leu Gly Arg Ala Leu Thr Ala His Leu Tyr Ser Leu Leu Gln Thr
145                 150                 155                 160
Gln His Ala Leu Gly Asp Ala Phe Ala Asp Leu Ser Gln Lys Ser Pro
                165                 170                 175
Glu Leu Gln Glu Glu Phe Gly Tyr Asn Ala Glu Thr Gln Lys Leu Leu
                180                 185                 190
Cys Lys Asn Gly Glu Thr Leu Leu Gly Ala Val Asn Phe Phe Val Ser
                195                 200                 205
Ser Ile Asn Thr Leu Val Thr Lys Thr Met Glu Asp Thr Leu Met Thr
    210                 215                 220
Val Lys Gln Tyr Glu Ala Ala Arg Leu Glu Tyr Asp Ala Tyr Arg Thr
225                 230                 235                 240
Asp Leu Glu Glu Leu Ser Leu Gly Pro Arg Asp Ala Gly Thr Arg Gly
                245                 250                 255
Arg Leu Glu Ser Ala Gln Ala Thr Phe Gln Ala His Arg Asp Lys Tyr
                260                 265                 270
Glu Lys Leu Arg Gly Asp Val Ala Ile Lys Leu Lys Phe Leu Glu Glu
                275                 280                 285
Asn Lys Ile Lys Val Met His Lys Gln Leu Leu Leu Phe His Asn Ala
    290                 295                 300
Val Ser Ala Tyr Phe Ala Gly Asn Gln Lys Gln Leu Glu Gln Thr Leu
305                 310                 315                 320
Gln Gln Phe Asn Ile Lys Leu Arg Pro Pro Gly Ala Glu Lys Pro Ser
                325                 330                 335
Trp Leu Glu Glu Gln
            340

<210> SEQ ID NO 42
<211> LENGTH: 888
<212> TYPE: PRT
<213> ORGANISM: Homo sapiens

<400> SEQUENCE: 42

Met Asp Glu Ser Ala Leu Leu Asp Leu Leu Glu Cys Pro Val Cys Leu
 1               5                  10                  15
Glu Arg Leu Asp Ala Ser Ala Lys Val Leu Pro Cys Gln His Thr Phe
                20                  25                  30
Cys Lys Arg Cys Leu Leu Gly Ile Val Gly Ser Arg Asn Glu Leu Arg
        35                  40                  45
Cys Pro Glu Cys Arg Thr Leu Val Gly Ser Gly Val Glu Glu Leu Pro
 50                  55                  60
```

-continued

```
Ser Asn Ile Leu Leu Val Arg Leu Leu Asp Gly Ile Lys Gln Arg Pro
 65                  70                  75                  80

Trp Lys Pro Gly Pro Gly Gly Ser Gly Thr Asn Cys Thr Asn Ala
             85                  90                  95

Leu Arg Ser Gln Ser Ser Thr Val Ala Asn Cys Ser Ser Lys Asp Leu
            100                 105                 110

Gln Ser Ser Gln Gly Gly Gln Gln Pro Arg Val Gln Ser Trp Ser Pro
            115                 120                 125

Pro Val Arg Gly Ile Pro Gln Leu Pro Cys Ala Lys Ala Leu Tyr Asn
            130                 135                 140

Tyr Glu Gly Lys Glu Pro Gly Asp Leu Lys Phe Ser Lys Gly Asp Ile
145                 150                 155                 160

Ile Ile Leu Arg Arg Gln Val Asp Glu Asn Trp Tyr His Gly Glu Val
                165                 170                 175

Asn Gly Ile His Gly Phe Phe Pro Thr Asn Phe Val Gln Ile Ile Lys
                180                 185                 190

Pro Leu Pro Gln Pro Pro Pro Gln Cys Lys Ala Leu Tyr Asp Phe Glu
            195                 200                 205

Val Lys Asp Lys Glu Ala Asp Lys Asp Cys Leu Pro Phe Ala Lys Asp
            210                 215                 220

Asp Val Leu Thr Val Ile Arg Arg Val Asp Glu Asn Trp Ala Glu Gly
225                 230                 235                 240

Met Leu Ala Asp Lys Ile Gly Ile Phe Pro Ile Ser Tyr Val Glu Phe
                245                 250                 255

Asn Ser Ala Ala Lys Gln Leu Ile Glu Trp Asp Lys Pro Pro Val Pro
            260                 265                 270

Gly Val Asp Ala Gly Glu Cys Ser Ser Ala Ala Ala Gln Ser Ser Thr
            275                 280                 285

Ala Pro Lys His Ser Asp Thr Lys Lys Asn Thr Lys Lys Arg His Ser
            290                 295                 300

Phe Thr Ser Leu Thr Met Ala Asn Lys Ser Ser Gln Ala Ser Gln Asn
305                 310                 315                 320

Arg His Ser Met Glu Ile Ser Pro Pro Val Leu Ile Ser Ser Ser Asn
                325                 330                 335

Pro Thr Ala Ala Arg Ile Ser Glu Leu Ser Gly Leu Ser Cys Ser
            340                 345                 350

Ala Pro Ser Gln Val His Ile Ser Thr Thr Gly Leu Ile Val Thr Pro
            355                 360                 365

Pro Pro Ser Ser Pro Val Thr Thr Gly Pro Ser Phe Thr Phe Pro Ser
370                 375                 380

Asp Val Pro Tyr Gln Ala Ala Leu Gly Thr Leu Asn Pro Pro Leu Pro
385                 390                 395                 400

Pro Pro Pro Leu Leu Ala Ala Thr Val Leu Ala Ser Thr Pro Pro Gly
                405                 410                 415

Ala Thr Ala Ala Ala Ala Ala Gly Met Gly Pro Arg Pro Met Ala
            420                 425                 430

Gly Ser Thr Asp Gln Ile Ala His Leu Arg Pro Gln Thr Arg Pro Ser
            435                 440                 445

Val Tyr Val Ala Ile Tyr Pro Tyr Thr Pro Arg Lys Glu Asp Glu Leu
            450                 455                 460

Glu Leu Arg Lys Gly Glu Met Phe Leu Val Phe Glu Arg Cys Gln Asp
465                 470                 475                 480
```

-continued

```
Gly Trp Phe Lys Gly Thr Ser Met His Thr Ser Lys Ile Gly Val Phe
            485                 490                 495
Pro Gly Asn Tyr Val Ala Pro Val Thr Arg Ala Val Thr Asn Ala Ser
        500                 505                 510
Gln Ala Lys Val Pro Met Ser Thr Ala Gly Gln Thr Ser Arg Gly Val
    515                 520                 525
Thr Met Val Ser Pro Ser Thr Ala Gly Gly Pro Ala Gln Lys Leu Gln
530                 535                 540
Gly Asn Gly Val Ala Gly Ser Pro Ser Val Val Pro Ala Ala Val Val
545                 550                 555                 560
Ser Ala Ala His Ile Gln Thr Ser Pro Gln Ala Lys Val Leu Leu His
                565                 570                 575
Met Thr Gly Gln Met Thr Val Asn Gln Ala Arg Asn Ala Val Arg Thr
            580                 585                 590
Val Ala Ala His Asn Gln Glu Arg Pro Thr Ala Ala Val Thr Pro Ile
        595                 600                 605
Gln Val Gln Asn Ala Ala Gly Leu Ser Pro Ala Ser Val Gly Leu Ser
    610                 615                 620
His His Ser Leu Ala Ser Pro Gln Pro Ala Pro Leu Met Pro Gly Ser
625                 630                 635                 640
Ala Thr His Thr Ala Ala Ile Ser Ile Ser Arg Ala Ser Ala Pro Leu
                645                 650                 655
Ala Cys Ala Ala Ala Pro Leu Thr Ser Pro Ser Ile Thr Ser Ala
            660                 665                 670
Ser Leu Glu Ala Glu Pro Ser Gly Arg Ile Val Thr Val Leu Pro Gly
        675                 680                 685
Leu Pro Thr Ser Pro Asp Ser Ala Ser Ser Ala Cys Gly Asn Ser Ser
    690                 695                 700
Ala Thr Lys Pro Asp Lys Asp Ser Lys Lys Glu Lys Lys Gly Leu Leu
705                 710                 715                 720
Lys Leu Leu Ser Gly Ala Ser Thr Lys Arg Lys Pro Arg Val Ser Pro
                725                 730                 735
Pro Ala Ser Pro Thr Leu Glu Val Glu Leu Gly Ser Ala Glu Leu Pro
            740                 745                 750
Leu Gln Gly Ala Val Gly Pro Glu Leu Pro Pro Gly Gly His Gly
    755                 760                 765
Arg Ala Gly Ser Cys Pro Val Asp Gly Asp Gly Pro Val Thr Thr Ala
770                 775                 780
Val Ala Gly Ala Ala Leu Ala Gln Asp Ala Phe His Arg Lys Ala Ser
785                 790                 795                 800
Ser Leu Asp Ser Ala Val Pro Ile Ala Pro Pro Arg Gln Ala Cys
                805                 810                 815
Ser Ser Leu Gly Pro Val Leu Asn Glu Ser Arg Pro Val Val Cys Glu
            820                 825                 830
Arg His Arg Val Val Val Ser Tyr Pro Pro Gln Ser Glu Ala Glu Leu
        835                 840                 845
Glu Leu Lys Glu Gly Asp Ile Val Phe Val His Lys Lys Arg Glu Asp
    850                 855                 860
Gly Trp Phe Lys Gly Thr Leu Gln Arg Asn Gly Lys Thr Gly Leu Phe
865                 870                 875                 880
Pro Gly Ser Phe Val Glu Asn Ile
                885
```

```
<210> SEQ ID NO 43
<211> LENGTH: 1253
<212> TYPE: PRT
<213> ORGANISM: Homo sapiens

<400> SEQUENCE: 43

Met Ala Ala Gln Val Thr Leu Glu Asp Ala Leu Ser Asn Val Asp Leu
1               5                   10                  15

Leu Glu Glu Leu Pro Leu Pro Asp Gln Gln Pro Cys Ile Glu Pro Pro
            20                  25                  30

Pro Ser Ser Leu Leu Tyr Gln Pro Asn Phe Asn Thr Asn Phe Glu Asp
        35                  40                  45

Arg Asn Ala Phe Val Thr Gly Ile Ala Arg Tyr Ile Glu Gln Ala Thr
    50                  55                  60

Val His Ser Ser Met Asn Glu Met Leu Glu Glu Gly Gln Glu Tyr Ala
65                  70                  75                  80

Val Met Leu Tyr Thr Trp Arg Ser Cys Ser Arg Ala Ile Pro Gln Val
                85                  90                  95

Lys Cys Asn Glu Gln Pro Asn Arg Val Glu Ile Tyr Glu Lys Thr Val
            100                 105                 110

Glu Val Leu Glu Pro Glu Val Thr Lys Leu Met Asn Phe Met Tyr Phe
        115                 120                 125

Gln Arg Asn Ala Ile Glu Arg Phe Cys Gly Glu Val Arg Arg Leu Cys
    130                 135                 140

His Ala Glu Arg Arg Lys Asp Phe Val Ser Glu Ala Tyr Leu Ile Thr
145                 150                 155                 160

Leu Gly Lys Phe Ile Asn Met Phe Ala Val Leu Asp Glu Leu Lys Asn
                165                 170                 175

Met Lys Cys Ser Val Lys Asn Asp His Ser Ala Tyr Lys Arg Ala Ala
            180                 185                 190

Gln Phe Leu Arg Lys Met Ala Asp Pro Gln Ser Ile Gln Glu Ser Gln
    195                 200                 205

Asn Leu Ser Met Phe Leu Ala Asn His Asn Lys Ile Thr Gln Ser Leu
    210                 215                 220

Gln Gln Gln Leu Glu Val Ile Ser Gly Tyr Glu Glu Leu Leu Ala Asp
225                 230                 235                 240

Ile Val Asn Leu Cys Val Asp Tyr Tyr Glu Asn Arg Met Tyr Leu Thr
                245                 250                 255

Pro Ser Glu Lys His Met Leu Leu Lys Val Met Gly Phe Gly Leu Tyr
            260                 265                 270

Leu Met Asp Gly Ser Val Ser Asn Ile Tyr Lys Leu Asp Ala Lys Lys
    275                 280                 285

Arg Ile Asn Leu Ser Lys Ile Asp Lys Tyr Phe Lys Gln Leu Gln Val
    290                 295                 300

Val Pro Leu Phe Gly Asp Met Gln Ile Glu Leu Ala Arg Tyr Ile Lys
305                 310                 315                 320

Thr Ser Ala His Tyr Glu Glu Asn Lys Ser Arg Trp Thr Cys Thr Ser
                325                 330                 335

Ser Gly Ser Ser Pro Gln Tyr Asn Ile Cys Glu Gln Met Ile Gln Ile
            340                 345                 350

Arg Glu Asp His Met Arg Phe Ile Ser Glu Leu Ala Arg Tyr Ser Asn
    355                 360                 365

Ser Glu Val Val Thr Gly Ser Gly Arg Gln Glu Ala Gln Lys Thr Asp
    370                 375                 380
```

-continued

```
Ala Glu Tyr Arg Lys Leu Phe Asp Leu Ala Leu Gln Gly Leu Gln Leu
385                 390                 395                 400

Leu Ser Gln Trp Ser Ala His Val Met Glu Val Tyr Ser Trp Lys Leu
            405                 410                 415

Val His Pro Thr Asp Lys Tyr Ser Asn Lys Asp Cys Pro Asp Ser Ala
        420                 425                 430

Glu Glu Tyr Glu Arg Ala Thr Arg Tyr Asn Tyr Thr Ser Glu Glu Lys
    435                 440                 445

Phe Ala Leu Val Glu Val Ile Ala Met Ile Lys Gly Leu Gln Val Leu
    450                 455                 460

Met Gly Arg Met Glu Ser Val Phe Asn His Ala Ile Arg His Thr Val
465                 470                 475                 480

Tyr Ala Ala Leu Gln Asp Phe Ser Gln Val Thr Leu Arg Glu Pro Leu
            485                 490                 495

Arg Gln Ala Ile Lys Lys Lys Asn Val Ile Gln Ser Val Leu Gln
        500                 505                 510

Ala Ile Arg Lys Thr Val Cys Asp Trp Glu Thr Gly His Glu Pro Phe
        515                 520                 525

Asn Asp Pro Ala Leu Arg Gly Glu Lys Asp Pro Lys Ser Gly Phe Asp
530                 535                 540

Ile Lys Val Pro Arg Arg Ala Val Gly Pro Ser Ser Thr Gln Leu Tyr
545                 550                 555                 560

Met Val Arg Thr Met Leu Glu Ser Leu Ile Ala Asp Lys Ser Gly Ser
            565                 570                 575

Lys Lys Thr Leu Arg Ser Ser Leu Glu Gly Pro Thr Ile Leu Asp Ile
            580                 585                 590

Glu Lys Phe His Arg Glu Ser Phe Phe Tyr Thr His Leu Ile Asn Phe
        595                 600                 605

Ser Glu Thr Leu Gln Gln Cys Cys Asp Leu Ser Gln Leu Trp Phe Arg
    610                 615                 620

Glu Phe Phe Leu Glu Leu Thr Met Gly Arg Arg Ile Gln Phe Pro Ile
625                 630                 635                 640

Glu Met Ser Met Pro Trp Ile Leu Thr Asp His Ile Leu Glu Thr Lys
            645                 650                 655

Glu Ala Ser Met Met Glu Tyr Val Leu Tyr Ser Leu Asp Leu Tyr Asn
            660                 665                 670

Asp Ser Ala His Tyr Ala Leu Thr Arg Phe Asn Lys Gln Phe Leu Tyr
        675                 680                 685

Asp Glu Ile Glu Ala Glu Val Asn Leu Cys Phe Asp Gln Phe Val Tyr
        690                 695                 700

Lys Leu Ala Asp Gln Ile Phe Ala Tyr Tyr Lys Val Met Ala Gly Ser
705                 710                 715                 720

Leu Leu Leu Asp Lys Arg Leu Arg Ser Glu Cys Lys Asn Gln Gly Ala
            725                 730                 735

Thr Ile His Leu Pro Pro Ser Asn Arg Tyr Glu Thr Leu Leu Lys Gln
            740                 745                 750

Arg His Val Gln Leu Leu Gly Arg Ser Ile Asp Leu Asn Arg Leu Ile
        755                 760                 765

Thr Gln Arg Val Ser Ala Ala Met Tyr Lys Ser Leu Glu Leu Ala Ile
        770                 775                 780

Gly Arg Phe Glu Ser Glu Asp Leu Thr Ser Ile Val Glu Leu Asp Gly
785                 790                 795                 800

Leu Leu Glu Ile Asn Arg Met Thr His Lys Leu Leu Ser Arg Tyr Leu
```

```
                    805                 810                 815
Thr Leu Asp Gly Phe Asp Ala Met Phe Arg Glu Ala Asn His Asn Val
                820                 825                 830

Ser Ala Pro Tyr Gly Arg Ile Thr Leu His Val Phe Trp Glu Leu Asn
            835                 840                 845

Tyr Asp Phe Leu Pro Asn Tyr Cys Tyr Asn Gly Ser Thr Asn Arg Phe
        850                 855                 860

Val Arg Thr Val Leu Pro Phe Ser Gln Glu Phe Gln Arg Asp Lys Gln
    865                 870                 875                 880

Pro Asn Ala Gln Pro Gln Tyr Leu His Gly Ser Lys Ala Leu Asn Leu
                885                 890                 895

Ala Tyr Ser Ser Ile Tyr Gly Ser Tyr Arg Asn Phe Val Gly Pro Pro
            900                 905                 910

His Phe Gln Val Ile Cys Arg Leu Leu Gly Tyr Gln Gly Ile Ala Val
        915                 920                 925

Val Met Glu Glu Leu Leu Lys Val Val Lys Ser Leu Leu Gln Gly Thr
    930                 935                 940

Ile Leu Gln Tyr Val Lys Thr Leu Met Glu Val Met Pro Lys Ile Cys
945                 950                 955                 960

Arg Leu Pro Arg His Glu Tyr Gly Ser Pro Gly Ile Leu Glu Phe Phe
                965                 970                 975

His His Gln Leu Lys Asp Ile Val Glu Tyr Ala Glu Leu Lys Thr Val
            980                 985                 990

Cys Phe Gln Asn Leu Arg Glu Val Gly Asn Ala Ile Leu Phe Cys Leu
        995                 1000                1005

Leu Ile Glu Gln Ser Leu Ser Leu Glu Val Cys Asp Leu Leu His
    1010                1015                1020

Ala Ala Pro Phe Gln Asn Ile Leu Pro Arg Val His Val Lys Glu Gly
1025                1030                1035                1040

Glu Arg Leu Asp Ala Lys Met Lys Arg Leu Glu Ser Lys Tyr Ala Pro
                1045                1050                1055

Leu His Leu Val Pro Leu Ile Glu Arg Leu Gly Thr Pro Gln Gln Ile
            1060                1065                1070

Ala Ile Ala Arg Glu Gly Asp Leu Leu Thr Lys Glu Arg Leu Cys Cys
        1075                1080                1085

Gly Leu Ser Met Phe Glu Val Ile Leu Thr Arg Ile Arg Ser Phe Leu
    1090                1095                1100

Asp Asp Pro Ile Trp Arg Gly Pro Leu Pro Ser Asn Gly Val Met His
1105                1110                1115                1120

Val Asp Glu Cys Val Glu Phe His Arg Leu Trp Ser Ala Met Gln Phe
                1125                1130                1135

Val Tyr Cys Ile Pro Val Gly Thr His Glu Phe Thr Val Glu Gln Cys
            1140                1145                1150

Phe Gly Asp Gly Leu His Trp Ala Gly Cys Met Ile Val Leu Leu
        1155                1160                1165

Gly Gln Gln Arg Arg Phe Ala Val Leu Asp Phe Cys Tyr His Leu Leu
    1170                1175                1180

Lys Val Gln Lys His Asp Gly Lys Asp Glu Ile Ile Lys Asn Val Pro
1185                1190                1195                1200

Leu Lys Lys Met Val Glu Arg Ile Arg Lys Phe Gln Ile Leu Asn Asp
                1205                1210                1215

Glu Ile Ile Thr Ile Leu Asp Lys Tyr Leu Lys Ser Gly Asp Gly Glu
            1220                1225                1230
```

```
Gly Thr Pro Val Glu His Val Arg Cys Phe Gln Pro Ile His Gln
        1235                1240                1245

Ser Leu Ala Ser Ser
    1250

<210> SEQ ID NO 44
<211> LENGTH: 1496
<212> TYPE: PRT
<213> ORGANISM: Homo sapiens

<400> SEQUENCE: 44

Met Ala Leu Ser Lys Gly Leu Arg Leu Leu Gly Arg Leu Gly Ala Glu
1               5                   10                  15

Gly Asp Cys Ser Val Leu Leu Glu Ala Arg Gly Arg Asp Asp Cys Leu
            20                  25                  30

Leu Phe Glu Ala Gly Thr Val Ala Thr Leu Ala Pro Glu Glu Lys Glu
        35                  40                  45

Val Ile Lys Gly Gln Tyr Gly Lys Leu Thr Asp Ala Tyr Gly Cys Leu
    50                  55                  60

Gly Glu Leu Arg Leu Lys Ser Gly Gly Thr Ser Leu Ser Phe Leu Val
65                  70                  75                  80

Leu Val Thr Gly Cys Thr Ser Val Gly Arg Ile Pro Asp Ala Glu Ile
                85                  90                  95

Tyr Lys Ile Thr Ala Thr Asp Phe Tyr Pro Leu Gln Glu Glu Ala Lys
            100                 105                 110

Glu Glu Glu Arg Leu Ile Ala Leu Lys Lys Ile Leu Ser Ser Gly Val
        115                 120                 125

Phe Tyr Phe Ser Trp Pro Asn Asp Gly Ser Arg Phe Asp Leu Thr Val
    130                 135                 140

Arg Thr Gln Lys Gln Gly Asp Asp Ser Ser Glu Trp Gly Asn Ser Phe
145                 150                 155                 160

Phe Trp Asn Gln Leu Leu His Val Pro Leu Arg Gln His Gln Val Ser
                165                 170                 175

Cys Cys Asp Trp Leu Leu Lys Ile Ile Cys Gly Val Val Thr Ile Arg
            180                 185                 190

Thr Val Tyr Ala Ser His Lys Gln Ala Lys Ala Cys Leu Val Ser Arg
        195                 200                 205

Val Ser Cys Glu Arg Thr Gly Thr Arg Phe His Thr Arg Gly Val Asn
    210                 215                 220

Asp Asp Gly His Val Ser Asn Phe Val Glu Thr Glu Gln Met Ile Tyr
225                 230                 235                 240

Met Asp Asp Gly Val Ser Ser Phe Val Gln Ile Arg Gly Ser Val Pro
                245                 250                 255

Leu Phe Trp Glu Gln Pro Gly Leu Gln Val Gly Ser His His Leu Arg
            260                 265                 270

Leu His Arg Gly Leu Glu Ala Asn Ala Pro Ala Phe Asp Arg His Met
        275                 280                 285

Val Leu Leu Lys Glu Gln Tyr Gly Gln Gln Val Val Asn Leu Leu
    290                 295                 300

Gly Ser Arg Gly Gly Glu Glu Val Leu Asn Arg Ala Phe Lys Lys Leu
305                 310                 315                 320

Leu Trp Ala Ser Cys His Ala Gly Asp Thr Pro Met Ile Asn Phe Asp
                325                 330                 335

Phe His Gln Phe Ala Lys Gly Gly Lys Leu Glu Lys Leu Glu Thr Leu
```

-continued

```
                340                 345                 350
Leu Arg Pro Gln Leu Lys Leu His Trp Glu Asp Phe Asp Val Phe Thr
            355                 360                 365
Lys Gly Glu Asn Val Ser Pro Arg Phe Gln Lys Gly Thr Leu Arg Met
        370                 375                 380
Asn Cys Leu Asp Cys Leu Asp Arg Thr Asn Thr Val Gln Ser Phe Ile
385                 390                 395                 400
Ala Leu Glu Val Leu His Leu Gln Leu Lys Thr Leu Gly Leu Ser Ser
                405                 410                 415
Lys Pro Ile Val Asp Arg Phe Val Glu Ser Phe Lys Ala Met Trp Ser
            420                 425                 430
Leu Asn Gly His Ser Leu Ser Lys Val Phe Thr Gly Ser Arg Ala Leu
        435                 440                 445
Glu Gly Lys Ala Lys Val Gly Lys Leu Lys Asp Gly Ala Arg Ser Met
    450                 455                 460
Ser Arg Thr Ile Gln Ser Asn Phe Phe Asp Gly Val Lys Gln Glu Ala
465                 470                 475                 480
Ile Lys Leu Leu Leu Val Gly Asp Val Tyr Gly Glu Glu Val Ala Asp
                485                 490                 495
Lys Gly Gly Met Leu Leu Asp Ser Thr Ala Leu Leu Val Thr Pro Arg
            500                 505                 510
Ile Leu Lys Ala Met Thr Glu Arg Gln Ser Glu Phe Thr Asn Phe Lys
        515                 520                 525
Arg Ile Arg Ile Ala Met Gly Thr Trp Asn Val Asn Gly Gly Lys Gln
    530                 535                 540
Phe Arg Ser Asn Val Leu Arg Thr Ala Glu Leu Thr Asp Trp Leu Leu
545                 550                 555                 560
Asp Ser Pro Gln Leu Ser Gly Ala Thr Asp Ser Gln Asp Asp Ser Ser
                565                 570                 575
Pro Ala Asp Ile Phe Ala Val Gly Phe Glu Glu Met Val Glu Leu Ser
            580                 585                 590
Ala Gly Asn Ile Val Asn Ala Ser Thr Thr Asn Lys Lys Met Trp Gly
        595                 600                 605
Glu Gln Leu Gln Lys Ala Ile Ser Arg Ser His Arg Tyr Ile Leu Leu
    610                 615                 620
Thr Ser Ala Gln Leu Val Gly Val Cys Leu Tyr Ile Phe Val Arg Pro
625                 630                 635                 640
Tyr His Val Pro Phe Ile Arg Asp Val Ala Ile Asp Thr Val Lys Thr
                645                 650                 655
Gly Met Gly Gly Lys Ala Gly Asn Lys Gly Ala Val Gly Ile Arg Phe
            660                 665                 670
Gln Phe His Ser Thr Ser Phe Cys Phe Ile Cys Ser His Leu Thr Ala
        675                 680                 685
Gly Gln Ser Gln Val Lys Glu Arg Asn Glu Asp Tyr Lys Glu Ile Thr
    690                 695                 700
Gln Lys Leu Cys Phe Pro Met Gly Arg Asn Val Phe Ser His Asp Tyr
705                 710                 715                 720
Val Phe Trp Cys Gly Asp Phe Asn Tyr Arg Ile Asp Leu Thr Tyr Glu
                725                 730                 735
Glu Val Phe Tyr Phe Val Lys Arg Gln Asp Trp Lys Lys Leu Leu Glu
            740                 745                 750
Phe Asp Gln Leu Gln Leu Gln Lys Ser Ser Gly Lys Ile Phe Lys Asp
        755                 760                 765
```

-continued

```
Phe His Glu Gly Ala Ile Asn Phe Gly Pro Thr Tyr Lys Tyr Asp Val
    770                 775                 780

Gly Ser Ala Ala Tyr Asp Thr Ser Asp Lys Cys Arg Thr Pro Ala Trp
785                 790                 795                 800

Thr Asp Arg Val Leu Trp Trp Arg Lys Lys His Pro Phe Asp Lys Thr
                    805                 810                 815

Ala Gly Glu Leu Asn Leu Leu Asp Ser Asp Leu Asp Val Asp Thr Lys
                820                 825                 830

Val Arg His Thr Trp Ser Pro Gly Ala Leu Gln Tyr Tyr Gly Arg Ala
                835                 840                 845

Glu Leu Gln Ala Ser Asp His Arg Pro Val Leu Ala Ile Val Glu Val
    850                 855                 860

Glu Val Gln Glu Val Asp Val Gly Ala Arg Glu Arg Val Phe Gln Glu
865                 870                 875                 880

Val Ser Ser Phe Gln Gly Pro Leu Asp Ala Thr Val Val Asn Leu
                    885                 890                 895

Gln Ser Pro Thr Leu Glu Glu Lys Asn Glu Phe Pro Glu Asp Leu Arg
                900                 905                 910

Thr Glu Leu Met Gln Thr Leu Gly Ser Tyr Gly Thr Ile Val Leu Val
                915                 920                 925

Arg Ile Asn Gln Gly Gln Met Leu Val Thr Phe Ala Asp Ser His Ser
    930                 935                 940

Ala Leu Ser Val Leu Asp Val Asp Gly Met Lys Val Lys Gly Arg Ala
945                 950                 955                 960

Val Lys Ile Arg Pro Lys Thr Lys Asp Trp Leu Lys Gly Leu Arg Glu
                965                 970                 975

Glu Ile Ile Arg Lys Arg Asp Ser Met Ala Pro Val Ser Pro Thr Ala
                980                 985                 990

Asn Ser Cys Leu Leu Glu Glu Asn Phe Asp Phe Thr Ser Leu Asp Tyr
    995                 1000                1005

Glu Ser Glu Gly Asp Ile Leu Glu Asp Glu Asp Tyr Leu Val Asp
    1010                1015                1020

Glu Phe Asn Gln Pro Gly Val Ser Asp Ser Glu Leu Gly Gly Asp Asp
1025                1030                1035                1040

Leu Ser Asp Val Pro Gly Pro Thr Ala Leu Ala Pro Ser Lys Ser
                    1045                1050                1055

Pro Ala Leu Thr Lys Lys Gln His Pro Thr Tyr Lys Asp Asp Ala
                    1060                1065                1070

Asp Leu Val Glu Leu Lys Arg Glu Leu Glu Ala Val Gly Glu Phe Arg
    1075                1080                1085

His Arg Ser Pro Ser Arg Ser Leu Ser Val Pro Asn Arg Pro Arg Pro
    1090                1095                1100

Pro Gln Pro Pro Gln Arg Pro Pro Pro Thr Gly Leu Met Val Lys
1105                1110                1115                1120

Lys Ser Ala Ser Asp Ala Ser Ile Ser Ser Gly Thr His Gly Gln Tyr
                    1125                1130                1135

Ser Ile Leu Gln Thr Ala Arg Leu Leu Pro Gly Ala Pro Gln Gln Pro
                1140                1145                1150

Pro Lys Ala Arg Thr Gly Ile Ser Lys Pro Tyr Asn Val Lys Gln Ile
                1155                1160                1165

Lys Thr Thr Asn Ala Gln Glu Ala Glu Ala Ala Ile Arg Cys Leu Leu
    1170                1175                1180
```

```
Glu Ala Arg Gly Gly Ala Ser Glu Glu Ala Leu Ser Ala Val Ala Pro
1185                1190                1195                1200

Arg Asp Leu Glu Ala Ser Ser Glu Pro Glu Pro Thr Pro Gly Ala Ala
            1205                1210                1215

Lys Pro Glu Thr Pro Gln Ala Pro Pro Leu Leu Pro Arg Pro Pro
        1220                1225                1230

Pro Arg Val Pro Ala Ile Lys Lys Pro Thr Leu Arg Arg Thr Gly Lys
        1235                1240                1245

Pro Leu Ser Pro Glu Glu Gln Phe Glu Gln Gln Thr Val His Phe Thr
    1250                1255                1260

Ile Gly Pro Pro Glu Thr Ser Val Glu Ala Pro Pro Val Val Thr Ala
1265                1270                1275                1280

Pro Arg Val Pro Pro Val Pro Lys Pro Arg Thr Phe Gln Pro Gly Lys
            1285                1290                1295

Ala Ala Glu Arg Pro Ser His Arg Lys Pro Ala Ser Asp Glu Ala Pro
            1300                1305                1310

Pro Gly Ala Gly Ala Ser Val Pro Pro Leu Glu Ala Pro Pro Leu
        1315                1320                1325

Val Pro Lys Val Pro Pro Arg Arg Lys Lys Ser Ala Pro Ala Ala Phe
    1330                1335                1340

His Leu Gln Val Leu Gln Ser Asn Ser Gln Leu Leu Gln Gly Leu Thr
1345                1350                1355                1360

Tyr Asn Ser Ser Asp Ser Pro Ser Gly His Pro Pro Ala Ala Gly Thr
            1365                1370                1375

Val Phe Pro Gln Gly Asp Phe Leu Ser Thr Ser Ser Ala Thr Ser Pro
        1380                1385                1390

Asp Ser Asp Gly Thr Lys Ala Met Lys Pro Glu Ala Ala Pro Leu Leu
        1395                1400                1405

Gly Asp Tyr Gln Asp Pro Phe Trp Asn Leu Leu His Pro Lys Leu
    1410                1415                1420

Leu Asn Asn Thr Trp Leu Ser Lys Ser Ser Asp Pro Leu Asp Ser Gly
1425                1430                1435                1440

Thr Arg Ser Pro Lys Arg Asp Pro Ile Asp Pro Val Ser Ala Gly Ala
            1445                1450                1455

Ser Ala Ala Lys Ala Glu Leu Pro Pro Asp His Glu His Lys Thr Leu
        1460                1465                1470

Gly His Trp Val Thr Ile Ser Asp Gln Glu Leu Arg Thr Ala Leu Gln
        1475                1480                1485

Val Phe Asp Pro Leu Ala Lys Thr
    1490                1495

<210> SEQ ID NO 45
<211> LENGTH: 12
<212> TYPE: PRT
<213> ORGANISM: Homo sapiens
<220> FEATURE:
<221> NAME/KEY: misc_feature
<222> LOCATION: (3), (5), (7), (9)
<223> OTHER INFORMATION: Xaa is any amino acid

<400> SEQUENCE: 45

Ile Ser Xaa Pro Xaa Phe Xaa His Xaa His Val Gly
1               5                   10

<210> SEQ ID NO 46
<211> LENGTH: 1038
<212> TYPE: PRT
```

<213> ORGANISM: Homo sapiens

<400> SEQUENCE: 46

```
Met Gln Pro Glu Glu Gly Thr Gly Trp Leu Leu Glu Leu Leu Ser Glu
1               5                   10                  15
Val Gln Leu Gln Gln Tyr Phe Leu Arg Leu Arg Asp Asp Leu Asn Val
                20                  25                  30
Thr Arg Leu Ser His Phe Glu Tyr Val Lys Asn Glu Asp Leu Glu Lys
            35                  40                  45
Ile Gly Met Gly Arg Pro Gly Gln Arg Arg Leu Trp Glu Ala Val Lys
        50                  55                  60
Arg Arg Lys Ala Leu Cys Lys Arg Lys Ser Trp Met Ser Lys Val Phe
65                  70                  75                  80
Ser Gly Lys Arg Leu Glu Ala Glu Phe Pro Pro His His Ser Gln Ser
                85                  90                  95
Thr Phe Arg Lys Thr Ser Pro Ala Pro Gly Gly Pro Ala Gly Glu Gly
            100                 105                 110
Pro Leu Gln Ser Leu Thr Cys Leu Ile Gly Glu Lys Asp Leu Arg Leu
        115                 120                 125
Leu Glu Lys Leu Gly Asp Gly Ser Phe Gly Val Val Arg Arg Gly Glu
130                 135                 140
Trp Asp Ala Pro Ser Gly Lys Thr Val Ser Val Ala Val Lys Cys Leu
145                 150                 155                 160
Lys Pro Asp Val Leu Ser Gln Pro Glu Ala Met Asp Asp Phe Ile Arg
                165                 170                 175
Glu Val Asn Ala Met His Ser Leu Asp His Arg Asn Leu Ile Arg Leu
            180                 185                 190
Tyr Gly Val Val Leu Thr Pro Pro Met Lys Met Val Thr Glu Leu Ala
        195                 200                 205
Pro Leu Gly Ser Leu Leu Asp Arg Leu Arg Lys His Gln Gly His Phe
210                 215                 220
Leu Leu Gly Thr Leu Ser Arg Tyr Ala Val Gln Val Ala Glu Gly Met
225                 230                 235                 240
Gly Tyr Leu Glu Ser Lys Arg Phe Ile His Arg Asp Leu Ala Ala Arg
                245                 250                 255
Asn Leu Leu Leu Ala Thr Arg Asp Leu Val Lys Ile Gly Asp Phe Gly
            260                 265                 270
Leu Met Arg Ala Leu Pro Gln Asn Asp Asp His Tyr Val Met Gln Glu
        275                 280                 285
His Arg Lys Val Pro Phe Ala Trp Cys Ala Pro Glu Ser Leu Lys Thr
290                 295                 300
Arg Thr Phe Ser His Ala Ser Asp Thr Trp Met Phe Gly Val Thr Leu
305                 310                 315                 320
Trp Glu Met Phe Thr Tyr Gly Gln Glu Pro Trp Ile Gly Leu Asn Gly
                325                 330                 335
Ser Gln Ile Leu His Lys Ile Asp Lys Glu Gly Glu Arg Leu Pro Arg
            340                 345                 350
Pro Glu Asp Cys Pro Gln Asp Ile Tyr Asn Val Met Val Gln Cys Trp
        355                 360                 365
Ala His Lys Pro Glu Asp Arg Pro Thr Phe Val Ala Leu Arg Asp Phe
370                 375                 380
Leu Leu Glu Ala Gln Pro Thr Asp Met Arg Ala Leu Gln Asp Phe Glu
385                 390                 395                 400
```

-continued

```
Glu Pro Asp Lys Leu His Ile Gln Met Asn Asp Val Ile Thr Val Ile
                405                 410                 415
Glu Gly Arg Ala Glu Asn Tyr Trp Trp Arg Gly Gln Asn Thr Arg Thr
            420                 425                 430
Leu Cys Val Gly Pro Phe Pro Arg Asn Val Val Thr Ser Val Ala Gly
        435                 440                 445
Leu Ser Ala Gln Asp Ile Ser Gln Pro Leu Gln Asn Ser Phe Ile His
    450                 455                 460
Thr Gly His Gly Asp Ser Asp Pro Arg His Cys Trp Gly Phe Pro Asp
465                 470                 475                 480
Arg Ile Asp Glu Leu Tyr Leu Gly Asn Pro Met Asp Pro Pro Asp Leu
                485                 490                 495
Leu Ser Val Glu Leu Ser Thr Ser Arg Pro Pro Gln His Leu Gly Gly
            500                 505                 510
Val Lys Lys Pro Thr Tyr Asp Pro Val Ser Glu Asp Gln Asp Pro Leu
        515                 520                 525
Ser Ser Asp Phe Lys Arg Leu Gly Leu Arg Lys Pro Gly Leu Pro Arg
    530                 535                 540
Gly Leu Trp Leu Ala Lys Pro Ser Ala Arg Val Pro Gly Thr Lys Ala
545                 550                 555                 560
Ser Arg Gly Ser Gly Ala Glu Val Thr Leu Ile Asp Phe Gly Glu Glu
                565                 570                 575
Pro Val Val Pro Ala Leu Arg Pro Cys Ala Pro Ser Leu Ala Gln Leu
            580                 585                 590
Ala Met Asp Ala Cys Ser Leu Leu Asp Glu Thr Pro Pro Gln Ser Pro
        595                 600                 605
Thr Arg Ala Leu Pro Arg Pro Leu His Pro Thr Pro Val Val Asp Trp
    610                 615                 620
Asp Ala Arg Pro Leu Pro Pro Pro Ala Tyr Asp Asp Val Ala Gln
625                 630                 635                 640
Asp Glu Asp Asp Phe Glu Ile Cys Ser Ile Asn Ser Thr Leu Val Gly
                645                 650                 655
Ala Gly Val Pro Ala Gly Pro Ser Gln Gly Gln Thr Asn Tyr Ala Phe
            660                 665                 670
Val Pro Glu Gln Ala Arg Pro Pro Pro Leu Glu Asp Asn Leu Phe
        675                 680                 685
Leu Pro Pro Gln Gly Gly Gly Lys Pro Pro Ser Ser Ala Gln Thr Ala
    690                 695                 700
Glu Ile Phe Gln Ala Leu Gln Gln Glu Cys Met Arg Gln Leu Gln Ala
705                 710                 715                 720
Pro Ala Gly Ser Pro Ala Pro Ser Pro Ser Pro Gly Gly Asp Asp Lys
                725                 730                 735
Pro Gln Val Pro Pro Arg Val Pro Ile Pro Pro Arg Pro Thr Arg Pro
            740                 745                 750
His Val Gln Leu Ser Pro Ala Pro Pro Gly Glu Glu Thr Ser Gln
        755                 760                 765
Trp Pro Gly Pro Ala Ser Pro Arg Val Pro Pro Arg Glu Pro Leu
    770                 775                 780
Ser Pro Gln Gly Ser Arg Thr Pro Ser Pro Leu Val Pro Pro Gly Ser
785                 790                 795                 800
Ser Pro Leu Pro Pro Arg Leu Ser Ser Pro Gly Lys Thr Met Pro
                805                 810                 815
Thr Thr Gln Ser Phe Ala Ser Asp Pro Lys Tyr Ala Thr Pro Gln Val
```

```
                820             825             830
Ile Gln Ala Pro Gly Pro Arg Ala Gly Pro Cys Ile Leu Pro Ile Val
            835             840             845
Arg Asp Gly Lys Lys Val Ser Ser Thr His Tyr Tyr Leu Leu Pro Glu
        850             855             860
Arg Pro Ser Tyr Leu Glu Arg Tyr Gln Arg Phe Leu Arg Glu Ala Gln
865             870             875             880
Ser Pro Glu Glu Pro Thr Pro Leu Pro Val Pro Leu Leu Leu Pro Pro
                885             890             895
Pro Ser Thr Pro Ala Pro Ala Ala Pro Thr Ala Thr Val Arg Pro Met
            900             905             910
Pro Gln Ala Ala Leu Asp Pro Lys Ala Asn Phe Ser Thr Asn Asn Ser
        915             920             925
Asn Pro Gly Ala Arg Pro Pro Pro Arg Ala Thr Ala Arg Leu Pro
    930             935             940
Gln Arg Gly Cys Pro Gly Asp Gly Pro Glu Ala Gly Arg Pro Ala Asp
945             950             955             960
Lys Ile Gln Met Ala Met Val His Gly Val Thr Thr Glu Glu Cys Gln
                965             970             975
Ala Ala Leu Gln Cys His Gly Trp Ser Val Gln Arg Ala Ala Gln Tyr
            980             985             990
Leu Lys Val Glu Gln Leu Phe Gly Leu Gly Leu Arg Pro Arg Gly Glu
        995             1000            1005
Cys His Lys Val Leu Glu Met Phe Asp Trp Asn Leu Glu Gln Ala Gly
    1010            1015            1020
Cys His Leu Leu Gly Ser Trp Gly Pro Ala His His Lys Arg
1025            1030            1035

<210> SEQ ID NO 47
<211> LENGTH: 747
<212> TYPE: PRT
<213> ORGANISM: Homo sapiens

<400> SEQUENCE: 47

Met Gln Pro Glu Glu Gly Thr Gly Trp Leu Leu Glu Leu Leu Ser Glu
1               5                   10                  15
Val Gln Leu Gln Gln Tyr Phe Leu Arg Leu Arg Asp Asp Leu Asn Val
            20                  25                  30
Thr Arg Leu Ser His Phe Glu Tyr Val Lys Asn Glu Asp Leu Glu Lys
        35                  40                  45
Ile Gly Met Gly Arg Pro Gly Gln Arg Arg Leu Trp Glu Ala Val Lys
    50                  55                  60
Arg Arg Lys Ala Met Cys Lys Arg Lys Ser Trp Met Ser Lys Val Phe
65                  70                  75                  80
Ser Gly Lys Arg Leu Glu Ala Glu Phe Pro Pro His His Ser Gln Ser
                85                  90                  95
Thr Phe Arg Lys Thr Ser Pro Thr Pro Gly Gly Ser Ala Gly Glu Gly
            100                 105                 110
Ser Leu Gln Ser Leu Thr Cys Leu Ile Gly Glu Lys Asp Leu His Leu
        115                 120                 125
Phe Glu Lys Leu Gly Asp Gly Ser Phe Gly Val Val Arg Arg Gly Glu
    130                 135                 140
Trp Asp Ala Pro Ser Gly Lys Thr Val Ser Val Ala Val Lys Cys Leu
145                 150                 155                 160
```

```
Lys Pro Asp Val Leu Ser Gln Pro Glu Ala Met Asp Phe Ile Arg
            165                 170                 175

Glu Val Asn Ala Met His Ser Leu Asp His Arg Asn Leu Ile Arg Leu
        180                 185                 190

Tyr Gly Val Val Leu Thr Pro Pro Met Lys Met Val Thr Glu Leu Ala
            195                 200                 205

Pro Leu Gly Ser Leu Leu Asp Arg Leu Arg Lys His Gln Gly His Phe
        210                 215                 220

Leu Leu Gly Thr Leu Ser Arg Tyr Ala Val Gln Val Ala Glu Gly Met
225                 230                 235                 240

Gly Tyr Leu Glu Ala Lys Arg Phe Ile His Arg Asp Leu Ala Ala Arg
            245                 250                 255

Asn Leu Leu Leu Ala Thr Arg Asp Leu Val Lys Ile Gly Asp Phe Gly
            260                 265                 270

Leu Met Arg Ala Leu Pro Gln Asn Asp Asp His Tyr Val Met Gln Glu
        275                 280                 285

His Arg Lys Val Pro Phe Ala Trp Cys Ala Pro Glu Ser Leu Lys Thr
        290                 295                 300

Arg Thr Phe Ser His Ala Ser Asp Thr Trp Met Phe Gly Val Thr Leu
305                 310                 315                 320

Trp Glu Met Phe Thr Tyr Gly Gln Glu Pro Trp Ile Gly Leu Asn Gly
                325                 330                 335

Ser Gln Ile Leu His Lys Ile Asp Lys Glu Gly Glu Arg Leu Pro Arg
            340                 345                 350

Pro Glu Asp Cys Pro Gln Asp Ile Tyr Asn Val Met Val Gln Cys Trp
        355                 360                 365

Ala His Lys Pro Glu Asp Arg Pro Thr Phe Val Ala Leu Arg Asp Phe
370                 375                 380

Leu Leu Glu Ala Gln Pro Thr Asp Met Arg Ala Leu Gln Asp Phe Glu
            385                 390                 395                 400

Glu Pro Asp Lys Leu His Ile Gln Met Asn Asp Val Ile Thr Val Ile
                405                 410                 415

Glu Gly Arg Ala Glu Asn Tyr Trp Trp Arg Gly Gln Asn Thr Arg Thr
            420                 425                 430

Leu Cys Val Gly Pro Phe Pro Arg Asn Val Val Thr Ser Val Ala Gly
        435                 440                 445

Leu Ser Ala Gln Asp Ile Ser Gln Pro Leu Gln Asn Ser Phe Ile His
    450                 455                 460

Thr Gly His Gly Asp Ser Asp Pro Arg His Cys Trp Gly Phe Pro Asp
465                 470                 475                 480

Lys Ile Asp Glu Leu Tyr Leu Gly Asn Pro Met Asp Pro Pro Asp Leu
            485                 490                 495

Leu Ser Val Glu Leu Ser Thr Ser Arg Pro Thr Gln His Leu Gly Arg
                500                 505                 510

Val Lys Arg Glu Pro Pro Pro Arg Pro Pro Gln Pro Ala Ile Phe Thr
        515                 520                 525

Gln Lys Pro Thr Tyr Asp Pro Val Ser Glu Asp Gln Asp Pro Leu Ser
    530                 535                 540

Ser Asp Phe Lys Lys Leu Gly Leu Arg Lys Pro Gly Leu Pro Arg Gly
545                 550                 555                 560

Leu Trp Leu Ala Lys Pro Ser Ala Arg Val Pro Gly Thr Lys Ala Gly
            565                 570                 575

Arg Gly Gly Gly Glu Val Thr Leu Ile Asp Phe Gly Glu Glu Pro Val
```

-continued

```
                580                 585                 590
Val Pro Ala Pro Arg Pro Cys Ala Pro Ser Leu Ala Gln Leu Ala Met
            595                 600                 605

Asp Ala Cys Ser Leu Leu Asp Lys Thr Pro Pro Gln Ser Pro Thr Arg
        610                 615                 620

Ala Leu Pro Arg Pro Leu His Pro Thr Pro Val Val Asp Trp Asp Ala
625                 630                 635                 640

Arg Pro Leu Pro Pro Pro Ala Tyr Asp Asp Val Ala Gln Asp Glu
                645                 650                 655

Asp Asp Phe Glu Val Cys Ser Ile Asn Ser Thr Leu Val Gly Ala Gly
            660                 665                 670

Val Ser Ala Glu Pro Ser Gln Gly Glu Thr Asn Tyr Ala Phe Val Pro
        675                 680                 685

Glu Pro Ala Arg Leu Leu Pro Ala Gly Gly Gln Pro Val Pro Pro
690                 695                 700

Thr Pro Glu Trp Gly Gln Ala Thr Gln Leu Gly Pro Asn Arg Arg Asp
705                 710                 715                 720

Leu Pro Gly Ala Ala Ala Gly Met His Ala Ala Ala Thr Gly Pro Ala
                725                 730                 735

Trp Leu Ser Gly Pro Leu Thr Gln Pro Trp Gly
            740                 745
```

<210> SEQ ID NO 48
<211> LENGTH: 591
<212> TYPE: PRT
<213> ORGANISM: Homo sapiens

<400> SEQUENCE: 48

```
Met Phe Gly Lys Arg Lys Lys Arg Val Glu Ile Ser Ala Pro Ser Asn
1               5                   10                  15

Phe Glu His Arg Val His Thr Gly Phe Asp Gln His Glu Gln Lys Phe
                20                  25                  30

Thr Gly Leu Pro Arg Gln Trp Gln Ser Leu Ile Glu Glu Ser Ala Arg
            35                  40                  45

Arg Pro Lys Pro Leu Val Asp Pro Ala Cys Ile Thr Ser Ile Gln Pro
        50                  55                  60

Gly Ala Pro Lys Thr Ile Val Arg Gly Ser Lys Gly Ala Lys Asp Gly
65                  70                  75                  80

Ala Leu Thr Leu Leu Leu Asp Glu Phe Glu Asn Met Ser Val Thr Arg
                85                  90                  95

Ser Asn Ser Leu Arg Arg Asp Ser Pro Pro Pro Ala Arg Ala Arg
            100                 105                 110

Gln Glu Asn Gly Met Pro Glu Glu Pro Ala Thr Thr Ala Arg Gly Gly
        115                 120                 125

Pro Gly Lys Ala Gly Ser Arg Gly Arg Phe Ala Gly His Ser Glu Ala
    130                 135                 140

Gly Gly Gly Ser Gly Asp Arg Arg Ala Gly Pro Glu Lys Arg Pro
145                 150                 155                 160

Lys Ser Ser Arg Glu Gly Ser Gly Pro Gln Glu Ser Ser Arg Asp
                165                 170                 175

Lys Arg Pro Leu Ser Gly Pro Asp Val Gly Thr Pro Gln Pro Ala Gly
            180                 185                 190

Leu Ala Ser Gly Ala Lys Leu Ala Ala Gly Arg Pro Phe Asn Thr Tyr
        195                 200                 205
```

```
Pro Arg Ala Asp Thr Asp His Pro Ser Arg Gly Ala Gln Gly Glu Pro
    210                 215                 220

His Asp Val Ala Pro Asn Gly Pro Ser Ala Gly Gly Leu Ala Ile Pro
225                 230                 235                 240

Gln Ser Ser Ser Ser Ser Arg Pro Pro Thr Arg Ala Arg Gly Ala
                245                 250                 255

Pro Ser Pro Gly Val Leu Gly Pro His Ala Ser Glu Pro Gln Leu Ala
            260                 265                 270

Pro Pro Ala Cys Thr Pro Ala Ala Pro Ala Val Pro Gly Pro Pro Gly
        275                 280                 285

Pro Arg Ser Pro Gln Arg Glu Pro Gln Arg Val Ser His Glu Gln Phe
    290                 295                 300

Arg Ala Ala Leu Gln Leu Val Asp Pro Gly Asp Pro Arg Ser Tyr
305                 310                 315                 320

Leu Asp Asn Phe Ile Lys Ile Gly Glu Gly Ser Thr Gly Ile Val Cys
                325                 330                 335

Ile Ala Thr Val Arg Ser Ser Gly Lys Leu Val Ala Val Lys Lys Met
            340                 345                 350

Asp Leu Arg Lys Gln Gln Arg Arg Glu Leu Leu Phe Asn Glu Val Val
        355                 360                 365

Ile Met Arg Asp Tyr Gln His Glu Asn Val Val Glu Met Tyr Asn Ser
370                 375                 380

Tyr Leu Val Gly Asp Glu Leu Trp Val Val Met Glu Phe Leu Glu Gly
385                 390                 395                 400

Gly Ala Leu Thr Asp Ile Val Thr His Thr Arg Met Asn Glu Glu Gln
                405                 410                 415

Ile Ala Ala Val Cys Leu Ala Val Leu Gln Ala Leu Ser Val Leu His
            420                 425                 430

Ala Gln Gly Val Ile His Arg Asp Ile Lys Ser Asp Ser Ile Leu Leu
        435                 440                 445

Thr His Asp Gly Arg Val Lys Leu Ser Asp Phe Gly Phe Cys Ala Gln
450                 455                 460

Val Ser Lys Glu Val Pro Arg Arg Lys Ser Leu Val Gly Thr Pro Tyr
465                 470                 475                 480

Trp Met Ala Pro Glu Leu Ile Ser Arg Leu Pro Tyr Gly Pro Glu Val
                485                 490                 495

Asp Ile Trp Ser Leu Gly Ile Met Val Ile Glu Met Val Asp Gly Glu
            500                 505                 510

Pro Pro Tyr Phe Asn Glu Pro Pro Leu Lys Ala Met Lys Met Ile Arg
        515                 520                 525

Asp Asn Leu Pro Pro Arg Leu Lys Asn Leu His Lys Val Ser Pro Ser
530                 535                 540

Leu Lys Gly Phe Leu Asp Arg Leu Leu Val Arg Asp Pro Ala Gln Arg
545                 550                 555                 560

Ala Thr Ala Ala Glu Leu Leu Lys His Pro Phe Leu Ala Lys Ala Gly
                565                 570                 575

Pro Pro Ala Ser Ile Val Pro Leu Met Arg Gln Asn Arg Thr Arg
            580                 585                 590

<210> SEQ ID NO 49
<211> LENGTH: 502
<212> TYPE: PRT
<213> ORGANISM: Homo sapiens

<400> SEQUENCE: 49
```

-continued

```
Met Ser Gly Gly Pro Met Gly Gly Arg Pro Gly Gly Arg Gly Ala Pro
1               5                  10                 15

Ala Val Gln Gln Asn Ile Pro Ser Thr Leu Leu Gln Asp His Glu Asn
            20                  25                  30

Gln Arg Leu Phe Glu Met Leu Gly Arg Lys Cys Leu Thr Leu Ala Thr
        35                  40                  45

Ala Val Val Gln Leu Tyr Leu Ala Leu Pro Pro Gly Ala Glu His Trp
    50                  55                  60

Thr Lys Glu His Cys Gly Ala Val Cys Phe Val Lys Asp Asn Pro Gln
65                  70                  75                  80

Lys Ser Tyr Phe Ile Arg Leu Tyr Gly Leu Gln Ala Gly Arg Leu Leu
                85                  90                  95

Trp Glu Gln Glu Leu Tyr Ser Gln Leu Val Tyr Ser Thr Pro Thr Pro
            100                 105                 110

Phe Phe His Thr Phe Ala Gly Asp Asp Cys Gln Ala Gly Leu Asn Phe
        115                 120                 125

Ala Asp Glu Asp Glu Ala Gln Ala Phe Arg Ala Leu Val Gln Glu Lys
    130                 135                 140

Ile Gln Lys Arg Asn Gln Arg Gln Ser Gly Asp Arg Arg Gln Leu Pro
145                 150                 155                 160

Pro Pro Pro Thr Pro Ala Asn Glu Glu Arg Arg Gly Gly Leu Pro Pro
                165                 170                 175

Leu Pro Leu His Pro Gly Gly Asp Gln Gly Gly Pro Pro Val Gly Pro
            180                 185                 190

Leu Ser Leu Gly Leu Ala Thr Val Asp Ile Gln Asn Pro Asp Ile Thr
        195                 200                 205

Ser Ser Arg Tyr Arg Gly Leu Pro Ala Pro Gly Pro Ser Pro Ala Asp
    210                 215                 220

Lys Lys Arg Ser Gly Lys Lys Ile Ser Lys Ala Asp Ile Gly Ala
225                 230                 235                 240

Pro Ser Gly Phe Lys His Val Ser His Val Gly Trp Asp Pro Gln Asn
                245                 250                 255

Gly Phe Asp Val Asn Asn Leu Asp Pro Asp Leu Arg Ser Leu Phe Ser
            260                 265                 270

Arg Ala Gly Ile Ser Glu Ala Gln Leu Thr Asp Ala Glu Thr Ser Lys
        275                 280                 285

Leu Ile Tyr Asp Phe Ile Glu Asp Gln Gly Gly Leu Glu Ala Val Arg
    290                 295                 300

Gln Glu Met Arg Arg Gln Glu Pro Leu Pro Pro Pro Pro Pro Pro Ser
305                 310                 315                 320

Arg Gly Gly Asn Gln Leu Pro Arg Pro Pro Ile Val Gly Gly Asn Lys
                325                 330                 335

Gly Arg Ser Gly Pro Leu Pro Pro Val Pro Leu Gly Ile Ala Pro Pro
            340                 345                 350

Pro Pro Thr Pro Arg Gly Pro Pro Pro Gly Arg Gly Gly Pro Pro
        355                 360                 365

Pro Pro Pro Pro Pro Ala Thr Gly Arg Ser Gly Pro Leu Pro Pro Pro
    370                 375                 380

Pro Pro Gly Ala Gly Gly Pro Pro Met Pro Pro Pro Pro Pro Pro Pro
385                 390                 395                 400

Pro Pro Pro Pro Ser Ser Gly Asn Gly Pro Ala Pro Pro Pro Leu Pro
                405                 410                 415
```

```
Pro Ala Leu Val Pro Ala Gly Gly Leu Ala Pro Gly Gly Gly Arg Gly
            420                 425                 430

Ala Leu Leu Asp Gln Ile Arg Gln Gly Ile Gln Leu Asn Lys Thr Pro
        435                 440                 445

Gly Ala Pro Glu Ser Ser Ala Leu Gln Pro Pro Gln Ser Ser Glu
    450                 455                 460

Gly Leu Val Gly Ala Leu Met His Val Met Gln Lys Arg Ser Arg Ala
465                 470                 475                 480

Ile His Ser Ser Asp Glu Gly Glu Asp Gln Ala Gly Asp Glu Asp Glu
                485                 490                 495

Asp Asp Glu Trp Asp Asp
            500

<210> SEQ ID NO 50
<211> LENGTH: 505
<212> TYPE: PRT
<213> ORGANISM: Homo sapiens

<400> SEQUENCE: 50

Met Ser Ser Val Gln Gln Pro Pro Pro Arg Arg Val Thr Asn
1               5                   10                  15

Val Gly Ser Leu Leu Leu Thr Pro Gln Glu Asn Glu Ser Leu Phe Thr
            20                  25                  30

Phe Leu Gly Lys Lys Cys Val Thr Met Ser Ser Ala Val Val Gln Leu
        35                  40                  45

Tyr Ala Ala Asp Arg Asn Cys Met Trp Ser Lys Lys Cys Ser Gly Val
    50                  55                  60

Ala Cys Leu Val Lys Asp Asn Pro Gln Arg Ser Tyr Phe Leu Arg Ile
65                  70                  75                  80

Phe Asp Ile Lys Asp Gly Lys Leu Leu Trp Glu Gln Glu Leu Tyr Asn
                85                  90                  95

Asn Phe Val Tyr Asn Ser Pro Arg Gly Tyr Phe His Thr Phe Ala Gly
            100                 105                 110

Asp Thr Cys Gln Val Ala Leu Asn Phe Ala Asn Glu Glu Glu Ala Lys
        115                 120                 125

Lys Phe Arg Lys Ala Val Thr Asp Leu Leu Gly Arg Arg Gln Arg Lys
    130                 135                 140

Ser Glu Lys Arg Arg Asp Pro Pro Asn Gly Pro Asn Leu Pro Met Ala
145                 150                 155                 160

Thr Val Asp Ile Lys Asn Pro Glu Ile Thr Thr Asn Arg Phe Tyr Gly
                165                 170                 175

Pro Gln Val Asn Asn Ile Ser His Thr Lys Glu Lys Lys Gly Lys
            180                 185                 190

Ala Lys Lys Lys Arg Leu Thr Lys Ala Asp Ile Gly Thr Pro Ser Asn
        195                 200                 205

Phe Gln His Ile Gly His Val Gly Trp Asp Pro Asn Thr Gly Phe Asp
    210                 215                 220

Leu Asn Asn Leu Asp Pro Glu Leu Lys Asn Leu Phe Asp Met Cys Gly
225                 230                 235                 240

Ile Ser Glu Ala Gln Leu Lys Asp Arg Glu Thr Ser Lys Val Ile Tyr
                245                 250                 255

Asp Phe Ile Glu Lys Thr Gly Gly Val Glu Ala Val Lys Asn Glu Leu
            260                 265                 270

Arg Arg Gln Ala Pro Pro Pro Pro Pro Ser Arg Gly Gly Pro Pro
        275                 280                 285
```

```
Pro Pro Pro Pro Pro His Asn Ser Gly Pro Pro Pro Pro Ala
        290                 295                 300

Arg Gly Arg Gly Ala Pro Pro Pro Ser Arg Ala Pro Thr Ala
305                 310                 315                 320

Ala Pro Pro Pro Pro Pro Ser Arg Pro Ser Val Ala Val Pro Pro
                325                 330                 335

Pro Pro Pro Asn Arg Met Tyr Pro Pro Pro Pro Ala Leu Pro Ser
            340                 345                 350

Ser Ala Pro Ser Gly Pro Pro Pro Pro Ser Val Leu Gly Val
        355                 360                 365

Gly Pro Val Ala Pro Pro Pro Pro Pro Pro Pro Pro Gly
    370                 375                 380

Pro Pro Pro Pro Pro Gly Leu Pro Ser Asp Gly Asp His Gln Val Pro
385                 390                 395                 400

Thr Thr Ala Gly Asn Lys Ala Ala Leu Leu Asp Gln Ile Arg Glu Gly
                405                 410                 415

Ala Gln Leu Lys Lys Val Glu Gln Asn Ser Arg Pro Val Ser Cys Ser
                420                 425                 430

Gly Arg Asp Ala Leu Leu Asp Gln Ile Arg Gln Gly Ile Gln Leu Lys
            435                 440                 445

Ser Val Ala Asp Gly Gln Glu Ser Thr Pro Pro Thr Pro Ala Pro Thr
450                 455                 460

Ser Gly Ile Val Gly Ala Leu Met Glu Val Met Gln Lys Arg Ser Lys
465                 470                 475                 480

Ala Ile His Ser Ser Asp Glu Asp Glu Asp Glu Asp Glu Asp
                485                 490                 495

Phe Glu Asp Asp Asp Glu Trp Glu Asp
            500                 505

<210> SEQ ID NO 51
<211> LENGTH: 391
<212> TYPE: PRT
<213> ORGANISM: Homo sapiens

<400> SEQUENCE: 51

Met Pro Gly Pro Gln Gly Gly Arg Gly Ala Ala Thr Met Ser Leu Gly
1               5                   10                  15

Lys Leu Ser Pro Val Gly Trp Val Ser Ser Gln Gly Lys Arg Arg
            20                  25                  30

Leu Thr Ala Asp Met Ile Ser His Pro Leu Gly Asp Phe Arg His Thr
            35                  40                  45

Met His Val Gly Arg Gly Gly Asp Val Phe Gly Asp Thr Ser Phe Leu
        50                  55                  60

Ser Asn His Gly Gly Ser Ser Gly Ser Thr His Arg Ser Pro Arg Ser
65                  70                  75                  80

Phe Leu Ala Lys Lys Leu Gln Leu Val Arg Arg Val Gly Ala Pro Pro
                85                  90                  95

Arg Arg Met Ala Ser Pro Pro Ala Pro Ser Pro Ala Pro Ala Ile
            100                 105                 110

Ser Pro Ile Ile Lys Asn Ala Ile Ser Leu Pro Gln Leu Asn Gln Ala
        115                 120                 125

Ala Tyr Asp Ser Leu Val Val Gly Lys Leu Ser Phe Asp Ser Ser Pro
    130                 135                 140

Thr Ser Ser Thr Asp Gly His Ser Ser Tyr Gly Leu Asp Ser Gly Phe
```

```
                145                 150                 155                 160
Cys Thr Ile Ser Arg Leu Pro Arg Ser Glu Lys Pro His Asp Arg Asp
                    165                 170                 175
Arg Asp Gly Ser Phe Pro Ser Glu Pro Gly Leu Arg Arg Ser Asp Ser
                180                 185                 190
Leu Leu Ser Phe Arg Leu Asp Leu Gly Pro Ser Leu Leu Ser
            195                 200                 205
Glu Leu Leu Gly Val Met Ser Leu Pro Glu Ala Pro Ala Ala Glu Thr
            210                 215                 220
Pro Ala Pro Ala Ala Asn Pro Pro Ala Pro Thr Ala Asn Pro Thr Gly
225                 230                 235                 240
Pro Ala Ala Asn Pro Pro Ala Thr Thr Ala Asn Pro Pro Ala Pro Ala
                245                 250                 255
Ala Asn Pro Ser Ala Pro Ala Ala Thr Pro Thr Gly Pro Ala Ala Asn
                260                 265                 270
Pro Pro Ala Pro Ala Ala Ser Ser Thr Pro His Gly His Cys Pro Asn
                275                 280                 285
Gly Val Thr Ala Gly Leu Gly Pro Val Ala Glu Val Lys Ser Ser Pro
            290                 295                 300
Val Gly Gly Gly Pro Arg Gly Pro Ala Gly Pro Ala Leu Gly Arg His
305                 310                 315                 320
Trp Gly Ala Gly Trp Asp Gly Gly His His Tyr Pro Glu Met Asp Ala
                    325                 330                 335
Arg Gln Glu Arg Val Glu Val Leu Pro Gln Ala Arg Ala Ser Trp Glu
                340                 345                 350
Ser Leu Asp Glu Glu Trp Arg Ala Pro Gln Ala Gly Ser Arg Thr Pro
            355                 360                 365
Val Pro Ser Thr Val Gln Ala Asn Thr Phe Glu Phe Ala Asp Ala Glu
            370                 375                 380
Glu Asp Asp Glu Val Lys Val
385                 390

<210> SEQ ID NO 52
<211> LENGTH: 210
<212> TYPE: PRT
<213> ORGANISM: Homo sapiens

<400> SEQUENCE: 52

Met Ser Thr Lys Val Pro Ile Tyr Leu Lys Arg Gly Ser Arg Lys Gly
1               5                   10                  15
Lys Lys Glu Lys Leu Arg Asp Leu Leu Ser Ser Asp Met Ile Ser Pro
                20                  25                  30
Pro Leu Gly Asp Phe Arg His Thr Ile His Ile Gly Ser Gly Gly Gly
            35                  40                  45
Ser Asp Met Phe Gly Asp Ile Ser Phe Leu Gln Gly Lys Phe His Leu
        50                  55                  60
Leu Pro Gly Thr Met Val Glu Gly Pro Glu Glu Asp Gly Thr Phe Asp
65                  70                  75                  80
Leu Pro Phe Gln Phe Thr Arg Thr Ala Thr Val Cys Gly Arg Glu Leu
                85                  90                  95
Pro Asp Gly Pro Ser Pro Leu Leu Lys Asn Ala Ile Ser Leu Pro Val
            100                 105                 110
Ile Gly Gly Pro Gln Ala Leu Thr Leu Pro Thr Ala Gln Ala Pro Pro
        115                 120                 125
```

-continued

Lys Pro Pro Arg Leu His Leu Glu Thr Pro Gln Pro Ser Pro Gln Glu
    130                 135                 140

Gly Gly Ser Val Asp Ile Trp Arg Ile Pro Glu Thr Gly Ser Pro Asn
145                 150                 155                 160

Ser Gly Leu Thr Pro Glu Ser Gly Ala Glu Pro Phe Leu Ser Asn
                165                 170                 175

Ala Ser Ser Leu Leu Ser Leu His Val Asp Leu Gly Pro Ser Ile Leu
            180                 185                 190

Asp Asp Val Leu Gln Ile Met Asp Gln Asp Leu Asp Ser Met Gln Ile
            195                 200                 205

Pro Thr
    210

<210> SEQ ID NO 53
<211> LENGTH: 254
<212> TYPE: PRT
<213> ORGANISM: Homo sapiens

<400> SEQUENCE: 53

Met Pro Ala Lys Thr Pro Ile Tyr Leu Lys Ala Ala Asn Asn Lys Lys
1               5                   10                  15

Gly Lys Lys Phe Lys Leu Arg Asp Ile Leu Ser Pro Asp Met Ile Ser
            20                  25                  30

Pro Pro Leu Gly Asp Phe Arg His Thr Ile His Ile Gly Lys Glu Gly
        35                  40                  45

Gln His Asp Val Phe Gly Asp Ile Ser Phe Leu Gln Gly Asn Tyr Glu
    50                  55                  60

Leu Leu Pro Gly Asn Gln Glu Lys Ala His Leu Gly Gln Phe Pro Gly
65                  70                  75                  80

His Asn Glu Phe Phe Arg Ala Asn Ser Thr Ser Asp Ser Val Phe Thr
                85                  90                  95

Glu Thr Pro Ser Pro Val Leu Lys Asn Ala Ile Ser Leu Pro Thr Ile
            100                 105                 110

Gly Gly Ser Gln Ala Leu Met Leu Pro Leu Leu Ser Pro Val Thr Phe
        115                 120                 125

Asn Ser Lys Gln Glu Ser Phe Gly Pro Ala Lys Leu Pro Arg Leu Ser
    130                 135                 140

Cys Glu Pro Val Met Glu Glu Lys Ala Gln Glu Lys Ser Ser Leu Leu
145                 150                 155                 160

Glu Asn Gly Thr Val His Gln Gly Asp Thr Ser Trp Gly Ser Ser Gly
                165                 170                 175

Ser Ala Ser Gln Ser Ser Gln Gly Arg Asp Ser His Ser Ser Ser Leu
            180                 185                 190

Ser Glu Gln Tyr Pro Asp Trp Pro Ala Glu Asp Met Phe Asp His Pro
    195                 200                 205

Thr Pro Cys Glu Leu Ile Lys Gly Lys Thr Lys Ser Glu Glu Ser Leu
    210                 215                 220

Ser Asp Leu Thr Gly Ser Leu Leu Ser Leu Gln Leu Asp Leu Gly Pro
225                 230                 235                 240

Ser Leu Leu Asp Glu Val Leu Asn Val Met Asp Lys Asn Lys
                245                 250

<210> SEQ ID NO 54
<211> LENGTH: 356
<212> TYPE: PRT
<213> ORGANISM: Homo sapiens

<400> SEQUENCE: 54

```
Met Pro Ile Leu Lys Gln Leu Val Ser Ser Val His Ser Lys Arg
1               5                   10                  15

Arg Ser Arg Ala Asp Leu Thr Ala Glu Met Ile Ser Ala Pro Leu Gly
            20                  25                  30

Asp Phe Arg His Thr Met His Val Gly Arg Ala Gly Asp Ala Phe Gly
        35                  40                  45

Asp Thr Ser Phe Leu Asn Ser Lys Ala Gly Glu Pro Asp Gly Glu Ser
    50                  55                  60

Leu Asp Glu Gln Pro Ser Ser Ser Lys Arg Ser Leu Leu Ser
65                  70                  75                  80

Arg Lys Phe Arg Gly Ser Lys Arg Ser Gln Ser Val Thr Arg Gly Glu
                85                  90                  95

Arg Glu Gln Arg Asp Met Leu Gly Ser Leu Arg Asp Ser Ala Leu Phe
            100                 105                 110

Val Lys Asn Ala Met Ser Leu Pro Gln Leu Asn Glu Lys Glu Ala Ala
        115                 120                 125

Glu Lys Gly Thr Ser Lys Leu Pro Lys Ser Leu Ser Ser Pro Val
    130                 135                 140

Lys Lys Ala Asn Asp Gly Glu Gly Gly Asp Glu Glu Ala Gly Thr Glu
145                 150                 155                 160

Glu Ala Val Pro Arg Arg Asn Gly Ala Ala Gly Pro His Ser Pro Asp
                165                 170                 175

Pro Leu Leu Asp Glu Gln Ala Phe Gly Asp Leu Thr Asp Leu Pro Val
            180                 185                 190

Val Pro Lys Ala Thr Tyr Gly Leu Lys His Ala Glu Ser Ile Met Ser
        195                 200                 205

Phe His Ile Asp Leu Gly Pro Ser Met Leu Gly Asp Val Leu Ser Ile
    210                 215                 220

Met Asp Lys Glu Glu Trp Asp Pro Glu Glu Gly Gly Gly Tyr His
225                 230                 235                 240

Gly Asp Glu Gly Ala Ala Gly Thr Ile Thr Gln Ala Pro Pro Tyr Ala
                245                 250                 255

Val Ala Pro Pro Leu Ala Arg Gln Glu Gly Lys Ala Gly Pro Asp
        260                 265                 270

Leu Pro Ser Leu Pro Ser His Ala Leu Glu Asp Glu Gly Trp Ala Ala
    275                 280                 285

Ala Ala Pro Ser Pro Gly Ser Ala Arg Ser Met Gly Ser His Thr Thr
290                 295                 300

Arg Asp Ser Ser Ser Leu Ser Ser Cys Thr Ser Gly Ile Leu Glu Glu
305                 310                 315                 320

Arg Ser Pro Ala Phe Arg Gly Pro Asp Arg Ala Arg Ala Ala Val Ser
                325                 330                 335

Arg Gln Pro Asp Lys Glu Phe Ser Phe Met Asp Glu Glu Glu Asp
            340                 345                 350

Glu Ile Arg Val
        355
```

<210> SEQ ID NO 55
<211> LENGTH: 148
<212> TYPE: PRT
<213> ORGANISM: Homo sapiens

<400> SEQUENCE: 55

```
Met Pro Val Leu Lys Gln Leu Gly Pro Ala Gln Pro Lys Arg Pro
1               5                   10                  15

Asp Arg Gly Ala Leu Ser Ile Ser Ala Pro Leu Gly Asp Phe Arg His
            20                  25                  30

Thr Leu His Val Gly Arg Gly Gly Asp Ala Phe Gly Asp Thr Ser Phe
            35                  40                  45

Leu Ser Arg His Gly Gly Pro Pro Glu Pro Arg Ala Pro Pro
        50                  55                  60

Ala Gly Ala Pro Arg Ser Pro Pro Pro Ala Val Pro Gln Ser Ala
65                  70                  75                  80

Ala Pro Ser Pro Ala Asp Pro Leu Leu Ser Phe His Leu Asp Leu Gly
            85                  90                  95

Pro Ser Met Leu Asp Ala Val Leu Gly Val Met Asp Ala Ala Arg Pro
            100                 105                 110

Glu Ala Ala Ala Lys Pro Asp Ala Glu Pro Arg Pro Gly Thr Gln
            115                 120                 125

Pro Pro Gln Ala Arg Cys Arg Pro Asn Ala Asp Leu Glu Leu Asn Asp
            130                 135                 140

Val Ile Gly Leu
145
```

<210> SEQ ID NO 56
<211> LENGTH: 545
<212> TYPE: PRT
<213> ORGANISM: Homo sapiens

<400> SEQUENCE: 56

```
Met Asp Trp Gly Thr Glu Leu Trp Asp Gln Phe Glu Val Leu Glu Arg
1               5                   10                  15

His Thr Gln Trp Gly Leu Asp Leu Leu Asp Arg Tyr Val Lys Phe Val
            20                  25                  30

Lys Glu Arg Thr Glu Val Glu Gln Ala Tyr Ala Lys Gln Leu Arg Ser
            35                  40                  45

Leu Val Lys Lys Tyr Leu Pro Lys Arg Pro Ala Lys Asp Asp Pro Glu
        50                  55                  60

Ser Lys Phe Ser Gln Gln Gln Ser Phe Val Gln Ile Leu Gln Glu Val
65                  70                  75                  80

Asn Asp Phe Ala Gly Gln Arg Glu Leu Val Ala Glu Asn Leu Ser Val
            85                  90                  95

Arg Val Cys Leu Glu Leu Thr Lys Tyr Ser Gln Glu Met Lys Gln Glu
            100                 105                 110

Arg Lys Met His Phe Gln Glu Gly Arg Arg Ala Gln Gln Leu Glu
            115                 120                 125

Asn Gly Phe Lys Gln Leu Glu Asn Ser Lys Arg Lys Phe Glu Arg Asp
        130                 135                 140

Cys Arg Glu Ala Glu Lys Ala Ala Gln Thr Ala Glu Arg Leu Asp Gln
145                 150                 155                 160

Asp Ile Asn Ala Thr Lys Ala Asp Val Glu Lys Ala Lys Gln Gln Ala
            165                 170                 175

His Leu Arg Ser His Met Ala Glu Glu Ser Lys Asn Glu Tyr Ala Ala
            180                 185                 190

Gln Leu Gln Arg Phe Asn Arg Asp Gln Ala His Phe Tyr Phe Ser Gln
            195                 200                 205

Met Pro Gln Ile Phe Asp Lys Leu Gln Asp Met Asp Glu Arg Arg Ala
```

```
                210                 215                 220
Thr Arg Leu Gly Ala Gly Tyr Gly Leu Leu Ser Glu Ala Glu Leu Glu
225                 230                 235                 240

Val Val Pro Ile Ile Ala Lys Cys Leu Glu Gly Met Lys Val Ala Ala
                245                 250                 255

Asn Ala Val Asp Pro Lys Asn Asp Ser His Val Leu Ile Glu Leu His
                260                 265                 270

Lys Ser Gly Phe Ala Arg Pro Gly Asp Val Glu Phe Glu Asp Phe Ser
                275                 280                 285

Gln Pro Met Asn Arg Ala Pro Ser Asp Ser Leu Gly Thr Pro Ser
290                 295                 300

Asp Gly Arg Pro Glu Leu Arg Gly Pro Gly Arg Ser Arg Thr Lys Arg
305                 310                 315                 320

Trp Pro Phe Gly Lys Lys Asn Lys Thr Val Val Thr Glu Asp Phe Ser
                325                 330                 335

His Leu Pro Pro Glu Gln Gln Arg Lys Arg Leu Gln Gln Gln Leu Glu
                340                 345                 350

Glu Arg Ser Arg Glu Leu Gln Lys Glu Val Asp Gln Arg Glu Ala Leu
                355                 360                 365

Lys Lys Met Lys Asp Val Tyr Glu Lys Thr Pro Gln Met Gly Asp Pro
370                 375                 380

Ala Ser Leu Glu Pro Gln Ile Ala Glu Thr Leu Ser Asn Ile Glu Arg
385                 390                 395                 400

Leu Lys Leu Glu Val Gln Lys Tyr Glu Ala Trp Leu Ala Glu Ala Glu
                405                 410                 415

Ser Arg Val Leu Ser Asn Arg Gly Asp Ser Leu Ser Arg His Ala Arg
                420                 425                 430

Pro Pro Asp Pro Pro Ala Ser Ala Pro Pro Asp Ser Ser Asn Ser
                435                 440                 445

Ala Ser Gln Asp Thr Lys Glu Ser Ser Glu Glu Pro Ser Glu Glu
                450                 455                 460

Ser Gln Asp Thr Pro Ile Tyr Thr Glu Phe Asp Glu Asp Phe Glu Glu
465                 470                 475                 480

Glu Pro Thr Ser Pro Ile Gly His Cys Val Ala Ile Tyr His Phe Glu
                485                 490                 495

Gly Ser Ser Glu Gly Thr Ile Ser Met Ala Glu Gly Glu Asp Leu Ser
                500                 505                 510

Leu Met Glu Glu Asp Lys Gly Asp Gly Trp Thr Arg Val Arg Arg Lys
                515                 520                 525

Glu Gly Gly Glu Gly Tyr Val Pro Thr Ser Tyr Leu Arg Val Thr Leu
                530                 535                 540

Asn
545

<210> SEQ ID NO 57
<211> LENGTH: 1224
<212> TYPE: PRT
<213> ORGANISM: Homo sapiens

<400> SEQUENCE: 57

Met Leu Thr Lys Phe Glu Thr Lys Ser Ala Arg Val Lys Gly Leu Ser
1               5                   10                  15

Phe His Pro Lys Arg Pro Trp Ile Leu Thr Ser Leu His Asn Gly Val
                20                  25                  30
```

-continued

```
Ile Gln Leu Trp Asp Tyr Arg Met Cys Thr Leu Ile Asp Lys Phe Asp
         35                  40                  45
Glu His Asp Gly Pro Val Arg Gly Ile Asp Phe His Lys Gln Gln Pro
 50                  55                  60
Leu Phe Val Ser Gly Gly Asp Tyr Lys Ile Lys Val Trp Asn Tyr
65                   70                  75                  80
Lys Leu Arg Arg Cys Leu Phe Thr Leu Leu Gly His Leu Asp Tyr Ile
                 85                  90                  95
Arg Thr Thr Phe Phe His His Glu Tyr Pro Trp Ile Leu Ser Ala Ser
             100                 105                 110
Asp Asp Gln Thr Ile Arg Val Trp Asn Trp Gln Ser Arg Thr Cys Val
         115                 120                 125
Cys Val Leu Thr Gly His Asn His Tyr Val Met Cys Ala Gln Phe His
         130                 135                 140
Pro Thr Glu Asp Leu Val Val Ser Ala Ser Leu Asp Gln Thr Val Arg
145                 150                 155                 160
Val Trp Asp Ile Ser Gly Leu Arg Lys Lys Asn Leu Ser Pro Gly Ala
                 165                 170                 175
Val Glu Ser Asp Val Arg Gly Ile Thr Gly Val Asp Leu Phe Gly Thr
             180                 185                 190
Thr Asp Ala Val Val Lys His Val Leu Glu Gly His Asp Arg Gly Val
         195                 200                 205
Asn Trp Ala Ala Phe His Pro Thr Met Pro Leu Ile Val Ser Gly Ala
         210                 215                 220
Asp Asp Arg Gln Val Lys Ile Trp Arg Met Asn Glu Ser Lys Ala Trp
225                 230                 235                 240
Glu Val Asp Thr Cys Arg Gly His Tyr Asn Asn Val Ser Cys Ala Val
                 245                 250                 255
Phe His Pro Arg Gln Glu Leu Ile Leu Ser Asn Ser Glu Asp Lys Ser
             260                 265                 270
Ile Arg Val Trp Asp Met Ser Lys Arg Thr Gly Val Gln Thr Phe Arg
         275                 280                 285
Arg Asp His Asp Arg Phe Trp Val Leu Ala Ala His Pro Asn Leu Asn
         290                 295                 300
Leu Phe Ala Ala Gly His Asp Gly Gly Met Ile Val Phe Lys Leu Glu
305                 310                 315                 320
Arg Glu Arg Pro Ala Tyr Ala Val His Gly Asn Met Leu His Tyr Val
                 325                 330                 335
Lys Asp Arg Phe Leu Arg Gln Leu Asp Phe Asn Ser Ser Lys Asp Val
             340                 345                 350
Ala Val Met Gln Leu Arg Ser Gly Ser Lys Phe Pro Val Phe Asn Met
         355                 360                 365
Ser Tyr Asn Pro Ala Glu Asn Ala Val Leu Leu Cys Thr Arg Ala Ser
370                 375                 380
Asn Leu Glu Asn Ser Thr Tyr Asp Leu Tyr Thr Ile Pro Lys Asp Ala
385                 390                 395                 400
Asp Ser Gln Asn Pro Asp Ala Pro Glu Gly Lys Arg Ser Ser Gly Leu
                 405                 410                 415
Thr Ala Val Trp Val Ala Arg Asn Arg Phe Ala Val Leu Asp Arg Met
             420                 425                 430
His Ser Leu Leu Ile Lys Asn Leu Lys Asn Glu Ile Thr Lys Lys Val
         435                 440                 445
Gln Val Pro Asn Cys Asp Glu Ile Phe Tyr Ala Gly Thr Gly Asn Leu
```

-continued

```
            450                 455                 460
Leu Leu Arg Asp Ala Asp Ser Ile Thr Leu Phe Asp Val Gln Gln Lys
465                 470                 475                 480

Arg Thr Leu Ala Ser Val Lys Ile Ser Lys Val Lys Tyr Val Ile Trp
                485                 490                 495

Ser Ala Asp Met Ser His Val Ala Leu Leu Ala Lys His Ala Ile Val
                500                 505                 510

Ile Cys Asn Arg Lys Leu Asp Ala Leu Cys Asn Ile His Glu Asn Ile
                515                 520                 525

Arg Val Lys Ser Gly Ala Trp Asp Glu Ser Gly Val Phe Ile Tyr Thr
530                 535                 540

Thr Ser Asn His Ile Lys Tyr Ala Val Thr Thr Gly Asp His Gly Ile
545                 550                 555                 560

Ile Arg Thr Leu Asp Leu Pro Ile Tyr Val Thr Arg Val Lys Gly Asn
                565                 570                 575

Asn Val Tyr Cys Leu Asp Arg Glu Cys Arg Pro Arg Val Leu Thr Ile
                580                 585                 590

Asp Pro Thr Glu Phe Lys Phe Lys Leu Ala Leu Ile Asn Arg Lys Tyr
            595                 600                 605

Asp Glu Val Leu His Met Val Arg Asn Ala Lys Leu Val Gly Gln Ser
            610                 615                 620

Ile Ile Ala Tyr Leu Gln Lys Lys Gly Tyr Pro Glu Val Ala Leu His
625                 630                 635                 640

Phe Val Lys Asp Glu Lys Thr Arg Phe Ser Leu Ala Leu Glu Cys Gly
                645                 650                 655

Asn Ile Glu Ile Ala Leu Glu Ala Ala Lys Ala Leu Asp Asp Lys Asn
                660                 665                 670

Cys Trp Glu Lys Leu Gly Glu Val Ala Leu Leu Gln Gly Asn His Gln
            675                 680                 685

Ile Val Glu Met Cys Tyr Gln Arg Thr Lys Asn Phe Asp Lys Val Ser
            690                 695                 700

Phe Leu Tyr Leu Ile Thr Gly Asn Leu Glu Lys Leu Arg Lys Met Met
705                 710                 715                 720

Lys Ile Ala Glu Ile Arg Lys Asp Met Ser Gly His Tyr Gln Asn Ala
                725                 730                 735

Leu Tyr Leu Gly Asp Val Ser Glu Arg Val Arg Ile Leu Lys Asn Cys
                740                 745                 750

Gly Gln Lys Ser Leu Ala Tyr Leu Thr Ala Ala Thr His Gly Leu Asp
            755                 760                 765

Glu Glu Ala Glu Ser Leu Lys Glu Thr Phe Asp Pro Glu Lys Glu Thr
770                 775                 780

Ile Pro Asp Ile Asp Pro Asn Ala Lys Leu Leu Gln Pro Pro Ala Pro
785                 790                 795                 800

Ile Met Pro Leu Asp Thr Asn Trp Pro Leu Leu Thr Val Ser Lys Gly
                805                 810                 815

Phe Phe Glu Gly Thr Ile Ala Ser Lys Gly Lys Gly Gly Ala Leu Ala
                820                 825                 830

Ala Asp Ile Asp Ile Asp Thr Val Gly Thr Glu Gly Trp Gly Glu Asp
            835                 840                 845

Ala Glu Leu Gln Leu Asp Glu Asp Gly Phe Val Glu Ala Thr Glu Gly
            850                 855                 860

Leu Gly Asp Asp Ala Leu Gly Lys Gly Gln Glu Gly Gly Gly Trp
865                 870                 875                 880
```

```
Asp Val Glu Glu Asp Leu Glu Leu Pro Pro Glu Leu Asp Ile Ser Pro
                885                 890                 895
Gly Ala Ala Gly Gly Ala Glu Asp Gly Phe Phe Val Pro Pro Thr Lys
            900                 905                 910
Gly Thr Ser Pro Thr Gln Ile Trp Cys Asn Asn Ser Gln Leu Pro Val
        915                 920                 925
Asp His Ile Leu Ala Gly Ser Phe Glu Thr Ala Met Arg Leu Leu His
    930                 935                 940
Asp Gln Val Gly Val Ile Gln Phe Gly Pro Tyr Lys Gln Leu Phe Leu
945                 950                 955                 960
Gln Thr Tyr Ala Arg Gly Arg Thr Thr Tyr Gln Ala Leu Pro Cys Leu
                965                 970                 975
Pro Ser Met Tyr Gly Tyr Pro Asn Arg Asn Trp Lys Asp Ala Gly Leu
            980                 985                 990
Lys Asn Gly Val Pro Ala Val Gly Leu Lys Leu Asn Asp Leu Ile Gln
        995                1000                1005
Arg Leu Gln Leu Cys Tyr Gln Leu Thr Thr Val Gly Lys Phe Glu Glu
    1010                1015                1020
Ala Val Glu Lys Phe Arg Ser Ile Leu Leu Ser Val Pro Leu Leu Val
1025                1030                1035                1040
Val Asp Asn Lys Gln Glu Ile Ala Glu Ala Gln Gln Leu Ile Thr Ile
                1045                1050                1055
Cys Arg Glu Tyr Ile Val Gly Leu Ser Val Gly Thr Glu Arg Lys Lys
            1060                1065                1070
Leu Pro Lys Glu Thr Leu Glu Gln Gln Lys Arg Ile Cys Glu Met Ala
        1075                1080                1085
Ala Tyr Phe Thr His Ser Asn Leu Gln Pro Val His Met Ile Leu Val
    1090                1095                1100
Leu Arg Thr Ala Leu Asn Leu Phe Phe Lys Leu Lys Asn Phe Lys Thr
1105                1110                1115                1120
Ala Ala Thr Phe Ala Arg Arg Leu Leu Glu Leu Gly Pro Lys Pro Glu
                1125                1130                1135
Val Ala Gln Gln Thr Arg Lys Ile Leu Ser Ala Cys Glu Lys Asn Pro
            1140                1145                1150
Thr Asp Ala Tyr Gln Leu Asn Tyr Asp Met His Asn Pro Phe Asp Ile
        1155                1160                1165
Cys Ala Ala Ser Tyr Arg Pro Ile Tyr Arg Gly Lys Pro Val Glu Lys
    1170                1175                1180
Cys Pro Leu Ser Gly Ala Cys Tyr Ser Pro Glu Phe Lys Gly Gln Ile
1185                1190                1195                1200
Cys Arg Val Thr Thr Val Thr Glu Ile Gly Lys Asp Val Ile Gly Leu
                1205                1210                1215
Arg Ile Ser Pro Leu Gln Phe Arg
            1220

<210> SEQ ID NO 58
<211> LENGTH: 874
<212> TYPE: PRT
<213> ORGANISM: Homo sapiens

<400> SEQUENCE: 58

Met Leu Lys Lys Phe Asp Lys Lys Asp Glu Glu Ser Gly Gly Gly Ser
1               5                   10                  15
Asn Pro Phe Gln His Leu Glu Lys Ser Ala Val Leu Gln Glu Ala Arg
```

-continued

```
                    20                  25                  30
Val Phe Asn Glu Thr Pro Ile Asn Pro Arg Lys Cys Ala His Ile Leu
         35                  40                  45
Thr Lys Ile Leu Tyr Leu Ile Asn Gln Gly Glu His Leu Gly Thr Thr
     50                  55                  60
Glu Ala Thr Glu Ala Phe Phe Ala Met Thr Lys Leu Phe Gln Ser Asn
 65                  70                  75                  80
Asp Pro Thr Leu Arg Arg Met Cys Tyr Leu Thr Ile Lys Glu Met Ser
                 85                  90                  95
Cys Ile Ala Glu Asp Val Ile Val Thr Ser Ser Leu Thr Lys Asp
             100                 105                 110
Met Thr Gly Lys Glu Asp Asn Tyr Arg Gly Pro Ala Val Arg Ala Leu
         115                 120                 125
Cys Gln Ile Thr Asp Ser Thr Met Leu Gln Ala Ile Glu Arg Tyr Met
     130                 135                 140
Lys Gln Ala Ile Val Asp Lys Val Pro Ser Val Ser Ser Ala Leu
145                 150                 155                 160
Val Ser Ser Leu His Leu Leu Lys Cys Ser Phe Asp Val Val Lys Arg
                 165                 170                 175
Trp Val Asn Glu Ala Gln Glu Ala Ala Ser Ser Asp Asn Ile Met Val
             180                 185                 190
Gln Tyr His Ala Leu Gly Leu Leu Tyr His Val Arg Lys Asn Asp Arg
         195                 200                 205
Leu Ala Val Asn Lys Met Ile Ser Lys Val Thr Arg His Gly Leu Lys
     210                 215                 220
Ser Pro Phe Ala Tyr Cys Met Met Ile Arg Val Ala Ser Lys Gln Leu
225                 230                 235                 240
Glu Glu Glu Asp Gly Ser Arg Asp Ser Pro Leu Phe Asp Phe Ile Glu
                 245                 250                 255
Ser Cys Leu Arg Asn Lys His Glu Met Val Val Tyr Glu Ala Ala Ser
             260                 265                 270
Ala Ile Val Asn Leu Pro Gly Cys Ser Ala Lys Glu Leu Ala Pro Ala
         275                 280                 285
Val Ser Val Leu Gln Leu Phe Cys Ser Pro Lys Ala Ala Leu Arg
     290                 295                 300
Tyr Ala Ala Val Arg Thr Leu Asn Lys Val Ala Met Lys His Pro Ser
305                 310                 315                 320
Ala Val Thr Ala Cys Asn Leu Asp Leu Glu Asn Leu Val Thr Asp Ser
                 325                 330                 335
Asn Arg Ser Ile Ala Thr Leu Ala Ile Thr Thr Leu Leu Lys Thr Gly
             340                 345                 350
Ser Glu Ser Ser Ile Asp Arg Leu Met Lys Gln Ile Ser Ser Phe Met
         355                 360                 365
Ser Glu Ile Ser Asp Glu Phe Lys Val Val Val Gln Ala Ile Ser
     370                 375                 380
Ala Leu Cys Gln Lys Tyr Pro Arg Lys His Ala Val Leu Met Asn Phe
385                 390                 395                 400
Leu Phe Thr Met Leu Arg Glu Glu Gly Gly Phe Glu Tyr Lys Arg Ala
                 405                 410                 415
Ile Val Asp Cys Ile Ile Ser Ile Ile Glu Glu Asn Ser Glu Ser Lys
             420                 425                 430
Glu Thr Gly Leu Ser His Leu Cys Glu Phe Ile Glu Asp Cys Glu Phe
         435                 440                 445
```

-continued

```
Thr Val Leu Ala Thr Arg Ile Leu His Leu Leu Gly Gln Glu Gly Pro
    450                 455                 460
Lys Thr Thr Asn Pro Ser Lys Tyr Ile Arg Phe Ile Tyr Asn Arg Val
465                 470                 475                 480
Val Leu Glu His Glu Glu Val Arg Ala Gly Ala Val Ser Ala Leu Ala
                485                 490                 495
Lys Phe Gly Ala Gln Asn Glu Glu Met Leu Pro Ser Ile Leu Val Leu
                500                 505                 510
Leu Lys Arg Cys Val Met Asp Asp Asn Glu Val Arg Asp Arg Ala
            515                 520                 525
Thr Phe Tyr Leu Asn Val Leu Glu Gln Lys Gln Lys Ala Leu Asn Ala
    530                 535                 540
Gly Tyr Ile Leu Asn Gly Leu Thr Val Ser Ile Pro Gly Leu Glu Arg
545                 550                 555                 560
Ala Leu Gln Gln Tyr Thr Leu Glu Pro Ser Glu Lys Pro Phe Asp Leu
                565                 570                 575
Lys Ser Val Pro Leu Ala Thr Ala Pro Met Ala Glu Gln Arg Thr Glu
            580                 585                 590
Ser Thr Pro Ile Thr Ala Val Lys Gln Pro Glu Lys Val Ala Ala Thr
    595                 600                 605
Arg Gln Glu Ile Phe Gln Glu Gln Leu Ala Ala Val Pro Glu Phe Arg
610                 615                 620
Gly Leu Gly Pro Leu Phe Lys Ser Ser Pro Glu Pro Val Ala Leu Thr
625                 630                 635                 640
Glu Ser Glu Thr Glu Tyr Val Ile Arg Cys Thr Lys His Thr Phe Thr
                645                 650                 655
Asn His Met Val Phe Gln Phe Asp Cys Thr Asn Thr Leu Asn Asp Gln
            660                 665                 670
Thr Leu Glu Asn Val Thr Val Gln Met Glu Pro Thr Glu Ala Tyr Glu
    675                 680                 685
Val Leu Cys Tyr Val Pro Ala Arg Ser Leu Pro Tyr Asn Gln Pro Gly
690                 695                 700
Thr Cys Tyr Thr Leu Val Ala Leu Pro Lys Glu Asp Pro Thr Ala Val
705                 710                 715                 720
Ala Cys Thr Phe Ser Cys Met Met Lys Phe Thr Val Lys Asp Cys Asp
                725                 730                 735
Pro Thr Thr Gly Glu Thr Asp Asp Glu Gly Tyr Glu Asp Glu Tyr Val
                740                 745                 750
Leu Glu Asp Leu Glu Val Thr Val Ala Asp His Ile Gln Lys Val Met
            755                 760                 765
Lys Leu Asn Phe Glu Ala Ala Trp Asp Glu Val Gly Asp Glu Phe Glu
    770                 775                 780
Lys Glu Glu Thr Phe Thr Leu Ser Thr Ile Lys Thr Leu Glu Glu Ala
785                 790                 795                 800
Val Gly Asn Ile Val Lys Phe Leu Gly Met His Pro Cys Glu Arg Ser
                805                 810                 815
Asp Lys Val Pro Asp Asn Lys Asn Thr His Thr Leu Leu Leu Ala Gly
                820                 825                 830
Val Phe Arg Gly Gly His Asp Ile Leu Val Arg Ser Arg Leu Leu Leu
            835                 840                 845
Leu Asp Thr Val Thr Met Gln Val Thr Ala Arg Ser Leu Glu Glu Leu
    850                 855                 860
```

-continued

Pro Val Asp Ile Ile Leu Ala Ser Val Gly
865                 870

<210> SEQ ID NO 59
<211> LENGTH: 849
<212> TYPE: PRT
<213> ORGANISM: Homo sapiens

<400> SEQUENCE: 59

Met Ser Glu Glu Arg Ser Leu Ser Leu Leu Ala Lys Ala Val Asp Pro
1               5                   10                  15

Arg His Pro Asn Met Met Thr Asp Val Val Lys Leu Leu Ser Ala Val
                20                  25                  30

Cys Ile Val Gly Glu Glu Ser Ile Leu Glu Glu Val Leu Glu Ala Leu
            35                  40                  45

Thr Ser Ala Gly Glu Glu Lys Lys Ile Asp Arg Phe Phe Cys Ile Val
        50                  55                  60

Glu Gly Leu Arg His Asn Ser Val Gln Leu Gln Val Ala Cys Met Gln
65                  70                  75                  80

Leu Ile Asn Ala Leu Val Thr Ser Pro Asp Asp Leu Asp Phe Arg Leu
                85                  90                  95

His Ile Arg Asn Glu Phe Met Arg Cys Gly Leu Lys Glu Ile Leu Pro
            100                 105                 110

Asn Leu Lys Cys Ile Lys Asn Asp Gly Leu Asp Ile Gln Leu Lys Val
        115                 120                 125

Phe Asp Glu His Lys Glu Glu Asp Leu Phe Glu Leu Ser His Arg Leu
130                 135                 140

Glu Asp Ile Arg Ala Glu Leu Asp Glu Ala Tyr Asp Val Tyr Asn Met
145                 150                 155                 160

Val Trp Ser Thr Val Lys Glu Thr Arg Ala Glu Gly Tyr Phe Ile Ser
                165                 170                 175

Ile Leu Gln His Leu Leu Leu Ile Arg Asn Asp Tyr Phe Ile Arg Gln
            180                 185                 190

Gln Tyr Phe Lys Leu Ile Asp Glu Cys Val Ser Gln Ile Val Leu His
        195                 200                 205

Arg Asp Gly Met Asp Pro Asp Phe Thr Tyr Arg Lys Arg Leu Asp Leu
210                 215                 220

Asp Leu Thr Gln Phe Val Asp Ile Cys Ile Asp Gln Ala Lys Leu Glu
225                 230                 235                 240

Glu Phe Glu Glu Lys Ala Ser Glu Leu Tyr Lys Lys Phe Glu Lys Glu
                245                 250                 255

Phe Thr Asp His Gln Glu Thr Gln Ala Glu Leu Gln Lys Lys Glu Ala
            260                 265                 270

Lys Ile Asn Glu Leu Gln Ala Glu Leu Gln Ala Phe Lys Ser Gln Phe
        275                 280                 285

Gly Ala Leu Pro Ala Asp Cys Asn Ile Pro Leu Pro Pro Ser Lys Glu
290                 295                 300

Gly Gly Thr Gly His Ser Ala Leu Pro Pro Pro Pro Leu Pro Ser
305                 310                 315                 320

Gly Gly Gly Val Pro Pro Pro Pro Pro Pro Pro Pro Leu
                325                 330                 335

Pro Gly Met Arg Met Pro Phe Ser Gly Pro Val Pro Pro Pro Pro
            340                 345                 350

Leu Gly Phe Leu Gly Gly Gln Asn Ser Pro Pro Leu Pro Ile Leu Pro
        355                 360                 365

```
Phe Gly Leu Lys Pro Lys Lys Glu Phe Lys Pro Glu Ile Ser Met Arg
    370                 375                 380

Arg Leu Asn Trp Leu Lys Ile Arg Pro His Glu Met Thr Glu Asn Cys
385                 390                 395                 400

Phe Trp Ile Lys Val Asn Glu Asn Lys Tyr Glu Asn Val Asp Leu Leu
                405                 410                 415

Cys Lys Leu Glu Asn Thr Phe Cys Cys Gln Gln Lys Gly Arg Arg Glu
                420                 425                 430

Glu Glu Asp Ile Glu Glu Lys Lys Ser Ile Lys Lys Ile Lys Glu
            435                 440                 445

Leu Lys Phe Leu Asp Ser Lys Ile Ala Gln Asn Leu Ser Ile Phe Leu
    450                 455                 460

Ser Ser Phe Arg Val Pro Tyr Glu Glu Ile Arg Met Met Ile Leu Glu
465                 470                 475                 480

Val Asp Glu Thr Arg Leu Ala Glu Ser Met Ile Gln Asn Leu Ile Lys
                485                 490                 495

His Leu Pro Asp Gln Glu Gln Leu Asn Ser Leu Ser Gln Phe Lys Ser
                500                 505                 510

Glu Tyr Ser Asn Leu Cys Glu Pro Glu Gln Phe Val Val Met Ser
                515                 520                 525

Asn Val Lys Arg Leu Arg Pro Arg Leu Ser Ala Ile Leu Phe Lys Leu
    530                 535                 540

Gln Phe Glu Glu Gln Val Asn Asn Ile Lys Pro Asp Ile Met Ala Val
545                 550                 555                 560

Ser Thr Ala Cys Glu Glu Ile Lys Lys Ser Lys Ser Phe Ser Lys Leu
                565                 570                 575

Leu Glu Leu Val Leu Leu Met Gly Asn Tyr Met Asn Ala Gly Ser Arg
                580                 585                 590

Asn Ala Gln Thr Phe Gly Phe Asn Leu Ser Ser Leu Cys Lys Leu Lys
                595                 600                 605

Asp Thr Lys Ser Ala Asp Gln Lys Thr Thr Leu Leu His Phe Leu Val
    610                 615                 620

Glu Ile Cys Glu Glu Lys Tyr Pro Asp Ile Leu Asn Phe Val Asp Asp
625                 630                 635                 640

Leu Glu Pro Leu Asp Lys Ala Ser Lys Val Ser Val Glu Thr Leu Glu
                645                 650                 655

Lys Asn Leu Arg Gln Met Gly Arg Gln Leu Gln Gln Leu Glu Lys Glu
                660                 665                 670

Leu Glu Thr Phe Pro Pro Pro Glu Asp Leu His Asp Lys Phe Val Thr
                675                 680                 685

Lys Met Ser Arg Phe Val Ile Ser Ala Lys Glu Gln Tyr Glu Thr Leu
    690                 695                 700

Ser Lys Leu His Glu Asn Met Glu Lys Leu Tyr Gln Ser Ile Ile Gly
705                 710                 715                 720

Tyr Tyr Ala Ile Asp Val Lys Lys Val Ser Val Glu Asp Phe Leu Thr
                725                 730                 735

Asp Leu Asn Asn Phe Arg Thr Thr Phe Met Gln Ala Ile Lys Glu Asn
                740                 745                 750

Ile Lys Lys Arg Glu Ala Glu Glu Lys Glu Lys Arg Val Arg Ile Ala
            755                 760                 765

Lys Glu Leu Ala Glu Arg Glu Arg Leu Glu Arg Gln Gln Lys Lys Lys
    770                 775                 780
```

-continued

```
Arg Leu Leu Glu Met Lys Thr Glu Gly Asp Glu Thr Gly Val Met Asp
785                 790                 795                 800

Asn Leu Leu Glu Ala Leu Gln Ser Gly Ala Ala Phe Arg Asp Arg Arg
            805                 810                 815

Lys Arg Thr Pro Met Pro Lys Asp Val Arg Gln Ser Leu Ser Pro Met
            820                 825                 830

Ser Gln Arg Pro Val Leu Lys Val Cys Asn His Gly Asn Lys Pro Tyr
        835                 840                 845

Leu
```

<210> SEQ ID NO 60
<211> LENGTH: 1638
<212> TYPE: PRT
<213> ORGANISM: Homo sapiens

<400> SEQUENCE: 60

```
Met Ser Gly Glu Val Arg Leu Arg Gln Leu Glu Gln Phe Ile Leu Asp
1               5                   10                  15

Gly Pro Ala Gln Thr Asn Gly Gln Cys Phe Ser Val Glu Thr Leu Leu
            20                  25                  30

Asp Ile Leu Ile Cys Leu Tyr Asp Glu Cys Asn Asn Ser Pro Leu Arg
        35                  40                  45

Arg Glu Lys Asn Ile Leu Glu Tyr Leu Glu Trp Ala Lys Pro Phe Thr
50                  55                  60

Ser Lys Val Lys Gln Met Arg Leu His Arg Glu Asp Phe Glu Ile Leu
65                  70                  75                  80

Lys Val Ile Gly Arg Gly Ala Phe Gly Glu Val Ala Val Val Lys Leu
                85                  90                  95

Lys Asn Ala Asp Lys Val Phe Ala Met Lys Ile Leu Asn Lys Trp Glu
            100                 105                 110

Met Leu Lys Arg Ala Glu Thr Ala Cys Phe Arg Glu Glu Arg Asp Val
        115                 120                 125

Leu Val Asn Gly Asp Asn Lys Trp Ile Thr Thr Leu His Tyr Ala Phe
130                 135                 140

Gln Asp Asp Asn Asn Leu Tyr Leu Val Met Asp Tyr Tyr Val Gly Gly
145                 150                 155                 160

Asp Leu Leu Thr Leu Leu Ser Lys Phe Glu Asp Arg Leu Pro Glu Asp
                165                 170                 175

Met Ala Arg Phe Tyr Leu Ala Glu Met Val Ile Ala Ile Asp Ser Val
            180                 185                 190

His Gln Leu His Tyr Val His Arg Asp Ile Lys Pro Asp Asn Ile Leu
        195                 200                 205

Met Asp Met Asn Gly His Ile Arg Leu Ala Asp Phe Gly Ser Cys Leu
210                 215                 220

Lys Leu Met Glu Asp Gly Thr Val Gln Ser Ser Val Ala Val Gly Thr
225                 230                 235                 240

Pro Asp Tyr Ile Ser Pro Glu Ile Leu Gln Ala Met Glu Asp Gly Lys
                245                 250                 255

Gly Arg Tyr Gly Pro Glu Cys Asp Trp Trp Ser Leu Gly Val Cys Met
            260                 265                 270

Tyr Glu Met Leu Tyr Gly Glu Thr Pro Phe Tyr Ala Glu Ser Leu Val
        275                 280                 285

Glu Thr Tyr Gly Lys Ile Met Asn His Lys Glu Arg Phe Gln Phe Pro
290                 295                 300
```

-continued

```
Ala Gln Val Thr Asp Val Ser Glu Asn Ala Lys Asp Leu Ile Arg Arg
305                 310                 315                 320

Leu Ile Cys Ser Arg Glu His Arg Leu Gly Gln Asn Gly Ile Glu Asp
            325                 330                 335

Phe Lys Lys His Pro Phe Phe Ser Gly Ile Asp Trp Asp Asn Ile Arg
        340                 345                 350

Asn Cys Glu Ala Pro Tyr Ile Pro Glu Val Ser Ser Pro Thr Asp Thr
    355                 360                 365

Ser Asn Phe Asp Val Asp Asp Cys Leu Lys Asn Ser Glu Thr Met
370                 375                 380

Pro Pro Pro Thr His Thr Ala Phe Ser Gly His His Leu Pro Phe Val
385                 390                 395                 400

Gly Phe Thr Tyr Thr Ser Ser Cys Val Leu Ser Asp Arg Ser Cys Leu
            405                 410                 415

Arg Val Thr Ala Gly Pro Thr Ser Leu Asp Leu Asp Val Asn Val Gln
        420                 425                 430

Arg Thr Leu Asp Asn Asn Leu Ala Thr Glu Ala Tyr Glu Arg Arg Ile
    435                 440                 445

Lys Arg Leu Glu Gln Glu Lys Leu Glu Leu Ser Arg Lys Leu Gln Glu
450                 455                 460

Ser Thr Gln Thr Val Gln Ala Leu Gln Tyr Ser Thr Val Asp Gly Pro
465                 470                 475                 480

Leu Thr Ala Ser Lys Asp Leu Glu Ile Lys Asn Leu Lys Glu Glu Ile
            485                 490                 495

Glu Lys Leu Arg Lys Gln Val Thr Glu Ser Ser His Leu Glu Gln Gln
        500                 505                 510

Leu Glu Glu Ala Asn Ala Val Arg Gln Glu Leu Asp Asp Ala Phe Arg
    515                 520                 525

Gln Ile Lys Ala Tyr Glu Lys Gln Ile Lys Thr Leu Gln Gln Glu Arg
530                 535                 540

Glu Asp Leu Asn Lys Leu Glu Val His Thr Glu Ala Leu Ala Ala Glu
545                 550                 555                 560

Ala Ser Lys Asp Arg Lys Leu Arg Glu Gln Ser Glu His Tyr Ser Lys
            565                 570                 575

Gln Leu Glu Asn Glu Leu Glu Gly Leu Lys Gln Lys Gln Ile Ser Tyr
        580                 585                 590

Ser Pro Gly Val Cys Ser Ile Glu His Gln Gln Glu Ile Thr Lys Leu
    595                 600                 605

Lys Thr Asp Leu Glu Lys Lys Ser Ile Phe Tyr Glu Glu Glu Leu Ser
610                 615                 620

Lys Arg Glu Gly Ile His Ala Asn Glu Ile Lys Asn Leu Lys Lys Glu
625                 630                 635                 640

Leu His Asp Ser Glu Gly Gln Gln Leu Ala Leu Asn Lys Glu Ile Met
            645                 650                 655

Ile Leu Lys Asp Lys Leu Glu Lys Thr Arg Arg Glu Ser Gln Ser Glu
        660                 665                 670

Arg Glu Glu Phe Glu Ser Glu Phe Lys Gln Gln Tyr Glu Arg Glu Lys
    675                 680                 685

Val Leu Leu Thr Glu Glu Asn Lys Lys Leu Thr Ser Glu Leu Asp Lys
690                 695                 700

Leu Thr Thr Leu Tyr Glu Asn Leu Ser Ile His Asn Gln Gln Leu Glu
705                 710                 715                 720

Glu Glu Val Lys Asp Leu Ala Asp Lys Lys Glu Ser Val Ala His Trp
```

-continued

```
                725                 730                 735
Glu Ala Gln Ile Thr Glu Ile Ile Gln Trp Val Ser Asp Glu Lys Asp
            740                 745                 750
Ala Arg Gly Tyr Leu Gln Ala Leu Ala Ser Lys Met Thr Glu Glu Leu
            755                 760                 765
Glu Ala Leu Arg Asn Ser Ser Leu Gly Thr Arg Ala Thr Asp Met Pro
            770                 775                 780
Trp Lys Met Arg Arg Phe Ala Lys Leu Asp Met Ser Ala Arg Leu Glu
785                 790                 795                 800
Leu Gln Ser Ala Leu Asp Ala Glu Ile Arg Ala Lys Gln Ala Ile Gln
                805                 810                 815
Glu Glu Leu Asn Lys Val Lys Ala Ser Asn Ile Ile Thr Glu Cys Lys
                820                 825                 830
Leu Lys Asp Ser Glu Lys Lys Asn Leu Glu Leu Leu Ser Glu Ile Glu
                835                 840                 845
Gln Leu Ile Lys Asp Thr Glu Glu Leu Arg Ser Glu Lys Gly Ile Glu
                850                 855                 860
His Gln Asp Ser Gln His Ser Phe Leu Ala Phe Leu Asn Thr Pro Thr
865                 870                 875                 880
Asp Ala Leu Asp Gln Phe Glu Thr Val Asp Ser Thr Pro Leu Ser Val
                885                 890                 895
His Thr Pro Thr Leu Arg Lys Lys Gly Cys Pro Gly Ser Thr Gly Phe
                900                 905                 910
Pro Pro Lys Arg Lys Thr His Gln Phe Phe Val Lys Ser Phe Thr Thr
                915                 920                 925
Pro Thr Lys Cys His Gln Cys Thr Ser Leu Met Val Gly Leu Ile Arg
                930                 935                 940
Gln Gly Cys Ser Cys Glu Val Cys Gly Phe Ser Cys His Ile Thr Cys
945                 950                 955                 960
Val Asn Lys Ala Pro Thr Thr Cys Pro Val Pro Pro Glu Gln Thr Lys
                965                 970                 975
Gly Pro Leu Gly Ile Asp Pro Gln Lys Gly Ile Gly Thr Ala Tyr Glu
                980                 985                 990
Gly His Val Arg Ile Pro Lys Pro Ala Gly Val Lys Lys Gly Trp Gln
                995                 1000                1005
Arg Ala Leu Ala Ile Val Cys Asp Phe Lys Leu Phe Leu Tyr Asp
            1010                1015                1020
Ile Ala Glu Gly Lys Ala Ser Gln Pro Ser Val Ile Ser Gln
            1025                1030                1035
Val Ile Asp Met Arg Asp Glu Glu Phe Ser Val Ser Ser Val Leu
            1040                1045                1050
Ala Ser Asp Val Ile His Ala Ser Arg Lys Asp Ile Pro Cys Ile
            1055                1060                1065
Phe Arg Val Thr Ala Ser Gln Leu Ser Ala Ser Asn Asn Lys Cys
            1070                1075                1080
Ser Ile Leu Met Leu Ala Asp Thr Glu Asn Glu Lys Asn Lys Trp
            1085                1090                1095
Val Gly Val Leu Ser Glu Leu His Lys Ile Leu Lys Lys Asn Lys
            1100                1105                1110
Phe Arg Asp Arg Ser Val Tyr Val Pro Lys Glu Ala Tyr Asp Ser
            1115                1120                1125
Thr Leu Pro Leu Ile Lys Thr Gln Ala Ala Ala Ile Ile Asp
            1130                1135                1140
```

-continued

```
His Glu Arg Ile Ala Leu Gly Asn Glu Glu Gly Leu Phe Val Val
    1145                1150                1155

His Val Thr Lys Asp Glu Ile Ile Arg Val Gly Asp Asn Lys Lys
    1160                1165                1170

Ile His Gln Ile Glu Leu Ile Pro Asn Asp Gln Leu Val Ala Val
    1175                1180                1185

Ile Ser Gly Arg Asn Arg His Val Arg Leu Phe Pro Met Ser Ala
    1190                1195                1200

Leu Asp Gly Arg Glu Thr Asp Phe Tyr Lys Leu Ser Glu Thr Lys
    1205                1210                1215

Gly Cys Gln Thr Val Thr Ser Gly Lys Val Arg His Gly Ala Leu
    1220                1225                1230

Thr Cys Leu Cys Val Ala Met Lys Arg Gln Val Leu Cys Tyr Glu
    1235                1240                1245

Leu Phe Gln Ser Lys Thr Arg His Arg Lys Phe Lys Glu Ile Gln
    1250                1255                1260

Val Pro Tyr Asn Val Gln Trp Met Ala Ile Phe Ser Glu Gln Leu
    1265                1270                1275

Cys Val Gly Phe Gln Ser Gly Phe Leu Arg Tyr Pro Leu Asn Gly
    1280                1285                1290

Glu Gly Asn Pro Tyr Ser Met Leu His Ser Asn Asp His Thr Leu
    1295                1300                1305

Ser Phe Ile Ala His Gln Pro Met Asp Ala Ile Cys Ala Val Glu
    1310                1315                1320

Ile Ser Ser Lys Glu Tyr Leu Leu Cys Phe Asn Ser Ile Gly Ile
    1325                1330                1335

Tyr Thr Asp Cys Gln Gly Arg Arg Ser Arg Gln Gln Glu Leu Met
    1340                1345                1350

Trp Pro Ala Asn Pro Ser Ser Cys Cys Tyr Asn Ala Pro Tyr Leu
    1355                1360                1365

Ser Val Tyr Ser Glu Asn Ala Val Asp Ile Phe Asp Val Asn Ser
    1370                1375                1380

Met Glu Trp Ile Gln Thr Leu Pro Leu Lys Lys Val Arg Pro Leu
    1385                1390                1395

Asn Asn Glu Gly Ser Leu Asn Leu Leu Gly Leu Glu Thr Ile Arg
    1400                1405                1410

Leu Ile Tyr Phe Lys Asn Lys Met Ala Glu Gly Asp Glu Leu Val
    1415                1420                1425

Val Pro Glu Thr Ser Asp Asn Ser Arg Lys Gln Met Val Arg Asn
    1430                1435                1440

Ile Asn Asn Lys Arg Arg Tyr Ser Phe Arg Val Pro Glu Glu Glu
    1445                1450                1455

Arg Met Gln Gln Arg Arg Glu Met Leu Arg Asp Pro Glu Met Arg
    1460                1465                1470

Asn Lys Leu Ile Ser Asn Pro Thr Asn Phe Asn His Ile Ala His
    1475                1480                1485

Met Gly Pro Gly Asp Gly Ile Gln Ile Leu Lys Asp Leu Pro Met
    1490                1495                1500

Asn Pro Arg Pro Gln Glu Ser Arg Thr Val Phe Ser Gly Ser Val
    1505                1510                1515

Ser Ile Pro Ser Ile Thr Lys Ser Arg Pro Glu Pro Gly Arg Ser
    1520                1525                1530
```

-continued

```
Met Ser Ala Ser Ser Gly Leu Ser Ala Arg Ser Ser Ala Gln Asn
    1535                1540                1545

Gly Ser Ala Leu Lys Arg Glu Phe Ser Gly Gly Ser Tyr Ser Ala
    1550                1555                1560

Lys Arg Gln Pro Met Pro Ser Pro Ser Glu Gly Ser Leu Ser Ser
    1565                1570                1575

Gly Gly Met Asp Gln Gly Ser Asp Ala Pro Ala Arg Asp Phe Asp
    1580                1585                1590

Gly Glu Asp Ser Asp Ser Pro Arg His Ser Thr Ala Ser Asn Ser
    1595                1600                1605

Ser Asn Leu Ser Ser Pro Pro Ser Pro Ala Ser Pro Arg Lys Thr
    1610                1615                1620

Lys Ser Leu Ser Leu Glu Ser Thr Asp Arg Gly Ser Trp Asp Pro
    1625                1630                1635

<210> SEQ ID NO 61
<211> LENGTH: 1711
<212> TYPE: PRT
<213> ORGANISM: Homo sapiens

<400> SEQUENCE: 61

Met Ser Ala Lys Val Arg Leu Lys Lys Leu Glu Gln Leu Leu Leu Asp
1               5                   10                  15

Gly Pro Trp Arg Asn Glu Ser Ala Leu Ser Val Glu Thr Leu Leu Asp
                20                  25                  30

Val Leu Val Cys Leu Tyr Thr Glu Cys Ser His Ser Ala Leu Arg Arg
            35                  40                  45

Asp Lys Tyr Val Ala Glu Phe Leu Glu Trp Ala Lys Pro Phe Thr Gln
        50                  55                  60

Leu Val Lys Glu Met Gln Leu His Arg Glu Asp Phe Glu Ile Ile Lys
65                  70                  75                  80

Val Ile Gly Arg Gly Ala Phe Gly Glu Val Ala Val Val Lys Met Lys
                85                  90                  95

Asn Thr Glu Arg Ile Tyr Ala Met Lys Ile Leu Asn Lys Trp Glu Met
            100                 105                 110

Leu Lys Arg Ala Glu Thr Ala Cys Phe Arg Glu Glu Arg Asp Val Leu
        115                 120                 125

Val Asn Gly Asp Cys Gln Trp Ile Thr Ala Leu His Tyr Ala Phe Gln
    130                 135                 140

Asp Glu Asn His Leu Tyr Leu Val Met Asp Tyr Tyr Val Gly Gly Asp
145                 150                 155                 160

Leu Leu Thr Leu Leu Ser Lys Phe Glu Asp Lys Leu Pro Glu Asp Met
                165                 170                 175

Ala Arg Phe Tyr Ile Gly Glu Met Val Leu Ala Ile Asp Ser Ile His
            180                 185                 190

Gln Leu His Tyr Val His Arg Asp Ile Lys Pro Asp Asn Val Leu Leu
        195                 200                 205

Asp Val Asn Gly His Ile Arg Leu Ala Asp Phe Gly Ser Cys Leu Lys
    210                 215                 220

Met Asn Asp Asp Gly Thr Val Gln Ser Val Ala Val Gly Thr Pro
225                 230                 235                 240

Asp Tyr Ile Ser Pro Glu Ile Leu Gln Ala Met Glu Asp Gly Met Gly
                245                 250                 255

Lys Tyr Gly Pro Glu Cys Asp Trp Trp Ser Leu Gly Val Cys Met Tyr
            260                 265                 270
```

-continued

```
Glu Met Leu Tyr Gly Glu Thr Pro Phe Tyr Ala Glu Ser Leu Val Glu
        275                 280                 285

Thr Tyr Gly Lys Ile Met Asn His Glu Glu Arg Phe Gln Phe Pro Ser
        290                 295                 300

His Val Thr Asp Val Ser Glu Glu Ala Lys Asp Leu Ile Gln Arg Leu
305                 310                 315                 320

Ile Cys Ser Arg Glu Arg Arg Leu Gly Gln Asn Gly Ile Glu Asp Phe
                325                 330                 335

Lys Lys His Ala Phe Phe Glu Gly Leu Asn Trp Glu Asn Ile Arg Asn
            340                 345                 350

Leu Glu Ala Pro Tyr Ile Pro Asp Val Ser Pro Ser Asp Thr Ser
        355                 360                 365

Asn Phe Asp Val Asp Asp Val Leu Arg Asn Thr Glu Ile Leu Pro
    370                 375                 380

Pro Gly Ser His Thr Gly Phe Ser Gly Leu His Leu Pro Phe Ile Gly
385                 390                 395                 400

Phe Thr Phe Thr Thr Glu Ser Cys Phe Ser Asp Arg Gly Ser Leu Lys
                405                 410                 415

Ser Ile Met Gln Ser Asn Thr Leu Thr Lys Asp Glu Asp Val Gln Arg
            420                 425                 430

Asp Leu Glu His Ser Leu Gln Met Glu Ala Tyr Glu Arg Arg Ile Arg
            435                 440                 445

Arg Leu Glu Gln Glu Lys Leu Glu Leu Ser Arg Lys Leu Gln Glu Ser
450                 455                 460

Thr Gln Thr Val Gln Ser Leu His Gly Ser Ser Arg Ala Leu Ser Asn
465                 470                 475                 480

Ser Asn Arg Asp Lys Glu Ile Lys Lys Leu Asn Glu Glu Ile Glu Arg
                485                 490                 495

Leu Lys Asn Lys Ile Ala Asp Ser Asn Arg Leu Glu Arg Gln Leu Glu
            500                 505                 510

Asp Thr Val Ala Leu Arg Gln Glu Arg Glu Asp Ser Thr Gln Arg Leu
            515                 520                 525

Arg Gly Leu Glu Lys Gln His Arg Val Val Arg Gln Glu Lys Glu Glu
        530                 535                 540

Leu His Lys Gln Leu Val Glu Ala Ser Glu Arg Leu Lys Ser Gln Ala
545                 550                 555                 560

Lys Glu Leu Lys Asp Ala His Gln Gln Arg Lys Leu Ala Leu Gln Glu
                565                 570                 575

Phe Ser Glu Leu Asn Glu Arg Met Ala Glu Leu Arg Ala Gln Lys Gln
            580                 585                 590

Lys Val Ser Arg Gln Leu Arg Asp Lys Glu Glu Met Glu Val Ala
        595                 600                 605

Thr Gln Lys Val Asp Ala Met Arg Gln Glu Met Arg Arg Ala Glu Lys
        610                 615                 620

Leu Arg Lys Glu Leu Glu Ala Gln Leu Asp Asp Ala Val Ala Glu Ala
625                 630                 635                 640

Ser Lys Glu Arg Lys Leu Arg Glu His Ser Glu Asn Phe Cys Lys Gln
                645                 650                 655

Met Glu Ser Glu Leu Glu Ala Leu Lys Val Lys Gln Gly Gly Arg Gly
            660                 665                 670

Ala Gly Ala Thr Leu Glu His Gln Gln Glu Ile Ser Lys Ile Lys Ser
        675                 680                 685
```

-continued

```
Glu Leu Glu Lys Lys Val Leu Phe Tyr Glu Glu Leu Val Arg Arg
    690                 695                 700

Glu Ala Ser His Val Leu Glu Val Lys Asn Val Lys Lys Glu Val His
705                 710                 715                 720

Asp Ser Glu Ser His Gln Leu Ala Leu Gln Lys Glu Ile Leu Met Leu
                725                 730                 735

Lys Asp Lys Leu Glu Lys Ser Lys Arg Glu Arg His Asn Glu Met Glu
            740                 745                 750

Glu Ala Val Gly Thr Ile Lys Asp Lys Tyr Glu Arg Glu Arg Ala Met
        755                 760                 765

Leu Phe Asp Glu Asn Lys Lys Leu Thr Ala Glu Asn Glu Lys Leu Cys
770                 775                 780

Ser Phe Val Asp Lys Leu Thr Ala Gln Asn Arg Gln Leu Glu Asp Glu
785                 790                 795                 800

Leu Gln Asp Leu Ala Ala Lys Lys Glu Ser Val Ala His Trp Glu Ala
                805                 810                 815

Gln Ile Ala Glu Ile Ile Gln Trp Val Ser Asp Glu Lys Asp Ala Arg
            820                 825                 830

Gly Tyr Leu Gln Ala Leu Ala Ser Lys Met Thr Glu Glu Leu Glu Ala
        835                 840                 845

Leu Arg Ser Ser Ser Leu Gly Ser Arg Thr Leu Asp Pro Leu Trp Lys
850                 855                 860

Val Arg Arg Ser Gln Lys Leu Asp Met Ser Ala Arg Leu Glu Leu Gln
865                 870                 875                 880

Ser Ala Leu Glu Ala Glu Ile Arg Ala Lys Gln Leu Val Gln Glu Glu
                885                 890                 895

Leu Arg Lys Val Lys Asp Ala Asn Leu Thr Leu Glu Ser Lys Leu Lys
            900                 905                 910

Asp Ser Glu Ala Lys Asn Arg Glu Leu Leu Glu Glu Met Glu Ile Leu
        915                 920                 925

Lys Lys Lys Met Glu Glu Lys Phe Arg Ala Asp Thr Gly Leu Lys Leu
930                 935                 940

Pro Asp Phe Gln Asp Ser Ile Phe Glu Tyr Phe Asn Thr Ala Pro Leu
945                 950                 955                 960

Ala His Asp Leu Thr Phe Arg Thr Ser Ser Ala Ser Glu Gln Glu Thr
                965                 970                 975

Gln Ala Pro Lys Pro Glu Ala Ser Pro Ser Met Ser Val Ala Ala Ser
            980                 985                 990

Glu Gln Gln Glu Asp Met Ala Arg Pro Pro Gln Arg Pro Ser Ala Val
        995                 1000                1005

Pro Leu Pro Thr Thr Gln Ala Leu Ala Leu Ala Gly Pro Lys Pro
    1010                1015                1020

Lys Ala His Gln Phe Ser Ile Lys Ser Phe Ser Ser Pro Thr Gln
    1025                1030                1035

Cys Ser His Cys Thr Ser Leu Met Val Gly Leu Ile Arg Gln Gly
    1040                1045                1050

Tyr Ala Cys Glu Val Cys Ser Phe Ala Cys His Val Ser Cys Lys
    1055                1060                1065

Asp Gly Ala Pro Gln Val Cys Pro Ile Pro Glu Gln Ser Lys
    1070                1075                1080

Arg Pro Leu Gly Val Asp Val Gln Arg Gly Ile Gly Thr Ala Tyr
    1085                1090                1095

Lys Gly His Val Lys Val Pro Lys Pro Thr Gly Val Lys Lys Gly
```

-continued

```
              1100                1105                1110
Trp Gln Arg Ala Tyr Ala Val Val Cys Glu Cys Lys Leu Phe Leu
      1115                1120                1125

Tyr Asp Leu Pro Glu Gly Lys Ser Thr Gln Pro Gly Val Ile Ala
      1130                1135                1140

Ser Gln Val Leu Asp Leu Arg Asp Asp Glu Phe Ser Val Ser Ser
      1145                1150                1155

Val Leu Ala Ser Asp Val Ile His Ala Thr Arg Arg Asp Ile Pro
      1160                1165                1170

Cys Ile Phe Arg Val Thr Ala Ser Leu Leu Gly Ala Pro Ser Lys
      1175                1180                1185

Thr Ser Ser Leu Leu Ile Leu Thr Glu Asn Glu Asn Glu Lys Arg
      1190                1195                1200

Lys Trp Val Gly Ile Leu Glu Gly Leu Gln Ser Ile Leu His Lys
      1205                1210                1215

Asn Arg Leu Arg Asn Gln Val Val His Val Pro Leu Glu Ala Tyr
      1220                1225                1230

Asp Ser Ser Leu Pro Leu Ile Lys Ala Ile Leu Thr Ala Ala Ile
      1235                1240                1245

Val Asp Ala Asp Arg Ile Ala Val Gly Leu Glu Gly Leu Tyr
      1250                1255                1260

Val Ile Glu Val Thr Arg Asp Val Ile Val Arg Ala Ala Asp Cys
      1265                1270                1275

Lys Lys Val His Gln Ile Glu Leu Ala Pro Arg Glu Lys Ile Val
      1280                1285                1290

Ile Leu Leu Cys Gly Arg Asn His His Val His Leu Tyr Pro Trp
      1295                1300                1305

Ser Ser Leu Asp Gly Ala Glu Gly Ser Phe Asp Ile Lys Leu Pro
      1310                1315                1320

Glu Thr Lys Gly Cys Gln Leu Met Ala Thr Ala Thr Leu Lys Arg
      1325                1330                1335

Asn Ser Gly Thr Cys Leu Phe Val Ala Val Lys Arg Leu Ile Leu
      1340                1345                1350

Cys Tyr Glu Ile Gln Arg Thr Lys Pro Phe His Arg Lys Phe Asn
      1355                1360                1365

Glu Ile Val Ala Pro Gly Ser Val Gln Cys Leu Ala Val Leu Arg
      1370                1375                1380

Asp Arg Leu Cys Val Gly Tyr Pro Ser Gly Phe Cys Leu Leu Ser
      1385                1390                1395

Ile Gln Gly Asp Gly Gln Pro Leu Asn Leu Val Asn Pro Asn Asp
      1400                1405                1410

Pro Ser Leu Ala Phe Leu Ser Gln Gln Ser Phe Asp Ala Leu Cys
      1415                1420                1425

Ala Val Glu Leu Glu Ser Glu Glu Tyr Leu Leu Cys Phe Ser His
      1430                1435                1440

Met Gly Leu Tyr Val Asp Pro Gln Gly Arg Arg Ala Arg Ala Gln
      1445                1450                1455

Glu Leu Met Trp Pro Ala Ala Pro Val Ala Cys Ser Cys Ser Pro
      1460                1465                1470

Thr His Val Thr Val Tyr Ser Glu Tyr Gly Val Asp Val Phe Asp
      1475                1480                1485

Val Arg Thr Met Glu Trp Val Gln Thr Ile Gly Leu Arg Arg Ile
      1490                1495                1500
```

```
Arg Pro Leu Asn Ser Glu Gly Thr Leu Asn Leu Leu Asn Cys Glu
    1505                1510                1515

Pro Pro Arg Leu Ile Tyr Phe Lys Ser Lys Phe Ser Gly Ala Val
    1520                1525                1530

Leu Asn Val Pro Asp Thr Ser Asp Asn Ser Lys Lys Gln Met Leu
    1535                1540                1545

Arg Thr Arg Ser Lys Arg Arg Phe Val Phe Lys Val Pro Glu Glu
    1550                1555                1560

Glu Arg Leu Gln Gln Arg Arg Glu Met Leu Arg Asp Pro Glu Leu
    1565                1570                1575

Arg Ser Lys Met Ile Ser Asn Pro Thr Asn Phe Asn His Val Ala
    1580                1585                1590

His Met Gly Pro Gly Asp Gly Met Gln Val Leu Met Asp Leu Pro
    1595                1600                1605

Leu Ser Ala Val Pro Pro Ser Gln Glu Glu Arg Pro Gly Pro Ala
    1610                1615                1620

Pro Thr Asn Leu Ala Arg Gln Pro Pro Ser Arg Asn Lys Pro Tyr
    1625                1630                1635

Ile Ser Trp Pro Ser Ser Gly Gly Ser Glu Pro Ser Val Thr Val
    1640                1645                1650

Pro Leu Arg Ser Met Ser Asp Pro Asp Gln Asp Phe Asp Lys Glu
    1655                1660                1665

Pro Asp Ser Asp Ser Thr Lys His Ser Thr Pro Ser Asn Ser Ser
    1670                1675                1680

Asn Pro Ser Gly Pro Pro Ser Pro Asn Ser Pro His Arg Ser Gln
    1685                1690                1695

Leu Pro Leu Glu Gly Leu Glu Gln Pro Ala Cys Asp Thr
    1700                1705                1710

<210> SEQ ID NO 62
<211> LENGTH: 79
<212> TYPE: PRT
<213> ORGANISM: Homo sapiens

<400> SEQUENCE: 62

Met Ser Glu Phe Trp His Lys Leu Gly Cys Cys Val Val Glu Lys Pro
1               5                   10                  15

Gln Pro Lys Lys Lys Arg Arg Ile Asp Arg Thr Met Ile Gly Glu
            20                  25                  30

Pro Met Asn Phe Val His Leu Thr His Ile Gly Ser Gly Glu Met Gly
            35                  40                  45

Ala Gly Asp Gly Leu Ala Met Thr Gly Ala Val Gln Glu Gln Met Arg
        50                  55                  60

Ser Lys Gly Asn Arg Asp Arg Pro Trp Ser Asn Ser Arg Gly Leu
65                  70                  75

<210> SEQ ID NO 63
<211> LENGTH: 84
<212> TYPE: PRT
<213> ORGANISM: Homo sapiens

<400> SEQUENCE: 63

Met Ser Glu Phe Trp Leu Cys Phe Asn Cys Cys Ile Ala Glu Gln Pro
1               5                   10                  15

Gln Pro Lys Arg Arg Arg Arg Ile Asp Arg Ser Met Ile Gly Glu Pro
            20                  25                  30
```

```
Thr Asn Phe Val His Thr Ala His Val Gly Ser Gly Asp Leu Phe Ser
        35                  40                  45

Gly Met Asn Ser Val Ser Ser Ile Gln Asn Gln Met Gln Ser Lys Gly
 50                  55                  60

Gly Tyr Gly Gly Gly Met Pro Ala Asn Val Gln Met Gln Leu Val Asp
 65                  70                  75                  80

Thr Lys Ala Gly

<210> SEQ ID NO 64
<211> LENGTH: 954
<212> TYPE: PRT
<213> ORGANISM: Homo sapiens

<400> SEQUENCE: 64

Met Glu Glu Glu Gly Ala Val Ala Lys Glu Trp Gly Thr Thr Pro
 1               5                  10                  15

Ala Gly Pro Val Trp Thr Ala Val Phe Asp Tyr Glu Ala Ala Gly Asp
                 20                  25                  30

Glu Glu Leu Thr Leu Arg Arg Gly Asp Arg Val Gln Val Leu Ser Gln
             35                  40                  45

Asp Cys Ala Val Ser Gly Asp Glu Gly Trp Trp Thr Gly Gln Leu Pro
         50                  55                  60

Ser Gly Arg Val Gly Val Phe Pro Ser Asn Tyr Val Ala Pro Gly Ala
 65                  70                  75                  80

Pro Ala Ala Pro Ala Gly Leu Gln Leu Pro Gln Glu Ile Pro Phe His
                 85                  90                  95

Glu Leu Gln Leu Glu Glu Ile Ile Gly Val Gly Gly Phe Gly Lys Val
            100                 105                 110

Tyr Arg Ala Leu Trp Arg Gly Glu Glu Val Ala Val Lys Ala Ala Arg
        115                 120                 125

Leu Asp Pro Glu Lys Asp Pro Ala Val Thr Ala Glu Gln Val Cys Gln
130                 135                 140

Glu Ala Arg Leu Phe Gly Ala Leu Gln His Pro Asn Ile Ile Ala Leu
145                 150                 155                 160

Arg Gly Ala Cys Leu Asn Pro Pro His Leu Cys Leu Val Met Glu Tyr
                165                 170                 175

Ala Arg Gly Gly Ala Leu Ser Arg Val Leu Ala Gly Arg Arg Val Pro
            180                 185                 190

Pro His Val Leu Val Asn Trp Ala Val Gln Val Ala Arg Gly Met Asn
        195                 200                 205

Tyr Leu His Asn Asp Ala Pro Val Pro Ile Ile His Arg Asp Leu Lys
    210                 215                 220

Ser Ile Asn Ile Leu Ile Leu Glu Ala Ile Glu Asn His Asn Leu Ala
225                 230                 235                 240

Asp Thr Val Leu Lys Ile Thr Asp Phe Gly Leu Ala Arg Glu Trp His
                245                 250                 255

Lys Thr Thr Lys Met Ser Ala Ala Gly Thr Tyr Ala Trp Met Ala Pro
            260                 265                 270

Glu Val Ile Arg Leu Ser Leu Phe Ser Lys Ser Ser Asp Val Trp Ser
        275                 280                 285

Phe Gly Val Leu Leu Trp Glu Leu Leu Thr Gly Glu Val Pro Tyr Arg
    290                 295                 300

Glu Ile Asp Ala Leu Ala Val Ala Tyr Gly Val Ala Met Asn Lys Leu
305                 310                 315                 320
```

-continued

```
Thr Leu Pro Ile Pro Ser Thr Cys Pro Glu Pro Phe Ala Arg Leu Leu
                325                 330                 335
Glu Glu Cys Trp Asp Pro Asp Pro His Gly Arg Pro Asp Phe Gly Ser
            340                 345                 350
Ile Leu Lys Arg Leu Glu Val Ile Glu Gln Ser Ala Leu Phe Gln Met
        355                 360                 365
Pro Leu Glu Ser Phe His Ser Leu Gln Glu Asp Trp Lys Leu Glu Ile
    370                 375                 380
Gln His Met Phe Asp Asp Leu Arg Thr Lys Glu Lys Glu Leu Arg Ser
385                 390                 395                 400
Arg Glu Glu Glu Leu Leu Arg Ala Ala Gln Glu Gln Arg Phe Gln Glu
                405                 410                 415
Glu Gln Leu Arg Arg Glu Gln Glu Leu Ala Glu Arg Glu Met Asp
            420                 425                 430
Ile Val Glu Arg Glu Leu His Leu Leu Met Cys Gln Leu Ser Gln Glu
        435                 440                 445
Lys Pro Arg Val Arg Lys Arg Lys Gly Asn Phe Lys Arg Ser Arg Leu
    450                 455                 460
Leu Lys Leu Arg Glu Gly Gly Ser His Ile Ser Leu Pro Ser Gly Phe
465                 470                 475                 480
Glu His Lys Ile Thr Val Gln Ala Ser Pro Thr Leu Asp Lys Arg Lys
                485                 490                 495
Gly Ser Asp Gly Ala Ser Pro Ala Ser Pro Ser Ile Ile Pro Arg
            500                 505                 510
Leu Arg Ala Ile Arg Leu Thr Pro Val Asp Cys Gly Gly Ser Ser Ser
        515                 520                 525
Gly Ser Ser Ser Gly Gly Ser Gly Thr Trp Ser Arg Gly Gly Pro Pro
    530                 535                 540
Lys Lys Glu Glu Leu Val Gly Gly Lys Lys Gly Arg Thr Trp Gly
545                 550                 555                 560
Pro Ser Ser Thr Leu Gln Lys Glu Arg Val Gly Gly Glu Glu Arg Leu
                565                 570                 575
Lys Gly Leu Gly Glu Gly Ser Lys Gln Trp Ser Ser Ser Ala Pro Asn
            580                 585                 590
Leu Gly Lys Ser Pro Lys His Thr Pro Ile Ala Pro Gly Phe Ala Ser
        595                 600                 605
Leu Asn Glu Met Glu Glu Phe Ala Glu Ala Glu Asp Gly Gly Ser Ser
    610                 615                 620
Val Pro Pro Ser Pro Tyr Ser Thr Pro Ser Tyr Leu Ser Val Pro Leu
625                 630                 635                 640
Pro Ala Glu Pro Ser Pro Gly Ala Arg Ala Pro Trp Glu Pro Thr Pro
                645                 650                 655
Ser Ala Pro Pro Ala Arg Trp Gly His Gly Ala Arg Arg Cys Asp
            660                 665                 670
Leu Ala Leu Leu Gly Cys Ala Thr Leu Leu Gly Ala Val Gly Leu Gly
        675                 680                 685
Ala Asp Val Ala Glu Ala Arg Ala Ala Asp Gly Glu Glu Gln Arg Arg
    690                 695                 700
Trp Leu Asp Gly Leu Phe Phe Pro Arg Ala Gly Arg Phe Pro Arg Gly
705                 710                 715                 720
Leu Ser Pro Pro Ala Arg Pro His Gly Arg Arg Glu Asp Val Gly Pro
                725                 730                 735
```

```
Gly Leu Gly Leu Ala Pro Ser Ala Thr Leu Val Ser Leu Ser Ser Val
            740                 745                 750

Ser Asp Cys Asn Ser Thr Arg Ser Leu Leu Arg Ser Asp Ser Asp Glu
            755                 760                 765

Ala Ala Pro Ala Ala Pro Ser Pro Pro Ser Pro Pro Ala Pro Thr
770                 775                 780

Pro Thr Pro Ser Pro Ser Thr Asn Pro Leu Val Asp Leu Glu Leu Glu
785                 790                 795                 800

Ser Phe Lys Lys Asp Pro Arg Gln Ser Leu Thr Pro Thr His Val Thr
            805                 810                 815

Ala Ala Cys Ala Val Ser Arg Gly His Arg Arg Thr Pro Ser Asp Gly
            820                 825                 830

Ala Leu Gly Gln Arg Gly Pro Pro Glu Pro Ala Gly His Gly Pro Gly
            835                 840                 845

Pro Arg Asp Leu Leu Asp Phe Pro Arg Leu Pro Asp Pro Gln Ala Leu
850                 855                 860

Phe Pro Ala Arg Arg Pro Pro Glu Phe Pro Gly Arg Pro Thr Thr
865                 870                 875                 880

Leu Thr Phe Ala Pro Arg Pro Arg Pro Ala Ala Ser Arg Pro Arg Leu
            885                 890                 895

Asp Pro Trp Lys Leu Val Ser Phe Gly Arg Thr Leu Thr Ile Ser Pro
            900                 905                 910

Pro Ser Arg Pro Asp Thr Pro Glu Ser Pro Gly Pro Pro Ser Val Gln
            915                 920                 925

Pro Thr Leu Leu Asp Met Asp Met Glu Gly Gln Asn Gln Asp Ser Thr
            930                 935                 940

Val Pro Leu Cys Gly Ala His Gly Ser His
945                 950

<210> SEQ ID NO 65
<211> LENGTH: 847
<212> TYPE: PRT
<213> ORGANISM: Homo sapiens

<400> SEQUENCE: 65

Met Glu Pro Leu Lys Ser Leu Phe Leu Lys Ser Pro Leu Gly Ser Trp
1               5                   10                  15

Asn Gly Ser Gly Ser Gly Gly Gly Gly Gly Gly Gly Gly Arg Pro
            20                  25                  30

Glu Gly Ser Pro Lys Ala Ala Gly Tyr Ala Asn Pro Val Trp Thr Ala
            35                  40                  45

Leu Phe Asp Tyr Glu Pro Ser Gly Gln Asp Glu Leu Ala Leu Arg Lys
        50                  55                  60

Gly Asp Arg Val Glu Val Leu Ser Arg Asp Ala Ala Ile Ser Gly Asp
65                  70                  75                  80

Glu Gly Trp Trp Ala Gly Gln Val Gly Gly Gln Val Gly Ile Phe Pro
                85                  90                  95

Ser Asn Tyr Val Ser Arg Gly Gly Gly Pro Pro Pro Cys Glu Val Ala
                100                 105                 110

Ser Phe Gln Glu Leu Arg Leu Glu Glu Val Ile Gly Ile Gly Gly Phe
            115                 120                 125

Gly Lys Val Tyr Arg Gly Ser Trp Arg Gly Glu Leu Val Ala Val Lys
130                 135                 140

Ala Ala Arg Gln Asp Pro Asp Glu Asp Ile Ser Val Thr Ala Glu Ser
145                 150                 155                 160
```

-continued

```
Val Arg Gln Glu Ala Arg Leu Phe Ala Met Leu Ala His Pro Asn Ile
                165                 170                 175

Ile Ala Leu Lys Ala Val Cys Leu Glu Glu Pro Asn Leu Cys Leu Val
            180                 185                 190

Met Glu Tyr Ala Ala Gly Gly Pro Leu Ser Arg Ala Leu Ala Gly Arg
        195                 200                 205

Arg Val Pro Pro His Val Leu Val Asn Trp Ala Val Gln Ile Ala Arg
    210                 215                 220

Gly Met His Tyr Leu His Cys Glu Ala Leu Val Pro Val Ile His Arg
225                 230                 235                 240

Asp Leu Lys Ser Asn Asn Ile Leu Leu Leu Gln Pro Ile Glu Ser Asp
                245                 250                 255

Asp Met Glu His Lys Thr Leu Lys Ile Thr Asp Phe Gly Leu Ala Arg
            260                 265                 270

Glu Trp His Lys Thr Thr Gln Met Ser Ala Ala Gly Thr Tyr Ala Trp
        275                 280                 285

Met Ala Pro Glu Val Ile Lys Ala Ser Thr Phe Ser Lys Gly Ser Asp
    290                 295                 300

Val Trp Ser Phe Gly Val Leu Leu Trp Glu Leu Leu Thr Gly Glu Val
305                 310                 315                 320

Pro Tyr Arg Gly Ile Asp Cys Leu Ala Val Ala Tyr Gly Val Ala Val
                325                 330                 335

Asn Lys Leu Thr Leu Pro Ile Pro Ser Thr Cys Pro Glu Pro Phe Ala
            340                 345                 350

Gln Leu Met Ala Asp Cys Trp Ala Gln Asp Pro His Arg Arg Pro Asp
        355                 360                 365

Phe Ala Ser Ile Leu Gln Gln Leu Glu Ala Leu Glu Ala Gln Val Leu
    370                 375                 380

Arg Glu Met Pro Arg Asp Ser Phe His Ser Met Gln Glu Gly Trp Lys
385                 390                 395                 400

Arg Glu Ile Gln Gly Leu Phe Asp Glu Leu Arg Ala Lys Glu Lys Glu
                405                 410                 415

Leu Leu Ser Arg Glu Glu Leu Thr Arg Ala Ala Arg Glu Gln Arg
            420                 425                 430

Ser Gln Ala Glu Gln Leu Arg Arg Glu His Leu Leu Ala Gln Trp
        435                 440                 445

Glu Leu Glu Val Phe Glu Arg Glu Leu Thr Leu Leu Gln Gln Val
    450                 455                 460

Asp Arg Glu Arg Pro His Val Arg Arg Arg Gly Thr Phe Lys Arg
465                 470                 475                 480

Ser Lys Leu Arg Ala Arg Asp Gly Gly Glu Arg Ile Ser Met Pro Leu
                485                 490                 495

Asp Phe Lys His Arg Ile Thr Val Gln Ala Ser Pro Gly Leu Asp Arg
            500                 505                 510

Arg Arg Asn Val Phe Glu Val Gly Pro Gly Asp Ser Pro Thr Phe Pro
        515                 520                 525

Arg Phe Arg Ala Ile Gln Leu Glu Pro Ala Glu Pro Gly Gln Ala Trp
    530                 535                 540

Gly Arg Gln Ser Pro Arg Arg Leu Glu Asp Ser Ser Asn Gly Glu Arg
545                 550                 555                 560

Arg Ala Cys Trp Ala Trp Gly Pro Ser Ser Pro Lys Pro Gly Glu Ala
                565                 570                 575
```

```
Gln Asn Gly Arg Arg Ser Arg Met Asp Glu Ala Thr Trp Tyr Leu
            580                 585                 590

Asp Ser Asp Ser Ser Pro Leu Gly Ser Pro Ser Thr Pro Pro Ala
            595                 600                 605

Leu Asn Gly Asn Pro Pro Arg Pro Ser Leu Glu Pro Glu Pro Lys
610                 615                 620

Arg Pro Val Pro Ala Glu Arg Gly Ser Ser Gly Thr Pro Lys Leu
625                 630                 635                 640

Ile Gln Arg Ala Leu Leu Arg Gly Thr Ala Leu Leu Ala Ser Leu Gly
            645                 650                 655

Leu Gly Arg Asp Leu Gln Pro Pro Gly Pro Gly Arg Glu Arg Gly
            660                 665                 670

Glu Ser Pro Thr Thr Pro Pro Thr Pro Thr Pro Ala Pro Cys Pro Thr
            675                 680                 685

Glu Pro Pro Pro Ser Pro Leu Ile Cys Phe Ser Leu Lys Thr Pro Asp
690                 695                 700

Ser Pro Pro Thr Pro Ala Pro Leu Leu Leu Asp Leu Gly Ile Pro Val
705                 710                 715                 720

Gly Gln Arg Ser Ala Lys Ser Pro Arg Arg Glu Glu Pro Arg Gly
            725                 730                 735

Gly Thr Val Ser Pro Pro Pro Gly Thr Ser Arg Ser Ala Pro Gly Thr
            740                 745                 750

Pro Gly Thr Pro Arg Ser Pro Pro Leu Gly Leu Ile Ser Arg Pro Arg
            755                 760                 765

Pro Ser Pro Leu Arg Ser Arg Ile Asp Pro Trp Ser Phe Val Ser Ala
770                 775                 780

Gly Pro Arg Pro Ser Pro Leu Pro Ser Pro Gln Pro Ala Pro Arg Arg
785                 790                 795                 800

Ala Pro Trp Thr Leu Phe Pro Asp Ser Asp Pro Phe Trp Asp Ser Pro
            805                 810                 815

Pro Ala Asn Pro Phe Gln Gly Gly Pro Gln Asp Cys Arg Ala Gln Thr
            820                 825                 830

Lys Asp Met Gly Ala Gln Ala Pro Trp Val Pro Glu Ala Gly Pro
            835                 840                 845

<210> SEQ ID NO 66
<211> LENGTH: 545
<212> TYPE: PRT
<213> ORGANISM: Homo sapiens

<400> SEQUENCE: 66

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
            35                  40                  45

Lys Lys Lys Asp Arg Phe Tyr Arg Ser Ile Leu Pro Gly Asp Lys Thr
50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110
```

```
Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
                180                 185                 190

Arg Pro Glu His Thr Lys Ser Val Tyr Thr Arg Ser Val Ile Glu Pro
            195                 200                 205

Leu Pro Val Thr Pro Thr Arg Asp Val Ala Thr Ser Pro Ile Ser Pro
        210                 215                 220

Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Glu Ile Leu Glu Lys
                245                 250                 255

Leu Arg Ser Ile Val Ser Val Gly Asp Pro Lys Lys Tyr Thr Arg
                260                 265                 270

Phe Glu Lys Ile Gly Gln Gly Ala Ser Gly Thr Val Tyr Thr Ala Met
            275                 280                 285

Asp Val Ala Thr Gly Gln Glu Val Ala Ile Lys Gln Met Asn Leu Gln
            290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
            340                 345                 350

Thr Asp Val Val Thr Glu Thr Cys Met Asp Glu Gly Gln Ile Ala Ala
            355                 360                 365

Val Cys Arg Glu Cys Leu Gln Ala Leu Glu Phe Leu His Ser Asn Gln
    370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
            420                 425                 430

Pro Glu Val Val Thr Arg Lys Ala Tyr Gly Pro Lys Val Asp Ile Trp
        435                 440                 445

Ser Leu Gly Ile Met Ala Ile Glu Met Ile Glu Gly Glu Pro Pro Tyr
        450                 455                 460

Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
                485                 490                 495

Phe Leu Asn Arg Cys Leu Glu Met Asp Val Glu Lys Arg Gly Ser Ala
                500                 505                 510

Lys Glu Leu Leu Gln His Gln Phe Leu Lys Ile Ala Lys Pro Leu Ser
            515                 520                 525
```

-continued

Ser Leu Thr Pro Leu Ile Ala Ala Lys Glu Ala Thr Lys Asn Asn
        530                 535                 540

His
545

<210> SEQ ID NO 67
<211> LENGTH: 524
<212> TYPE: PRT
<213> ORGANISM: Homo sapiens

<400> SEQUENCE: 67

Met Ser Asp Asn Gly Glu Leu Glu Asp Lys Pro Pro Ala Pro Pro Val
  1               5                  10                  15

Arg Met Ser Ser Thr Ile Phe Ser Thr Gly Gly Lys Asp Pro Leu Ser
                 20                  25                  30

Ala Asn His Ser Leu Lys Pro Leu Pro Ser Val Pro Glu Glu Lys Lys
             35                  40                  45

Pro Arg His Lys Ile Ile Ser Ile Phe Ser Gly Thr Glu Lys Gly Ser
         50                  55                  60

Lys Lys Lys Glu Lys Glu Arg Pro Glu Ile Ser Pro Pro Ser Asp Phe
 65                  70                  75                  80

Glu His Thr Ile His Val Gly Phe Asp Ala Val Thr Gly Glu Phe Thr
                 85                  90                  95

Gly Met Pro Glu Gln Trp Ala Arg Leu Leu Gln Thr Ser Asn Ile Thr
                100                 105                 110

Lys Leu Glu Gln Lys Lys Asn Pro Gln Ala Val Leu Asp Val Leu Lys
            115                 120                 125

Phe Tyr Asp Ser Asn Thr Val Lys Gln Lys Tyr Leu Ser Phe Thr Pro
130                 135                 140

Pro Glu Lys Asp Gly Phe Pro Ser Gly Thr Pro Ala Leu Asn Ala Lys
145                 150                 155                 160

Gly Thr Glu Ala Pro Ala Val Val Thr Glu Glu Asp Asp Asp Glu
                165                 170                 175

Glu Thr Ala Pro Pro Val Ile Ala Pro Arg Pro Asp His Thr Lys Ser
                180                 185                 190

Ile Tyr Thr Arg Ser Val Ile Asp Pro Val Pro Ala Pro Val Gly Asp
            195                 200                 205

Ser His Val Asp Gly Ala Ala Lys Ser Leu Asp Lys Gln Lys Lys
        210                 215                 220

Thr Lys Met Thr Asp Glu Glu Ile Met Glu Lys Leu Arg Thr Ile Val
225                 230                 235                 240

Ser Ile Gly Asp Pro Lys Lys Lys Tyr Thr Arg Tyr Glu Lys Ile Gly
                245                 250                 255

Gln Gly Ala Ser Gly Thr Val Phe Thr Ala Thr Asp Val Ala Leu Gly
                260                 265                 270

Gln Glu Val Ala Ile Lys Gln Ile Asn Leu Gln Lys Gln Pro Lys Lys
            275                 280                 285

Glu Leu Ile Ile Asn Glu Ile Leu Val Met Lys Glu Leu Lys Asn Pro
        290                 295                 300

Asn Ile Val Asn Phe Leu Asp Ser Tyr Leu Val Gly Asp Glu Leu Phe
305                 310                 315                 320

Val Val Met Glu Tyr Leu Ala Gly Gly Ser Leu Thr Asp Val Val Thr
                325                 330                 335

Glu Thr Cys Met Asp Glu Ala Gln Ile Ala Ala Val Cys Arg Glu Cys
                340                 345                 350

```
Leu Gln Ala Leu Glu Phe Leu His Ala Asn Gln Val Ile His Arg Asp
        355                 360                 365

Ile Lys Ser Asp Asn Val Leu Leu Gly Met Glu Gly Ser Val Lys Leu
    370                 375                 380

Thr Asp Phe Gly Phe Cys Ala Gln Ile Thr Pro Glu Gln Ser Lys Arg
385                 390                 395                 400

Ser Thr Met Val Gly Thr Pro Tyr Trp Met Ala Pro Glu Val Val Thr
                405                 410                 415

Arg Lys Ala Tyr Gly Pro Lys Val Asp Ile Trp Ser Leu Gly Ile Met
                420                 425                 430

Ala Ile Glu Met Val Glu Gly Glu Pro Pro Tyr Leu Asn Glu Asn Pro
        435                 440                 445

Leu Arg Ala Leu Tyr Leu Ile Ala Thr Asn Gly Thr Pro Glu Leu Gln
    450                 455                 460

Asn Pro Glu Lys Leu Ser Pro Ile Phe Arg Asp Phe Leu Asn Arg Cys
465                 470                 475                 480

Leu Glu Met Asp Val Glu Lys Arg Gly Ser Ala Lys Glu Leu Leu Gln
                485                 490                 495

His Pro Phe Leu Lys Leu Ala Lys Pro Leu Ser Ser Leu Thr Pro Leu
                500                 505                 510

Ile Met Ala Ala Lys Glu Ala Met Lys Ser Asn Arg
        515                 520

<210> SEQ ID NO 68
<211> LENGTH: 544
<212> TYPE: PRT
<213> ORGANISM: Homo sapiens

<400> SEQUENCE: 68

Met Ser Asp Gly Leu Asp Asn Glu Glu Lys Pro Pro Ala Pro Pro Leu
1               5                   10                  15

Arg Met Asn Ser Asn Asn Arg Asp Ser Ser Ala Leu Asn His Ser Ser
                20                  25                  30

Lys Pro Leu Pro Met Ala Pro Glu Glu Lys Asn Lys Lys Ala Arg Leu
            35                  40                  45

Arg Ser Ile Phe Pro Gly Gly Gly Asp Lys Thr Asn Lys Lys Lys Glu
        50                  55                  60

Lys Glu Arg Pro Glu Ile Ser Leu Pro Ser Asp Phe Glu His Thr Ile
65                  70                  75                  80

His Val Gly Phe Asp Ala Val Thr Gly Glu Phe Thr Gly Ile Pro Glu
                85                  90                  95

Gln Trp Ala Arg Leu Leu Gln Thr Ser Asn Ile Thr Lys Leu Glu Gln
            100                 105                 110

Lys Lys Asn Pro Gln Ala Val Leu Asp Val Leu Lys Phe Tyr Asp Ser
        115                 120                 125

Lys Glu Thr Val Asn Asn Gln Lys Tyr Met Ser Phe Thr Ser Gly Asp
    130                 135                 140

Lys Ser Ala His Gly Tyr Ile Ala Ala His Pro Ser Ser Thr Lys Thr
145                 150                 155                 160

Ala Ser Glu Pro Pro Leu Ala Pro Pro Val Ser Glu Glu Asp Glu
                165                 170                 175

Glu Glu Glu Glu Glu Glu Asp Glu Asn Glu Pro Pro Val Ile Ala
            180                 185                 190

Pro Arg Pro Glu His Thr Lys Ser Ile Tyr Thr Arg Ser Val Val Glu
```

-continued

```
            195                 200                 205
Ser Ile Ala Ser Pro Ala Val Pro Asn Lys Glu Val Thr Pro Pro Ser
    210                 215                 220
Ala Glu Asn Ala Asn Ser Ser Thr Leu Tyr Arg Asn Thr Asp Arg Gln
225                 230                 235                 240
Arg Lys Lys Ser Lys Met Thr Asp Glu Glu Ile Leu Glu Lys Leu Arg
                245                 250                 255
Ser Ile Val Ser Val Gly Asp Pro Lys Lys Tyr Thr Arg Phe Glu
            260                 265                 270
Lys Ile Gly Gln Gly Ala Ser Gly Thr Val Tyr Thr Ala Leu Asp Ile
        275                 280                 285
Ala Thr Gly Gln Glu Val Ala Ile Lys Gln Met Asn Leu Gln Gln Gln
    290                 295                 300
Pro Lys Lys Glu Leu Ile Ile Asn Glu Ile Leu Val Met Arg Glu Asn
305                 310                 315                 320
Lys Asn Pro Asn Ile Val Asn Tyr Leu Asp Ser Tyr Leu Val Gly Asp
                325                 330                 335
Glu Leu Trp Val Val Met Glu Tyr Leu Ala Gly Gly Ser Leu Thr Asp
            340                 345                 350
Val Val Thr Glu Thr Cys Met Asp Glu Gly Gln Ile Ala Ala Val Cys
        355                 360                 365
Arg Glu Cys Leu Gln Ala Leu Asp Phe Leu His Ser Asn Gln Val Ile
    370                 375                 380
His Arg Asp Ile Lys Ser Asp Asn Ile Leu Leu Gly Met Asp Gly Ser
385                 390                 395                 400
Val Lys Leu Thr Asp Phe Gly Phe Cys Ala Gln Ile Thr Pro Glu Gln
                405                 410                 415
Ser Lys Arg Ser Thr Met Val Gly Thr Pro Tyr Trp Met Ala Pro Glu
            420                 425                 430
Val Val Thr Arg Lys Ala Tyr Gly Pro Lys Val Asp Ile Trp Ser Leu
        435                 440                 445
Gly Ile Met Ala Ile Glu Met Val Glu Gly Glu Pro Pro Tyr Leu Asn
    450                 455                 460
Glu Asn Pro Leu Arg Ala Leu Tyr Leu Ile Ala Thr Asn Gly Thr Pro
465                 470                 475                 480
Glu Leu Gln Asn Pro Glu Arg Leu Ser Ala Val Phe Arg Asp Phe Leu
                485                 490                 495
Asn Arg Cys Leu Glu Met Asp Val Asp Arg Arg Gly Ser Ala Lys Glu
            500                 505                 510
Leu Leu Gln His Pro Phe Leu Lys Leu Ala Lys Pro Leu Ser Ser Leu
        515                 520                 525
Thr Pro Leu Ile Ile Ala Ala Lys Glu Ala Ile Lys Asn Ser Ser Arg
    530                 535                 540

<210> SEQ ID NO 69
<211> LENGTH: 719
<212> TYPE: PRT
<213> ORGANISM: Homo sapiens

<400> SEQUENCE: 69

Met Phe Gly Lys Lys Lys Lys Ile Glu Ile Ser Gly Pro Ser Asn
1               5                   10                  15

Phe Glu His Arg Val His Thr Gly Phe Asp Pro Gln Glu Gln Lys Phe
                20                  25                  30
```

```
Thr Gly Leu Pro Gln Gln Trp His Ser Leu Leu Ala Asp Thr Ala Asn
        35                  40                  45

Arg Pro Lys Pro Met Val Asp Pro Ser Cys Ile Thr Pro Ile Gln Leu
 50                  55                  60

Ala Pro Met Lys Thr Ile Val Arg Gly Asn Lys Pro Cys Lys Glu Thr
 65                  70                  75                  80

Ser Ile Asn Gly Leu Leu Glu Asp Phe Asp Asn Ile Ser Val Thr Arg
                 85                  90                  95

Ser Asn Ser Leu Arg Lys Glu Ser Pro Pro Thr Pro Asp Gln Gly Ala
            100                 105                 110

Ser Ser His Gly Pro Gly His Ala Glu Glu Asn Gly Phe Ile Thr Phe
            115                 120                 125

Ser Gln Tyr Ser Ser Glu Ser Asp Thr Thr Ala Asp Tyr Thr Thr Glu
        130                 135                 140

Lys Tyr Arg Glu Lys Ser Leu Tyr Gly Asp Asp Leu Asp Pro Tyr Tyr
145                 150                 155                 160

Arg Gly Ser His Ala Ala Lys Gln Asn Gly His Val Met Lys Met Lys
                165                 170                 175

His Gly Glu Ala Tyr Tyr Ser Glu Val Lys Pro Leu Lys Ser Asp Phe
            180                 185                 190

Ala Arg Phe Ser Ala Asp Tyr His Ser His Leu Asp Ser Leu Ser Lys
        195                 200                 205

Pro Ser Glu Tyr Ser Asp Leu Lys Trp Glu Tyr Gln Arg Ala Ser Ser
    210                 215                 220

Ser Ser Pro Leu Asp Tyr Ser Phe Gln Phe Thr Pro Ser Arg Thr Ala
225                 230                 235                 240

Gly Thr Ser Gly Cys Ser Lys Glu Ser Leu Ala Tyr Ser Glu Ser Glu
                245                 250                 255

Trp Gly Pro Ser Leu Asp Asp Tyr Asp Arg Arg Pro Lys Ser Ser Tyr
            260                 265                 270

Leu Asn Gln Thr Ser Pro Gln Pro Thr Met Arg Gln Arg Ser Arg Ser
        275                 280                 285

Gly Ser Gly Leu Gln Glu Pro Met Met Pro Phe Gly Ala Ser Ala Phe
    290                 295                 300

Lys Thr His Pro Gln Gly His Ser Tyr Asn Ser Tyr Thr Tyr Pro Arg
305                 310                 315                 320

Leu Ser Glu Pro Thr Met Cys Ile Pro Lys Val Asp Tyr Asp Arg Ala
                325                 330                 335

Gln Met Val Leu Ser Pro Leu Ser Gly Ser Asp Thr Tyr Pro Arg
            340                 345                 350

Gly Pro Ala Lys Leu Pro Gln Ser Gln Ser Lys Ser Gly Tyr Ser Ser
        355                 360                 365

Ser Ser His Gln Tyr Pro Ser Gly Tyr His Lys Ala Thr Leu Tyr His
    370                 375                 380

His Pro Ser Leu Gln Ser Ser Gln Tyr Ile Ser Thr Ala Ser Tyr
385                 390                 395                 400

Leu Ser Ser Leu Ser Leu Ser Ser Thr Tyr Pro Pro Ser Trp
                405                 410                 415

Gly Ser Ser Asp Gln Gln Pro Ser Arg Val Ser His Glu Gln Phe
            420                 425                 430

Arg Ala Ala Leu Gln Leu Val Val Ser Pro Gly Asp Pro Arg Glu Tyr
        435                 440                 445

Leu Ala Asn Phe Ile Lys Ile Gly Glu Gly Ser Thr Gly Ile Val Cys
```

```
                450                 455                 460
Ile Ala Thr Glu Lys His Thr Gly Lys Gln Val Ala Val Lys Met
465                 470                 475                 480

Asp Leu Arg Lys Gln Gln Arg Arg Glu Leu Leu Phe Asn Val Val
                485                 490                 495

Ile Met Arg Asp Tyr His His Asp Asn Val Val Asp Met Tyr Ser Ser
                500                 505                 510

Tyr Leu Val Gly Asp Glu Leu Trp Val Val Met Glu Phe Leu Glu Gly
                515                 520                 525

Gly Ala Leu Thr Asp Ile Val Thr His Thr Arg Met Asn Glu Glu Gln
530                 535                 540

Ile Ala Thr Val Cys Leu Ser Val Leu Arg Ala Leu Ser Tyr Leu His
545                 550                 555                 560

Asn Gln Gly Val Ile His Arg Asp Ile Lys Ser Asp Ser Ile Leu Leu
                565                 570                 575

Thr Ser Asp Gly Arg Ile Lys Leu Ser Asp Phe Gly Phe Cys Ala Gln
                580                 585                 590

Val Ser Lys Glu Val Pro Lys Arg Lys Ser Leu Val Gly Thr Pro Tyr
                595                 600                 605

Trp Met Ala Pro Glu Val Ile Ser Arg Leu Pro Tyr Gly Thr Glu Val
                610                 615                 620

Asp Ile Trp Ser Leu Gly Ile Met Val Ile Glu Met Ile Asp Gly Glu
625                 630                 635                 640

Pro Pro Tyr Phe Asn Glu Pro Pro Leu Gln Ala Met Arg Arg Ile Arg
                645                 650                 655

Asp Ser Leu Pro Pro Arg Val Lys Asp Leu His Lys Val Ser Ser Val
                660                 665                 670

Leu Arg Gly Phe Leu Asp Leu Met Leu Val Arg Glu Pro Ser Gln Arg
                675                 680                 685

Ala Thr Ala Gln Glu Leu Leu Gly His Pro Phe Leu Lys Leu Ala Gly
                690                 695                 700

Pro Pro Ser Cys Ile Val Pro Leu Met Arg Gln Tyr Arg His His
705                 710                 715

<210> SEQ ID NO 70
<211> LENGTH: 681
<212> TYPE: PRT
<213> ORGANISM: Homo sapiens

<400> SEQUENCE: 70

Met Phe Arg Lys Lys Lys Lys Arg Pro Glu Ile Ser Ala Pro Gln
1               5                   10                  15

Asn Phe Gln His Arg Val His Thr Ser Phe Asp Pro Lys Glu Gly Lys
                20                  25                  30

Phe Val Gly Leu Pro Pro Gln Trp Gln Asn Ile Leu Asp Thr Leu Arg
            35                  40                  45

Arg Pro Lys Pro Val Val Asp Pro Ser Arg Ile Thr Arg Val Gln Leu
        50                  55                  60

Gln Pro Met Lys Thr Val Val Arg Gly Ser Ala Met Pro Val Asp Gly
65                  70                  75                  80

Tyr Ile Ser Gly Leu Leu Asn Asp Ile Gln Lys Leu Ser Val Ile Ser
                85                  90                  95

Ser Asn Thr Leu Arg Gly Arg Ser Pro Thr Ser Arg Arg Arg Ala Gln
                100                 105                 110
```

-continued

```
Ser Leu Gly Leu Leu Gly Asp Glu His Trp Ala Thr Asp Pro Asp Met
            115                 120                 125

Tyr Leu Gln Ser Pro Gln Ser Glu Arg Thr Asp Pro His Gly Leu Tyr
        130                 135                 140

Leu Ser Cys Asn Gly Gly Thr Pro Ala Gly His Lys Gln Met Pro Trp
145                 150                 155                 160

Pro Glu Pro Gln Ser Pro Arg Val Leu Pro Asn Gly Leu Ala Ala Lys
                165                 170                 175

Ala Gln Ser Leu Gly Pro Ala Glu Phe Gln Gly Ala Ser Gln Arg Cys
            180                 185                 190

Leu Gln Leu Gly Ala Cys Leu Gln Ser Ser Pro Gly Ala Ser Pro
        195                 200                 205

Pro Thr Gly Thr Asn Arg His Gly Met Lys Ala Lys His Gly Ser
    210                 215                 220

Glu Glu Ala Arg Pro Gln Ser Cys Leu Val Gly Ser Ala Thr Gly Arg
225                 230                 235                 240

Pro Gly Gly Glu Gly Ser Pro Ser Pro Lys Thr Arg Glu Ser Ser Leu
                245                 250                 255

Lys Arg Arg Leu Phe Arg Ser Met Phe Leu Ser Thr Ala Ala Thr Ala
            260                 265                 270

Pro Pro Ser Ser Ser Lys Pro Gly Pro Pro Gln Ser Lys Pro Asn
        275                 280                 285

Ser Ser Phe Arg Pro Pro Gln Lys Asp Asn Pro Pro Ser Leu Val Ala
290                 295                 300

Lys Ala Gln Ser Leu Pro Ser Asp Gln Pro Val Gly Thr Phe Ser Pro
305                 310                 315                 320

Leu Thr Thr Ser Asp Thr Ser Ser Pro Gln Lys Ser Leu Arg Thr Ala
                325                 330                 335

Pro Ala Thr Gly Gln Leu Pro Gly Arg Ser Ser Pro Ala Gly Ser Pro
            340                 345                 350

Arg Thr Trp His Ala Gln Ile Ser Thr Ser Asn Leu Tyr Leu Pro Gln
        355                 360                 365

Asp Pro Thr Val Ala Lys Gly Ala Leu Ala Gly Glu Asp Thr Gly Val
    370                 375                 380

Val Thr His Glu Gln Phe Lys Ala Ala Leu Arg Met Val Val Asp Gln
385                 390                 395                 400

Gly Asp Pro Arg Leu Leu Asp Ser Tyr Val Lys Ile Gly Glu Gly
                405                 410                 415

Ser Thr Gly Ile Val Cys Leu Ala Arg Glu Lys His Ser Gly Arg Gln
            420                 425                 430

Val Ala Val Lys Met Met Asp Leu Arg Lys Gln Gln Arg Arg Glu Leu
        435                 440                 445

Leu Phe Asn Glu Val Val Ile Met Arg Asp Tyr Gln His Phe Asn Val
    450                 455                 460

Val Glu Met Tyr Lys Ser Tyr Leu Val Gly Glu Glu Leu Trp Val Leu
465                 470                 475                 480

Met Glu Phe Leu Gln Gly Gly Ala Leu Thr Asp Ile Val Ser Gln Val
                485                 490                 495

Arg Leu Asn Glu Glu Gln Ile Ala Thr Val Cys Glu Ala Val Leu Gln
            500                 505                 510

Ala Leu Ala Tyr Leu His Ala Gln Gly Val Ile His Arg Asp Ile Lys
        515                 520                 525

Ser Asp Ser Ile Leu Leu Thr Leu Asp Gly Arg Val Lys Leu Ser Asp
```

-continued

```
              530                 535                 540
Phe Gly Phe Cys Ala Gln Ile Ser Lys Asp Val Pro Lys Arg Lys Ser
545                 550                 555                 560

Leu Val Gly Thr Pro Tyr Trp Met Ala Pro Glu Val Ile Ser Arg Ser
                565                 570                 575

Leu Tyr Ala Thr Glu Val Asp Ile Trp Ser Leu Gly Ile Met Val Ile
                580                 585                 590

Glu Met Val Asp Gly Glu Pro Pro Tyr Phe Ser Asp Ser Pro Val Gln
            595                 600                 605

Ala Met Lys Arg Leu Arg Asp Ser Pro Pro Lys Leu Lys Asn Ser
        610                 615                 620

His Lys Val Ser Pro Val Leu Arg Asp Phe Leu Glu Arg Met Leu Val
625                 630                 635                 640

Arg Asp Pro Gln Glu Arg Ala Thr Ala Gln Glu Leu Leu Asp His Pro
                645                 650                 655

Phe Leu Leu Gln Thr Gly Leu Pro Glu Cys Leu Val Pro Leu Ile Gln
                660                 665                 670

Leu Tyr Arg Lys Gln Thr Ser Thr Cys
                675                 680

<210> SEQ ID NO 71
<211> LENGTH: 346
<212> TYPE: PRT
<213> ORGANISM: Homo sapiens

<400> SEQUENCE: 71

Met Ala Arg Pro Gln Arg Thr Pro Ala Arg Ser Pro Asp Ser Ile Val
1               5                   10                  15

Glu Val Lys Ser Lys Phe Asp Ala Glu Phe Arg Arg Phe Ala Leu Pro
                20                  25                  30

Arg Ala Ser Val Ser Gly Phe Gln Glu Phe Ser Arg Leu Leu Arg Ala
            35                  40                  45

Val His Gln Ile Pro Gly Leu Asp Val Leu Gly Tyr Thr Asp Ala
        50                  55                  60

His Gly Asp Leu Leu Pro Leu Thr Asn Asp Asp Ser Leu His Arg Ala
65                  70                  75                  80

Leu Ala Ser Gly Pro Pro Leu Arg Leu Leu Gln Lys Arg Ala
                85                  90                  95

Glu Ala Asp Ser Ser Gly Leu Ala Phe Ala Ser Asn Ser Leu Gln Arg
                100                 105                 110

Arg Lys Lys Gly Leu Leu Leu Arg Pro Val Ala Pro Leu Arg Thr Arg
            115                 120                 125

Pro Pro Leu Leu Ile Ser Leu Pro Gln Asp Phe Arg Gln Val Ser Ser
        130                 135                 140

Val Ile Asp Val Asp Leu Leu Pro Glu Thr His Arg Val Arg Leu
145                 150                 155                 160

His Lys His Gly Ser Asp Arg Pro Leu Gly Phe Tyr Ile Arg Asp Gly
                165                 170                 175

Met Ser Val Arg Val Ala Pro Gln Gly Leu Glu Arg Val Pro Gly Ile
            180                 185                 190

Phe Ile Ser Arg Leu Val Arg Gly Gly Leu Ala Glu Ser Thr Gly Leu
        195                 200                 205

Leu Ala Val Ser Asp Glu Ile Leu Glu Val Asn Gly Ile Glu Val Ala
    210                 215                 220
```

```
Gly Lys Thr Leu Asp Gln Val Thr Asp Met Met Val Ala Asn Ser His
225                 230                 235                 240

Asn Leu Ile Val Thr Val Lys Pro Ala Asn Gln Arg Asn Asn Val Val
                245                 250                 255

Arg Gly Ala Ser Gly Arg Leu Thr Gly Pro Pro Ser Ala Gly Pro Gly
            260                 265                 270

Pro Ala Glu Pro Asp Ser Asp Asp Ser Ser Asp Leu Val Ile Glu
        275                 280                 285

Asn Arg Gln Pro Pro Ser Ser Asn Gly Leu Ser Gln Gly Pro Pro Cys
290                 295                 300

Trp Asp Leu His Pro Gly Cys Arg His Pro Gly Thr Arg Ser Ser Leu
305                 310                 315                 320

Pro Ser Leu Asp Asp Gln Glu Gln Ala Ser Ser Gly Trp Gly Ser Arg
                325                 330                 335

Ile Arg Gly Asp Gly Ser Gly Phe Ser Leu
            340                 345

<210> SEQ ID NO 72
<211> LENGTH: 552
<212> TYPE: PRT
<213> ORGANISM: Homo sapiens

<400> SEQUENCE: 72

Met Ser Leu Ser Arg Ser Glu Glu Met His Arg Leu Thr Glu Asn Val
1               5                   10                  15

Tyr Lys Thr Ile Met Glu Gln Phe Asn Pro Ser Leu Arg Asn Phe Ile
            20                  25                  30

Ala Met Gly Lys Asn Tyr Glu Lys Ala Leu Ala Gly Val Thr Tyr Ala
        35                  40                  45

Ala Lys Gly Tyr Phe Asp Ala Leu Val Lys Met Gly Glu Leu Ala Ser
    50                  55                  60

Glu Ser Gln Gly Ser Lys Glu Leu Gly Asp Val Leu Phe Gln Met Ala
65                  70                  75                  80

Glu Val His Arg Gln Ile Gln Asn Gln Leu Glu Glu Met Leu Lys Ser
                85                  90                  95

Phe His Asn Glu Leu Leu Thr Gln Leu Glu Gln Lys Val Glu Leu Asp
            100                 105                 110

Ser Arg Tyr Leu Ser Ala Ala Leu Lys Lys Tyr Gln Thr Glu Gln Arg
        115                 120                 125

Ser Lys Gly Asp Ala Leu Asp Lys Cys Gln Ala Glu Leu Lys Lys Leu
    130                 135                 140

Arg Lys Lys Ser Gln Gly Ser Lys Asn Pro Gln Lys Tyr Ser Asp Lys
145                 150                 155                 160

Glu Leu Gln Tyr Ile Asp Ala Ile Ser Asn Lys Gln Gly Glu Leu Glu
                165                 170                 175

Asn Tyr Val Ser Asp Gly Tyr Lys Thr Ala Leu Thr Glu Glu Arg Arg
            180                 185                 190

Arg Phe Cys Phe Leu Val Glu Lys Gln Cys Ala Val Ala Lys Asn Ser
        195                 200                 205

Ala Ala Tyr His Ser Lys Gly Lys Glu Leu Leu Ala Gln Lys Leu Pro
    210                 215                 220

Leu Trp Gln Gln Ala Cys Ala Asp Pro Ser Lys Ile Pro Glu Arg Ala
225                 230                 235                 240

Val Gln Leu Met Gln Gln Val Ala Ser Asn Gly Ala Thr Leu Pro Ser
                245                 250                 255
```

Ala Leu Ser Ala Ser Lys Ser Asn Leu Val Ile Ser Asp Pro Ile Pro
            260                 265                 270

Gly Ala Lys Pro Leu Pro Val Pro Pro Glu Leu Ala Pro Phe Val Gly
            275                 280                 285

Arg Met Ser Ala Gln Glu Ser Thr Pro Ile Met Asn Gly Val Thr Gly
            290                 295                 300

Pro Asp Gly Glu Asp Tyr Ser Pro Trp Ala Asp Arg Lys Ala Ala Gln
305                 310                 315                 320

Pro Lys Ser Leu Ser Pro Gln Ser Gln Ser Lys Leu Ser Asp Ser
            325                 330                 335

Tyr Ser Asn Thr Leu Pro Val Arg Lys Ser Val Thr Pro Lys Asn Ser
            340                 345                 350

Tyr Ala Thr Thr Glu Asn Lys Thr Leu Pro Arg Ser Ser Ser Met Ala
            355                 360                 365

Ala Gly Leu Glu Arg Asn Gly Arg Met Arg Val Lys Ala Ile Phe Ser
            370                 375                 380

His Ala Ala Gly Asp Asn Ser Thr Leu Leu Ser Phe Lys Glu Gly Asp
385                 390                 395                 400

Leu Ile Thr Leu Leu Val Pro Glu Ala Arg Asp Gly Trp His Tyr Gly
            405                 410                 415

Glu Ser Glu Lys Thr Lys Met Arg Gly Trp Phe Pro Phe Ser Tyr Thr
            420                 425                 430

Arg Val Leu Asp Ser Asp Gly Ser Asp Arg Leu His Met Ser Leu Gln
            435                 440                 445

Gln Gly Lys Ser Ser Ser Thr Gly Asn Leu Leu Asp Lys Asp Asp Leu
            450                 455                 460

Ala Ile Pro Pro Pro Asp Tyr Gly Ala Ala Ser Arg Ala Phe Pro Ala
465                 470                 475                 480

Gln Thr Ala Ser Gly Phe Lys Gln Arg Pro Tyr Ser Val Ala Val Pro
            485                 490                 495

Ala Phe Ser Gln Gly Leu Asp Asp Tyr Gly Ala Arg Ser Met Ser Arg
            500                 505                 510

Asn Pro Phe Ala His Val Gln Leu Lys Pro Thr Val Thr Asn Asp Arg
            515                 520                 525

Cys Asp Leu Ser Ala Gln Gly Pro Glu Gly Arg Glu His Gly Asp Gly
            530                 535                 540

Ser Ala Arg Thr Leu Ala Gly Arg
545                 550

<210> SEQ ID NO 73
<211> LENGTH: 1657
<212> TYPE: PRT
<213> ORGANISM: Homo sapiens

<400> SEQUENCE: 73

Met Ser Ala Ala Asp Glu Val Asp Gly Leu Gly Val Ala Arg Pro His
1               5                   10                  15

Tyr Gly Ser Val Leu Asp Asn Glu Arg Leu Thr Ala Glu Glu Met Asp
            20                  25                  30

Glu Arg Arg Arg Gln Asn Val Ala Tyr Glu Tyr Leu Cys His Leu Glu
            35                  40                  45

Glu Ala Lys Arg Trp Met Glu Ala Cys Leu Gly Glu Asp Leu Pro Pro
        50                  55                  60

Thr Thr Glu Leu Glu Glu Gly Leu Arg Asn Gly Val Tyr Leu Ala Lys

-continued

```
            65                  70                  75                  80
Leu Gly Asn Phe Phe Ser Pro Lys Val Val Ser Leu Lys Lys Ile Tyr
                        85                  90                  95

Asp Arg Glu Gln Thr Arg Tyr Lys Ala Thr Gly Leu His Phe Arg His
                100                 105                 110

Thr Asp Asn Val Ile Gln Trp Leu Asn Ala Met Asp Glu Ile Gly Leu
            115                 120                 125

Pro Lys Ile Phe Tyr Pro Glu Thr Thr Asp Ile Tyr Asp Arg Lys Asn
        130                 135                 140

Met Pro Arg Cys Ile Tyr Cys Ile His Ala Leu Ser Leu Tyr Leu Phe
145                 150                 155                 160

Lys Leu Gly Leu Ala Pro Gln Ile Gln Asp Leu Tyr Gly Lys Val Asp
                165                 170                 175

Phe Thr Glu Glu Glu Ile Asn Asn Met Lys Thr Glu Leu Glu Lys Tyr
                180                 185                 190

Gly Ile Gln Met Pro Ala Phe Ser Lys Ile Gly Gly Ile Leu Ala Asn
            195                 200                 205

Glu Leu Ser Val Asp Glu Ala Ala Leu His Ala Ala Val Ile Ala Ile
        210                 215                 220

Asn Glu Ala Ile Asp Arg Arg Ile Pro Ala Asp Thr Phe Ala Ala Leu
225                 230                 235                 240

Lys Asn Pro Asn Ala Met Leu Val Asn Leu Glu Pro Leu Ala Ser
                245                 250                 255

Thr Tyr Gln Asp Ile Leu Tyr Gln Ala Lys Gln Asp Lys Met Thr Asn
                260                 265                 270

Ala Lys Asn Arg Thr Glu Asn Ser Glu Arg Glu Arg Asp Val Tyr Glu
            275                 280                 285

Glu Leu Leu Thr Gln Ala Glu Ile Gln Gly Asn Ile Asn Lys Val Asn
        290                 295                 300

Thr Phe Ser Ala Leu Ala Asn Ile Asp Leu Ala Leu Glu Gln Gly Asp
305                 310                 315                 320

Ala Leu Ala Leu Phe Arg Ala Leu Gln Ser Pro Ala Leu Gly Leu Arg
                325                 330                 335

Gly Leu Gln Gln Gln Asn Ser Asp Trp Tyr Leu Lys Gln Leu Leu Ser
                340                 345                 350

Asp Lys Gln Gln Lys Arg Gln Ser Gly Gln Thr Asp Pro Leu Gln Lys
            355                 360                 365

Glu Glu Leu Gln Ser Gly Val Asp Ala Ala Asn Ser Ala Ala Gln Gln
        370                 375                 380

Tyr Gln Arg Arg Leu Ala Ala Val Ala Leu Ile Asn Ala Ala Ile Gln
385                 390                 395                 400

Lys Gly Val Ala Glu Lys Thr Val Leu Glu Leu Met Asn Pro Glu Ala
                405                 410                 415

Gln Leu Pro Gln Val Tyr Pro Phe Ala Ala Asp Leu Tyr Gln Lys Glu
                420                 425                 430

Leu Ala Thr Leu Gln Arg Gln Ser Pro Glu His Asn Leu Thr His Pro
            435                 440                 445

Glu Leu Ser Val Ala Val Glu Met Leu Ser Ser Val Ala Leu Ile Asn
        450                 455                 460

Arg Ala Leu Glu Ser Gly Asp Val Asn Thr Val Trp Lys Gln Leu Ser
465                 470                 475                 480

Ser Ser Val Thr Gly Leu Thr Asn Ile Glu Glu Glu Asn Cys Gln Arg
                485                 490                 495
```

-continued

```
Tyr Leu Asp Glu Leu Met Lys Leu Lys Ala Gln Ala His Ala Glu Asn
            500                 505                 510
Asn Glu Phe Ile Thr Trp Asn Asp Ile Gln Ala Cys Val Asp His Val
        515                 520                 525
Asn Leu Val Val Gln Glu His Glu Arg Ile Leu Ala Ile Gly Leu
    530                 535                 540
Ile Asn Glu Ala Leu Asp Glu Gly Asp Ala Gln Lys Thr Leu Gln Ala
545                 550                 555                 560
Leu Gln Ile Pro Ala Ala Lys Leu Glu Gly Val Leu Ala Glu Val Ala
                565                 570                 575
Gln His Tyr Gln Asp Thr Leu Ile Arg Ala Lys Arg Glu Lys Ala Gln
            580                 585                 590
Glu Ile Gln Asp Glu Ser Ala Val Leu Trp Leu Asp Glu Ile Gln Gly
        595                 600                 605
Gly Ile Trp Gln Ser Asn Lys Asp Thr Gln Glu Ala Gln Lys Phe Ala
    610                 615                 620
Leu Gly Ile Phe Ala Ile Asn Glu Ala Val Glu Ser Gly Asp Val Gly
625                 630                 635                 640
Lys Thr Leu Ser Ala Leu Arg Ser Pro Asp Val Gly Leu Tyr Gly Val
                645                 650                 655
Ile Pro Glu Cys Gly Glu Thr Tyr His Ser Asp Leu Ala Glu Ala Lys
            660                 665                 670
Lys Lys Lys Leu Ala Val Gly Asp Asn Asn Ser Lys Trp Val Lys His
        675                 680                 685
Trp Val Lys Gly Gly Tyr Tyr Tyr His Asn Leu Glu Thr Gln Glu
    690                 695                 700
Gly Gly Trp Asp Glu Pro Pro Asn Phe Val Gln Asn Ser Met Gln Leu
705                 710                 715                 720
Ser Arg Glu Glu Ile Gln Ser Ser Ile Ser Gly Val Thr Ala Ala Tyr
                725                 730                 735
Asn Arg Glu Gln Leu Trp Leu Ala Asn Glu Gly Leu Ile Thr Arg Leu
            740                 745                 750
Gln Ala Arg Cys Arg Gly Tyr Leu Val Arg Gln Glu Phe Arg Ser Arg
        755                 760                 765
Met Asn Phe Leu Lys Lys Gln Ile Pro Ala Ile Thr Cys Ile Gln Ser
    770                 775                 780
Gln Trp Arg Gly Tyr Lys Gln Lys Lys Ala Tyr Gln Asp Arg Leu Ala
785                 790                 795                 800
Tyr Leu Arg Ser His Lys Asp Glu Val Val Lys Ile Gln Ser Leu Ala
                805                 810                 815
Arg Met His Gln Ala Arg Lys Arg Tyr Arg Asp Arg Leu Gln Tyr Phe
            820                 825                 830
Arg Asp His Ile Asn Asp Ile Ile Lys Ile Gln Ala Phe Ile Arg Ala
        835                 840                 845
Asn Lys Ala Arg Asp Asp Tyr Lys Thr Leu Ile Asn Ala Glu Asp Pro
    850                 855                 860
Pro Met Val Val Val Arg Lys Phe Val His Leu Leu Asp Gln Ser Asp
865                 870                 875                 880
Gln Asp Phe Gln Glu Glu Leu Asp Leu Met Lys Met Arg Glu Glu Val
                885                 890                 895
Ile Thr Leu Ile Arg Ser Asn Gln Gln Leu Glu Asn Asp Leu Asn Leu
            900                 905                 910
```

-continued

```
Met Asp Ile Lys Ile Gly Leu Leu Val Lys Asn Lys Ile Thr Leu Gln
        915                 920                 925

Asp Val Val Ser His Ser Lys Lys Leu Thr Lys Lys Asn Lys Glu Gln
    930                 935                 940

Leu Ser Asp Met Met Met Ile Asn Lys Gln Lys Gly Gly Leu Lys Ala
945                 950                 955                 960

Leu Ser Lys Glu Lys Arg Glu Lys Leu Glu Ala Tyr Gln His Leu Phe
                965                 970                 975

Tyr Leu Leu Gln Thr Asn Pro Thr Tyr Leu Ala Lys Leu Ile Phe Gln
            980                 985                 990

Met Pro Gln Asn Lys Ser Thr Lys Phe Met Asp Ser Val Ile Phe Thr
        995                 1000                1005

Leu Tyr Asn Tyr Ala Ser Asn Gln Arg Glu Glu Tyr Leu Leu Leu
    1010                1015                1020

Arg Leu Phe Lys Thr Ala Leu Gln Glu Glu Ile Lys Ser Lys Val
    1025                1030                1035

Asp Gln Ile Gln Glu Ile Val Thr Gly Asn Pro Thr Val Ile Lys
    1040                1045                1050

Met Val Val Ser Phe Asn Arg Gly Ala Arg Gly Gln Asn Ala Leu
    1055                1060                1065

Arg Gln Ile Leu Ala Pro Val Val Lys Glu Ile Met Asp Asp Lys
    1070                1075                1080

Ser Leu Asn Ile Lys Thr Asp Pro Val Asp Ile Tyr Lys Ser Trp
    1085                1090                1095

Val Asn Gln Met Glu Ser Gln Thr Gly Glu Ala Ser Lys Leu Pro
    1100                1105                1110

Tyr Asp Val Thr Pro Glu Gln Ala Leu Ala His Glu Glu Val Lys
    1115                1120                1125

Thr Arg Leu Asp Ser Ser Ile Arg Asn Met Arg Ala Val Thr Asp
    1130                1135                1140

Lys Phe Leu Ser Ala Ile Val Ser Ser Val Asp Lys Ile Pro Tyr
    1145                1150                1155

Gly Met Arg Phe Ile Ala Lys Val Leu Lys Asp Ser Leu His Glu
    1160                1165                1170

Lys Phe Pro Asp Ala Gly Glu Asp Glu Leu Leu Lys Ile Ile Gly
    1175                1180                1185

Asn Leu Leu Tyr Tyr Arg Tyr Met Asn Pro Ala Ile Val Ala Pro
    1190                1195                1200

Asp Ala Phe Asp Ile Ile Asp Leu Ser Ala Gly Gly Gln Leu Thr
    1205                1210                1215

Thr Asp Gln Arg Arg Asn Leu Gly Ser Ile Ala Lys Met Leu Gln
    1220                1225                1230

His Ala Ala Ser Asn Lys Met Phe Leu Gly Asp Asn Ala His Leu
    1235                1240                1245

Ser Ile Ile Asn Glu Tyr Leu Ser Gln Ser Tyr Gln Lys Phe Arg
    1250                1255                1260

Arg Phe Phe Gln Thr Ala Cys Asp Val Pro Glu Leu Gln Asp Lys
    1265                1270                1275

Phe Asn Val Asp Glu Tyr Ser Asp Leu Val Thr Leu Thr Lys Pro
    1280                1285                1290

Val Ile Tyr Ile Ser Ile Gly Glu Ile Ile Asn Thr His Thr Leu
    1295                1300                1305

Leu Leu Asp His Gln Asp Ala Ile Ala Pro Glu His Asn Asp Pro
```

-continued

```
                1310                1315                1320
Ile His Glu Leu Leu Asp Asp Leu Gly Glu Val Pro Thr Ile Glu
    1325                1330                1335

Ser Leu Ile Gly Glu Ser Ser Gly Asn Leu Asn Asp Pro Asn Lys
    1340                1345                1350

Glu Ala Leu Ala Lys Thr Glu Val Ser Leu Thr Leu Thr Asn Lys
    1355                1360                1365

Phe Asp Val Pro Gly Asp Glu Asn Ala Glu Met Asp Ala Arg Thr
    1370                1375                1380

Ile Leu Leu Asn Thr Lys Arg Leu Ile Val Asp Val Ile Arg Phe
    1385                1390                1395

Gln Pro Gly Glu Thr Leu Thr Glu Ile Leu Glu Thr Pro Ala Thr
    1400                1405                1410

Ser Glu Gln Glu Ala Glu His Gln Arg Ala Met Gln Arg Arg Ala
    1415                1420                1425

Ile Arg Asp Ala Lys Thr Pro Asp Lys Met Lys Lys Ser Lys Ser
    1430                1435                1440

Val Lys Glu Asp Ser Asn Leu Thr Leu Gln Glu Lys Lys Glu Lys
    1445                1450                1455

Ile Gln Thr Gly Leu Lys Lys Leu Thr Glu Leu Gly Thr Val Asp
    1460                1465                1470

Pro Lys Asn Lys Tyr Gln Glu Leu Ile Asn Asp Ile Ala Arg Asp
    1475                1480                1485

Ile Arg Asn Gln Arg Arg Tyr Arg Gln Arg Lys Ala Glu Leu
    1490                1495                1500

Val Lys Leu Gln Gln Thr Tyr Ala Ala Leu Asn Ser Lys Ala Thr
    1505                1510                1515

Phe Tyr Gly Glu Gln Val Asp Tyr Tyr Lys Ser Tyr Ile Lys Thr
    1520                1525                1530

Cys Leu Asp Asn Leu Ala Ser Lys Gly Lys Val Ser Lys Lys Pro
    1535                1540                1545

Arg Glu Met Lys Gly Lys Lys Ser Lys Lys Ile Ser Leu Lys Tyr
    1550                1555                1560

Thr Ala Ala Arg Leu His Glu Lys Gly Val Leu Leu Glu Ile Glu
    1565                1570                1575

Asp Leu Gln Val Asn Gln Phe Lys Asn Val Ile Phe Glu Ile Ser
    1580                1585                1590

Pro Thr Glu Glu Val Gly Asp Phe Glu Val Lys Ala Lys Phe Met
    1595                1600                1605

Gly Val Gln Met Glu Thr Phe Met Leu His Tyr Gln Asp Leu Leu
    1610                1615                1620

Gln Leu Gln Tyr Glu Gly Val Ala Val Met Lys Leu Phe Asp Arg
    1625                1630                1635

Ala Lys Val Asn Val Asn Leu Leu Ile Phe Leu Leu Asn Lys Lys
    1640                1645                1650

Phe Tyr Gly Lys
    1655

<210> SEQ ID NO 74
<211> LENGTH: 1575
<212> TYPE: PRT
<213> ORGANISM: Homo sapiens

<400> SEQUENCE: 74
```

-continued

```
Met Pro His Glu Glu Leu Pro Ser Leu Gln Arg Pro Arg Tyr Gly Ser
1               5                   10                  15

Ile Val Asp Asp Glu Arg Leu Ser Ala Glu Glu Met Asp Glu Arg Arg
            20                  25                  30

Arg Gln Asn Ile Ala Tyr Glu Tyr Leu Cys His Leu Glu Glu Ala Lys
        35                  40                  45

Arg Trp Met Glu Val Cys Leu Val Glu Glu Leu Pro Pro Thr Thr Glu
    50                  55                  60

Leu Glu Glu Gly Leu Arg Asn Gly Val Tyr Leu Ala Lys Leu Ala Lys
65                  70                  75                  80

Phe Phe Ala Pro Lys Met Val Ser Glu Lys Lys Ile Tyr Asp Val Glu
                85                  90                  95

Gln Thr Arg Tyr Lys Lys Ser Gly Leu His Phe Arg His Thr Asp Asn
            100                 105                 110

Thr Val Gln Trp Leu Arg Ala Met Glu Ser Ile Gly Leu Pro Lys Ile
            115                 120                 125

Phe Tyr Pro Glu Thr Thr Asp Val Tyr Asp Arg Lys Asn Ile Pro Arg
    130                 135                 140

Met Ile Tyr Cys Ile His Ala Leu Ser Leu Tyr Leu Phe Lys Leu Gly
145                 150                 155                 160

Ile Ala Pro Gln Ile Gln Asp Leu Leu Gly Lys Val Asp Phe Thr Glu
                165                 170                 175

Glu Glu Ile Ser Asn Met Arg Lys Glu Leu Glu Lys Tyr Gly Ile Gln
            180                 185                 190

Met Pro Ser Phe Ser Lys Ile Gly Gly Ile Leu Ala Asn Glu Leu Ser
    195                 200                 205

Val Asp Glu Ala Leu His Ala Ala Val Ile Ala Ile Asn Glu Ala
210                 215                 220

Val Glu Lys Gly Ile Ala Glu Gln Thr Val Val Thr Leu Arg Asn Pro
225                 230                 235                 240

Asn Ala Val Leu Thr Leu Val Asp Asp Asn Leu Ala Pro Glu Tyr Gln
                245                 250                 255

Lys Glu Leu Trp Asp Ala Lys Lys Lys Glu Glu Asn Ala Arg Leu
            260                 265                 270

Lys Asn Ser Cys Ile Ser Glu Glu Arg Asp Ala Tyr Glu Glu Leu
            275                 280                 285

Leu Thr Gln Ala Glu Ile Gln Gly Asn Ile Asn Lys Val Asn Arg Gln
290                 295                 300

Ala Ala Val Asp His Ile Asn Ala Val Ile Pro Glu Gly Asp Pro Glu
305                 310                 315                 320

Asn Thr Leu Leu Ala Leu Lys Lys Pro Glu Ala Gln Leu Pro Ala Val
                325                 330                 335

Tyr Pro Phe Ala Ala Met Tyr Gln Asn Glu Leu Phe Asn Leu Gln
            340                 345                 350

Lys Gln Asn Thr Met Asn Tyr Leu Ala His Glu Glu Leu Leu Ile Ala
            355                 360                 365

Val Glu Met Leu Ser Ala Val Ala Leu Leu Asn Gln Ala Leu Glu Ser
    370                 375                 380

Asn Asp Leu Val Ser Val Gln Asn Gln Leu Arg Ser Pro Ala Ile Gly
385                 390                 395                 400

Leu Asn Asn Leu Asp Lys Ala Tyr Val Glu Arg Tyr Ala Asn Thr Leu
                405                 410                 415

Leu Ser Val Lys Leu Glu Val Leu Ser Gln Gly Gln Asp Asn Leu Ser
```

```
                420                 425                 430
Trp Asn Glu Ile Gln Asn Cys Ile Asp Met Val Asn Ala Gln Ile Gln
        435                 440                 445
Glu Glu Asn Asp Arg Val Val Ala Val Gly Tyr Ile Asn Glu Ala Ile
    450                 455                 460
Asp Glu Gly Asn Pro Leu Arg Thr Leu Glu Thr Leu Leu Pro Thr
465                 470                 475                 480
Ala Asn Ile Ser Asp Val Asp Pro Ala His Ala Gln His Tyr Gln Asp
                485                 490                 495
Val Leu Tyr His Ala Lys Ser Gln Lys Leu Gly Asp Ser Glu Ser Val
            500                 505                 510
Ser Lys Val Leu Trp Leu Asp Glu Ile Gln Gln Ala Val Asp Glu Ala
            515                 520                 525
Asn Val Asp Glu Asp Arg Ala Lys Gln Trp Val Thr Leu Val Val Asp
    530                 535                 540
Val Asn Gln Cys Leu Glu Gly Lys Lys Ser Ser Asp Ile Leu Ser Val
545                 550                 555                 560
Leu Lys Ser Ser Thr Ser Asn Ala Asn Asp Ile Ile Pro Glu Cys Ala
                565                 570                 575
Asp Lys Tyr Tyr Asp Ala Leu Val Lys Ala Lys Glu Leu Lys Ser Glu
            580                 585                 590
Arg Val Ser Ser Asp Gly Ser Trp Leu Lys Leu Asn Leu His Lys Lys
        595                 600                 605
Tyr Asp Tyr Tyr Asn Thr Asp Ser Lys Glu Ser Ser Trp Val Thr
    610                 615                 620
Pro Glu Ser Cys Phe Tyr Lys Glu Ser Trp Leu Thr Gly Lys Glu Ile
625                 630                 635                 640
Glu Asp Ile Ile Glu Glu Val Thr Val Gly Tyr Ile Arg Glu Asn Ile
                645                 650                 655
Trp Ser Ala Ser Glu Glu Leu Leu Arg Phe Gln Ala Thr Ser Ser
            660                 665                 670
Gly Pro Ile Leu Arg Glu Glu Phe Glu Ala Arg Lys Ser Phe Leu His
        675                 680                 685
Glu Gln Glu Glu Asn Val Val Lys Ile Gln Ala Phe Trp Lys Gly Tyr
    690                 695                 700
Lys Gln Arg Lys Glu Tyr Met His Arg Gln Thr Phe Ile Asp Asn
705                 710                 715                 720
Thr Asp Ser Val Val Lys Ile Gln Ser Trp Phe Arg Met Ala Thr Ala
                725                 730                 735
Arg Lys Ser Tyr Leu Ser Arg Leu Gln Tyr Phe Arg Asp His Asn Asn
            740                 745                 750
Glu Ile Val Lys Ile Gln Ser Leu Leu Arg Ala Asn Lys Ala Arg Asp
        755                 760                 765
Asp Tyr Lys Thr Leu Val Gly Ser Glu Asn Pro Leu Thr Val Ile
    770                 775                 780
Arg Lys Phe Val Tyr Leu Leu Asp Gln Ser Asp Leu Asp Phe Gln Glu
785                 790                 795                 800
Glu Leu Glu Val Ala Arg Leu Arg Glu Glu Val Val Thr Lys Ile Arg
                805                 810                 815
Ala Asn Gln Gln Leu Glu Lys Asp Leu Asn Leu Met Asp Ile Lys Ile
            820                 825                 830
Gly Leu Leu Val Lys Asn Arg Ile Thr Leu Glu Asp Val Ile Ser His
        835                 840                 845
```

```
Ser Lys Lys Leu Asn Lys Lys Gly Gly Glu Met Glu Ile Leu Asn
    850             855             860

Asn Thr Asp Asn Gln Gly Ile Lys Ser Leu Ser Lys Glu Arg Arg Lys
865             870             875             880

Thr Leu Glu Thr Tyr Gln Gln Leu Phe Tyr Leu Leu Gln Thr Asn Pro
                885             890             895

Leu Tyr Leu Ala Lys Leu Ile Phe Gln Met Pro Gln Asn Lys Ser Thr
                900             905             910

Lys Phe Met Asp Thr Val Ile Phe Thr Leu Tyr Asn Tyr Ala Ser Asn
            915             920             925

Gln Arg Glu Glu Tyr Leu Leu Leu Lys Leu Phe Lys Thr Ala Leu Glu
        930             935             940

Glu Glu Ile Lys Ser Lys Val Asp Gln Val Gln Asp Ile Val Thr Gly
945             950             955             960

Asn Pro Thr Val Ile Lys Met Val Val Ser Phe Asn Arg Gly Ala Arg
                965             970             975

Gly Gln Asn Thr Leu Arg Gln Leu Leu Ala Pro Val Val Lys Glu Ile
            980             985             990

Ile Asp Asp Lys Ser Leu Ile Ile Asn Thr Asn Pro Val Glu Val Tyr
        995             1000            1005

Lys Ala Trp Val Asn Gln Leu Gly Thr Gln Thr Gly Glu Ala Ser
    1010            1015            1020

Lys Leu Pro Tyr Asp Val Thr Thr Glu Gln Ala Leu Thr Tyr Pro
    1025            1030            1035

Glu Val Lys Asn Lys Leu Glu Ala Ser Ile Glu Asn Leu Arg Arg
    1040            1045            1050

Val Thr Asp Lys Val Leu Asn Ser Ile Ile Ser Ser Leu Asp Leu
    1055            1060            1065

Leu Pro Tyr Gly Leu Arg Tyr Ile Ala Lys Val Leu Lys Asn Ser
    1070            1075            1080

Ile His Glu Lys Phe Pro Asp Ala Thr Glu Asp Glu Leu Leu Lys
    1085            1090            1095

Ile Val Gly Asn Leu Leu Tyr Tyr Arg Tyr Met Asn Pro Ala Ile
    1100            1105            1110

Val Ala Pro Asp Gly Phe Asp Ile Ile Asp Met Thr Ala Gly Gly
    1115            1120            1125

Gln Ile Asn Ser Asp Gln Arg Arg Asn Leu Gly Ser Val Ala Lys
    1130            1135            1140

Val Leu Gln His Ala Ala Ser Asn Lys Leu Phe Glu Gly Glu Asn
    1145            1150            1155

Glu His Leu Ser Ser Met Asn Asn Tyr Leu Ser Glu Thr Tyr Gln
    1160            1165            1170

Glu Phe Arg Lys Tyr Phe Lys Glu Ala Cys Asn Val Pro Glu Pro
    1175            1180            1185

Glu Glu Lys Phe Asn Met Asp Lys Tyr Thr Asp Leu Val Thr Val
    1190            1195            1200

Ser Lys Pro Val Ile Tyr Ile Ser Ile Glu Glu Ile Ile Ser Thr
    1205            1210            1215

His Ser Leu Leu Leu Glu His Gln Asp Ala Ile Ala Pro Glu Lys
    1220            1225            1230

Asn Asp Leu Leu Ser Glu Leu Leu Gly Ser Leu Gly Glu Val Pro
    1235            1240            1245
```

```
Thr Val Glu Ser Phe Leu Gly Glu Gly Ala Val Asp Pro Asn Asp
    1250                1255                1260

Pro Asn Lys Ala Asn Thr Leu Ser Gln Leu Ser Lys Thr Glu Ile
    1265                1270                1275

Ser Leu Val Leu Thr Ser Lys Tyr Asp Ile Glu Asp Gly Glu Ala
    1280                1285                1290

Ile Asp Ser Arg Ser Leu Met Ile Lys Thr Lys Lys Leu Ile Ile
    1295                1300                1305

Asp Val Ile Arg Asn Gln Pro Gly Asn Thr Leu Thr Glu Ile Leu
    1310                1315                1320

Glu Thr Pro Ala Thr Ala Gln Gln Glu Val Asp His Ala Thr Asp
    1325                1330                1335

Met Val Ser Arg Ala Met Ile Asp Ser Arg Thr Pro Glu Glu Met
    1340                1345                1350

Lys His Ser Gln Ser Met Ile Glu Asp Ala Gln Leu Pro Leu Glu
    1355                1360                1365

Gln Lys Lys Arg Lys Ile Gln Arg Asn Leu Arg Thr Leu Glu Gln
    1370                1375                1380

Thr Gly His Val Ser Ser Glu Asn Lys Tyr Gln Asp Ile Leu Asn
    1385                1390                1395

Glu Ile Ala Lys Asp Ile Arg Asn Gln Arg Ile Tyr Arg Lys Leu
    1400                1405                1410

Arg Lys Ala Glu Leu Ala Lys Leu Gln Gln Thr Leu Asn Ala Leu
    1415                1420                1425

Asn Lys Lys Ala Ala Phe Tyr Glu Glu Gln Ile Asn Tyr Tyr Asp
    1430                1435                1440

Thr Tyr Ile Lys Thr Cys Leu Asp Asn Leu Lys Arg Lys Asn Thr
    1445                1450                1455

Arg Arg Ser Ile Lys Leu Asp Gly Lys Gly Glu Pro Lys Gly Ala
    1460                1465                1470

Lys Arg Ala Lys Pro Val Lys Tyr Thr Ala Ala Lys Leu His Glu
    1475                1480                1485

Lys Gly Val Leu Leu Asp Ile Asp Asp Leu Gln Thr Asn Gln Phe
    1490                1495                1500

Lys Asn Val Thr Phe Asp Ile Ile Ala Thr Glu Asp Val Gly Ile
    1505                1510                1515

Phe Asp Val Arg Ser Lys Phe Leu Gly Val Glu Met Glu Lys Val
    1520                1525                1530

Gln Leu Asn Ile Gln Asp Leu Leu Gln Met Gln Tyr Glu Gly Val
    1535                1540                1545

Ala Val Met Lys Met Phe Asp Lys Val Lys Val Asn Val Asn Leu
    1550                1555                1560

Leu Ile Tyr Leu Leu Asn Lys Lys Phe Tyr Gly Lys
    1565                1570                1575

<210> SEQ ID NO 75
<211> LENGTH: 1646
<212> TYPE: PRT
<213> ORGANISM: Homo sapiens

<400> SEQUENCE: 75

Met Gly Ser Gln Ala Leu Gln Glu Trp Gly Gln Arg Glu Pro Gly Arg
1               5                   10                  15

Trp Pro Asp Pro Ala Gly Lys Lys Asp Val Arg Arg Glu Ala Ser Asp
                20                  25                  30
```

-continued

```
Ser Gly Arg Ala Gly Thr Trp Pro Arg Thr Ala Lys Glu Lys Leu Lys
        35                  40                  45

Ile Asp Gly Asp Thr Arg Leu Pro Ser Ser Pro Gln Arg Phe Leu Arg
50                  55                  60

Gly Cys Gly Asp Leu His Gln Lys Pro Lys Leu Glu Leu Ile Leu Ser
65                  70                  75                  80

Phe Gly Arg Cys Asn Ser Pro Pro Ala Ser Ala Val Pro Gly Arg
                85                  90                  95

Asp Cys Arg Glu Glu Ala Ala Gln Arg Cys Arg Gln Gly Ser Ser Cys
            100                 105                 110

Arg Arg Cys Gly Arg Asp Tyr Leu Ala Ala Arg Arg Gly Pro Ser Glu
            115                 120                 125

Cys Ser Pro Arg Glu Lys Met Ala Ala Ala Gly Asn Arg Ala Ser
    130                 135                 140

Ser Ser Gly Phe Pro Gly Ala Arg Ala Thr Ser Pro Glu Ala Gly Gly
145                 150                 155                 160

Gly Gly Gly Ala Leu Lys Ala Ser Ser Ala Pro Ala Ala Ala Gly
                165                 170                 175

Leu Leu Arg Glu Ala Gly Ser Gly Gly Arg Glu Arg Ala Asp Trp Arg
            180                 185                 190

Arg Arg Gln Leu Arg Lys Val Arg Ser Val Glu Leu Asp Gln Leu Pro
        195                 200                 205

Glu Gln Pro Leu Phe Leu Ala Ala Ser Pro Ala Ser Ser Thr Ser
210                 215                 220

Pro Ser Pro Glu Pro Ala Asp Ala Ala Gly Ser Gly Thr Gly Phe Gln
225                 230                 235                 240

Pro Val Ala Val Pro Pro His Gly Ala Ala Ser Arg Gly Gly Ala
                245                 250                 255

His Leu Thr Glu Ser Val Ala Ala Pro Asp Ser Gly Ala Ser Ser Pro
            260                 265                 270

Ala Ala Ala Glu Pro Gly Glu Lys Arg Ala Pro Ala Ala Glu Pro Ser
        275                 280                 285

Pro Ala Ala Ala Pro Ala Gly Arg Glu Met Glu Asn Lys Glu Thr Leu
290                 295                 300

Lys Gly Leu His Lys Met Asp Asp Arg Pro Glu Glu Arg Met Ile Arg
305                 310                 315                 320

Glu Lys Leu Lys Ala Thr Cys Met Pro Ala Trp Lys His Glu Trp Leu
                325                 330                 335

Glu Arg Arg Asn Arg Arg Gly Pro Val Val Val Lys Pro Ile Pro Val
            340                 345                 350

Lys Gly Asp Gly Ser Glu Met Asn His Leu Ala Ala Glu Ser Pro Gly
        355                 360                 365

Glu Val Gln Ala Ser Ala Ala Ser Pro Ala Ser Lys Gly Arg Arg Ser
        370                 375                 380

Pro Ser Pro Gly Asn Ser Pro Ser Gly Arg Thr Val Lys Ser Glu Ser
385                 390                 395                 400

Pro Gly Val Arg Arg Lys Arg Val Ser Pro Val Pro Phe Gln Ser Gly
                405                 410                 415

Arg Ile Thr Pro Pro Arg Arg Ala Pro Ser Pro Asp Gly Phe Ser Pro
            420                 425                 430

Tyr Ser Pro Glu Glu Thr Asn Arg Arg Val Asn Lys Val Met Arg Ala
        435                 440                 445
```

```
Arg Leu Tyr Leu Leu Gln Gln Ile Gly Pro Asn Ser Phe Leu Ile Gly
    450                 455                 460

Gly Asp Ser Pro Asp Asn Lys Tyr Arg Val Phe Ile Gly Pro Gln Asn
465                 470                 475                 480

Cys Ser Cys Ala Arg Gly Thr Phe Cys Ile His Leu Leu Phe Val Met
                485                 490                 495

Leu Arg Val Phe Gln Leu Glu Pro Ser Asp Pro Met Leu Trp Arg Lys
            500                 505                 510

Thr Leu Lys Asn Phe Glu Val Glu Ser Leu Phe Gln Lys Tyr His Ser
        515                 520                 525

Arg Arg Ser Ser Arg Ile Lys Ala Pro Ser Arg Asn Thr Ile Gln Lys
    530                 535                 540

Phe Val Ser Arg Met Ser Asn Ser His Thr Leu Ser Ser Ser Ser Thr
545                 550                 555                 560

Ser Thr Ser Ser Ser Glu Asn Ser Ile Lys Asp Glu Glu Gln Met
                565                 570                 575

Cys Pro Ile Cys Leu Leu Gly Met Leu Asp Glu Glu Ser Leu Thr Val
            580                 585                 590

Cys Glu Asp Gly Cys Arg Asn Lys Leu His His Cys Met Ser Ile
    595                 600                 605

Trp Ala Glu Glu Cys Arg Arg Asn Arg Glu Pro Leu Ile Cys Pro Leu
    610                 615                 620

Cys Arg Ser Lys Trp Arg Ser His Asp Phe Tyr Ser His Glu Leu Ser
625                 630                 635                 640

Ser Pro Val Asp Ser Pro Ser Ser Leu Arg Ala Ala Gln Gln Gln Thr
                645                 650                 655

Val Gln Gln Gln Pro Leu Ala Gly Ser Arg Arg Asn Gln Glu Ser Asn
                660                 665                 670

Phe Asn Leu Thr His Tyr Gly Thr Gln Gln Ile Pro Pro Ala Tyr Lys
        675                 680                 685

Asp Leu Ala Glu Pro Trp Ile Gln Val Phe Gly Met Glu Leu Val Gly
    690                 695                 700

Cys Leu Phe Ser Arg Asn Trp Asn Val Arg Glu Met Ala Leu Arg Arg
705                 710                 715                 720

Leu Ser His Asp Val Ser Gly Ala Leu Leu Ala Asn Gly Glu Ser
                725                 730                 735

Thr Gly Asn Ser Gly Gly Ser Ser Gly Ser Ser Pro Ser Gly Gly Ala
                740                 745                 750

Thr Ser Gly Ser Ser Gln Thr Ser Ile Ser Gly Asp Val Val Glu Ala
            755                 760                 765

Cys Cys Ser Val Leu Ser Met Val Cys Ala Asp Pro Val Tyr Lys Val
    770                 775                 780

Tyr Val Ala Ala Leu Lys Thr Leu Arg Ala Met Leu Val Tyr Thr Pro
785                 790                 795                 800

Cys His Ser Leu Ala Glu Arg Ile Lys Leu Gln Arg Leu Leu Gln Pro
                805                 810                 815

Val Val Asp Thr Ile Leu Val Lys Cys Ala Asp Ala Asn Ser Arg Thr
            820                 825                 830

Ser Gln Leu Ser Ile Ser Thr Leu Leu Glu Leu Cys Lys Gly Gln Ala
        835                 840                 845

Gly Glu Leu Ala Val Gly Arg Glu Ile Leu Lys Ala Gly Ser Ile Gly
    850                 855                 860

Ile Gly Gly Val Asp Tyr Val Leu Asn Cys Ile Leu Gly Asn Gln Thr
```

-continued

```
           865                 870                 875                 880
Glu Ser Asn Asn Trp Gln Glu Leu Leu Gly Arg Leu Cys Leu Ile Asp
                    885                 890                 895

Arg Leu Leu Leu Glu Phe Pro Ala Glu Phe Tyr Pro His Ile Val Ser
            900                 905                 910

Thr Asp Val Ser Gln Ala Glu Pro Val Glu Ile Arg Tyr Lys Lys Leu
            915                 920                 925

Leu Ser Leu Leu Thr Phe Ala Leu Gln Ser Ile Asp Asn Ser His Ser
        930                 935                 940

Met Val Gly Lys Leu Ser Arg Arg Ile Tyr Leu Ser Ser Ala Arg Met
945                 950                 955                 960

Val Thr Thr Val Pro His Val Phe Ser Lys Leu Leu Glu Met Leu Ser
                965                 970                 975

Val Ser Ser Ser Thr His Phe Thr Arg Met Arg Arg Leu Met Ala
            980                 985                 990

Ile Ala Asp Glu Val Glu Ile Ala Glu Ala Ile Gln Leu Gly Val Glu
                995                 1000                1005

Asp Thr Leu Asp Gly Gln Gln Asp Ser Phe Leu Gln Ala Ser Val
    1010                1015                1020

Pro Asn Asn Tyr Leu Glu Thr Thr Glu Asn Ser Ser Pro Glu Cys
    1025                1030                1035

Thr Val His Leu Glu Lys Thr Gly Lys Gly Leu Cys Ala Thr Lys
    1040                1045                1050

Leu Ser Ala Ser Ser Glu Asp Ile Ser Glu Arg Leu Ala Ser Ile
    1055                1060                1065

Ser Val Gly Pro Ser Ser Ser Thr Thr Thr Thr Thr Thr Thr Thr
    1070                1075                1080

Glu Gln Pro Lys Pro Met Val Gln Thr Lys Gly Arg Pro His Ser
    1085                1090                1095

Gln Cys Leu Asn Ser Ser Pro Leu Ser His His Ser Gln Leu Met
    1100                1105                1110

Phe Pro Ala Leu Ser Thr Pro Ser Ser Ser Thr Pro Ser Val Pro
    1115                1120                1125

Ala Gly Thr Ala Thr Asp Val Ser Lys His Arg Leu Gln Gly Phe
    1130                1135                1140

Ile Pro Cys Arg Ile Pro Ser Ala Ser Pro Gln Thr Gln Arg Lys
    1145                1150                1155

Phe Ser Leu Gln Phe His Arg Asn Cys Pro Glu Asn Lys Asp Ser
    1160                1165                1170

Asp Lys Leu Ser Pro Val Phe Thr Gln Ser Arg Pro Leu Pro Ser
    1175                1180                1185

Ser Asn Ile His Arg Pro Lys Pro Ser Arg Pro Thr Pro Gly Asn
    1190                1195                1200

Thr Ser Lys Gln Gly Asp Pro Ser Lys Asn Ser Met Thr Leu Asp
    1205                1210                1215

Leu Asn Ser Ser Ser Lys Cys Asp Asp Ser Phe Gly Cys Ser Ser
    1220                1225                1230

Asn Ser Ser Asn Ala Val Ile Pro Ser Asp Glu Thr Val Phe Thr
    1235                1240                1245

Pro Val Glu Glu Lys Cys Arg Leu Asp Val Asn Thr Glu Leu Asn
    1250                1255                1260

Ser Ser Ile Glu Asp Leu Leu Glu Ala Ser Met Pro Ser Ser Asp
    1265                1270                1275
```

```
Thr Thr Val Thr Phe Lys Ser Glu Val Ala Val Leu Ser Pro Glu
            1280                1285                1290

Lys Ala Glu Asn Asp Asp Thr Tyr Lys Asp Val Asn His Asn
    1295                1300                1305

Gln Lys Cys Lys Glu Lys Met Glu Ala Glu Glu Glu Ala Leu
1310                1315                1320

Ala Ile Ala Met Ala Met Ser Ala Ser Gln Asp Ala Leu Pro Ile
        1325                1330                1335

Val Pro Gln Leu Gln Val Glu Asn Gly Glu Asp Ile Ile Ile Ile
    1340                1345                1350

Gln Gln Asp Thr Pro Glu Thr Leu Pro Gly His Thr Lys Ala Lys
        1355                1360                1365

Gln Pro Tyr Arg Glu Asp Thr Glu Trp Leu Lys Gly Gln Gln Ile
    1370                1375                1380

Gly Leu Gly Ala Phe Ser Ser Cys Tyr Gln Ala Gln Asp Val Gly
        1385                1390                1395

Thr Gly Thr Leu Met Ala Val Lys Gln Val Thr Tyr Val Arg Asn
1400                1405                1410

Thr Ser Ser Glu Gln Glu Glu Val Val Glu Ala Leu Arg Glu Glu
        1415                1420                1425

Ile Arg Met Met Ser His Leu Asn His Pro Asn Ile Ile Arg Met
    1430                1435                1440

Leu Gly Ala Thr Cys Glu Lys Ser Asn Tyr Asn Leu Phe Ile Glu
        1445                1450                1455

Trp Met Ala Gly Gly Ser Val Ala His Leu Leu Ser Lys Tyr Gly
1460                1465                1470

Ala Phe Lys Glu Ser Val Val Ile Asn Tyr Thr Glu Gln Leu Leu
        1475                1480                1485

Arg Gly Leu Ser Tyr Leu His Glu Asn Gln Ile Ile His Arg Asp
    1490                1495                1500

Val Lys Gly Ala Asn Leu Leu Ile Asp Ser Thr Gly Gln Arg Leu
1505                1510                1515

Arg Ile Ala Asp Phe Gly Ala Ala Ala Arg Leu Ala Ser Lys Gly
    1520                1525                1530

Thr Gly Ala Gly Glu Phe Gln Gly Gln Leu Leu Gly Thr Ile Ala
        1535                1540                1545

Phe Met Ala Pro Glu Val Leu Arg Gly Gln Gln Tyr Gly Arg Ser
    1550                1555                1560

Cys Asp Val Trp Ser Val Gly Cys Ala Ile Ile Glu Met Ala Cys
    1565                1570                1575

Ala Lys Pro Pro Trp Asn Ala Glu Lys His Ser Asn His Leu Ala
    1580                1585                1590

Leu Ile Phe Lys Ile Ala Ser Ala Thr Thr Ala Pro Ser Ile Pro
        1595                1600                1605

Ser His Leu Ser Pro Gly Leu Arg Asp Val Ala Leu Arg Cys Leu
    1610                1615                1620

Glu Leu Gln Pro Gln Asp Arg Pro Pro Ser Arg Glu Leu Leu Lys
    1625                1630                1635

His Pro Val Phe Arg Thr Thr Trp
    1640                1645

<210> SEQ ID NO 76
<211> LENGTH: 1608
```

<212> TYPE: PRT
<213> ORGANISM: Homo sapiens

<400> SEQUENCE: 76

```
Met Arg Glu Ala Ala Ala Leu Val Pro Pro Pro Ala Phe Ala Val
1               5                  10                  15

Thr Pro Ala Ala Ala Met Glu Glu Pro Pro Pro Pro Pro Pro Pro
               20                  25                  30

Pro Pro Pro Pro Glu Pro Glu Thr Glu Ser Glu Pro Glu Cys Cys Leu
           35                  40                  45

Ala Ala Arg Gln Glu Gly Thr Leu Gly Asp Ser Ala Cys Lys Ser Pro
       50                  55                  60

Glu Ser Asp Leu Glu Asp Phe Ser Asp Glu Thr Asn Thr Glu Asn Leu
65                  70                  75                  80

Tyr Gly Thr Ser Pro Pro Ser Thr Pro Arg Gln Met Lys Arg Met Ser
               85                  90                  95

Thr Lys His Gln Arg Asn Asn Val Gly Arg Pro Ala Ser Arg Ser Asn
               100                 105                 110

Leu Lys Glu Lys Met Asn Ala Pro Asn Gln Pro Pro His Lys Asp Thr
           115                 120                 125

Gly Lys Thr Val Glu Asn Val Glu Glu Tyr Ser Tyr Lys Gln Glu Lys
       130                 135                 140

Lys Ile Arg Ala Ala Leu Arg Thr Thr Glu Arg Asp His Lys Lys Asn
145                 150                 155                 160

Val Gln Cys Ser Phe Met Leu Asp Ser Val Gly Gly Ser Leu Pro Lys
               165                 170                 175

Lys Ser Ile Pro Asp Val Asp Leu Asn Lys Pro Tyr Leu Ser Leu Gly
               180                 185                 190

Cys Ser Asn Ala Lys Leu Pro Val Ser Val Pro Met Pro Ile Ala Arg
           195                 200                 205

Pro Ala Arg Gln Thr Ser Arg Thr Asp Cys Pro Ala Asp Arg Leu Lys
       210                 215                 220

Phe Phe Glu Thr Leu Arg Leu Leu Leu Lys Leu Thr Ser Val Ser Lys
225                 230                 235                 240

Lys Lys Asp Arg Glu Gln Arg Gly Gln Glu Asn Thr Ser Gly Phe Trp
               245                 250                 255

Leu Asn Arg Ser Asn Glu Leu Ile Trp Leu Glu Leu Gln Ala Trp His
               260                 265                 270

Ala Gly Arg Thr Ile Asn Asp Gln Asp Phe Phe Leu Tyr Thr Ala Arg
           275                 280                 285

Gln Ala Ile Pro Asp Ile Ile Asn Glu Ile Leu Thr Phe Lys Val Asp
       290                 295                 300

Tyr Gly Ser Phe Ala Phe Val Arg Asp Arg Ala Gly Phe Asn Gly Thr
305                 310                 315                 320

Ser Val Glu Gly Gln Cys Lys Ala Thr Pro Gly Thr Lys Ile Val Gly
               325                 330                 335

Tyr Ser Thr His His Glu His Leu Gln Arg Gln Arg Val Ser Phe Glu
               340                 345                 350

Gln Val Lys Arg Ile Met Glu Leu Leu Glu Tyr Ile Glu Ala Leu Tyr
           355                 360                 365

Pro Ser Leu Gln Ala Leu Gln Lys Asp Tyr Glu Lys Tyr Ala Ala Lys
       370                 375                 380

Asp Phe Gln Asp Arg Val Gln Ala Leu Cys Leu Trp Leu Asn Ile Thr
385                 390                 395                 400
```

-continued

```
Lys Asp Leu Asn Gln Lys Leu Arg Ile Met Gly Thr Val Leu Gly Ile
                405                 410                 415
Lys Asn Leu Ser Asp Ile Gly Trp Pro Val Phe Glu Ile Pro Ser Pro
            420                 425                 430
Arg Pro Ser Lys Gly Asn Glu Pro Glu Tyr Glu Gly Asp Asp Thr Glu
        435                 440                 445
Gly Glu Leu Lys Glu Leu Glu Ser Ser Thr Asp Glu Ser Glu Glu Glu
    450                 455                 460
Gln Ile Ser Asp Pro Arg Val Pro Glu Ile Arg Gln Pro Ile Asp Asn
465                 470                 475                 480
Ser Phe Asp Ile Gln Ser Arg Asp Cys Ile Ser Lys Lys Leu Glu Arg
                485                 490                 495
Leu Glu Ser Glu Asp Asp Ser Leu Gly Trp Gly Ala Pro Asp Trp Ser
            500                 505                 510
Thr Glu Ala Gly Phe Ser Arg His Cys Leu Thr Ser Ile Tyr Arg Pro
        515                 520                 525
Phe Val Asp Lys Ala Leu Lys Gln Met Gly Leu Arg Lys Leu Ile Leu
    530                 535                 540
Arg Leu His Lys Leu Met Asp Gly Ser Leu Gln Arg Ala Arg Ile Ala
545                 550                 555                 560
Leu Val Lys Asn Asp Arg Pro Val Glu Phe Ser Glu Phe Pro Asp Pro
                565                 570                 575
Met Trp Gly Ser Asp Tyr Val Gln Leu Ser Arg Thr Pro Pro Ser Ser
            580                 585                 590
Glu Glu Lys Cys Ser Ala Val Ser Trp Glu Glu Leu Lys Ala Met Asp
        595                 600                 605
Leu Pro Ser Phe Glu Pro Ala Phe Leu Val Leu Cys Arg Val Leu Leu
    610                 615                 620
Asn Val Ile His Glu Cys Leu Lys Leu Arg Leu Glu Gln Arg Pro Ala
625                 630                 635                 640
Gly Glu Pro Ser Leu Leu Ser Ile Lys Gln Leu Val Arg Glu Cys Lys
                645                 650                 655
Glu Val Leu Lys Gly Gly Leu Leu Met Lys Gln Tyr Tyr Gln Phe Met
            660                 665                 670
Leu Gln Glu Val Leu Glu Asp Leu Glu Lys Pro Asp Cys Asn Ile Asp
        675                 680                 685
Ala Phe Glu Glu Asp Leu His Lys Met Leu Met Val Tyr Phe Asp Tyr
    690                 695                 700
Met Arg Ser Trp Ile Gln Met Leu Gln Gln Leu Pro Gln Ala Ser His
705                 710                 715                 720
Ser Leu Lys Asn Leu Leu Glu Glu Trp Asn Phe Thr Lys Glu Ile
                725                 730                 735
Thr His Tyr Ile Arg Gly Gly Glu Ala Gln Ala Gly Lys Leu Phe Cys
            740                 745                 750
Asp Ile Ala Gly Met Leu Leu Lys Ser Thr Gly Ser Phe Leu Glu Phe
        755                 760                 765
Gly Leu Gln Glu Ser Cys Ala Glu Phe Trp Thr Ser Ala Asp Asp Ser
    770                 775                 780
Ser Ala Ser Asp Glu Ile Arg Arg Ser Val Ile Glu Ile Ser Arg Ala
785                 790                 795                 800
Leu Lys Glu Leu Phe His Glu Ala Arg Glu Arg Ala Ser Lys Ala Leu
                805                 810                 815
```

-continued

```
Gly Phe Ala Lys Met Leu Arg Lys Asp Leu Glu Ile Ala Ala Glu Phe
            820                 825                 830

Arg Leu Ser Ala Pro Val Arg Asp Leu Leu Asp Val Leu Lys Ser Lys
            835                 840                 845

Gln Tyr Val Lys Val Gln Ile Pro Gly Leu Glu Asn Leu Gln Met Phe
            850                 855                 860

Val Pro Asp Thr Leu Ala Glu Glu Lys Ser Ile Ile Leu Gln Leu Leu
865                 870                 875                 880

Asn Ala Ala Ala Gly Lys Asp Cys Ser Lys Asp Ser Asp Asp Val Leu
                885                 890                 895

Ile Asp Ala Tyr Leu Leu Leu Thr Lys His Gly Asp Arg Ala Arg Asp
            900                 905                 910

Ser Glu Asp Ser Trp Gly Thr Trp Glu Ala Gln Pro Val Lys Val Val
            915                 920                 925

Pro Gln Val Glu Thr Val Asp Thr Leu Arg Ser Met Gln Val Asp Asn
            930                 935                 940

Leu Leu Leu Val Val Met Gln Ser Ala His Leu Thr Ile Gln Arg Lys
945                 950                 955                 960

Ala Phe Gln Gln Ser Ile Glu Gly Leu Met Thr Leu Cys Gln Glu Gln
                965                 970                 975

Thr Ser Ser Gln Pro Val Ile Ala Lys Ala Leu Gln Gln Leu Lys Asn
            980                 985                 990

Asp Ala Leu Glu Leu Cys Asn Arg Ile Ser Asn Ala Ile Asp Arg Val
            995                 1000                1005

Asp His Met Phe Thr Ser Glu Phe Asp Ala Glu Val Asp Glu Ser
    1010                1015                1020

Glu Ser Val Thr Leu Gln Gln Tyr Tyr Arg Glu Ala Met Ile Gln
    1025                1030                1035

Gly Tyr Asn Phe Gly Phe Glu Tyr His Lys Glu Val Val Arg Leu
    1040                1045                1050

Met Ser Gly Glu Phe Arg Gln Lys Ile Gly Asp Lys Tyr Ile Ser
    1055                1060                1065

Phe Ala Arg Lys Trp Met Asn Tyr Val Leu Thr Lys Cys Glu Ser
    1070                1075                1080

Gly Arg Gly Thr Arg Pro Arg Trp Ala Thr Gln Gly Phe Asp Phe
    1085                1090                1095

Leu Gln Ala Ile Glu Pro Ala Phe Ile Ser Ala Leu Pro Glu Asp
    1100                1105                1110

Asp Phe Leu Ser Leu Gln Ala Leu Met Asn Glu Cys Ile Gly His
    1115                1120                1125

Val Ile Gly Lys Pro His Ser Pro Val Thr Gly Leu Tyr Leu Ala
    1130                1135                1140

Ile His Arg Asn Ser Pro Arg Pro Met Lys Val Pro Arg Cys His
    1145                1150                1155

Ser Asp Pro Pro Asn Pro His Leu Ile Ile Pro Thr Pro Glu Gly
    1160                1165                1170

Phe Ser Thr Arg Ser Met Pro Ser Asp Ala Arg Ser His Gly Ser
    1175                1180                1185

Pro Ala Ala Ala Ala Ala Ala Ala Ala Val Ala Ala Ser
    1190                1195                1200

Arg Pro Ser Pro Ser Gly Gly Asp Ser Val Leu Pro Lys Ser Ile
    1205                1210                1215

Ser Ser Ala His Asp Thr Arg Gly Ser Ser Val Pro Glu Asn Asp
```

-continued

```
                1220                1225                1230
Arg Leu Ala Ser Ile Ala Ala Glu Leu Gln Phe Arg Ser Leu Ser
                1235                1240                1245
Arg His Ser Ser Pro Thr Glu Glu Arg Asp Glu Pro Ala Tyr Pro
                1250                1255                1260
Arg Gly Asp Ser Ser Gly Ser Thr Arg Arg Ser Trp Glu Leu Arg
                1265                1270                1275
Thr Leu Ile Ser Gln Ser Lys Asp Thr Ala Ser Lys Leu Gly Pro
                1280                1285                1290
Ile Glu Ala Ile Gln Lys Ser Val Arg Leu Phe Glu Glu Lys Arg
                1295                1300                1305
Tyr Arg Glu Met Arg Arg Lys Asn Ile Ile Gly Gln Val Cys Asp
                1310                1315                1320
Thr Pro Lys Ser Tyr Asp Asn Val Met His Val Gly Leu Arg Lys
                1325                1330                1335
Val Thr Phe Lys Trp Gln Arg Gly Asn Lys Ile Gly Glu Gly Gln
                1340                1345                1350
Tyr Gly Lys Val Tyr Thr Cys Ile Ser Val Asp Thr Gly Glu Leu
                1355                1360                1365
Met Ala Met Lys Glu Ile Arg Phe Gln Pro Asn Asp His Lys Thr
                1370                1375                1380
Ile Lys Glu Thr Ala Asp Glu Leu Lys Ile Phe Glu Gly Ile Lys
                1385                1390                1395
His Pro Asn Leu Val Arg Tyr Phe Gly Val Glu Leu His Arg Glu
                1400                1405                1410
Glu Met Tyr Ile Phe Met Glu Tyr Cys Asp Glu Gly Thr Leu Glu
                1415                1420                1425
Glu Val Ser Arg Leu Gly Leu Gln Glu His Val Ile Arg Leu Tyr
                1430                1435                1440
Ser Lys Gln Ile Thr Ile Ala Ile Asn Val Leu His Glu His Gly
                1445                1450                1455
Ile Val His Arg Asp Ile Lys Gly Ala Asn Ile Phe Leu Thr Ser
                1460                1465                1470
Ser Gly Leu Ile Lys Leu Gly Asp Phe Gly Cys Ser Val Lys Leu
                1475                1480                1485
Lys Asn Asn Ala Gln Thr Met Pro Gly Glu Val Asn Ser Thr Leu
                1490                1495                1500
Gly Thr Ala Ala Tyr Met Ala Pro Glu Val Ile Thr Arg Ala Lys
                1505                1510                1515
Gly Glu Gly His Gly Arg Ala Ala Asp Ile Trp Ser Leu Gly Cys
                1520                1525                1530
Val Val Ile Glu Met Val Thr Gly Lys Arg Pro Trp His Glu Tyr
                1535                1540                1545
Glu His Asn Phe Gln Ile Met Tyr Lys Val Gly Met Gly His Lys
                1550                1555                1560
Pro Pro Ile Pro Glu Arg Leu Ser Pro Glu Gly Lys Asp Phe Leu
                1565                1570                1575
Ser His Cys Leu Glu Ser Asp Pro Lys Met Arg Trp Thr Ala Ser
                1580                1585                1590
Gln Leu Leu Asp His Ser Phe Val Lys Val Cys Thr Asp Glu Glu
                1595                1600                1605

<210> SEQ ID NO 77
```

<211> LENGTH: 525
<212> TYPE: PRT
<213> ORGANISM: Homo sapiens

<400> SEQUENCE: 77

Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
    290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
            340                 345                 350

Arg His Ile Asn Trp Glu Glu Leu Leu Ala Arg Lys Val Glu Pro Pro
        355                 360                 365

Phe Lys Pro Leu Leu Gln Ser Glu Glu Asp Val Ser Gln Phe Asp Ser
    370                 375                 380

Lys Phe Thr Arg Gln Thr Pro Val Asp Ser Pro Asp Asp Ser Thr Leu

-continued

```
           385                 390                 395                 400
    Ser Glu Ser Ala Asn Gln Val Phe Leu Gly Phe Thr Tyr Val Ala Pro
                    405                 410                 415

Ser Val Leu Glu Ser Val Lys Glu Lys Phe Ser Phe Glu Pro Lys Ile
                    420                 425                 430

Arg Ser Pro Arg Arg Phe Ile Gly Ser Pro Arg Thr Pro Val Ser Pro
                    435                 440                 445

Val Lys Phe Ser Pro Gly Asp Phe Trp Gly Arg Gly Ala Ser Ala Ser
                    450                 455                 460

Thr Ala Asn Pro Gln Thr Pro Val Glu Tyr Pro Met Glu Thr Ser Gly
    465                 470                 475                 480

Ile Glu Gln Met Asp Val Thr Met Ser Gly Glu Ala Ser Ala Pro Leu
                    485                 490                 495

Pro Ile Arg Gln Pro Asn Ser Gly Pro Tyr Lys Lys Gln Ala Phe Pro
                    500                 505                 510

Met Ile Ser Lys Arg Pro Glu His Leu Arg Met Asn Leu
                    515                 520                 525

<210> SEQ ID NO 78
<211> LENGTH: 724
<212> TYPE: PRT
<213> ORGANISM: Homo sapiens

<400> SEQUENCE: 78

Met Ser Ala Glu Gly Tyr Gln Tyr Arg Ala Leu Tyr Asp Tyr Lys Lys
1               5                   10                  15

Glu Arg Glu Glu Asp Ile Asp Leu His Leu Gly Asp Ile Leu Thr Val
                20                  25                  30

Asn Lys Gly Ser Leu Val Ala Leu Gly Phe Ser Asp Gly Gln Glu Ala
            35                  40                  45

Arg Pro Glu Glu Ile Gly Trp Leu Asn Gly Tyr Asn Glu Thr Thr Gly
        50                  55                  60

Glu Arg Gly Asp Phe Pro Gly Thr Tyr Val Glu Tyr Ile Gly Arg Lys
65                  70                  75                  80

Lys Ile Ser Pro Pro Thr Pro Lys Pro Arg Pro Pro Arg Pro Leu Pro
                85                  90                  95

Val Ala Pro Gly Ser Ser Lys Thr Glu Ala Asp Val Glu Gln Gln Ala
            100                 105                 110

Leu Thr Leu Pro Asp Leu Ala Glu Gln Phe Ala Pro Pro Asp Ile Ala
        115                 120                 125

Pro Pro Leu Leu Ile Lys Leu Val Glu Ala Ile Glu Lys Lys Gly Leu
    130                 135                 140

Glu Cys Ser Thr Leu Tyr Arg Thr Gln Ser Ser Ser Asn Leu Ala Glu
145                 150                 155                 160

Leu Arg Gln Leu Leu Asp Cys Asp Thr Pro Ser Val Asp Leu Glu Met
                165                 170                 175

Ile Asp Val His Val Leu Ala Asp Ala Phe Lys Arg Tyr Leu Leu Asp
            180                 185                 190

Leu Pro Asn Pro Val Ile Pro Ala Ala Val Tyr Ser Glu Met Ile Ser
        195                 200                 205

Leu Ala Pro Glu Val Gln Ser Ser Glu Glu Tyr Ile Gln Leu Leu Lys
    210                 215                 220

Lys Leu Ile Arg Ser Pro Ser Ile Pro His Gln Tyr Trp Leu Thr Leu
225                 230                 235                 240
```

-continued

```
Gln Tyr Leu Leu Lys His Phe Lys Leu Ser Gln Thr Ser Ser Lys
            245                 250                 255

Asn Leu Leu Asn Ala Arg Val Leu Ser Glu Ile Phe Ser Pro Met Leu
        260                 265                 270

Phe Arg Phe Ser Ala Ala Ser Ser Asp Asn Thr Glu Asn Leu Ile Lys
    275                 280                 285

Val Ile Glu Ile Leu Ile Ser Thr Glu Trp Asn Glu Arg Gln Pro Ala
290                 295                 300

Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                325                 330                 335

Asp Ile Ser Arg Glu Glu Val Asn Glu Lys Leu Arg Asp Thr Ala Asp
            340                 345                 350

Gly Thr Phe Leu Val Arg Asp Ala Ser Thr Lys Met His Gly Asp Tyr
        355                 360                 365

Thr Leu Thr Leu Arg Lys Gly Gly Asn Asn Lys Leu Ile Lys Ile Phe
    370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                405                 410                 415

Asn Pro Lys Leu Asp Val Lys Leu Leu Tyr Pro Val Ser Lys Tyr Gln
            420                 425                 430

Gln Asp Gln Val Val Lys Glu Asp Asn Ile Glu Ala Val Gly Lys Lys
        435                 440                 445

Leu His Glu Tyr Asn Thr Gln Phe Gln Glu Lys Ser Arg Glu Tyr Asp
    450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
            500                 505                 510

Lys Arg Glu Gly Asn Glu Lys Glu Ile Gln Arg Ile Met His Asn Tyr
        515                 520                 525

Asp Lys Leu Lys Ser Arg Ile Ser Glu Ile Ile Asp Ser Arg Arg Arg
    530                 535                 540

Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Asp Glu Asp Leu Pro His His Asp Glu Lys Thr Trp
    610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
```

```
                    660                 665                 670
Asn Lys Thr Ala Thr Gly Tyr Gly Phe Ala Glu Pro Tyr Asn Leu Tyr
            675                 680                 685

Ser Ser Leu Lys Glu Leu Val Leu His Tyr Gln His Thr Ser Leu Val
        690                 695                 700

Gln His Asn Asp Ser Leu Asn Val Thr Leu Ala Tyr Pro Val Tyr Ala
705                 710                 715                 720

Gln Gln Arg Arg

<210> SEQ ID NO 79
<211> LENGTH: 2098
<212> TYPE: PRT
<213> ORGANISM: Homo sapiens

<400> SEQUENCE: 79

Met Ala Thr Asp Asp Lys Thr Ser Pro Thr Leu Asp Ser Ala Asn Asp
1               5                   10                  15

Leu Pro Arg Ser Pro Thr Ser Pro Ser His Leu Thr His Phe Lys Pro
            20                  25                  30

Leu Thr Pro Asp Gln Asp Glu Pro Pro Phe Lys Ser Ala Tyr Ser Ser
        35                  40                  45

Phe Val Asn Leu Phe Arg Phe Asn Lys Glu Arg Ala Glu Gly Gly Gln
50                  55                  60

Gly Glu Gln Gln Pro Leu Ser Gly Ser Trp Thr Ser Pro Gln Leu Pro
65                  70                  75                  80

Ser Arg Thr Gln Ser Val Arg Ser Pro Thr Pro Tyr Lys Lys Gln Leu
                85                  90                  95

Asn Glu Glu Leu Gln Arg Arg Ser Ser Ala Leu Asp Thr Arg Arg Lys
            100                 105                 110

Ala Glu Pro Thr Phe Gly Gly His Asp Pro Arg Thr Ala Val Gln Leu
        115                 120                 125

Arg Ser Leu Ser Thr Val Leu Lys Arg Leu Lys Glu Ile Met Glu Gly
130                 135                 140

Lys Ser Gln Asp Ser Asp Leu Lys Gln Tyr Trp Met Pro Asp Ser Gln
145                 150                 155                 160

Cys Lys Glu Cys Tyr Asp Cys Ser Glu Lys Phe Thr Thr Phe Arg Arg
                165                 170                 175

Arg His His Cys Arg Leu Cys Gly Gln Ile Phe Cys Ser Arg Cys Cys
            180                 185                 190

Asn Gln Glu Ile Pro Gly Lys Phe Met Gly Tyr Thr Gly Asp Leu Arg
        195                 200                 205

Ala Cys Thr Tyr Cys Arg Lys Ile Ala Leu Ser Tyr Ala His Ser Thr
210                 215                 220

Asp Ser Asn Ser Ile Gly Glu Asp Leu Asn Ala Leu Ser Asp Ser Ala
225                 230                 235                 240

Cys Ser Val Ser Val Leu Asp Pro Ser Glu Pro Arg Thr Pro Val Gly
                245                 250                 255

Ser Arg Lys Ala Ser Arg Asn Ile Phe Leu Glu Asp Asp Leu Ala Trp
            260                 265                 270

Gln Ser Leu Ile His Pro Asp Ser Ser Asn Thr Pro Leu Ser Thr Arg
        275                 280                 285

Leu Val Ser Val Gln Glu Asp Ala Gly Lys Ser Pro Ala Arg Asn Arg
290                 295                 300

Ser Ala Ser Ile Thr Asn Leu Ser Leu Asp Arg Ser Gly Ser Pro Met
```

-continued

```
            305                 310                 315                 320
Val Pro Ser Tyr Glu Thr Ser Val Ser Pro Gln Ala Asn Arg Thr Tyr
                    325                 330                 335
Val Arg Thr Glu Thr Thr Glu Asp Arg Lys Ile Leu Leu Asp Ser
                340                 345                 350
Val Gln Leu Lys Asp Leu Trp Lys Lys Ile Cys His Ser Ser Gly
                355                 360                 365
Met Glu Phe Gln Asp His Arg Tyr Trp Leu Arg Thr His Pro Asn Cys
            370                 375                 380
Ile Val Gly Lys Glu Leu Val Asn Trp Leu Ile Arg Asn Gly His Ile
385                 390                 395                 400
Ala Thr Arg Ala Gln Ala Ile Ala Ile Gly Gln Ala Met Val Asp Gly
                405                 410                 415
Arg Trp Leu Asp Cys Val Ser His Asp Gln Leu Phe Arg Asp Glu
                420                 425                 430
Tyr Ala Leu Tyr Arg Pro Leu Gln Ser Thr Glu Phe Ser Glu Thr Pro
                435                 440                 445
Ser Pro Asp Ser Asp Ser Val Asn Ser Val Glu Gly His Ser Glu Pro
                450                 455                 460
Ser Trp Phe Lys Asp Ile Lys Phe Asp Asp Ser Asp Thr Glu Gln Ile
465                 470                 475                 480
Ala Glu Glu Gly Asp Asp Asn Leu Ala Asn Ser Ala Ser Pro Ser Lys
                485                 490                 495
Arg Thr Ser Val Ser Ser Phe Gln Ser Thr Val Asp Ser Asp Ser Ala
                500                 505                 510
Ala Ser Ile Ser Leu Asn Val Glu Leu Asp Asn Val Asn Phe His Ile
                515                 520                 525
Lys Lys Pro Ser Lys Tyr Pro His Val Pro Pro His Pro Ala Asp Gln
                530                 535                 540
Lys Glu Tyr Leu Ile Ser Asp Thr Gly Gly Gln Gln Leu Ser Ile Ser
545                 550                 555                 560
Asp Ala Phe Ile Lys Glu Ser Leu Phe Asn Arg Arg Val Glu Glu Lys
                565                 570                 575
Ser Lys Glu Leu Pro Phe Thr Pro Leu Gly Trp His His Asn Asn Leu
                580                 585                 590
Glu Leu Leu Arg Glu Glu Asn Gly Glu Lys Gln Ala Met Glu Arg Leu
                595                 600                 605
Leu Ser Ala Asn His Asn His Met Met Ala Leu Leu Gln Gln Leu Leu
            610                 615                 620
His Ser Asp Ser Leu Ser Ser Ser Trp Arg Asp Ile Ile Val Ser Leu
625                 630                 635                 640
Val Cys Gln Val Val Gln Thr Val Arg Pro Asp Val Lys Asn Gln Asp
                645                 650                 655
Asp Asp Met Asp Ile Arg Gln Phe Val His Ile Lys Lys Ile Pro Gly
                660                 665                 670
Gly Lys Lys Phe Asp Ser Val Val Val Asn Gly Phe Val Cys Thr Lys
                675                 680                 685
Asn Ile Ala His Lys Lys Met Asn Ser Cys Ile Lys Asn Pro Lys Ile
            690                 695                 700
Leu Leu Leu Lys Cys Ser Ile Glu Tyr Leu Tyr Arg Glu Glu Thr Lys
705                 710                 715                 720
Phe Thr Cys Ile Asp Pro Ile Val Leu Gln Glu Arg Glu Phe Leu Lys
                725                 730                 735
```

-continued

```
Asn Tyr Val Gln Arg Ile Val Asp Val Arg Pro Thr Leu Val Leu Val
            740                 745                 750
Glu Lys Thr Val Ser Arg Ile Ala Gln Asp Met Leu Leu Glu His Gly
            755                 760                 765
Ile Thr Leu Val Ile Asn Val Lys Ser Gln Val Leu Glu Arg Ile Ser
            770                 775                 780
Arg Met Thr Gln Gly Asp Leu Val Met Ser Met Asp Gln Leu Leu Thr
785                 790                 795                 800
Lys Pro His Leu Gly Thr Cys His Lys Phe Tyr Met Gln Ile Phe Gln
                805                 810                 815
Leu Pro Asn Glu Gln Thr Lys Thr Leu Met Phe Phe Glu Gly Cys Pro
            820                 825                 830
Gln His Leu Gly Cys Thr Ile Lys Leu Arg Gly Gly Ser Asp Tyr Glu
            835                 840                 845
Leu Ala Arg Val Lys Glu Ile Leu Ile Phe Met Ile Cys Val Ala Tyr
850                 855                 860
His Ser Gln Leu Glu Ile Ser Phe Leu Met Asp Glu Phe Ala Met Pro
865                 870                 875                 880
Pro Thr Leu Met Gln Asn Pro Ser Phe His Ser Leu Ile Glu Gly Arg
                885                 890                 895
Gly His Glu Gly Ala Val Gln Glu Gln Tyr Gly Gly Gly Ser Ile Pro
            900                 905                 910
Trp Asp Pro Asp Ile Pro Pro Glu Ser Leu Pro Cys Asp Asp Ser Ser
            915                 920                 925
Leu Leu Glu Ser Arg Ile Val Phe Glu Lys Gly Glu Gln Glu Asn Lys
            930                 935                 940
Asn Leu Pro Gln Ala Val Ala Ser Val Lys His Gln Glu His Ser Thr
945                 950                 955                 960
Thr Ala Cys Pro Ala Gly Leu Pro Cys Ala Phe Phe Ala Pro Val Pro
                965                 970                 975
Glu Ser Leu Leu Pro Leu Pro Val Asp Asp Gln Gln Asp Ala Leu Gly
            980                 985                 990
Ser Glu Leu Pro Glu Ser Leu Gln Gln Thr Val Val Leu Gln Asp Pro
            995                 1000                1005
Lys Ser Gln Ile Arg Ala Phe Arg Asp Pro Leu Gln Asp Asp Thr
            1010                1015                1020
Gly Leu Tyr Val Thr Glu Glu Val Thr Ser Ser Glu Asp Lys Arg
            1025                1030                1035
Lys Thr Tyr Ser Leu Ala Phe Lys Gln Glu Leu Lys Asp Val Ile
            1040                1045                1050
Leu Cys Ile Ser Pro Val Ile Thr Phe Arg Glu Pro Phe Leu Leu
            1055                1060                1065
Thr Glu Lys Gly Met Arg Cys Ser Thr Arg Asp Tyr Phe Ala Glu
            1070                1075                1080
Gln Val Tyr Trp Ser Pro Leu Leu Asn Lys Glu Phe Lys Glu Met
            1085                1090                1095
Glu Asn Arg Arg Lys Lys Gln Leu Leu Arg Asp Leu Ser Gly Leu
            1100                1105                1110
Gln Gly Met Asn Gly Ser Ile Gln Ala Lys Ser Ile Gln Val Leu
            1115                1120                1125
Pro Ser His Glu Leu Val Ser Thr Arg Ile Ala Glu His Leu Gly
            1130                1135                1140
```

-continued

```
Asp Ser Gln Ser Leu Gly Arg Met Leu Ala Asp Tyr Arg Ala Arg
    1145                1150                1155

Gly Gly Arg Ile Gln Pro Lys Asn Ser Asp Pro Phe Ala His Ser
    1160                1165                1170

Lys Asp Ala Ser Ser Thr Ser Ser Gly Lys Ser Gly Ser Lys Asn
    1175                1180                1185

Glu Gly Asp Glu Glu Arg Gly Leu Ile Leu Ser Asp Ala Val Trp
    1190                1195                1200

Ser Thr Lys Val Asp Cys Leu Asn Pro Ile Asn His Gln Arg Leu
    1205                1210                1215

Cys Val Leu Phe Ser Ser Ser Ala Gln Ser Ser Asn Ala Pro
    1220                1225                1230

Ser Ala Cys Val Ser Pro Trp Ile Val Thr Met Glu Phe Tyr Gly
    1235                1240                1245

Lys Asn Asp Leu Thr Leu Gly Ile Phe Leu Glu Arg Tyr Cys Phe
    1250                1255                1260

Arg Pro Ser Tyr Gln Cys Pro Ser Met Phe Cys Asp Thr Pro Met
    1265                1270                1275

Val His His Ile Arg Arg Phe Val His Gly Gln Gly Cys Val Gln
    1280                1285                1290

Ile Ile Leu Lys Glu Leu Asp Ser Pro Val Pro Gly Tyr Gln His
    1295                1300                1305

Thr Ile Leu Thr Tyr Ser Trp Cys Arg Ile Cys Lys Gln Val Thr
    1310                1315                1320

Pro Val Val Ala Leu Ser Asn Glu Ser Trp Ser Met Ser Phe Ala
    1325                1330                1335

Lys Tyr Leu Glu Leu Arg Phe Tyr Gly His Gln Tyr Thr Arg Arg
    1340                1345                1350

Ala Asn Ala Glu Pro Cys Gly His Ser Ile His His Asp Tyr His
    1355                1360                1365

Gln Tyr Phe Ser Tyr Asn Gln Met Val Ala Ser Phe Ser Tyr Ser
    1370                1375                1380

Pro Ile Arg Leu Leu Glu Val Cys Val Pro Leu Pro Lys Ile Phe
    1385                1390                1395

Ile Lys Arg Gln Ala Pro Leu Lys Val Ser Leu Leu Gln Asp Leu
    1400                1405                1410

Lys Asp Phe Phe Gln Lys Val Ser Gln Val Tyr Val Ala Ile Asp
    1415                1420                1425

Glu Arg Leu Ala Ser Leu Lys Thr Asp Thr Phe Ser Lys Thr Arg
    1430                1435                1440

Glu Glu Lys Met Glu Asp Ile Phe Ala Gln Lys Glu Met Glu Glu
    1445                1450                1455

Gly Glu Phe Lys Asn Trp Ile Glu Lys Met Gln Ala Arg Leu Met
    1460                1465                1470

Ser Ser Ser Val Asp Thr Pro Gln Gln Leu Gln Ser Val Phe Glu
    1475                1480                1485

Ser Leu Ile Ala Lys Lys Gln Ser Leu Cys Glu Val Leu Gln Ala
    1490                1495                1500

Trp Asn Asn Arg Leu Gln Asp Leu Phe Gln Glu Lys Gly Arg
    1505                1510                1515

Lys Arg Pro Ser Val Pro Pro Ser Pro Gly Arg Leu Arg Gln Gly
    1520                1525                1530

Glu Glu Ser Lys Ile Ser Ala Met Asp Ala Ser Pro Arg Asn Ile
```

```
          1535                1540                1545

Ser Pro Gly Leu Gln Asn Gly Glu Lys Glu Asp Arg Phe Leu Thr
    1550                1555                1560

Thr Leu Ser Ser Gln Ser Ser Thr Ser Ser Thr His Leu Gln Leu
    1565                1570                1575

Pro Thr Pro Pro Glu Val Met Ser Glu Gln Ser Val Gly Gly Pro
    1580                1585                1590

Pro Glu Leu Asp Thr Ala Ser Ser Ser Glu Asp Val Phe Asp Gly
    1595                1600                1605

His Leu Leu Gly Ser Thr Asp Ser Gln Val Lys Glu Lys Ser Thr
    1610                1615                1620

Met Lys Ala Ile Phe Ala Asn Leu Leu Pro Gly Asn Ser Tyr Asn
    1625                1630                1635

Pro Ile Pro Phe Pro Phe Asp Pro Asp Lys His Tyr Leu Met Tyr
    1640                1645                1650

Glu His Glu Arg Val Pro Ile Ala Val Cys Glu Lys Glu Pro Ser
    1655                1660                1665

Ser Ile Ile Ala Phe Ala Leu Ser Cys Lys Glu Tyr Arg Asn Ala
    1670                1675                1680

Leu Glu Glu Leu Ser Lys Ala Thr Gln Trp Asn Ser Ala Glu Glu
    1685                1690                1695

Gly Leu Pro Thr Asn Ser Thr Ser Asp Ser Arg Pro Lys Ser Ser
    1700                1705                1710

Ser Pro Ile Arg Leu Pro Glu Met Ser Gly Gly Gln Thr Asn Arg
    1715                1720                1725

Thr Thr Glu Thr Glu Pro Gln Pro Thr Lys Lys Ala Ser Gly Met
    1730                1735                1740

Leu Ser Phe Phe Arg Gly Thr Ala Gly Lys Ser Pro Asp Leu Ser
    1745                1750                1755

Ser Gln Lys Arg Glu Thr Leu Arg Gly Ala Asp Ser Ala Tyr Tyr
    1760                1765                1770

Gln Val Gly Gln Thr Gly Lys Glu Gly Thr Glu Asn Gln Gly Val
    1775                1780                1785

Glu Pro Gln Asp Glu Val Asp Gly Gly Asp Thr Gln Lys Lys Gln
    1790                1795                1800

Leu Ile Asn Pro His Val Glu Leu Gln Phe Ser Asp Ala Asn Ala
    1805                1810                1815

Lys Phe Tyr Cys Arg Leu Tyr Tyr Ala Gly Glu Phe His Lys Met
    1820                1825                1830

Arg Glu Val Ile Leu Asp Ser Ser Glu Glu Asp Phe Ile Arg Ser
    1835                1840                1845

Leu Ser His Ser Ser Pro Trp Gln Ala Arg Gly Gly Lys Ser Gly
    1850                1855                1860

Ala Ala Phe Tyr Ala Thr Glu Asp Asp Arg Phe Ile Leu Lys Gln
    1865                1870                1875

Met Pro Arg Leu Glu Val Gln Ser Phe Leu Asp Phe Ala Pro His
    1880                1885                1890

Tyr Phe Asn Tyr Ile Thr Asn Ala Val Gln Gln Lys Arg Pro Thr
    1895                1900                1905

Ala Leu Ala Lys Ile Leu Gly Val Tyr Arg Ile Gly Tyr Lys Asn
    1910                1915                1920

Ser Gln Asn Asn Thr Glu Lys Lys Leu Asp Leu Leu Val Met Glu
    1925                1930                1935
```

-continued

```
Asn Leu Phe Tyr Gly Arg Lys Met Ala Gln Val Phe Asp Leu Lys
    1940                1945                1950

Gly Ser Leu Arg Asn Arg Asn Val Lys Thr Asp Thr Gly Lys Glu
    1955                1960                1965

Ser Cys Asp Val Val Leu Leu Asp Glu Asn Leu Leu Lys Met Val
    1970                1975                1980

Arg Asp Asn Pro Leu Tyr Ile Arg Ser His Ser Lys Ala Val Leu
    1985                1990                1995

Arg Thr Ser Ile His Ser Asp Ser His Phe Leu Ser Ser His Leu
    2000                2005                2010

Ile Ile Asp Tyr Ser Leu Leu Val Gly Arg Asp Asp Thr Ser Asn
    2015                2020                2025

Glu Leu Val Val Gly Ile Ile Asp Tyr Ile Arg Thr Phe Thr Trp
    2030                2035                2040

Asp Lys Lys Leu Glu Met Val Val Lys Ser Thr Gly Ile Leu Gly
    2045                2050                2055

Gly Gln Gly Lys Met Pro Thr Val Val Ser Pro Glu Leu Tyr Arg
    2060                2065                2070

Thr Arg Phe Cys Glu Ala Met Asp Lys Tyr Phe Leu Met Val Pro
    2075                2080                2085

Asp His Trp Thr Gly Leu Gly Leu Asn Cys
    2090                2095

<210> SEQ ID NO 80
<211> LENGTH: 1074
<212> TYPE: PRT
<213> ORGANISM: Homo sapiens

<400> SEQUENCE: 80

Met Ser Leu Lys Asn Glu Pro Arg Val Asn Thr Ser Ala Leu Gln Lys
1               5                   10                  15

Ile Ala Ala Asp Met Ser Asn Ile Ile Glu Asn Leu Asp Thr Arg Glu
                20                  25                  30

Leu His Phe Glu Gly Glu Val Asp Tyr Asp Val Ser Pro Ser Asp
            35                  40                  45

Pro Lys Ile Gln Glu Val Tyr Ile Pro Phe Ser Ala Ile Tyr Asn Thr
    50                  55                  60

Gln Gly Phe Lys Glu Pro Asn Ile Gln Thr Tyr Leu Ser Gly Cys Pro
65                  70                  75                  80

Ile Lys Ala Gln Val Leu Glu Val Glu Arg Phe Thr Ser Thr Thr Arg
                85                  90                  95

Val Pro Ser Ile Asn Leu Tyr Thr Ile Glu Leu Thr His Gly Glu Phe
            100                 105                 110

Lys Trp Gln Val Lys Arg Lys Phe Lys His Phe Gln Glu Phe His Arg
        115                 120                 125

Glu Leu Leu Lys Tyr Lys Ala Phe Ile Arg Ile Pro Ile Pro Thr Arg
    130                 135                 140

Arg His Thr Phe Arg Arg Gln Asn Val Arg Glu Glu Pro Arg Glu Met
145                 150                 155                 160

Pro Ser Leu Pro Arg Ser Ser Glu Asn Met Ile Arg Glu Glu Gln Phe
                165                 170                 175

Leu Gly Arg Arg Lys Gln Leu Glu Asp Tyr Leu Thr Lys Ile Leu Lys
            180                 185                 190

Met Pro Met Tyr Arg Asn Tyr His Ala Thr Thr Glu Phe Leu Asp Ile
```

-continued

```
                195                 200                 205
Ser Gln Leu Ser Phe Ile His Asp Leu Gly Pro Lys Gly Ile Glu Gly
    210                 215                 220

Met Ile Met Lys Arg Ser Gly His Arg Ile Pro Gly Leu Asn Cys
225                 230                 235                 240

Cys Gly Gln Gly Arg Ala Cys Tyr Arg Trp Ser Lys Arg Trp Leu Ile
                245                 250                 255

Val Lys Asp Ser Phe Leu Leu Tyr Met Lys Pro Asp Ser Gly Ala Ile
                260                 265                 270

Ala Phe Val Leu Leu Val Asp Lys Glu Phe Lys Ile Lys Val Gly Lys
    275                 280                 285

Lys Glu Thr Glu Thr Lys Tyr Gly Ile Arg Ile Asp Asn Leu Ser Arg
    290                 295                 300

Thr Leu Ile Leu Lys Cys Asn Ser Tyr Arg His Ala Arg Trp Trp Gly
305                 310                 315                 320

Gly Ala Ile Glu Glu Phe Ile Gln Lys His Gly Thr Asn Phe Leu Lys
                325                 330                 335

Asp His Arg Phe Gly Ser Tyr Ala Ala Ile Gln Glu Asn Ala Leu Ala
                340                 345                 350

Lys Trp Tyr Val Asn Ala Lys Gly Tyr Phe Glu Asp Val Ala Asn Ala
                355                 360                 365

Met Glu Glu Ala Asn Glu Glu Ile Phe Ile Thr Asp Trp Trp Leu Ser
    370                 375                 380

Pro Glu Ile Phe Leu Lys Arg Pro Val Val Glu Gly Asn Arg Trp Arg
385                 390                 395                 400

Leu Asp Cys Ile Leu Lys Arg Lys Ala Gln Gln Gly Val Arg Ile Phe
                405                 410                 415

Ile Met Leu Tyr Lys Glu Val Glu Leu Ala Leu Gly Ile Asn Ser Glu
                420                 425                 430

Tyr Thr Lys Arg Thr Leu Met Arg Leu His Pro Asn Ile Lys Val Met
    435                 440                 445

Arg His Pro Asp His Val Ser Ser Thr Val Tyr Leu Trp Ala His His
450                 455                 460

Glu Lys Leu Val Ile Ile Asp Gln Ser Val Ala Phe Val Gly Gly Ile
465                 470                 475                 480

Asp Leu Ala Tyr Gly Arg Trp Asp Asp Asn Glu His Arg Leu Thr Asp
                485                 490                 495

Val Gly Ser Val Lys Arg Val Thr Ser Gly Pro Ser Leu Gly Ser Leu
                500                 505                 510

Pro Pro Ala Ala Met Glu Ser Met Glu Ser Leu Arg Leu Lys Asp Lys
                515                 520                 525

Asn Glu Pro Val Gln Asn Leu Pro Ile Gln Lys Ser Ile Asp Asp Val
    530                 535                 540

Asp Ser Lys Leu Lys Gly Ile Gly Lys Pro Arg Lys Phe Ser Lys Phe
545                 550                 555                 560

Ser Leu Tyr Lys Gln Leu His Arg His Leu His Asp Ala Asp Ser
                565                 570                 575

Ile Ser Ser Ile Asp Ser Thr Ser Ser Tyr Phe Asn His Tyr Arg Ser
                580                 585                 590

His His Asn Leu Ile His Gly Leu Lys Pro His Phe Lys Leu Phe His
    595                 600                 605

Pro Ser Ser Glu Ser Glu Gln Gly Leu Thr Arg Pro His Ala Asp Thr
610                 615                 620
```

```
Gly Ser Ile Arg Ser Leu Gln Thr Gly Val Gly Glu Leu His Gly Glu
625                 630                 635                 640

Thr Arg Phe Trp His Gly Lys Asp Tyr Cys Asn Phe Val Phe Lys Asp
            645                 650                 655

Trp Val Gln Leu Asp Lys Pro Phe Ala Asp Phe Ile Asp Arg Tyr Ser
                660                 665                 670

Thr Pro Arg Met Pro Trp His Asp Ile Ala Ser Ala Val His Gly Lys
            675                 680                 685

Ala Ala Arg Asp Val Ala Arg His Phe Ile Gln Arg Trp Asn Phe Thr
690                 695                 700

Lys Ile Met Lys Ser Lys Tyr Arg Ser Leu Ser Tyr Pro Phe Leu Leu
705                 710                 715                 720

Pro Lys Ser Gln Thr Thr Ala His Glu Leu Arg Tyr Gln Val Pro Gly
                725                 730                 735

Ser Val His Ala Asn Val Gln Leu Leu Arg Ser Ala Ala Asp Trp Ser
            740                 745                 750

Ala Gly Ile Lys Tyr His Glu Glu Ser Ile His Ala Ala Tyr Val His
            755                 760                 765

Val Ile Glu Asn Ser Arg His Tyr Ile Tyr Ile Glu Asn Gln Phe Phe
770                 775                 780

Ile Ser Cys Ala Asp Asp Lys Val Val Phe Asn Lys Ile Gly Asp Ala
785                 790                 795                 800

Ile Ala Gln Arg Ile Leu Lys Ala His Arg Glu Asn Gln Lys Tyr Arg
                805                 810                 815

Val Tyr Val Val Ile Pro Leu Leu Pro Gly Phe Glu Gly Asp Ile Ser
                820                 825                 830

Thr Gly Gly Gly Asn Ala Leu Gln Ala Ile Met His Phe Asn Tyr Arg
            835                 840                 845

Thr Met Cys Arg Gly Glu Asn Ser Ile Leu Gly Gln Leu Lys Ala Glu
850                 855                 860

Leu Gly Asn Gln Trp Ile Asn Tyr Ile Ser Phe Cys Gly Leu Arg Thr
865                 870                 875                 880

His Ala Glu Leu Glu Gly Asn Leu Val Thr Glu Leu Ile Tyr Val His
                885                 890                 895

Ser Lys Leu Leu Ile Ala Asp Asp Asn Thr Val Ile Ile Gly Ser Ala
                900                 905                 910

Asn Ile Asn Asp Arg Ser Met Leu Gly Lys Arg Asp Ser Glu Met Ala
            915                 920                 925

Val Ile Val Gln Asp Thr Glu Thr Val Pro Ser Val Met Asp Gly Lys
            930                 935                 940

Glu Tyr Gln Ala Gly Arg Phe Ala Arg Gly Leu Arg Leu Gln Cys Phe
945                 950                 955                 960

Arg Val Val Leu Gly Tyr Leu Asp Asp Pro Ser Glu Asp Ile Gln Asp
                965                 970                 975

Pro Val Ser Asp Lys Phe Phe Lys Glu Val Trp Val Ser Thr Ala Ala
            980                 985                 990

Arg Asn Ala Thr Ile Tyr Asp Lys Val Phe Arg Cys Leu Pro Asn Asp
            995                 1000                1005

Glu Val His Asn Leu Ile Gln Leu Arg Asp Phe Ile Asn Lys Pro
    1010                1015                1020

Val Leu Ala Lys Glu Asp Pro Ile Arg Ala Glu Glu Leu Lys
    1025                1030                1035
```

```
Lys Ile Arg Gly Phe Leu Val Gln Phe Pro Phe Tyr Phe Leu Ser
    1040                1045                1050

Glu Glu Ser Leu Leu Pro Ser Val Gly Thr Lys Glu Ala Ile Val
    1055                1060                1065

Pro Met Glu Val Trp Thr
    1070

<210> SEQ ID NO 81
<211> LENGTH: 845
<212> TYPE: PRT
<213> ORGANISM: Homo sapiens

<400> SEQUENCE: 81

Met Glu Leu Trp Arg Gln Cys Thr His Trp Leu Ile Gln Cys Arg Val
1               5                   10                  15

Leu Pro Pro Ser His Arg Val Thr Trp Asp Gly Ala Gln Val Cys Glu
                20                  25                  30

Leu Ala Gln Ala Leu Arg Asp Gly Val Leu Leu Cys Gln Leu Leu Asn
            35                  40                  45

Asn Leu Leu Pro His Ala Ile Asn Leu Arg Glu Val Asn Leu Arg Pro
        50                  55                  60

Gln Met Ser Gln Phe Leu Cys Leu Lys Asn Ile Arg Thr Phe Leu Ser
65                  70                  75                  80

Thr Cys Cys Glu Lys Phe Gly Leu Lys Arg Ser Glu Leu Phe Glu Ala
                85                  90                  95

Phe Asp Leu Phe Asp Val Gln Asp Phe Gly Lys Val Ile Tyr Thr Leu
                100                 105                 110

Ser Ala Leu Ser Trp Thr Pro Ile Ala Gln Asn Arg Gly Ile Met Pro
            115                 120                 125

Phe Pro Thr Glu Glu Glu Ser Val Gly Asp Glu Asp Ile Tyr Ser Gly
        130                 135                 140

Leu Ser Asp Gln Ile Asp Asp Thr Val Glu Glu Asp Glu Asp Leu Tyr
145                 150                 155                 160

Asp Cys Val Glu Asn Glu Glu Ala Glu Gly Asp Glu Ile Tyr Glu Asp
                165                 170                 175

Leu Met Arg Ser Glu Pro Val Ser Met Pro Pro Lys Met Thr Glu Tyr
                180                 185                 190

Asp Lys Arg Cys Cys Cys Leu Arg Glu Ile Gln Gln Thr Glu Glu Lys
            195                 200                 205

Tyr Thr Asp Thr Leu Gly Ser Ile Gln Gln His Phe Leu Lys Pro Leu
        210                 215                 220

Gln Arg Phe Leu Lys Pro Gln Asp Ile Glu Ile Ile Phe Ile Asn Ile
225                 230                 235                 240

Glu Asp Leu Leu Arg Val His Thr His Phe Leu Lys Glu Met Lys Glu
                245                 250                 255

Ala Leu Gly Thr Pro Gly Ala Ala Asn Leu Tyr Gln Val Phe Ile Lys
                260                 265                 270

Tyr Lys Glu Arg Phe Leu Val Tyr Gly Arg Tyr Cys Ser Gln Val Glu
            275                 280                 285

Ser Ala Ser Lys His Leu Asp Arg Val Ala Ala Ala Arg Glu Asp Val
        290                 295                 300

Gln Met Lys Leu Glu Glu Cys Ser Gln Arg Ala Asn Asn Gly Arg Phe
305                 310                 315                 320

Thr Leu Arg Asp Leu Leu Met Val Pro Met Gln Arg Val Leu Lys Tyr
                325                 330                 335
```

```
His Leu Leu Leu Gln Glu Leu Val Lys His Thr Gln Glu Ala Met Glu
            340                 345                 350

Lys Glu Asn Leu Arg Leu Ala Leu Asp Ala Met Arg Asp Leu Ala Gln
            355                 360                 365

Cys Val Asn Glu Val Lys Arg Asp Asn Glu Thr Leu Arg Gln Ile Thr
            370                 375                 380

Asn Phe Gln Leu Ser Ile Glu Asn Leu Asp Gln Ser Leu Ala His Tyr
385                 390                 395                 400

Gly Arg Pro Lys Ile Asp Gly Glu Leu Lys Ile Thr Ser Val Glu Arg
                405                 410                 415

Arg Ser Lys Met Asp Arg Tyr Ala Phe Leu Leu Asp Lys Ala Leu Leu
            420                 425                 430

Ile Cys Lys Arg Arg Gly Asp Ser Tyr Asp Leu Lys Asp Phe Val Asn
            435                 440                 445

Leu His Ser Phe Gln Val Arg Asp Asp Ser Ser Gly Asp Arg Asp Asn
450                 455                 460

Lys Lys Trp Ser His Met Phe Leu Leu Ile Glu Asp Gln Gly Ala Gln
465                 470                 475                 480

Gly Tyr Glu Leu Phe Phe Lys Thr Arg Glu Leu Lys Lys Lys Trp Met
                485                 490                 495

Glu Gln Phe Glu Met Ala Ile Ser Asn Ile Tyr Pro Glu Asn Ala Thr
                500                 505                 510

Ala Asn Gly His Asp Phe Gln Met Phe Ser Phe Glu Glu Thr Thr Ser
            515                 520                 525

Cys Lys Ala Cys Gln Met Leu Leu Arg Gly Thr Phe Tyr Gln Gly Tyr
            530                 535                 540

Arg Cys His Arg Cys Arg Ala Ser Ala His Lys Glu Cys Leu Gly Arg
545                 550                 555                 560

Val Pro Pro Cys Gly Arg His Gly Gln Asp Phe Pro Gly Thr Met Lys
                565                 570                 575

Lys Asp Lys Leu His Arg Arg Ala Gln Asp Lys Lys Arg Asn Glu Leu
            580                 585                 590

Gly Leu Pro Lys Met Glu Val Phe Gln Glu Tyr Tyr Gly Leu Pro Pro
            595                 600                 605

Pro Pro Gly Ala Ile Gly Pro Phe Leu Arg Leu Asn Pro Gly Asp Ile
            610                 615                 620

Val Glu Leu Thr Lys Ala Glu Ala Glu Gln Asn Trp Trp Glu Gly Arg
625                 630                 635                 640

Asn Thr Ser Thr Asn Glu Ile Gly Trp Phe Pro Cys Asn Arg Val Lys
                645                 650                 655

Pro Tyr Val His Gly Pro Pro Gln Asp Leu Ser Val His Leu Trp Tyr
                660                 665                 670

Ala Gly Pro Met Glu Arg Ala Gly Ala Glu Ser Ile Leu Ala Asn Arg
            675                 680                 685

Ser Asp Gly Thr Phe Leu Val Arg Gln Arg Val Lys Asp Ala Ala Glu
690                 695                 700

Phe Ala Ile Ser Ile Lys Tyr Asn Val Glu Val Lys His Ile Lys Ile
705                 710                 715                 720

Met Thr Ala Glu Gly Leu Tyr Arg Ile Thr Lys Lys Ala Phe Arg
                725                 730                 735

Gly Leu Thr Glu Leu Val Glu Phe Tyr Gln Gln Asn Ser Leu Lys Asp
            740                 745                 750
```

```
Cys Phe Lys Ser Leu Asp Thr Thr Leu Gln Phe Pro Phe Lys Glu Pro
        755                 760                 765

Glu Lys Arg Thr Ile Ser Arg Pro Ala Val Gly Ser Thr Lys Tyr Phe
        770                 775                 780

Gly Thr Ala Lys Ala Arg Tyr Asp Phe Cys Ala Arg Asp Arg Ser Glu
785                 790                 795                 800

Leu Ser Leu Lys Glu Gly Asp Ile Ile Lys Ile Leu Asn Lys Lys Gly
                805                 810                 815

Gln Gln Gly Trp Trp Arg Gly Glu Ile Tyr Gly Arg Val Gly Trp Phe
                820                 825                 830

Pro Ala Asn Tyr Val Glu Glu Asp Tyr Ser Glu Tyr Cys
                835                 840                 845

<210> SEQ ID NO 82
<211> LENGTH: 93
<212> TYPE: PRT
<213> ORGANISM: Homo sapiens

<400> SEQUENCE: 82

Gly Ser Gly Ser Ala Ser Pro Arg Lys Ser Thr Val Ile Ser Ser Pro
1               5                   10                  15

Phe Asp Pro Lys His Val Thr His Val Gly Phe Asn Tyr Asp Thr Gly
                20                  25                  30

Glu Phe Thr Gly Met Pro Thr Glu Trp Gln Ala Leu Leu Lys Val Ser
            35                  40                  45

Gly Ile Thr Lys Ser Glu Gln Val Gln His Pro Gln Ala Val Leu Asp
        50                  55                  60

Ala Met Ala Phe Tyr Ser Gln Ser Lys Lys Tyr Leu Glu Glu Gly Ala
65                  70                  75                  80

Lys Pro Pro Phe Pro Arg Glu Ser Thr Glu Lys Pro Leu
                85                  90

<210> SEQ ID NO 83
<211> LENGTH: 609
<212> TYPE: PRT
<213> ORGANISM: Homo sapiens

<400> SEQUENCE: 83

Met Glu Gly Pro Ser Leu Arg Gly Pro Ala Leu Arg Leu Ala Gly Leu
1               5                   10                  15

Pro Thr Gln Gln Asp Cys Asn Ile Gln Glu Lys Ile Asp Leu Glu Ile
                20                  25                  30

Arg Met Arg Glu Gly Ile Trp Lys Leu Leu Ser Leu Thr Gln Lys
            35                  40                  45

Asp Gln Val Leu His Ala Val Lys Asn Leu Met Val Cys Asn Ala Arg
        50                  55                  60

Leu Met Ala Tyr Thr Ser Glu Leu Gln Lys Leu Glu Glu Gln Ile Ala
65                  70                  75                  80

Asn Gln Thr Gly Arg Cys Asp Val Lys Phe Glu Ser Lys Glu Arg Thr
                85                  90                  95

Ala Cys Lys Gly Lys Ile Ala Ile Ser Asp Ile Arg Ile Pro Leu Met
                100                 105                 110

Trp Lys Asp Ser Asp His Phe Ser Asn Lys Glu Arg Ser Arg Arg Tyr
            115                 120                 125

Ala Ile Phe Cys Leu Phe Lys Met Gly Ala Asn Val Phe Asp Thr Asp
        130                 135                 140
```

-continued

```
Val Val Asn Val Asp Lys Thr Ile Thr Asp Ile Cys Phe Glu Asn Val
145                 150                 155                 160

Thr Ile Phe Asn Glu Ala Gly Pro Asp Phe Gln Ile Lys Val Glu Val
                165                 170                 175

Tyr Ser Cys Cys Thr Glu Glu Ser Ser Ile Thr Asn Thr Pro Lys Lys
            180                 185                 190

Leu Ala Lys Lys Leu Lys Thr Ser Ile Ser Lys Ala Thr Gly Lys Lys
        195                 200                 205

Ile Ser Ser Val Leu Gln Glu Asp Asp Glu Met Cys Leu Leu Leu
    210                 215                 220

Ser Ser Ala Val Phe Gly Val Lys Tyr Asn Leu Ala His Thr Thr
225                 230                 235                 240

Leu Thr Leu Glu Ser Ala Glu Asp Ser Phe Lys Thr His Asn Leu Ser
                245                 250                 255

Ile Asn Gly Asn Glu Glu Ser Ser Phe Trp Leu Pro Leu Tyr Gly Asn
            260                 265                 270

Met Cys Cys Arg Leu Val Ala Gln Pro Ala Cys Met Ala Glu Asp Ala
        275                 280                 285

Phe Ala Gly Phe Leu Asn Gln Gln Gln Met Val Glu Gly Leu Ile Ser
290                 295                 300

Trp Arg Arg Leu Tyr Cys Val Leu Arg Gly Gly Lys Leu Tyr Cys Phe
305                 310                 315                 320

Tyr Ser Pro Glu Glu Ile Glu Ala Lys Val Glu Pro Ala Leu Val Val
                325                 330                 335

Pro Ile Asn Lys Glu Thr Arg Ile Arg Ala Met Asp Lys Asp Ala Lys
            340                 345                 350

Lys Arg Ile His Asn Phe Ser Val Ile Asn Pro Val Pro Gly Gln Ala
        355                 360                 365

Ile Thr Gln Ile Phe Ala Val Asp Asn Arg Glu Asp Leu Gln Lys Trp
    370                 375                 380

Met Glu Ala Phe Trp Gln His Phe Asp Leu Ser Gln Trp Lys His
385                 390                 395                 400

Cys Cys Glu Glu Leu Met Lys Ile Glu Ile Met Ser Pro Arg Lys Pro
                405                 410                 415

Pro Leu Phe Leu Thr Lys Glu Ala Thr Ser Val Tyr His Asp Met Ser
            420                 425                 430

Ile Asp Ser Pro Met Lys Leu Glu Ser Leu Thr Asp Ile Ile Gln Lys
        435                 440                 445

Lys Ile Glu Glu Thr Asn Gly Gln Phe Leu Ile Gly Gln His Glu Glu
    450                 455                 460

Ser Leu Pro Pro Pro Trp Ala Thr Leu Phe Asp Gly Asn His Gln Met
465                 470                 475                 480

Val Ile Gln Lys Lys Val Leu Tyr Pro Ala Ser Glu Pro Leu His Asp
                485                 490                 495

Glu Lys Gly Lys Lys Arg Gln Ala Pro Leu Pro Ser Asp Lys Leu
            500                 505                 510

Pro Phe Ser Leu Lys Ser Gln Ser Asn Thr Asp Gln Leu Val Lys Asp
        515                 520                 525

Asn Trp Gly Lys Thr Ser Val Ser Gln Thr Ser Ser Leu Asp Thr Lys
    530                 535                 540

Leu Ser Thr Leu Met His His Leu Gln Lys Pro Met Ala Ala Pro Arg
545                 550                 555                 560

Lys Leu Leu Pro Ala Arg Arg Asn Arg Leu Ser Asp Gly Glu His Thr
```

```
                            565                 570                 575
Asp Thr Lys Thr Asn Phe Glu Ala Lys Pro Val Pro Ala Pro Arg Gln
        580                 585                 590

Lys Ser Ile Lys Asp Ile Leu Asp Pro Arg Ser Trp Leu Gln Ala Gln
        595                 600                 605

Val

<210> SEQ ID NO 84
<211> LENGTH: 211
<212> TYPE: PRT
<213> ORGANISM: Homo sapiens

<400> SEQUENCE: 84

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
            35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Val Gly Glu Thr Tyr
65                  70                  75                  80

Gly Lys Asp Ile Thr Ser Arg Gly Lys Asp Lys Pro Ile Ala Asp Val
                85                  90                  95

Phe Leu Ile Cys Phe Ser Leu Val Ser Pro Ala Ser Phe Glu Asn Val
            100                 105                 110

Arg Ala Lys Trp Tyr Pro Glu Val Arg His His Cys Pro Asn Thr Pro
        115                 120                 125

Ile Ile Leu Val Gly Thr Lys Leu Asp Leu Arg Asp Asp Lys Asp Thr
130                 135                 140

Ile Glu Lys Leu Lys Glu Lys Lys Leu Thr Pro Ile Thr Tyr Pro Gln
145                 150                 155                 160

Gly Leu Ala Met Ala Lys Glu Ile Gly Ala Val Lys Tyr Leu Glu Cys
                165                 170                 175

Ser Ala Leu Thr Gln Arg Gly Leu Lys Thr Val Phe Asp Glu Ala Ile
            180                 185                 190

Arg Ala Val Leu Cys Pro Pro Val Lys Lys Arg Lys Arg Lys Cys
        195                 200                 205

Leu Leu Leu
    210

<210> SEQ ID NO 85
<211> LENGTH: 499
<212> TYPE: PRT
<213> ORGANISM: Homo sapiens

<400> SEQUENCE: 85

Met Ala Met Ala Glu Gly Glu Arg Thr Glu Cys Ala Glu Pro Pro Arg
1               5                   10                  15

Asp Glu Pro Pro Ala Asp Gly Ala Leu Lys Arg Ala Glu Glu Leu Lys
                20                  25                  30

Thr Gln Ala Asn Asp Tyr Phe Lys Ala Lys Asp Tyr Glu Asn Ala Ile
            35                  40                  45

Lys Phe Tyr Ser Gln Ala Ile Glu Leu Asn Pro Ser Asn Ala Ile Tyr
        50                  55                  60
```

-continued

```
Tyr Gly Asn Arg Ser Leu Ala Tyr Leu Arg Thr Glu Cys Tyr Gly Tyr
 65                  70                  75                  80

Ala Leu Gly Asp Ala Thr Arg Ala Ile Glu Leu Asp Lys Lys Tyr Ile
                 85                  90                  95

Lys Gly Tyr Tyr Arg Arg Ala Ala Ser Asn Met Ala Leu Gly Lys Phe
            100                 105                 110

Arg Ala Ala Leu Arg Asp Tyr Glu Thr Val Val Lys Val Lys Pro His
        115                 120                 125

Asp Lys Asp Ala Lys Met Lys Tyr Gln Glu Cys Asn Lys Ile Val Lys
    130                 135                 140

Gln Lys Ala Phe Glu Arg Ala Ile Ala Gly Asp His Lys Arg Ser
145                 150                 155                 160

Val Val Asp Ser Leu Asp Ile Glu Ser Met Thr Ile Glu Asp Glu Tyr
                165                 170                 175

Ser Gly Pro Lys Leu Glu Asp Gly Lys Val Thr Ile Ser Phe Met Lys
            180                 185                 190

Glu Leu Met Gln Trp Tyr Lys Asp Gln Lys Lys Leu His Arg Lys Cys
        195                 200                 205

Ala Tyr Gln Ile Leu Val Gln Val Lys Glu Val Leu Ser Lys Leu Ser
    210                 215                 220

Thr Leu Val Glu Thr Thr Leu Lys Glu Thr Glu Lys Ile Thr Val Cys
225                 230                 235                 240

Gly Asp Thr His Gly Gln Phe Tyr Asp Leu Leu Asn Ile Phe Glu Leu
                245                 250                 255

Asn Gly Leu Pro Ser Glu Thr Asn Pro Tyr Ile Phe Asn Gly Asp Phe
            260                 265                 270

Val Asp Arg Gly Ser Phe Ser Val Glu Val Ile Leu Thr Leu Phe Gly
        275                 280                 285

Phe Lys Leu Leu Tyr Pro Asp His Phe His Leu Leu Arg Gly Asn His
    290                 295                 300

Glu Thr Asp Asn Met Asn Gln Ile Tyr Gly Phe Glu Gly Glu Val Lys
305                 310                 315                 320

Ala Lys Tyr Thr Ala Gln Met Tyr Glu Leu Phe Ser Glu Val Phe Glu
                325                 330                 335

Trp Leu Pro Leu Ala Gln Cys Ile Asn Gly Lys Val Leu Ile Met His
            340                 345                 350

Gly Gly Leu Phe Ser Glu Asp Gly Val Thr Leu Asp Asp Ile Arg Lys
        355                 360                 365

Ile Glu Arg Asn Arg Gln Pro Pro Asp Ser Gly Pro Met Cys Asp Leu
    370                 375                 380

Leu Trp Ser Asp Pro Gln Pro Gln Asn Gly Arg Ser Ile Ser Lys Arg
385                 390                 395                 400

Gly Val Ser Cys Gln Phe Gly Pro Asp Val Thr Lys Ala Phe Leu Glu
                405                 410                 415

Glu Asn Asn Leu Asp Tyr Ile Ile Arg Ser His Glu Val Lys Ala Glu
            420                 425                 430

Gly Tyr Glu Val Ala His Gly Gly Arg Cys Val Thr Val Phe Ser Ala
        435                 440                 445

Pro Asn Tyr Cys Asp Gln Met Gly Asn Lys Ala Ser Tyr Ile His Leu
    450                 455                 460

Gln Gly Ser Asp Leu Arg Pro Gln Phe His Gln Phe Thr Ala Val Pro
465                 470                 475                 480
```

His Pro Asn Val Lys Pro Met Ala Tyr Ala Asn Thr Leu Leu Gln Leu
              485                 490                 495
Gly Met Met

<210> SEQ ID NO 86
<211> LENGTH: 344
<212> TYPE: PRT
<213> ORGANISM: Homo sapiens

<400> SEQUENCE: 86

Met Pro Val Asp Val Ala Ser Pro Ala Gly Lys Thr Val Cys Val Thr
1               5                   10                  15

Gly Ala Gly Gly Tyr Ile Ala Ser Trp Ile Val Lys Ile Leu Leu Glu
            20                  25                  30

Arg Gly Tyr Thr Val Lys Gly Thr Val Arg Asn Pro Asp Asp Pro Lys
        35                  40                  45

Asn Thr His Leu Arg Glu Leu Glu Gly Gly Lys Glu Arg Leu Ile Leu
    50                  55                  60

Cys Lys Ala Asp Leu Gln Asp Tyr Glu Ala Leu Lys Ala Ala Ile Asp
65                  70                  75                  80

Gly Cys Asp Gly Val Phe His Thr Ala Ser Pro Val Thr Asp Asp Pro
                85                  90                  95

Glu Gln Met Val Glu Pro Ala Val Asn Gly Ala Lys Phe Val Ile Asn
            100                 105                 110

Ala Ala Ala Glu Ala Lys Val Lys Arg Val Val Ile Thr Ser Ser Ile
        115                 120                 125

Gly Ala Val Tyr Met Asp Pro Asn Arg Asp Pro Glu Ala Val Val Asp
    130                 135                 140

Glu Ser Cys Trp Ser Asp Leu Asp Phe Cys Lys Asn Thr Lys Asn Trp
145                 150                 155                 160

Tyr Cys Tyr Gly Lys Met Val Ala Glu Gln Ala Ala Trp Glu Thr Ala
                165                 170                 175

Lys Glu Lys Gly Val Asp Leu Val Val Leu Asn Pro Val Leu Val Leu
            180                 185                 190

Gly Pro Pro Leu Gln Pro Thr Ile Asn Ala Ser Leu Tyr His Val Leu
        195                 200                 205

Lys Tyr Leu Thr Gly Ser Ala Lys Thr Tyr Ala Asn Leu Thr Gln Ala
    210                 215                 220

Tyr Val Asp Val Arg Asp Val Ala Leu Ala His Val Leu Val Tyr Glu
225                 230                 235                 240

Ala Pro Ser Ala Ser Gly Arg Tyr Leu Leu Ala Glu Ser Ala Arg His
                245                 250                 255

Arg Gly Glu Val Val Glu Ile Leu Ala Lys Leu Phe Pro Glu Tyr Pro
            260                 265                 270

Leu Pro Thr Lys Cys Lys Asp Glu Lys Asn Pro Arg Ala Lys Pro Tyr
        275                 280                 285

Lys Phe Thr Asn Gln Lys Ile Lys Asp Leu Gly Leu Glu Phe Thr Ser
    290                 295                 300

Thr Lys Gln Ser Leu Tyr Asp Thr Val Lys Ser Leu Gln Glu Lys Gly
305                 310                 315                 320

His Leu Ala Pro Pro Pro Pro Pro Ser Ala Ser Gln Glu Ser Val
                325                 330                 335

Glu Asn Gly Ile Lys Ile Gly Ser
            340

<210> SEQ ID NO 87
<211> LENGTH: 784
<212> TYPE: PRT
<213> ORGANISM: Homo sapiens

<400> SEQUENCE: 87

```
Met Tyr Ile Leu Ile Tyr Ile Ser Ile Pro Lys His Pro Gln Thr Asp
1               5                   10                  15

Lys Thr Arg Pro Ile Tyr Pro Ser Thr Leu Gly Thr Glu Leu Arg Thr
            20                  25                  30

Glu Leu Gly Lys Thr Gly Gln Gly Lys Gln Lys Ile Tyr Cys Ala Lys
        35                  40                  45

Cys Thr Lys Lys Cys Ser Gly Glu Val Leu Arg Val Ala Asp Asn His
    50                  55                  60

Phe His Lys Ala Cys Phe Gln Cys Cys Gln Cys Lys Lys Ser Leu Ala
65                  70                  75                  80

Thr Gly Gly Phe Phe Thr Lys Asp Asn Ala Tyr Cys Ile Pro Asp
                85                  90                  95

Tyr Gln Arg Leu Tyr Gly Thr Lys Cys Ala Asn Cys Gln Gln Tyr Val
            100                 105                 110

Glu Gly Glu Val Val Ser Thr Met Gly Lys Thr Tyr His Gln Lys Cys
        115                 120                 125

Phe Thr Cys Ser Lys Cys Lys Gln Pro Phe Lys Ser Gly Ser Lys Val
    130                 135                 140

Thr Asn Thr Gly Lys Glu Val Leu Cys Glu Gln Cys Val Thr Gly Ala
145                 150                 155                 160

Pro Val Ser Pro Ser Arg Gln Ala Thr Gly Gly Val Ser Pro
                165                 170                 175

Ala Pro Pro Ala Glu Ser Pro Thr Arg Ala Thr Ala His Gln Gln His
            180                 185                 190

Gly Ser Val Ile Ser His Lys Ala His Leu Lys Glu Asp Tyr Asp Pro
        195                 200                 205

Asn Asp Cys Ala Gly Cys Gly Glu Leu Leu Lys Glu Gly Gln Ala Leu
    210                 215                 220

Val Ala Leu Asp Arg Gln Trp His Val Ser Cys Phe Arg Cys Lys Ala
225                 230                 235                 240

Cys Gln Ala Val Leu Asn Gly Glu Tyr Met Gly Lys Asp Ala Val Pro
                245                 250                 255

Tyr Cys Glu Lys Cys Tyr Gln Lys Gly Phe Gly Val Lys Cys Ala Tyr
            260                 265                 270

Cys Ser Arg Phe Ile Ser Gly Lys Val Leu Gln Ala Gly Asp Asn His
        275                 280                 285

His Phe His Pro Thr Cys Ala Arg Cys Thr Lys Cys Gly Asp Pro Phe
    290                 295                 300

Gly Asp Gly Glu Glu Met Tyr Leu Gln Gly Ser Ala Ile Trp His Pro
305                 310                 315                 320

Arg Cys Gly Pro Gly Pro Ser Glu Ser Gly Ile Ile Leu Asn Gly Gly
                325                 330                 335

Gly Gly Thr Ser Ser Val Val Gly Gly Ala Ser Asn Gly Asn Phe Thr
            340                 345                 350

Asp Thr Glu Cys Asp Arg Met Ser Ser Ser Ala Leu Ser Glu Met Tyr
        355                 360                 365

Ile Arg Ser Arg Thr Pro Ser Phe Asn Gly Ser Leu Tyr Ser Ser Ser
    370                 375                 380
```

-continued

```
Arg Lys His Tyr Arg Thr Val Ser Pro Gly Leu Ile Leu Arg Glu Tyr
385                 390                 395                 400

Gly Arg Pro Asn Ala Glu Asp Ile Ser Arg Ile Tyr Thr Tyr Ser Tyr
            405                 410                 415

Leu Thr Asp Ala Pro His Tyr Leu Arg Lys Pro Ile Asp Pro Tyr Asp
            420                 425                 430

Lys Thr Pro Leu Ser Pro His Phe His Arg Pro Ser Ser Tyr Ala Thr
            435                 440                 445

Thr Ala Ser Asn Ala Gly Ser Val Ala Gly Ser Arg Pro Pro Ser Arg
450                 455                 460

Pro His Ser Arg Thr Arg Ser Ala Met Lys Val Leu Val Asp Ala Ile
465                 470                 475                 480

Arg Ser Glu Thr Pro Arg Pro Lys Ser Pro Gly Met Asn Asn Glu Glu
                485                 490                 495

Pro Ile Glu Leu Ser His Tyr Pro Ala Ala Lys Lys Pro Pro Pro Gly
                500                 505                 510

Glu Gln Pro Lys Ile Glu Arg Asp Asp Phe Pro Ala Pro Pro Tyr Pro
            515                 520                 525

Tyr Thr Asp Pro Glu Arg Arg Arg Tyr Ser Asp Thr Tyr Lys Gly
            530                 535                 540

Val Pro Ala Ser Asp Asp Glu Asp Glu Asn Val Glu Asn Gly Lys Pro
545                 550                 555                 560

Asn Gly Lys Val Lys Asn Gly Glu Glu Gln Gln Arg Leu Gln Arg Glu
                565                 570                 575

Ala Glu Gln Leu Glu Lys Leu Asn Ser Gly Ile Gly Ser Ala Ile Ala
            580                 585                 590

Lys Asp Leu Lys Glu His Ala Lys Tyr Arg Lys Trp Lys Gln Asn Asn
            595                 600                 605

Leu Asp Pro Arg Asn Ala Ser Arg Thr Pro Ser Ala Ser Lys Glu Pro
            610                 615                 620

Leu Tyr Lys Leu Arg Tyr Glu Ser Pro Ile Gly Ala Ser Pro Ser Arg
625                 630                 635                 640

Asn Leu Asp His Gln Lys Pro Phe Tyr Glu Asp Met Phe Asp Arg
                645                 650                 655

Ser Thr Ser Tyr Arg Gly Ser Leu Gly Lys Ser Leu Gly Asn Ala Pro
                660                 665                 670

Ser Tyr Asn Ala Ile His Ser Tyr Arg Ser Pro Pro Lys Pro Gly Tyr
            675                 680                 685

Gly Phe Lys Thr Thr Leu Pro Tyr Ile Arg Asn Gly Phe Ser Ser
690                 695                 700

Asp Phe Ser Tyr Gly Gly Leu Gly Asp Lys Thr His Ser Thr Asp Leu
705                 710                 715                 720

Ser Cys Gly Lys Ser Glu Ala Ser Val Asp Ser Ile Thr Glu Gly Asp
                725                 730                 735

Arg Arg Ala Leu Met Gly Gly Asp Leu Pro Ala Ser Ser Thr Tyr Ser
                740                 745                 750

Gly Ala Leu Ser Tyr His Tyr Pro Gln Ala Gly Leu Ile Arg Arg Ser
            755                 760                 765

Leu Pro Asn Met Ser His Ser Ile Ile Ser Cys Ala Asn Ala Lys Leu
770                 775                 780

<210> SEQ ID NO 88
<211> LENGTH: 559
```

<212> TYPE: PRT
<213> ORGANISM: Homo sapiens

<400> SEQUENCE: 88

Met Pro Leu Val Lys Arg Asn Ile Asp Pro Arg His Leu Cys His Thr
1               5                   10                  15

Ala Leu Pro Arg Gly Ile Lys Asn Glu Leu Glu Cys Val Thr Asn Ile
            20                  25                  30

Ser Leu Ala Asn Ile Ile Arg Gln Leu Ser Ser Leu Ser Lys Tyr Ala
        35                  40                  45

Glu Asp Ile Phe Gly Glu Leu Phe Asn Glu Ala His Ser Phe Ser Phe
50                  55                  60

Arg Val Asn Ser Leu Gln Glu Arg Val Asp Arg Leu Ser Val Ser Val
65                  70                  75                  80

Thr Gln Leu Asp Pro Lys Glu Glu Leu Ser Leu Gln Asp Ile Thr
            85                  90                  95

Met Arg Lys Ala Phe Arg Ser Ser Thr Ile Gln Asp Gln Gln Leu Phe
            100                 105                 110

Asp Arg Lys Thr Leu Pro Ile Pro Leu Gln Glu Thr Tyr Asp Val Cys
            115                 120                 125

Glu Gln Pro Pro Pro Leu Asn Ile Leu Thr Pro Tyr Arg Asp Asp Gly
130                 135                 140

Lys Glu Gly Leu Lys Phe Tyr Thr Asn Pro Ser Tyr Phe Phe Asp Leu
145                 150                 155                 160

Trp Lys Glu Lys Met Leu Gln Asp Thr Glu Asp Lys Arg Lys Glu Lys
            165                 170                 175

Arg Lys Gln Lys Gln Lys Asn Leu Asp Arg Pro His Glu Pro Glu Lys
            180                 185                 190

Val Pro Arg Ala Pro His Asp Arg Arg Glu Trp Gln Lys Leu Ala
            195                 200                 205

Gln Gly Pro Glu Leu Ala Glu Asp Ala Asn Leu His Lys His
210                 215                 220

Ile Glu Val Ala Asn Gly Pro Ala Ser His Phe Glu Thr Arg Pro Gln
225                 230                 235                 240

Thr Tyr Val Asp His Met Asp Gly Ser Tyr Ser Leu Ser Ala Leu Pro
            245                 250                 255

Phe Ser Gln Met Ser Glu Leu Leu Thr Arg Ala Glu Glu Arg Val Leu
            260                 265                 270

Val Arg Pro His Glu Pro Pro Pro Pro Met His Gly Ala Gly
            275                 280                 285

Asp Ala Lys Pro Ile Pro Thr Cys Ile Ser Ser Ala Thr Gly Leu Ile
            290                 295                 300

Glu Asn Arg Pro Gln Ser Pro Ala Thr Gly Arg Thr Pro Val Phe Val
305                 310                 315                 320

Ser Pro Thr Pro Pro Pro Pro Pro Pro Leu Pro Ser Ala Leu Ser
            325                 330                 335

Thr Ser Ser Leu Arg Ala Ser Met Thr Ser Thr Pro Pro Pro Val
            340                 345                 350

Pro Pro Pro Pro Pro Pro Ala Thr Ala Leu Gln Ala Pro Ala Val
            355                 360                 365

Pro Pro Pro Pro Ala Pro Leu Gln Ile Ala Pro Gly Val Leu His Pro
            370                 375                 380

Ala Pro Pro Pro Ile Ala Pro Leu Val Gln Pro Ser Pro Pro Val
385                 390                 395                 400

```
Ala Arg Ala Ala Pro Val Cys Glu Thr Val Pro Val His Pro Leu Pro
            405                 410                 415

Gln Gly Glu Val Gln Gly Leu Pro Pro Pro Pro Pro Pro Pro Pro Leu
            420                 425                 430

Pro Pro Pro Gly Ile Arg Pro Ser Ser Pro Val Thr Val Thr Ala Leu
            435                 440                 445

Ala His Pro Pro Ser Gly Leu His Pro Thr Pro Ser Thr Ala Pro Gly
            450                 455                 460

Pro His Val Pro Leu Met Pro Pro Ser Pro Pro Ser Gln Val Ile Pro
465                 470                 475                 480

Ala Ser Glu Pro Lys Arg His Pro Ser Thr Leu Pro Val Ile Ser Asp
                485                 490                 495

Ala Arg Ser Val Leu Leu Glu Ala Ile Arg Lys Gly Ile Gln Leu Arg
                500                 505                 510

Lys Val Glu Glu Gln Arg Glu Gln Ala Lys His Glu Arg Ile Glu
            515                 520                 525

Asn Asp Val Ala Thr Ile Leu Ser Arg Arg Ile Ala Val Glu Tyr Ser
530                 535                 540

Asp Ser Glu Asp Asp Ser Glu Phe Asp Glu Val Asp Trp Leu Glu
545                 550                 555
```

<210> SEQ ID NO 89
<211> LENGTH: 2135
<212> TYPE: PRT
<213> ORGANISM: Homo sapiens

<400> SEQUENCE: 89

```
Met Pro Ala Leu Gly Pro Ala Leu Leu Gln Ala Leu Trp Ala Gly Trp
1               5                   10                  15

Val Leu Thr Leu Gln Pro Leu Pro Pro Thr Ala Phe Thr Pro Asn Gly
            20                  25                  30

Thr Tyr Leu Gln His Leu Ala Arg Asp Pro Thr Ser Gly Thr Leu Tyr
        35                  40                  45

Leu Gly Ala Thr Asn Phe Leu Phe Gln Leu Ser Pro Gly Leu Gln Leu
    50                  55                  60

Glu Ala Thr Val Ser Thr Gly Pro Val Leu Asp Ser Arg Asp Cys Leu
65                  70                  75                  80

Pro Pro Val Met Pro Asp Glu Cys Pro Gln Ala Gln Pro Thr Asn Asn
                85                  90                  95

Pro Asn Gln Leu Leu Leu Val Ser Pro Gly Ala Leu Val Val Cys Gly
            100                 105                 110

Ser Val His Gln Gly Val Cys Glu Gln Arg Arg Leu Gly Gln Leu Glu
        115                 120                 125

Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Ala Gly Glu Pro Leu Leu Phe Val Gly Arg Gly Tyr Thr Ser Arg Gly
                165                 170                 175

Val Gly Gly Gly Ile Pro Pro Ile Thr Thr Arg Ala Leu Trp Pro Pro
            180                 185                 190

Asp Pro Gln Ala Ala Phe Ser Tyr Glu Glu Thr Ala Lys Leu Ala Val
        195                 200                 205

Gly Arg Leu Ser Glu Tyr Ser His His Phe Val Ser Ala Phe Ala Arg
```

-continued

```
            210                 215                 220
Gly Ala Ser Ala Tyr Phe Leu Phe Leu Arg Arg Asp Leu Gln Ala Gln
225                 230                 235                 240

Ser Arg Ala Phe Arg Ala Tyr Val Ser Arg Val Cys Leu Arg Asp Gln
                245                 250                 255

His Tyr Tyr Ser Tyr Val Glu Leu Pro Leu Ala Cys Glu Gly Gly Arg
                260                 265                 270

Tyr Gly Leu Ile Gln Ala Ala Val Ala Thr Ser Arg Glu Val Ala
                275                 280                 285

His Gly Glu Val Leu Phe Ala Ala Phe Ser Ser Ala Pro Pro Thr
290                 295                 300

Val Gly Arg Pro Pro Ser Ala Ala Gly Ala Ser Gly Ala Ser Ala
305                 310                 315                 320

Leu Cys Ala Phe Pro Leu Asp Glu Val Asp Arg Leu Ala Asn Arg Thr
                325                 330                 335

Arg Asp Ala Cys Tyr Thr Arg Glu Gly Arg Ala Glu Asp Gly Thr Glu
                340                 345                 350

Val Ala Tyr Ile Glu Tyr Asp Val Asn Ser Asp Cys Ala Gln Leu Pro
                355                 360                 365

Val Asp Thr Leu Asp Ala Tyr Pro Cys Gly Ser Asp His Thr Pro Ser
370                 375                 380

Pro Met Ala Ser Arg Val Pro Leu Glu Ala Thr Pro Ile Leu Glu Trp
385                 390                 395                 400

Pro Gly Ile Gln Leu Thr Ala Val Ala Val Thr Met Glu Asp Gly His
                405                 410                 415

Thr Ile Ala Phe Leu Gly Asp Ser Gln Gly Gln Leu His Arg Val Tyr
                420                 425                 430

Leu Gly Pro Gly Ser Asp Gly His Pro Tyr Ser Thr Gln Ser Ile Gln
                435                 440                 445

Gln Gly Ser Ala Val Ser Arg Asp Leu Thr Phe Asp Gly Thr Phe Glu
                450                 455                 460

His Leu Tyr Val Met Thr Gln Ser Thr Leu Leu Lys Val Pro Val Ala
465                 470                 475                 480

Ser Cys Ala Gln His Leu Asp Cys Ala Ser Cys Leu Ala His Arg Asp
                485                 490                 495

Pro Tyr Cys Gly Trp Cys Val Leu Leu Gly Arg Cys Ser Arg Arg Ser
                500                 505                 510

Glu Cys Ser Arg Gly Gln Gly Pro Glu Gln Trp Leu Trp Ser Phe Gln
                515                 520                 525

Pro Glu Leu Gly Cys Leu Gln Val Ala Ala Met Ser Pro Ala Asn Ile
                530                 535                 540

Ser Arg Glu Glu Thr Arg Glu Val Phe Leu Ser Val Pro Asp Leu Pro
545                 550                 555                 560

Pro Leu Trp Pro Gly Glu Ser Tyr Ser Cys His Phe Gly Glu His Gln
                565                 570                 575

Ser Pro Ala Leu Leu Thr Gly Ser Gly Val Met Cys Pro Ser Pro Asp
                580                 585                 590

Pro Ser Glu Ala Pro Val Leu Pro Arg Gly Ala Asp Tyr Val Ser Val
                595                 600                 605

Ser Val Glu Leu Arg Phe Gly Ala Val Val Ile Ala Lys Thr Ser Leu
                610                 615                 620

Ser Phe Tyr Asp Cys Val Ala Val Thr Glu Leu Arg Pro Ser Ala Gln
625                 630                 635                 640
```

```
Cys Gln Ala Cys Val Ser Ser Arg Trp Gly Cys Asn Trp Cys Val Trp
                645                 650                 655

Gln His Leu Cys Thr His Lys Ala Ser Cys Asp Ala Gly Pro Met Val
                660                 665                 670

Ala Ser His Gln Ser Pro Leu Val Ser Pro Asp Pro Ala Arg Gly
                675                 680             685

Gly Pro Ser Pro Ser Pro Pro Thr Ala Pro Lys Ala Leu Ala Thr Pro
690                 695                 700

Ala Pro Asp Thr Leu Pro Val Glu Pro Gly Ala Pro Ser Thr Ala Thr
705                 710                 715                 720

Ala Ser Asp Ile Ser Pro Gly Ala Ser Pro Ser Leu Leu Ser Pro Trp
                725                 730                 735

Gly Pro Trp Ala Gly Ser Gly Ser Ile Ser Ser Pro Gly Ser Thr Gly
                740                 745                 750

Ser Pro Leu His Glu Glu Pro Ser Pro Ser Pro Gln Asn Gly Pro
                755                 760                 765

Gly Thr Ala Val Pro Ala Pro Thr Asp Phe Arg Pro Ser Ala Thr Pro
770                 775                 780

Glu Asp Leu Leu Ala Ser Pro Leu Ser Pro Ser Glu Val Ala Ala Val
785                 790                 795                 800

Pro Pro Ala Asp Pro Gly Pro Glu Ala Leu His Pro Thr Val Pro Leu
                805                 810                 815

Asp Leu Pro Pro Ala Thr Val Pro Ala Thr Thr Phe Pro Gly Ala Met
                820                 825                 830

Gly Ser Val Lys Pro Ala Leu Asp Trp Leu Thr Arg Glu Gly Gly Glu
                835                 840                 845

Leu Pro Glu Ala Asp Glu Trp Thr Gly Gly Asp Ala Pro Ala Phe Ser
850                 855                 860

Thr Ser Thr Leu Leu Ser Gly Asp Gly Asp Ser Ala Glu Leu Glu Gly
865                 870                 875                 880

Pro Pro Ala Pro Leu Ile Leu Pro Ser Ser Leu Asp Tyr Gln Tyr Asp
                885                 890                 895

Thr Pro Gly Leu Trp Glu Leu Glu Glu Ala Thr Leu Gly Ala Ser Ser
                900                 905                 910

Cys Pro Cys Val Glu Ser Val Gln Gly Ser Thr Leu Met Pro Val His
                915                 920                 925

Val Glu Arg Glu Ile Arg Leu Leu Gly Arg Asn Leu His Leu Phe Gln
930                 935                 940

Asp Gly Pro Gly Asp Asn Glu Cys Val Met Glu Leu Glu Gly Leu Glu
945                 950                 955                 960

Val Val Val Glu Ala Arg Val Glu Cys Glu Pro Pro Asp Thr Gln
                965                 970                 975

Cys His Val Thr Cys Gln Gln His Gln Leu Ser Tyr Glu Ala Leu Gln
                980                 985                 990

Pro Glu Leu Arg Val Gly Leu Phe Leu Arg Arg Ala Gly Arg Leu Arg
                995                 1000                1005

Val Asp Ser Ala Glu Gly Leu His Val Val Leu Tyr Asp Cys Ser
     1010                1015                1020

Val Gly His Gly Asp Cys Ser Arg Cys Gln Thr Ala Met Pro Gln
     1025                1030                1035

Tyr Gly Cys Val Trp Cys Glu Gly Glu Arg Pro Arg Cys Val Thr
     1040                1045                1050
```

-continued

Arg Glu Ala Cys Gly Glu Ala Glu Ala Val Ala Thr Gln Cys Pro
1055                1060                1065

Ala Pro Leu Ile His Ser Val Glu Pro Leu Thr Gly Pro Val Asp
1070                1075                1080

Gly Gly Thr Arg Val Thr Ile Arg Gly Ser Asn Leu Gly Gln His
1085                1090                1095

Val Gln Asp Val Leu Gly Met Val Thr Val Ala Gly Val Pro Cys
1100                1105                1110

Ala Val Asp Ala Gln Glu Tyr Glu Val Ser Ser Leu Val Cys
1115                1120                1125

Ile Thr Gly Ala Ser Gly Glu Val Ala Gly Ala Thr Ala Val
1130                1135                1140

Glu Val Pro Gly Arg Gly Arg Gly Val Ser Glu His Asp Phe Ala
1145                1150                1155

Tyr Gln Asp Pro Lys Val His Ser Ile Phe Pro Ala Arg Gly Pro
1160                1165                1170

Arg Ala Gly Gly Thr Arg Leu Thr Leu Asn Gly Ser Lys Leu Leu
1175                1180                1185

Thr Gly Arg Leu Glu Asp Ile Arg Val Val Gly Asp Gln Pro
1190                1195                1200

Cys His Leu Leu Pro Glu Gln Gln Ser Glu Gln Leu Arg Cys Glu
1205                1210                1215

Thr Ser Pro Arg Pro Thr Pro Ala Thr Leu Pro Val Ala Val Trp
1220                1225                1230

Phe Gly Ala Thr Glu Arg Arg Leu Gln Arg Gly Gln Phe Lys Tyr
1235                1240                1245

Thr Leu Asp Pro Asn Ile Thr Ser Ala Gly Pro Thr Lys Ser Phe
1250                1255                1260

Leu Ser Gly Gly Arg Glu Ile Cys Val Arg Gly Gln Asn Leu Asp
1265                1270                1275

Val Val Gln Thr Pro Arg Ile Arg Val Thr Val Val Ser Arg Met
1280                1285                1290

Leu Gln Pro Ser Gln Gly Leu Gly Arg Arg Arg Val Val Pro
1295                1300                1305

Glu Thr Ala Cys Ser Leu Gly Pro Ser Cys Ser Ser Gln Gln Phe
1310                1315                1320

Glu Glu Pro Cys His Val Asn Ser Ser Gln Leu Ile Thr Cys Arg
1325                1330                1335

Thr Pro Ala Leu Pro Gly Leu Pro Glu Asp Pro Trp Val Arg Val
1340                1345                1350

Glu Phe Ile Leu Asp Asn Leu Val Phe Asp Phe Ala Thr Leu Asn
1355                1360                1365

Pro Thr Pro Phe Ser Tyr Glu Ala Asp Pro Thr Leu Gln Pro Leu
1370                1375                1380

Asn Pro Glu Asp Pro Thr Met Pro Phe Arg His Lys Pro Gly Ser
1385                1390                1395

Val Phe Ser Val Glu Gly Glu Asn Leu Asp Leu Ala Met Ser Lys
1400                1405                1410

Glu Glu Val Val Ala Met Ile Gly Asp Gly Pro Cys Val Val Lys
1415                1420                1425

Thr Leu Thr Arg His His Leu Tyr Cys Glu Pro Pro Val Glu Gln
1430                1435                1440

Pro Leu Pro Arg His His Ala Leu Arg Glu Ala Pro Asp Ser Leu

-continued

```
             1445                1450                1455

Pro Glu Phe Thr Val Gln Met Gly Asn Leu Arg Phe Ser Leu Gly
    1460                1465                1470

His Val Gln Tyr Asp Gly Glu Ser Pro Gly Ala Phe Pro Val Ala
    1475                1480                1485

Ala Gln Val Gly Leu Gly Val Gly Thr Ser Leu Leu Ala Leu Gly
    1490                1495                1500

Val Ile Ile Ile Val Leu Met Tyr Arg Arg Lys Ser Lys Gln Ala
    1505                1510                1515

Leu Arg Asp Tyr Lys Lys Val Gln Ile Gln Leu Glu Asn Leu Glu
    1520                1525                1530

Ser Ser Val Arg Asp Arg Cys Lys Lys Glu Phe Thr Asp Leu Met
    1535                1540                1545

Thr Glu Met Thr Asp Leu Thr Ser Asp Leu Leu Gly Ser Gly Ile
    1550                1555                1560

Pro Phe Leu Asp Tyr Lys Val Tyr Ala Glu Arg Ile Phe Phe Pro
    1565                1570                1575

Gly His Arg Glu Ser Pro Leu His Arg Asp Leu Gly Val Pro Glu
    1580                1585                1590

Ser Arg Arg Pro Thr Val Glu Gln Gly Leu Gly Gln Leu Ser Asn
    1595                1600                1605

Leu Leu Asn Ser Lys Leu Phe Leu Thr Lys Phe Ile His Thr Leu
    1610                1615                1620

Glu Ser Gln Arg Thr Phe Ser Ala Arg Asp Arg Ala Tyr Val Ala
    1625                1630                1635

Ser Leu Leu Thr Val Ala Leu His Gly Lys Leu Glu Tyr Phe Thr
    1640                1645                1650

Asp Ile Leu Arg Thr Leu Leu Ser Asp Leu Val Ala Gln Tyr Val
    1655                1660                1665

Ala Lys Asn Pro Lys Leu Met Leu Arg Arg Thr Glu Thr Val Val
    1670                1675                1680

Glu Lys Leu Leu Thr Asn Trp Met Ser Ile Cys Leu Tyr Thr Phe
    1685                1690                1695

Val Arg Asp Ser Val Gly Glu Pro Leu Tyr Met Leu Phe Arg Gly
    1700                1705                1710

Ile Lys His Gln Val Asp Lys Gly Pro Val Asp Ser Val Thr Gly
    1715                1720                1725

Lys Ala Lys Tyr Thr Leu Asn Asp Asn Arg Leu Leu Arg Glu Asp
    1730                1735                1740

Val Glu Tyr Arg Pro Leu Thr Leu Asn Ala Leu Leu Ala Val Gly
    1745                1750                1755

Pro Gly Ala Gly Glu Ala Gln Gly Val Pro Val Lys Val Leu Asp
    1760                1765                1770

Cys Asp Thr Ile Ser Gln Ala Lys Glu Lys Met Leu Asp Gln Leu
    1775                1780                1785

Tyr Lys Gly Val Pro Leu Thr Gln Arg Pro Asp Pro Arg Thr Leu
    1790                1795                1800

Asp Val Glu Trp Arg Ser Gly Val Ala Gly His Leu Ile Leu Ser
    1805                1810                1815

Asp Glu Asp Val Thr Ser Glu Val Gln Gly Leu Trp Arg Arg Leu
    1820                1825                1830

Asn Thr Leu Gln His Tyr Lys Val Pro Asp Gly Ala Thr Val Ala
    1835                1840                1845
```

```
Leu Val Pro Cys Leu Thr Lys His Val Leu Arg Glu Asn Gln Asp
    1850                1855                1860

Tyr Val Pro Gly Glu Arg Thr Pro Met Leu Glu Asp Val Asp Glu
    1865                1870                1875

Gly Gly Ile Arg Pro Trp His Leu Val Lys Pro Ser Asp Glu Pro
    1880                1885                1890

Glu Pro Pro Arg Pro Arg Arg Gly Ser Leu Arg Gly Gly Glu Arg
    1895                1900                1905

Glu Arg Ala Lys Ala Ile Pro Glu Ile Tyr Leu Thr Arg Leu Leu
    1910                1915                1920

Ser Met Lys Gly Thr Leu Gln Lys Phe Val Asp Asp Leu Phe Gln
    1925                1930                1935

Val Ile Leu Ser Thr Ser Arg Pro Val Pro Leu Ala Val Lys Tyr
    1940                1945                1950

Phe Phe Asp Leu Leu Asp Glu Gln Ala Gln Gln His Gly Ile Ser
    1955                1960                1965

Asp Gln Asp Thr Ile His Ile Trp Lys Thr Asn Ser Leu Pro Leu
    1970                1975                1980

Arg Phe Trp Ile Asn Ile Ile Lys Asn Pro Gln Phe Val Phe Asp
    1985                1990                1995

Val Gln Thr Ser Asp Asn Met Asp Ala Val Leu Val Ile Ala
    2000                2005                2010

Gln Thr Phe Met Asp Ala Cys Thr Leu Ala Asp His Lys Leu Gly
    2015                2020                2025

Arg Asp Ser Pro Ile Asn Lys Leu Leu Tyr Ala Arg Asp Ile Pro
    2030                2035                2040

Arg Tyr Lys Arg Met Val Glu Arg Tyr Tyr Ala Asp Ile Arg Gln
    2045                2050                2055

Thr Val Pro Ala Ser Asp Gln Glu Met Asn Ser Val Leu Ala Glu
    2060                2065                2070

Leu Ser Trp Asn Tyr Ser Gly Asp Leu Gly Ala Arg Val Ala Leu
    2075                2080                2085

His Glu Leu Tyr Lys Tyr Ile Asn Lys Tyr Tyr Asp Gln Ile Ile
    2090                2095                2100

Thr Ala Leu Glu Glu Asp Gly Thr Ala Gln Lys Met Gln Leu Gly
    2105                2110                2115

Tyr Arg Leu Gln Gln Ile Ala Ala Ala Val Glu Asn Lys Val Thr
    2120                2125                2130

Asp Leu
    2135

<210> SEQ ID NO 90
<211> LENGTH: 307
<212> TYPE: PRT
<213> ORGANISM: Homo sapiens

<400> SEQUENCE: 90

Met Gly Thr Val Leu Ser Leu Ser Pro Ser Tyr Arg Lys Ala Thr Leu
1               5                   10                  15

Phe Glu Asp Gly Ala Ala Thr Val Gly His Tyr Thr Ala Val Gln Asn
                20                  25                  30

Ser Lys Asn Ala Lys Asp Lys Asn Leu Lys Arg His Ser Ile Ile Ser
        35                  40                  45

Val Leu Pro Trp Lys Arg Ile Val Ala Val Ser Ala Lys Lys Lys Asn
```

```
                50                  55                  60
Ser Lys Lys Val Gln Pro Asn Ser Ser Tyr Gln Asn Asn Ile Thr His
 65                  70                  75                  80

Leu Asn Asn Glu Asn Leu Lys Lys Ser Leu Ser Cys Ala Asn Leu Ser
                 85                  90                  95

Thr Phe Ala Gln Pro Pro Ala Gln Pro Ala Pro Pro Ala Ser
                100                 105                 110

Gln Leu Ser Gly Ser Gln Thr Gly Gly Ser Ser Val Lys Lys Ala
                115                 120                 125

Pro His Pro Ala Val Thr Ser Ala Gly Thr Pro Lys Arg Val Ile Val
130                 135                 140

Gln Ala Ser Thr Ser Glu Leu Leu Arg Cys Leu Gly Glu Phe Leu Cys
145                 150                 155                 160

Arg Arg Cys Tyr Arg Leu Lys His Leu Ser Pro Thr Asp Pro Val Leu
                165                 170                 175

Trp Leu Arg Ser Val Asp Arg Ser Leu Leu Gln Gly Trp Gln Asp
                180                 185                 190

Gln Gly Phe Ile Thr Pro Ala Asn Val Val Phe Leu Tyr Met Leu Cys
                195                 200                 205

Arg Asp Val Ile Ser Ser Glu Val Gly Ser Asp His Glu Leu Gln Ala
210                 215                 220

Val Leu Leu Thr Cys Leu Tyr Leu Ser Tyr Ser Tyr Met Gly Asn Glu
225                 230                 235                 240

Ile Ser Tyr Pro Leu Lys Pro Phe Leu Val Glu Ser Cys Lys Glu Ala
                245                 250                 255

Phe Trp Asp Arg Cys Leu Ser Val Ile Asn Leu Met Ser Ser Lys Met
                260                 265                 270

Leu Gln Ile Asn Ala Asp Pro His Tyr Phe Thr Gln Val Phe Ser Asp
                275                 280                 285

Leu Lys Asn Glu Ser Gly Gln Glu Asp Lys Lys Arg Leu Leu Leu Gly
                290                 295                 300

Leu Asp Arg
305

<210> SEQ ID NO 91
<211> LENGTH: 1406
<212> TYPE: PRT
<213> ORGANISM: Homo sapiens

<400> SEQUENCE: 91

Met Asp Met Val Glu Asn Ala Asp Ser Leu Gln Ala Gln Glu Arg Lys
 1               5                  10                  15

Asp Ile Leu Met Lys Tyr Asp Lys Gly His Arg Ala Gly Leu Pro Glu
                 20                  25                  30

Asp Lys Gly Pro Glu Pro Val Gly Ile Asn Ser Ser Ile Asp Arg Phe
                 35                  40                  45

Gly Ile Leu His Glu Thr Glu Leu Pro Pro Val Thr Ala Arg Glu Ala
                 50                  55                  60

Lys Lys Ile Arg Arg Glu Met Thr Arg Thr Ser Lys Trp Met Glu Met
 65                  70                  75                  80

Leu Gly Glu Trp Glu Thr Tyr Lys His Ser Ser Lys Leu Ile Asp Arg
                 85                  90                  95

Val Tyr Lys Gly Ile Pro Met Asn Ile Arg Gly Pro Val Trp Ser Val
                100                 105                 110
```

-continued

```
Leu Leu Asn Ile Gln Glu Ile Lys Leu Lys Asn Pro Gly Arg Tyr Gln
        115                 120                 125

Ile Met Lys Glu Arg Gly Lys Arg Ser Ser Glu His Ile His His Ile
    130                 135                 140

Asp Leu Asp Val Arg Thr Thr Leu Arg Asn His Val Phe Phe Arg Asp
145                 150                 155                 160

Arg Tyr Gly Ala Lys Gln Arg Glu Leu Phe Tyr Ile Leu Leu Ala Tyr
                165                 170                 175

Ser Glu Tyr Asn Pro Glu Val Gly Tyr Cys Arg Asp Leu Ser His Ile
            180                 185                 190

Thr Ala Leu Phe Leu Leu Tyr Leu Pro Glu Glu Asp Ala Phe Trp Ala
        195                 200                 205

Leu Val Gln Leu Leu Ala Ser Glu Arg His Ser Leu Pro Gly Phe His
    210                 215                 220

Ser Pro Asn Gly Gly Thr Val Gln Gly Leu Gln Asp Gln Glu His
225                 230                 235                 240

Val Val Pro Lys Ser Gln Pro Lys Thr Met Trp His Gln Asp Lys Glu
                245                 250                 255

Gly Leu Cys Gly Gln Cys Ala Ser Leu Gly Cys Leu Leu Arg Asn Leu
            260                 265                 270

Ile Asp Gly Ile Ser Leu Gly Leu Thr Leu Arg Leu Trp Asp Val Tyr
        275                 280                 285

Leu Val Glu Gly Glu Gln Val Leu Met Pro Ile Thr Ser Ile Ala Leu
    290                 295                 300

Lys Val Gln Gln Lys Arg Leu Met Lys Thr Ser Arg Cys Gly Leu Trp
305                 310                 315                 320

Ala Arg Leu Arg Asn Gln Phe Phe Asp Thr Trp Ala Met Asn Asp Asp
                325                 330                 335

Thr Val Leu Lys His Leu Arg Ala Ser Thr Lys Leu Thr Arg Lys
            340                 345                 350

Gln Gly Asp Leu Pro Pro Ala Lys Arg Glu Gln Gly Ser Leu Ala
        355                 360                 365

Pro Arg Pro Val Pro Ala Ser Arg Gly Gly Lys Thr Leu Cys Lys Gly
    370                 375                 380

Tyr Arg Gln Ala Pro Pro Gly Pro Pro Ala Gln Phe Gln Arg Pro Ile
385                 390                 395                 400

Cys Ser Ala Ser Pro Pro Trp Ala Ser Arg Phe Ser Thr Pro Cys Pro
                405                 410                 415

Gly Gly Ala Val Arg Glu Asp Thr Tyr Pro Val Gly Thr Gln Gly Val
            420                 425                 430

Pro Ser Leu Ala Leu Ala Gln Gly Gly Pro Gln Gly Ser Trp Arg Phe
        435                 440                 445

Leu Glu Trp Lys Ser Met Pro Arg Leu Pro Thr Asp Leu Asp Ile Gly
    450                 455                 460

Gly Pro Trp Phe Pro His Tyr Asp Phe Glu Trp Ser Cys Trp Val Arg
465                 470                 475                 480

Ala Ile Ser Gln Glu Asp Gln Leu Ala Thr Cys Trp Gln Ala Glu His
                485                 490                 495

Cys Gly Glu Val His Asn Lys Asp Met Ser Trp Pro Glu Glu Met Ser
            500                 505                 510

Phe Thr Ala Asn Ser Ser Lys Ile Asp Arg Gln Lys Val Pro Thr Glu
        515                 520                 525

Lys Gly Ala Thr Gly Leu Ser Asn Leu Gly Asn Thr Cys Phe Met Asn
```

-continued

```
        530              535              540
Ser Ser Ile Gln Cys Val Ser Asn Thr Gln Pro Leu Thr Gln Tyr Phe
545              550              555              560

Ile Ser Gly Arg His Leu Tyr Glu Leu Asn Arg Thr Asn Pro Ile Gly
             565              570              575

Met Lys Gly His Met Ala Lys Cys Tyr Gly Asp Leu Val Gln Glu Leu
             580              585              590

Trp Ser Gly Thr Gln Lys Ser Val Ala Pro Leu Lys Leu Arg Arg Thr
             595              600              605

Ile Ala Lys Tyr Ala Pro Lys Phe Asp Gly Phe Gln Gln Gln Asp Ser
     610              615              620

Gln Glu Leu Leu Ala Phe Leu Leu Asp Gly Leu His Glu Asp Leu Asn
625              630              635              640

Arg Val His Glu Lys Pro Tyr Val Glu Leu Lys Asp Ser Asp Gly Arg
                 645              650              655

Pro Asp Trp Glu Val Ala Ala Glu Ala Trp Asp Asn His Leu Arg Arg
             660              665              670

Asn Arg Ser Ile Ile Val Asp Leu Phe His Gly Gln Leu Arg Ser Gln
         675              680              685

Val Lys Cys Lys Thr Cys Gly His Ile Ser Val Arg Phe Asp Pro Phe
690              695              700

Asn Phe Leu Ser Leu Pro Leu Pro Met Asp Ser Tyr Met Asp Leu Glu
705              710              715              720

Ile Thr Val Ile Lys Leu Asp Gly Thr Thr Pro Val Arg Tyr Gly Leu
                 725              730              735

Arg Leu Asn Met Asp Glu Lys Tyr Thr Gly Leu Lys Lys Gln Leu Arg
             740              745              750

Asp Leu Cys Gly Leu Asn Ser Glu Gln Ile Leu Leu Ala Glu Val His
             755              760              765

Asp Ser Asn Ile Lys Asn Phe Pro Gln Asp Asn Gln Lys Val Gln Leu
         770              775              780

Ser Val Ser Gly Phe Leu Cys Ala Phe Glu Ile Pro Val Pro Ser Ser
785              790              795              800

Pro Ile Ser Ala Ser Ser Pro Thr Gln Ile Asp Phe Ser Ser Ser Pro
             805              810              815

Ser Thr Asn Gly Met Phe Thr Leu Thr Thr Asn Gly Asp Leu Pro Lys
             820              825              830

Pro Ile Phe Ile Pro Asn Gly Met Pro Asn Thr Val Val Pro Cys Gly
             835              840              845

Thr Glu Lys Asn Phe Thr Asn Gly Met Val Asn Gly His Met Pro Ser
850              855              860

Leu Pro Asp Ser Pro Phe Thr Gly Tyr Ile Ile Ala Val His Arg Lys
865              870              875              880

Met Met Arg Thr Glu Leu Tyr Phe Leu Ser Pro Gln Glu Asn Arg Pro
                 885              890              895

Ser Leu Phe Gly Met Pro Leu Ile Val Pro Cys Thr Val His Thr Arg
             900              905              910

Lys Lys Asp Leu Tyr Asp Ala Val Trp Ile Gln Val Ser Trp Leu Ala
         915              920              925

Arg Pro Leu Pro Pro Gln Glu Ala Ser Ile His Ala Gln Asp Arg Asp
         930              935              940

Asn Cys Met Gly Tyr Gln Tyr Pro Phe Thr Leu Arg Val Val Gln Lys
945              950              955              960
```

-continued

```
Asp Gly Asn Ser Cys Ala Trp Cys Pro Gln Tyr Arg Phe Cys Arg Gly
            965                 970                 975
Cys Lys Ile Asp Cys Gly Glu Asp Arg Ala Phe Ile Gly Asn Ala Tyr
            980                 985                 990
Ile Ala Val Asp Trp His Pro Thr Ala Leu His Leu Arg Tyr Gln Thr
            995                 1000                1005
Ser Gln Glu Arg Val Val Asp Lys His Glu Ser Val Glu Gln Ser
    1010                1015                1020
Arg Arg Ala Gln Ala Glu Pro Ile Asn Leu Asp Ser Cys Leu Arg
    1025                1030                1035
Ala Phe Thr Ser Glu Glu Leu Gly Glu Ser Glu Met Tyr Tyr
    1040                1045                1050
Cys Ser Lys Cys Lys Thr His Cys Leu Ala Thr Lys Lys Leu Asp
    1055                1060                1065
Leu Trp Arg Leu Pro Pro Phe Leu Ile Ile His Leu Lys Arg Phe
    1070                1075                1080
Gln Phe Val Asn Asp Gln Trp Ile Lys Ser Gln Lys Ile Val Arg
    1085                1090                1095
Phe Leu Arg Glu Ser Phe Asp Pro Ser Ala Phe Leu Val Pro Arg
    1100                1105                1110
Asp Pro Ala Leu Cys Gln His Lys Pro Leu Thr Pro Gln Gly Asp
    1115                1120                1125
Glu Leu Ser Lys Pro Arg Ile Leu Ala Arg Glu Val Lys Lys Val
    1130                1135                1140
Asp Ala Gln Ser Ser Ala Gly Lys Glu Asp Met Leu Leu Ser Lys
    1145                1150                1155
Ser Pro Ser Ser Leu Ser Ala Asn Ile Ser Ser Pro Lys Gly
    1160                1165                1170
Ser Pro Ser Ser Arg Lys Ser Gly Thr Ser Cys Pro Ser Ser
    1175                1180                1185
Lys Asn Ser Ser Pro Asn Ser Ser Pro Arg Thr Leu Gly Arg Ser
    1190                1195                1200
Lys Gly Arg Leu Arg Leu Pro Gln Ile Gly Ser Lys Asn Lys Pro
    1205                1210                1215
Ser Ser Ser Lys Lys Asn Leu Asp Ala Ser Lys Glu Asn Gly Ala
    1220                1225                1230
Gly Gln Ile Cys Glu Leu Ala Asp Ala Leu Ser Arg Gly His Met
    1235                1240                1245
Arg Gly Gly Ser Gln Pro Glu Leu Val Thr Pro Gln Asp His Glu
    1250                1255                1260
Val Ala Leu Ala Asn Gly Phe Leu Tyr Glu His Glu Ala Cys Gly
    1265                1270                1275
Asn Gly Cys Gly Asp Gly Tyr Ser Asn Gly Gln Leu Gly Asn His
    1280                1285                1290
Ser Glu Glu Asp Ser Thr Asp Asp Gln Arg Glu Asp Thr His Ile
    1295                1300                1305
Lys Pro Ile Tyr Asn Leu Tyr Ala Ile Ser Cys His Ser Gly Ile
    1310                1315                1320
Leu Ser Gly Gly His Tyr Ile Thr Tyr Ala Lys Asn Pro Asn Cys
    1325                1330                1335
Lys Trp Tyr Cys Tyr Asn Asp Ser Ser Cys Glu Glu Leu His Pro
    1340                1345                1350
```

```
Asp Glu Ile Asp Thr Asp Ser Ala Tyr Ile Leu Phe Tyr Glu Gln
    1355                1360                1365

Gln Gly Ile Asp Tyr Ala Gln Phe Leu Pro Lys Ile Asp Gly Lys
    1370                1375                1380

Lys Met Ala Asp Thr Ser Ser Thr Asp Glu Asp Ser Glu Ser Asp
    1385                1390                1395

Tyr Glu Lys Tyr Ser Met Leu Gln
    1400                1405

<210> SEQ ID NO 92
<211> LENGTH: 141
<212> TYPE: PRT
<213> ORGANISM: Homo sapiens

<400> SEQUENCE: 92

Met Ala Gly Glu Glu Ile Asn Glu Asp Tyr Pro Val Glu Ile His Glu
1               5                   10                  15

Tyr Leu Ser Ala Phe Glu Asn Ser Ile Gly Ala Val Asp Glu Met Leu
                20                  25                  30

Lys Thr Met Met Ser Val Ser Arg Asn Glu Leu Leu Gln Lys Leu Asp
            35                  40                  45

Pro Leu Glu Gln Ala Lys Val Asp Leu Val Ser Ala Tyr Thr Leu Asn
        50                  55                  60

Ser Met Phe Trp Val Tyr Leu Ala Thr Gln Gly Val Asn Pro Lys Glu
65                  70                  75                  80

His Pro Val Lys Gln Glu Leu Glu Arg Ile Arg Val Tyr Met Asn Arg
                85                  90                  95

Val Lys Glu Ile Thr Asp Lys Lys Lys Ala Gly Lys Leu Asp Arg Gly
                100                 105                 110

Ala Ala Ser Arg Phe Val Lys Asn Ala Leu Trp Glu Pro Lys Ser Lys
            115                 120                 125

Asn Ala Ser Lys Val Ala Asn Lys Gly Lys Ser Lys Ser
        130                 135                 140

<210> SEQ ID NO 93
<211> LENGTH: 521
<212> TYPE: PRT
<213> ORGANISM: Homo sapiens

<400> SEQUENCE: 93

Met Glu Ala Asn Trp Thr Ala Phe Leu Phe Gln Ala His Glu Ala Ser
1               5                   10                  15

His His Gln Gln Gln Ala Ala Gln Asn Ser Leu Leu Pro Leu Leu Ser
                20                  25                  30

Ser Ala Val Glu Pro Pro Asp Gln Lys Pro Leu Leu Pro Ile Pro Ile
            35                  40                  45

Thr Gln Lys Pro Gln Gly Ala Pro Glu Thr Leu Lys Asp Ala Ile Gly
        50                  55                  60

Ile Lys Lys Glu Lys Pro Lys Thr Ser Phe Val Cys Thr Tyr Cys Ser
65                  70                  75                  80

Lys Ala Phe Arg Asp Ser Tyr His Leu Arg Arg His Glu Ser Cys His
                85                  90                  95

Thr Gly Ile Lys Leu Val Ser Arg Pro Lys Lys Thr Pro Thr Thr Val
                100                 105                 110

Val Pro Leu Ile Ser Thr Ile Ala Gly Asp Ser Ser Arg Thr Ser Leu
            115                 120                 125
```

-continued

```
Val Ser Thr Ile Ala Gly Ile Leu Ser Thr Val Thr Ser Ser Ser
        130                 135                 140

Gly Thr Asn Pro Ser Ser Ser Ala Ser Thr Thr Ala Met Pro Val Thr
145                 150                 155                 160

Gln Ser Val Lys Lys Pro Ser Lys Pro Val Lys Lys Asn His Ala Cys
                165                 170                 175

Glu Met Cys Gly Lys Ala Phe Arg Asp Val Tyr His Leu Asn Arg His
            180                 185                 190

Lys Leu Ser His Ser Asp Glu Lys Pro Phe Glu Cys Pro Ile Cys Asn
        195                 200                 205

Gln Arg Phe Lys Arg Lys Asp Arg Met Thr Tyr His Val Arg Ser His
    210                 215                 220

Glu Gly Gly Ile Thr Lys Pro Tyr Thr Cys Ser Val Cys Gly Lys Gly
225                 230                 235                 240

Phe Ser Arg Pro Asp His Leu Ser Cys His Val Lys His Val His Ser
                245                 250                 255

Thr Glu Arg Pro Phe Lys Cys Gln Thr Cys Thr Ala Ala Phe Ala Thr
            260                 265                 270

Lys Asp Arg Leu Arg Thr His Met Val Arg His Glu Gly Lys Val Ser
        275                 280                 285

Cys Asn Ile Cys Gly Lys Leu Leu Ser Ala Ala Tyr Ile Thr Ser His
    290                 295                 300

Leu Lys Thr His Gly Gln Ser Gln Ser Ile Asn Cys Asn Thr Cys Lys
305                 310                 315                 320

Gln Gly Ile Ser Lys Thr Cys Met Ser Glu Glu Thr Ser Asn Gln Lys
                325                 330                 335

Gln Gln Gln Gln Gln Gln Gln Gln Gln Gln Gln Gln Gln Gln Gln Gln
            340                 345                 350

Gln Gln His Val Thr Ser Trp Pro Gly Lys Gln Val Glu Thr Leu Arg
        355                 360                 365

Leu Trp Glu Glu Ala Val Lys Ala Arg Lys Lys Glu Ala Ala Asn Leu
    370                 375                 380

Cys Gln Thr Ser Thr Ala Ala Thr Thr Pro Val Thr Leu Thr Thr Pro
385                 390                 395                 400

Phe Ser Ile Thr Ser Ser Val Ser Ser Gly Thr Met Ser Asn Pro Val
                405                 410                 415

Thr Val Ala Ala Ala Met Ser Met Arg Ser Pro Val Asn Val Ser Ser
            420                 425                 430

Ala Val Asn Ile Thr Ser Pro Met Asn Ile Gly His Pro Val Thr Ile
        435                 440                 445

Thr Ser Pro Leu Ser Met Thr Ser Pro Leu Thr Leu Thr Thr Pro Val
    450                 455                 460

Asn Leu Pro Thr Pro Val Thr Ala Pro Val Asn Ile Ala His Pro Val
465                 470                 475                 480

Thr Ile Thr Ser Pro Met Asn Leu Pro Thr Pro Met Thr Leu Ala Ala
                485                 490                 495

Pro Leu Asn Ile Ala Met Arg Pro Val Glu Ser Met Pro Phe Leu Pro
            500                 505                 510

Gln Ala Leu Pro Thr Ser Pro Pro Trp
        515                 520

<210> SEQ ID NO 94
<211> LENGTH: 686
<212> TYPE: PRT
```

<213> ORGANISM: Homo sapiens

<400> SEQUENCE: 94

Met Thr Asp Ala Leu Leu Pro Ala Ala Pro Gln Pro Leu Glu Lys Lys
1               5                   10                  15

Asn Asp Gly Tyr Phe Arg Lys Gly Cys Asn Pro Leu Ala Gln Thr Gly
            20                  25                  30

Arg Ser Lys Leu Gln Asn Gln Arg Ala Ala Leu Asn Gln Gln Ile Leu
        35                  40                  45

Lys Ala Val Arg Met Arg Thr Gly Ala Glu Asn Leu Leu Lys Val Ala
50                  55                  60

Thr Asn Ser Lys Val Arg Glu Gln Val Arg Leu Glu Leu Ser Phe Val
65                  70                  75                  80

Asn Ser Asp Leu Gln Met Leu Lys Glu Glu Leu Glu Gly Leu Asn Ile
                85                  90                  95

Ser Val Gly Val Tyr Gln Asn Thr Glu Glu Ala Phe Thr Ile Pro Leu
            100                 105                 110

Ile Pro Leu Gly Leu Lys Glu Thr Lys Asp Val Asp Phe Ala Val Val
        115                 120                 125

Leu Lys Asp Phe Ile Leu Glu His Tyr Ser Glu Asp Gly Tyr Leu Tyr
130                 135                 140

Glu Asp Glu Ile Ala Asp Leu Met Asp Leu Arg Gln Ala Cys Arg Thr
145                 150                 155                 160

Pro Ser Arg Asp Glu Ala Gly Val Glu Leu Leu Met Thr Tyr Phe Ile
                165                 170                 175

Gln Leu Gly Phe Val Glu Ser Arg Phe Phe Pro Thr Arg Gln Met
            180                 185                 190

Gly Leu Leu Phe Thr Trp Tyr Asp Ser Leu Thr Gly Val Pro Val Ser
        195                 200                 205

Gln Gln Asn Leu Leu Glu Lys Ala Ser Val Leu Phe Asn Thr Gly
210                 215                 220

Ala Leu Tyr Thr Gln Ile Gly Thr Arg Cys Asp Arg Gln Thr Gln Ala
225                 230                 235                 240

Gly Leu Glu Ser Ala Ile Asp Ala Phe Gln Arg Ala Ala Gly Val Leu
                245                 250                 255

Asn Tyr Leu Lys Asp Thr Phe Thr His Thr Pro Ser Tyr Asp Met Ser
            260                 265                 270

Pro Ala Met Leu Ser Val Leu Val Lys Met Met Leu Ala Gln Ala Gln
        275                 280                 285

Glu Ser Val Phe Glu Lys Ile Ser Leu Pro Gly Ile Arg Asn Glu Phe
290                 295                 300

Phe Met Leu Val Lys Val Ala Gln Glu Ala Ala Lys Val Gly Glu Val
305                 310                 315                 320

Tyr Gln Gln Leu His Ala Ala Met Ser Gln Ala Pro Val Lys Glu Asn
                325                 330                 335

Ile Pro Tyr Ser Trp Ala Ser Leu Ala Cys Val Lys Ala His His Tyr
            340                 345                 350

Ala Ala Leu Ala His Tyr Phe Thr Ala Ile Leu Leu Ile Asp His Gln
        355                 360                 365

Val Lys Pro Gly Thr Asp Leu Asp His Gln Glu Lys Cys Leu Ser Gln
370                 375                 380

Leu Tyr Asp His Met Pro Glu Gly Leu Thr Pro Leu Ala Thr Leu Lys
385                 390                 395                 400

```
Asn Asp Gln Gln Arg Arg Gln Leu Gly Lys Ser His Leu Arg Arg Ala
                405                 410                 415
Met Ala His His Glu Ser Val Arg Glu Ala Ser Leu Cys Lys Lys
        420                 425                 430
Leu Arg Ser Ile Glu Val Leu Gln Lys Val Leu Cys Ala Ala Gln Glu
            435                 440                 445
Arg Ser Arg Leu Thr Tyr Ala Gln His Gln Glu Glu Asp Asp Leu Leu
450                 455                 460
Asn Leu Ile Asp Ala Pro Ser Val Val Ala Lys Thr Glu Gln Glu Val
465                 470                 475                 480
Asp Ile Ile Leu Pro Gln Phe Ser Lys Leu Thr Val Thr Asp Phe Phe
                485                 490                 495
Gln Lys Leu Gly Pro Leu Ser Val Phe Ser Ala Asn Lys Arg Trp Thr
                500                 505                 510
Pro Pro Arg Ser Ile Arg Phe Thr Ala Glu Glu Gly Asp Leu Gly Phe
            515                 520                 525
Thr Leu Arg Gly Asn Ala Pro Val Gln Val His Phe Leu Asp Pro Tyr
530                 535                 540
Cys Ser Ala Ser Val Ala Gly Ala Arg Glu Gly Asp Tyr Ile Val Ser
545                 550                 555                 560
Ile Gln Leu Val Asp Cys Lys Trp Leu Thr Leu Ser Glu Val Met Lys
                565                 570                 575
Leu Leu Lys Ser Phe Gly Glu Asp Glu Ile Glu Met Lys Val Val Ser
                580                 585                 590
Leu Leu Asp Ser Thr Ser Ser Met His Asn Lys Ser Ala Thr Tyr Ser
            595                 600                 605
Val Gly Met Gln Lys Thr Tyr Ser Met Ile Cys Leu Ala Ile Asp Asp
        610                 615                 620
Asp Asp Lys Thr Asp Lys Thr Lys Lys Ile Ser Lys Lys Leu Ser Phe
625                 630                 635                 640
Leu Ser Trp Gly Thr Asn Lys Asn Arg Gln Lys Ser Ala Ser Thr Leu
                645                 650                 655
Cys Leu Pro Ser Val Gly Ala Ala Arg Pro Gln Val Lys Lys Lys Leu
            660                 665                 670
Pro Ser Pro Phe Ser Leu Leu Asn Ser Asp Ser Ser Trp Tyr
            675                 680                 685

<210> SEQ ID NO 95
<211> LENGTH: 462
<212> TYPE: PRT
<213> ORGANISM: Homo sapiens

<400> SEQUENCE: 95

Met Ser Ala Gly Gly Pro Cys Pro Ala Ala Gly Gly Gly Pro Gly
1               5                   10                  15
Gly Ala Ser Cys Ser Val Gly Ala Pro Gly Gly Val Ser Met Phe Arg
                20                  25                  30
Trp Leu Glu Val Leu Glu Lys Glu Phe Asp Lys Ala Phe Val Asp Val
            35                  40                  45
Asp Leu Leu Leu Gly Glu Ile Asp Pro Asp Gln Ala Asp Ile Thr Tyr
        50                  55                  60
Glu Gly Arg Gln Lys Met Thr Ser Leu Ser Ser Cys Phe Ala Gln Leu
65                  70                  75                  80
Cys His Lys Ala Gln Ser Val Ser Gln Ile Asn His Lys Leu Glu Ala
                85                  90                  95
```

Gln Leu Val Asp Leu Lys Ser Glu Leu Thr Glu Thr Gln Ala Glu Lys
            100                 105                 110

Val Val Leu Glu Lys Glu Val His Asp Gln Leu Leu Gln Leu His Ser
        115                 120                 125

Ile Gln Leu Gln Leu His Ala Lys Thr Gly Gln Ser Ala Asp Ser Gly
    130                 135                 140

Thr Ile Lys Ala Lys Leu Ser Gly Pro Ser Val Glu Glu Leu Glu Arg
145                 150                 155                 160

Glu Leu Glu Ala Asn Lys Lys Glu Lys Met Lys Glu Ala Gln Leu Glu
                165                 170                 175

Ala Glu Val Lys Leu Leu Arg Lys Glu Asn Glu Ala Leu Arg Arg His
            180                 185                 190

Ile Ala Val Leu Gln Ala Glu Val Tyr Gly Ala Arg Leu Ala Ala Lys
        195                 200                 205

Tyr Leu Asp Lys Glu Leu Ala Gly Arg Val Gln Gln Ile Gln Leu Leu
    210                 215                 220

Gly Arg Asp Met Lys Gly Pro Ala His Asp Lys Leu Trp Asn Gln Leu
225                 230                 235                 240

Glu Ala Glu Ile His Leu His Arg His Lys Thr Val Ile Arg Ala Cys
                245                 250                 255

Arg Gly Arg Asn Asp Leu Lys Arg Pro Met Gln Ala Pro Pro Gly His
            260                 265                 270

Asp Gln Asp Ser Leu Lys Lys Ser Gln Gly Val Gly Pro Ile Arg Lys
        275                 280                 285

Val Leu Leu Lys Glu Asp His Glu Gly Leu Gly Ile Ser Ile Thr
    290                 295                 300

Gly Gly Lys Glu His Gly Val Pro Ile Leu Ile Ser Glu Ile His Pro
305                 310                 315                 320

Gly Gln Pro Ala Asp Arg Cys Gly Gly Leu His Val Gly Asp Ala Ile
                325                 330                 335

Leu Ala Val Asn Gly Val Asn Leu Arg Asp Thr Lys His Lys Glu Ala
            340                 345                 350

Val Thr Ile Leu Ser Gln Gln Arg Gly Glu Ile Glu Phe Glu Val Val
        355                 360                 365

Tyr Val Ala Pro Glu Val Asp Ser Asp Glu Asn Val Glu Tyr Glu
    370                 375                 380

Asp Glu Ser Gly His Arg Tyr Arg Leu Tyr Leu Asp Glu Leu Glu Gly
385                 390                 395                 400

Gly Gly Asn Pro Gly Ala Ser Cys Lys Asp Thr Ser Gly Glu Ile Lys
                405                 410                 415

Val Leu Gln Gly Phe Asn Lys Lys Ala Val Thr Asp Thr His Glu Asn
            420                 425                 430

Gly Asp Leu Gly Thr Ala Ser Glu Thr Pro Leu Asp Asp Gly Ala Ser
        435                 440                 445

Lys Leu Asp Asp Leu His Thr Leu Tyr His Lys Lys Ser Tyr
    450                 455                 460

<210> SEQ ID NO 96
<211> LENGTH: 617
<212> TYPE: PRT
<213> ORGANISM: Homo sapiens

<400> SEQUENCE: 96

Met Ser Trp Gly Thr Glu Leu Trp Asp Gln Phe Asp Asn Leu Glu Lys

-continued

```
1               5                   10                  15
His Thr Gln Trp Gly Ile Asp Ile Leu Glu Lys Tyr Ile Lys Phe Val
                20                  25                  30
Lys Glu Arg Thr Glu Ile Glu Leu Ser Tyr Ala Lys Gln Leu Arg Asn
                35                  40              45
Leu Ser Lys Lys Tyr Gln Pro Lys Lys Asn Ser Lys Glu Glu Glu Glu
 50                  55                  60
Tyr Lys Tyr Thr Ser Cys Lys Ala Phe Ile Ser Asn Leu Asn Glu Met
 65                  70                  75                  80
Asn Asp Tyr Ala Gly Gln His Glu Val Ile Ser Glu Asn Met Ala Ser
                85                  90                  95
Gln Ile Ile Val Asp Leu Ala Arg Tyr Val Gln Glu Leu Lys Gln Glu
                100                 105                 110
Arg Lys Ser Asn Phe His Asp Gly Arg Lys Ala Gln His Ile Glu
                115                 120             125
Thr Cys Trp Lys Gln Leu Glu Ser Ser Lys Arg Arg Phe Glu Arg Asp
                130                 135             140
Cys Lys Glu Ala Asp Arg Ala Gln Gln Tyr Phe Glu Lys Met Asp Ala
145                 150                 155                 160
Asp Ile Asn Val Thr Lys Ala Asp Val Glu Lys Ala Arg Gln Gln Ala
                165                 170                 175
Gln Ile Arg His Gln Met Ala Glu Asp Ser Lys Ala Asp Tyr Ser Ser
                180                 185                 190
Ile Leu Gln Lys Phe Asn His Glu Gln His Glu Tyr Tyr His Thr His
                195                 200                 205
Ile Pro Asn Ile Phe Gln Lys Ile Gln Glu Met Glu Glu Arg Arg Ile
                210                 215                 220
Val Arg Met Gly Glu Ser Met Lys Thr Tyr Ala Glu Val Asp Arg Gln
225                 230                 235                 240
Val Ile Pro Ile Ile Gly Lys Cys Leu Asp Gly Ile Val Lys Ala Ala
                245                 250                 255
Glu Ser Ile Asp Gln Lys Asn Asp Ser Gln Leu Val Ile Glu Ala Tyr
                260                 265                 270
Lys Ser Gly Phe Glu Pro Pro Gly Asp Ile Glu Phe Glu Asp Tyr Thr
                275                 280                 285
Gln Pro Met Lys Arg Thr Val Ser Asp Asn Ser Leu Ser Asn Ser Arg
                290                 295                 300
Gly Glu Gly Lys Pro Asp Leu Lys Phe Gly Gly Lys Ser Lys Gly Lys
305                 310                 315                 320
Leu Trp Pro Phe Ile Lys Lys Asn Lys Leu Met Ser Leu Leu Thr Ser
                325                 330                 335
Pro His Gln Pro Pro Pro Pro Ala Ser Ala Ser Pro Ser Ala
                340                 345                 350
Val Pro Asn Gly Pro Gln Ser Pro Lys Gln Lys Glu Pro Leu Ser
                355                 360                 365
His Arg Phe Asn Glu Phe Met Thr Ser Lys Pro Lys Ile His Cys Phe
                370                 375                 380
Arg Ser Leu Lys Arg Gly Leu Ser Leu Lys Leu Gly Ala Thr Pro Glu
385                 390                 395                 400
Asp Phe Ser Asn Leu Pro Pro Glu Gln Arg Arg Lys Lys Leu Gln Gln
                405                 410                 415
Lys Val Asp Glu Leu Asn Lys Glu Ile Gln Lys Glu Met Asp Gln Arg
                420                 425                 430
```

-continued

```
Asp Ala Ile Thr Lys Met Lys Asp Val Tyr Leu Lys Asn Pro Gln Met
        435                 440                 445
Gly Asp Pro Ala Ser Leu Asp His Lys Leu Ala Glu Val Ser Gln Asn
    450                 455                 460
Ile Glu Lys Leu Arg Val Glu Thr Gln Lys Phe Glu Ala Trp Leu Ala
465                 470                 475                 480
Glu Val Glu Gly Arg Leu Pro Ala Arg Ser Glu Gln Ala Arg Arg Gln
                485                 490                 495
Ser Gly Leu Tyr Asp Ser Gln Asn Pro Pro Thr Val Asn Asn Cys Ala
        500                 505                 510
Gln Asp Arg Glu Ser Pro Asp Gly Ser Tyr Thr Glu Glu Gln Ser Gln
    515                 520                 525
Glu Ser Glu Met Lys Val Leu Ala Thr Asp Phe Asp Asp Glu Phe Asp
    530                 535                 540
Asp Glu Glu Pro Leu Pro Ala Ile Gly Thr Cys Lys Ala Leu Tyr Thr
545                 550                 555                 560
Phe Glu Gly Gln Asn Glu Gly Thr Ile Ser Val Val Glu Gly Glu Thr
                565                 570                 575
Leu Tyr Val Ile Glu Glu Asp Lys Gly Asp Gly Trp Thr Arg Ile Arg
        580                 585                 590
Arg Asn Glu Asp Glu Glu Gly Tyr Val Pro Thr Ser Tyr Val Glu Val
    595                 600                 605
Cys Leu Asp Lys Asn Ala Lys Asp Ser
    610                 615

<210> SEQ ID NO 97
<211> LENGTH: 1402
<212> TYPE: PRT
<213> ORGANISM: Homo sapiens

<400> SEQUENCE: 97

Met His Gln Thr Leu Cys Leu Asn Pro Glu Ser Leu Lys Met Ser Ala
1               5                   10                  15
Cys Ser Asp Phe Val Glu His Ile Trp Lys Pro Gly Ser Cys Lys Asn
                20                  25                  30
Cys Phe Cys Leu Arg Ser Asp His Gln Leu Val Ala Gly Pro Pro Gln
            35                  40                  45
Pro Arg Ala Gly Ser Leu Pro Pro Pro Arg Leu Pro Arg Pro
    50                  55                  60
Glu Asn Cys Arg Leu Glu Asp Glu Gly Val Asn Ser Ser Pro Tyr Ser
65                  70                  75                  80
Lys Pro Thr Ile Ala Val Lys Pro Thr Met Met Ser Ser Glu Ala Ser
                85                  90                  95
Asp Val Trp Thr Glu Ala Asn Leu Ser Ala Glu Val Ser Gln Val Ile
                100                 105                 110
Trp Arg Arg Ala Pro Gly Lys Leu Pro Leu Pro Lys Gln Glu Asp Ala
            115                 120                 125
Pro Val Val Tyr Leu Gly Ser Phe Arg Gly Val Gln Lys Pro Ala Gly
        130                 135                 140
Pro Ser Thr Ser Pro Asp Gly Asn Ser Arg Cys Pro Pro Ala Tyr Thr
145                 150                 155                 160
Met Val Gly Leu His Asn Leu Glu Pro Arg Gly Glu Arg Asn Ile Ala
                165                 170                 175
Phe His Pro Val Ser Phe Pro Glu Glu Lys Ala Val His Lys Glu Lys
```

-continued

```
                180                 185                 190
Pro Ser Phe Pro Tyr Gln Asp Arg Pro Ser Thr Gln Glu Ser Phe Arg
            195                 200                 205
Gln Lys Leu Ala Ala Phe Ala Gly Thr Thr Ser Gly Cys His Gln Gly
        210                 215                 220
Pro Gly Pro Leu Arg Glu Ser Leu Pro Ser Glu Asp Ser Asp Gln
225                 230                 235                 240
Arg Cys Ser Pro Ser Gly Asp Ser Glu Gly Glu Tyr Cys Ser Ile
                245                 250                 255
Leu Asp Cys Cys Pro Gly Ser Pro Val Ala Lys Ala Ala Ser Gln Thr
            260                 265                 270
Ala Gly Ser Arg Gly Arg His Gly Gly Arg Asp Cys Ser Pro Thr Cys
        275                 280                 285
Trp Glu Gln Gly Lys Cys Ser Gly Pro Ala Glu Gln Glu Lys Arg Gly
        290                 295                 300
Pro Ser Phe Pro Lys Glu Cys Cys Ser Gln Gly Pro Thr Ala His Pro
305                 310                 315                 320
Ser Cys Leu Gly Pro Lys Lys Leu Ser Leu Thr Ser Glu Ala Ala Ile
                325                 330                 335
Ser Ser Asp Gly Leu Ser Cys Gly Ser Gly Ser Gly Ser Gly Ala Ser
            340                 345                 350
Ser Pro Phe Val Pro His Leu Glu Ser Asp Tyr Cys Ser Leu Met Lys
        355                 360                 365
Glu Pro Ala Pro Glu Lys Gln Gln Asp Pro Gly Cys Pro Gly Val Thr
        370                 375                 380
Pro Ser Arg Cys Leu Gly Leu Thr Gly Glu Pro Gln Pro Pro Ala His
385                 390                 395                 400
Pro Arg Glu Ala Thr Gln Pro Glu Pro Ile Tyr Ala Glu Ser Thr Lys
                405                 410                 415
Arg Lys Lys Ala Ala Pro Val Pro Ser Lys Ser Gln Ala Lys Ile Glu
            420                 425                 430
His Ala Ala Ala Gln Gly Gln Gly Gln Val Cys Thr Gly Asn Ala
        435                 440                 445
Trp Ala Gln Lys Ala Ala Ser Gly Trp Gly Arg Asp Ser Pro Asp Pro
        450                 455                 460
Thr Pro Gln Val Ser Ala Thr Ile Thr Val Met Ala Ala His Pro Glu
465                 470                 475                 480
Glu Asp His Arg Thr Ile Tyr Leu Ser Ser Pro Asp Ser Ala Val Gly
                485                 490                 495
Val Gln Trp Pro Arg Gly Pro Val Ser Gln Asn Ser Glu Val Gly Glu
            500                 505                 510
Glu Glu Thr Ser Ala Gly Gln Gly Leu Ser Ser Arg Glu Ser His Ala
        515                 520                 525
His Ser Ala Ser Glu Ser Lys Pro Lys Glu Arg Pro Ala Ile Pro Pro
        530                 535                 540
Lys Leu Ser Lys Ser Ser Pro Val Gly Ser Pro Val Ser Pro Ser Ala
545                 550                 555                 560
Gly Gly Pro Pro Val Ser Pro Leu Ala Asp Leu Ser Asp Gly Ser Ser
                565                 570                 575
Gly Gly Ser Ser Ile Gly Pro Gln Pro Ser Gln Gly Pro Ala Asp
            580                 585                 590
Pro Ala Pro Ser Cys Arg Thr Asn Gly Val Ala Ile Ser Asp Pro Ser
        595                 600                 605
```

-continued

```
Arg Cys Pro Gln Pro Ala Ala Ser Ser Ala Ser Glu Gln Arg Arg Pro
    610                 615                 620
Arg Phe Gln Ala Gly Thr Trp Ser Arg Gln Cys Arg Ile Glu Glu Glu
625                 630                 635                 640
Glu Glu Val Glu Gln Glu Leu Leu Ser His Ser Trp Gly Arg Glu Thr
            645                 650                 655
Lys Asn Gly Pro Thr Asp His Ser Asn Ser Thr Thr Trp His Arg Leu
            660                 665                 670
His Pro Thr Asp Gly Ser Ser Gly Gln Asn Ser Lys Val Gly Thr Gly
            675                 680                 685
Met Ser Lys Ser Ala Ser Phe Ala Phe Glu Phe Pro Lys Asp Arg Ser
    690                 695                 700
Gly Ile Glu Thr Phe Ser Pro Pro Pro Pro Lys Ser Arg His
    705                 710                 715                 720
Leu Leu Lys Met Asn Lys Ser Ser Asp Leu Glu Lys Val Ser Gln
                725                 730                 735
Gly Ser Ala Glu Ser Leu Ser Pro Ser Phe Arg Gly Val His Val Ser
            740                 745                 750
Phe Thr Thr Gly Ser Thr Asp Ser Leu Ala Ser Asp Ser Arg Thr Cys
    755                 760                 765
Ser Asp Gly Gly Pro Ser Ser Glu Leu Ala His Ser Pro Thr Asn Ser
770                 775                 780
Gly Lys Lys Leu Phe Ala Pro Val Pro Phe Pro Ser Gly Ser Thr Glu
785                 790                 795                 800
Asp Val Ser Pro Ser Gly Pro Gln Gln Pro Pro Leu Pro Gln Lys
            805                 810                 815
Lys Ile Val Ser Arg Ala Ala Ser Ser Pro Asp Gly Phe Phe Trp Thr
            820                 825                 830
Gln Gly Ser Pro Lys Pro Gly Thr Ala Ser Pro Lys Leu Asn Leu Ser
        835                 840                 845
His Ser Glu Thr Asn Val His Asp Glu Ser His Phe Ser Tyr Ser Leu
    850                 855                 860
Ser Pro Gly Asn Arg His His Pro Val Phe Ser Ser Ser Asp Pro Leu
865                 870                 875                 880
Glu Lys Ala Phe Lys Gly Ser Gly His Trp Leu Pro Ala Ala Gly Leu
                885                 890                 895
Ala Gly Asn Arg Gly Gly Cys Gly Ser Pro Gly Leu Gln Cys Lys Gly
            900                 905                 910
Ala Pro Ser Ala Ser Ser Ser Gln Leu Ser Val Ser Ser Gln Ala Ser
            915                 920                 925
Thr Gly Ser Thr Gln Leu Gln Leu His Gly Leu Leu Ser Asn Ile Ser
    930                 935                 940
Ser Lys Glu Gly Thr Tyr Ala Lys Leu Gly Gly Leu Tyr Thr Gln Ser
945                 950                 955                 960
Leu Ala Arg Leu Val Ala Lys Cys Glu Asp Leu Phe Met Gly Gly Gln
                965                 970                 975
Lys Lys Glu Leu His Phe Asn Glu Asn Asn Trp Ser Leu Phe Lys Leu
            980                 985                 990
Thr Cys Asn Lys Pro Cys Cys Asp Ser Gly Asp Ala Ile Tyr Tyr Cys
            995                1000                1005
Ala Thr Cys Ser Glu Asp Pro Gly Ser Thr Tyr Ala Val Lys Ile
    1010                1015                1020
```

```
Cys Lys Ala Pro Glu Pro Lys Thr Val Ser Tyr Cys Ser Pro Ser
1025                1030                1035

Val Pro Val His Phe Asn Ile Gln Gln Asp Cys Gly His Phe Val
    1040                1045                1050

Ala Ser Val Pro Ser Ser Met Leu Ser Ser Pro Asp Ala Pro Lys
1055                1060                1065

Asp Pro Val Pro Ala Leu Pro Thr His Pro Ala Gln Glu Gln
    1070                1075                1080

Asp Cys Val Val Ile Thr Arg Glu Val Pro His Gln Thr Ala
1085                1090                1095

Ser Asp Phe Val Arg Asp Ser Ala Ala Ser His Gln Ala Glu Pro
    1100                1105                1110

Glu Ala Tyr Glu Arg Arg Val Cys Phe Leu Leu Leu Gln Leu Cys
    1115                1120                1125

Asn Gly Leu Glu His Leu Lys Glu His Gly Ile Ile His Arg Asp
1130                1135                1140

Leu Cys Leu Glu Asn Leu Leu Leu Val His Cys Thr Leu Gln Ala
    1145                1150                1155

Gly Pro Gly Pro Ala Pro Ala Pro Ala Pro Ala Pro Ala Ala Ala
1160                1165                1170

Ala Pro Pro Cys Ser Ser Ala Ala Pro Pro Ala Gly Gly Thr Leu
    1175                1180                1185

Ser Pro Ala Ala Gly Pro Ala Ser Pro Glu Gly Pro Arg Glu Lys
    1190                1195                1200

Gln Leu Pro Arg Leu Ile Ile Ser Asn Phe Leu Lys Ala Lys Gln
    1205                1210                1215

Lys Pro Gly Gly Thr Pro Asn Leu Gln Gln Lys Lys Ser Gln Ala
1220                1225                1230

Arg Leu Ala Pro Glu Ile Val Ser Ala Ser Gln Tyr Arg Lys Phe
    1235                1240                1245

Asp Glu Phe Gln Thr Gly Ile Leu Ile Tyr Glu Leu Leu His Gln
1250                1255                1260

Pro Asn Pro Phe Glu Val Arg Ala Gln Leu Arg Glu Arg Asp Tyr
1265                1270                1275

Arg Gln Glu Asp Leu Pro Pro Leu Pro Ala Leu Ser Leu Tyr Ser
    1280                1285                1290

Pro Gly Leu Gln Gln Leu Ala His Leu Leu Leu Glu Ala Asp Pro
1295                1300                1305

Ile Lys Arg Ile Arg Ile Gly Glu Ala Lys Arg Val Leu Gln Cys
1310                1315                1320

Leu Leu Trp Gly Pro Arg Arg Glu Leu Val Gln Gln Pro Gly Thr
    1325                1330                1335

Ser Glu Glu Ala Leu Cys Gly Thr Leu His Asn Trp Ile Asp Met
1340                1345                1350

Lys Arg Ala Leu Met Met Met Lys Phe Ala Glu Lys Ala Val Asp
    1355                1360                1365

Arg Arg Arg Gly Val Glu Leu Glu Asp Trp Leu Cys Cys Gln Tyr
    1370                1375                1380

Leu Ala Ser Ala Glu Pro Gly Ala Leu Leu Gln Ser Leu Lys Leu
    1385                1390                1395

Leu Gln Leu Leu
    1400
```

```
<210> SEQ ID NO 98
<211> LENGTH: 32
<212> TYPE: DNA
<213> ORGANISM: Mus musculus

<400> SEQUENCE: 98
caggatccat tctggaagat ctgaacatgc tg                           32

<210> SEQ ID NO 99
<211> LENGTH: 29
<212> TYPE: DNA
<213> ORGANISM: Mus musculus

<400> SEQUENCE: 99
cagaattcgc ccccaccagt tttttcgag                              29

<210> SEQ ID NO 100
<211> LENGTH: 30
<212> TYPE: DNA
<213> ORGANISM: Homo sapiens

<400> SEQUENCE: 100
accgaattcg aagctgagca atatttctcg                             30

<210> SEQ ID NO 101
<211> LENGTH: 39
<212> TYPE: DNA
<213> ORGANISM: Homo sapiens

<400> SEQUENCE: 101
accgaattct caacattgtg tattagcttt ctttctata                   39

<210> SEQ ID NO 102
<211> LENGTH: 29
<212> TYPE: DNA
<213> ORGANISM: Homo sapiens

<400> SEQUENCE: 102
caggatcctc tgcatcatat ggggatgat                              29

<210> SEQ ID NO 103
<211> LENGTH: 32
<212> TYPE: DNA
<213> ORGANISM: Homo sapiens

<400> SEQUENCE: 103
cagaattctc atagaataca aagagcagaa ag                          32

<210> SEQ ID NO 104
<211> LENGTH: 31
<212> TYPE: DNA
<213> ORGANISM: Homo sapiens

<400> SEQUENCE: 104
caggatccaa agagaaagag cggccagaga t                           31

<210> SEQ ID NO 105
<211> LENGTH: 39
<212> TYPE: DNA
<213> ORGANISM: Homo sapiens

<400> SEQUENCE: 105
cagaattctc aacactcagc tgacttatct gtaaagctc                   39
```

```
<210> SEQ ID NO 106
<211> LENGTH: 29
<212> TYPE: DNA
<213> ORGANISM: Homo sapiens

<400> SEQUENCE: 106
caggatccaa gcaccccgac accaagaag                                    29

<210> SEQ ID NO 107
<211> LENGTH: 31
<212> TYPE: DNA
<213> ORGANISM: Homo sapiens

<400> SEQUENCE: 107
cagaattcac ccagtggtgc ttatatggac c                                 31

<210> SEQ ID NO 108
<211> LENGTH: 32
<212> TYPE: DNA
<213> ORGANISM: Homo sapiens

<400> SEQUENCE: 108
caggatccga catccagaac cctgacatca cg                                32

<210> SEQ ID NO 109
<211> LENGTH: 36
<212> TYPE: DNA
<213> ORGANISM: Homo sapiens

<400> SEQUENCE: 109
cagaattctc aacatcgaga tggcggtggg ggcggc                            36

<210> SEQ ID NO 110
<211> LENGTH: 24
<212> TYPE: PRT
<213> ORGANISM: Homo sapiens

<400> SEQUENCE: 110

Cys Asp Glu His Thr Arg Arg Glu Leu Ala Lys Met Lys Gln Glu Pro
1               5                   10                  15

Val Lys Pro Glu Glu Gly Arg Asp
            20

<210> SEQ ID NO 111
<211> LENGTH: 261
<212> TYPE: DNA
<213> ORGANISM: Homo sapiens

<400> SEQUENCE: 111
atcctggagg acctcaatat gctctacatc cggcagatgg cactcagcct ggaggacaca    60
gacctgcaga ggaaactaga tcatgagatc cggatgaggg atggggcctg caagctgctg   120
gcagcctgct cccagcgaga gcaggctctg gaagccacca agagcctgct ggtgtgcaac   180
agccgtattc tcagctacat gggtgagctg cagcggcgaa aggaggccca ggtgctggag   240
aagacaggca ggcgaccttc g                                            261

<210> SEQ ID NO 112
<211> LENGTH: 87
<212> TYPE: PRT
<213> ORGANISM: Homo sapiens

<400> SEQUENCE: 112
```

```
Ile Leu Glu Asp Leu Asn Met Leu Tyr Ile Arg Gln Met Ala Leu Ser
1               5                   10                  15

Leu Glu Asp Thr Glu Leu Gln Arg Lys Leu Asp His Glu Ile Arg Met
            20                  25                  30

Arg Asp Gly Ala Cys Lys Leu Leu Ala Ala Cys Ser Gln Arg Glu Gln
        35                  40                  45

Ala Leu Glu Ala Thr Lys Ser Leu Leu Val Cys Asn Ser Arg Ile Leu
    50                  55                  60

Ser Tyr Met Gly Glu Leu Gln Arg Arg Lys Glu Ala Gln Val Leu Glu
65              70                  75                  80

Lys Thr Gly Arg Arg Pro Ser
                85

<210> SEQ ID NO 113
<211> LENGTH: 261
<212> TYPE: DNA
<213> ORGANISM: Homo sapiens

<400> SEQUENCE: 113
attctggaag atctgaacat gctgtacatt cggcagatgg cgctgtcttt agaagatacg        60
gaacttcaac gtaaattaga tcatgaaatc cgcatgcgtg atggtgccga aaaactcctg       120
gccgcgttgt cccagagaga acaggcactg gaagcaacca atcattgct ggtgtcgaat        180 agccgtatcc tgagttatat gggcgaactt cagcgccgca agaagcaca agttctcgaa        240 aaaactggtg ggggctgcta a                                                 261

<210> SEQ ID NO 114
<211> LENGTH: 87
<212> TYPE: PRT
<213> ORGANISM: Homo sapiens

<400> SEQUENCE: 114

Ile Leu Glu Asp Leu Asn Met Leu Tyr Ile Arg Gln Met Ala Leu Ser
1               5                   10                  15

Leu Glu Asp Thr Glu Leu Gln Arg Lys Leu Asp His Glu Ile Arg Met
            20                  25                  30

Arg Asp Gly Ala Glu Lys Leu Leu Ala Ala Leu Ser Gln Arg Glu Gln
        35                  40                  45

Ala Leu Glu Ala Thr Lys Ser Leu Leu Val Ser Asn Ser Arg Ile Leu
    50                  55                  60

Ser Tyr Met Gly Glu Leu Gln Arg Arg Lys Glu Ala Gln Val Leu Glu
65              70                  75                  80

Lys Thr Gly Arg Arg Cys Ser
                85
```